United States Patent
Wu et al.

(10) Patent No.: US 9,695,180 B2
(45) Date of Patent: Jul. 4, 2017

(54) SUBSTITUTED IMIDAZO[1,2-A]PYRAZINES AS LSD1 INHIBITORS

(71) Applicant: Incyte Corporation, Wilmington, DE (US)

(72) Inventors: Liangxing Wu, Wilmington, PA (US); Joel R. Courter, Glen Mills, PA (US); Chunhong He, Chadds Ford, PA (US); Jingwei Li, Westfield, NJ (US); Liang Lu, Hockessin, DE (US); Yaping Sun, Hockessin, DE (US); Xiaozhao Wang, Drexel Hill, PA (US); Wenqing Yao, Chadds Ford, PA (US); Colin Zhang, Ambler, PA (US); Jincong Zhuo, Garnet Valley, PA (US)

(73) Assignee: Incyte Corporation, Wilmington, DE (US)

( * ) Notice: Subject to any disclaimer, the term of this patent is extended or adjusted under 35 U.S.C. 154(b) by 48 days.

(21) Appl. No.: 14/795,466

(22) Filed: Jul. 9, 2015

(65) Prior Publication Data
US 2016/0009720 A1 Jan. 14, 2016

Related U.S. Application Data

(60) Provisional application No. 62/022,913, filed on Jul. 10, 2014.

(51) Int. Cl.
*A61K 31/4985* (2006.01)
*C07D 487/04* (2006.01)
*C07D 519/00* (2006.01)

(52) U.S. Cl.
CPC ......... *C07D 487/04* (2013.01); *C07D 519/00* (2013.01)

(58) Field of Classification Search
CPC ...................... A61K 31/4985; C07D 487/04
USPC .......................................... 514/249; 544/350
See application file for complete search history.

(56) References Cited

U.S. PATENT DOCUMENTS

| | | | |
|---|---|---|---|
| 5,658,857 A | 8/1997 | Andree et al. |
| 8,115,000 B2 | 2/2012 | Rajagopalan et al. |
| 8,349,210 B2 | 1/2013 | Xu et al. |
| 8,546,394 B2 | 10/2013 | Li |
| 8,853,408 B2 | 10/2014 | Johnson |
| 2002/0151549 A1 | 10/2002 | Hayakawa et al. |
| 2004/0023972 A1 | 2/2004 | Sundermann et al. |
| 2004/0058938 A1 | 3/2004 | Cullmann et al. |
| 2004/0082635 A1 | 4/2004 | Hashimoto et al. |
| 2004/0082781 A1 | 4/2004 | Hibi et al. |
| 2004/0220189 A1 | 11/2004 | Sun et al. |
| 2005/0009832 A1 | 1/2005 | Sun et al. |
| 2005/0113283 A1 | 5/2005 | Solow-Cordero et al. |
| 2006/0178399 A1 | 8/2006 | Nishizawa et al. |
| 2006/0194842 A1 | 8/2006 | Uchida et al. |
| 2007/0004772 A1 | 1/2007 | Sun et al. |
| 2007/0191395 A1 | 8/2007 | Kawakami |
| 2008/0249154 A1 | 10/2008 | Ohmoto et al. |
| 2009/0203690 A1 | 8/2009 | Akritopoulou-Zanze et al. |
| 2009/0318436 A1 | 12/2009 | Albrecht et al. |
| 2010/0113441 A1 | 5/2010 | Siegel et al. |
| 2011/0105457 A1 | 5/2011 | Taniyama et al. |
| 2011/0112067 A1 | 5/2011 | Hartmann et al. |
| 2012/0004262 A1 | 1/2012 | Guibourt et al. |
| 2012/0108500 A1 | 5/2012 | Sakane et al. |
| 2012/0220582 A1 | 8/2012 | Mitchell et al. |
| 2012/0283266 A1 | 11/2012 | Ortega Munoz et al. |
| 2012/0322877 A1 | 12/2012 | Casero et al. |
| 2013/0035377 A1 | 2/2013 | Minucci et al. |
| 2013/0040946 A1 | 2/2013 | Siegel et al. |
| 2013/0090386 A1 | 4/2013 | Ortega Munoz et al. |
| 2013/0095067 A1 | 4/2013 | Baker et al. |
| 2013/0109751 A1 | 5/2013 | Salvatore |
| 2013/0197013 A1 | 8/2013 | Fyfe et al. |
| 2013/0203754 A1 | 8/2013 | Yang et al. |
| 2013/0217878 A1 | 8/2013 | Lizuka et al. |
| 2013/0231342 A1 | 9/2013 | Munoz et al. |
| 2013/0303545 A1 | 11/2013 | Maes et al. |
| 2014/0011857 A1 | 1/2014 | Casero et al. |

(Continued)

FOREIGN PATENT DOCUMENTS

| CA | 2831143 | 10/2012 |
|---|---|---|
| CA | 2844525 | 2/2013 |

(Continued)

OTHER PUBLICATIONS

Jordan, V. C. Nature Reviews: Drug Discovery, 2, 2003, 205.*

(Continued)

*Primary Examiner* — Douglas M Willis
(74) *Attorney, Agent, or Firm* — Fish & Richardson P.C.

(57) ABSTRACT

The present invention is directed to imidazo[1,2-a]pyrazine derivatives of Formula I, or a pharmaceutically acceptable salt thereof, which are LSD1 inhibitors useful in the treatment of diseases such as cancer.

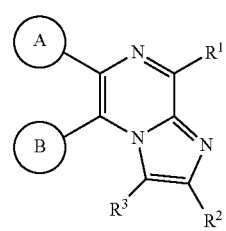

I

53 Claims, No Drawings

(56) References Cited

U.S. PATENT DOCUMENTS

| | | | |
|---|---|---|---|
| 2014/0018393 A1 | 1/2014 | Johnson et al. |
| 2014/0094445 A1 | 4/2014 | Vakayalapati et al. |
| 2014/0206757 A1 | 7/2014 | Shi et al. |
| 2014/0213657 A1 | 7/2014 | Munoz et al. |
| 2014/0228405 A1 | 8/2014 | Tomita et al. |
| 2014/0256742 A1 | 9/2014 | Baker et al. |
| 2014/0296255 A1 | 10/2014 | Maes et al. |
| 2014/0329833 A1 | 11/2014 | Maes et al. |
| 2014/0343118 A1 | 11/2014 | McCafferty et al. |
| 2015/0065434 A1 | 3/2015 | Woster et al. |
| 2015/0065495 A1 | 3/2015 | Vankayalapati et al. |
| 2015/0133564 A1 | 5/2015 | Oh et al. |
| 2015/0225375 A1 | 8/2015 | Wu et al. |
| 2015/0225379 A1 | 8/2015 | Wu et al. |
| 2015/0225394 A1 | 8/2015 | Wu et al. |
| 2015/0225401 A1 | 8/2015 | Wu et al. |
| 2015/0232436 A1 | 8/2015 | Baker et al. |
| 2016/0009711 A1 | 1/2016 | Wu et al. |
| 2016/0009712 A1 | 1/2016 | Wu et al. |
| 2016/0009721 A1 | 1/2016 | Wu et al. |
| 2016/0289238 A1 | 10/2016 | He et al. |

FOREIGN PATENT DOCUMENTS

| | | |
|---|---|---|
| CA | 2887598 | 4/2014 |
| CN | 103054869 | 4/2013 |
| CN | 103124724 | 5/2013 |
| CN | 103373996 | 10/2013 |
| CN | 103893163 | 7/2014 |
| CN | 103933036 | 7/2014 |
| CN | 103961340 | 8/2014 |
| CN | 104119280 | 10/2014 |
| DE | 102006041292 | 3/2008 |
| EP | 0404190 | 12/1990 |
| EP | 0430385 | 6/1991 |
| EP | 2524918 | 11/2012 |
| EP | 2740474 | 6/2014 |
| EP | 2743256 | 6/2014 |
| FR | 2662163 | 11/1991 |
| FR | 2920090 | 2/2009 |
| FR | 2920091 | 2/2009 |
| JP | 2000319277 | 11/2000 |
| JP | 2000319278 | 11/2000 |
| JP | 2001006877 | 1/2001 |
| JP | 2001035664 | 2/2001 |
| JP | 2001057292 | 2/2001 |
| JP | 2001114780 | 4/2001 |
| JP | 2005089352 | 4/2005 |
| JP | 2010070503 | 4/2010 |
| WO | WO 8804298 | 6/1988 |
| WO | WO 9325553 | 12/1993 |
| WO | WO 9418198 | 8/1994 |
| WO | WO 95/12594 * | 5/1995 |
| WO | WO 9924434 | 5/1999 |
| WO | WO 01/27119 | 4/2001 |
| WO | WO 01/83481 | 8/2001 |
| WO | WO 02/00196 | 1/2002 |
| WO | WO 02/06286 | 1/2002 |
| WO | WO 02/34748 | 5/2002 |
| WO | WO 02/38562 | 5/2002 |
| WO | WO 02/051831 | 7/2002 |
| WO | WO 02/072549 | 9/2002 |
| WO | WO 03/006471 | 1/2003 |
| WO | WO 03/044021 | 5/2003 |
| WO | WO 03/062392 | 7/2003 |
| WO | WO 2004/017950 | 3/2004 |
| WO | WO 2004/021989 | 3/2004 |
| WO | WO 2004/058762 | 7/2004 |
| WO | WO 2004/072081 | 8/2004 |
| WO | WO 2004/074290 | 9/2004 |
| WO | WO 2004/089380 | 10/2004 |
| WO | WO 2004/089416 | 10/2004 |
| WO | WO 2004/096131 | 11/2004 |
| WO | WO 2004/108692 | 12/2004 |
| WO | WO 2005/007658 | 1/2005 |
| WO | WO 2005/025558 | 3/2005 |
| WO | WO 2005/035532 | 4/2005 |
| WO | WO 2005/042537 | 5/2005 |
| WO | WO 2005/044793 | 5/2005 |
| WO | WO 2005/097052 | 10/2005 |
| WO | WO 2006/015263 | 2/2006 |
| WO | WO 2006/018727 | 2/2006 |
| WO | WO 2006/038116 | 4/2006 |
| WO | WO 2006/057946 | 6/2006 |
| WO | WO 2006/058752 | 6/2006 |
| WO | WO 2006/073938 | 7/2006 |
| WO | WO 2006/074041 | 7/2006 |
| WO | WO 2006/113704 | 10/2006 |
| WO | WO 2006/131003 | 12/2006 |
| WO | WO 2006/135667 | 12/2006 |
| WO | WO 2006/135795 | 12/2006 |
| WO | WO 2006/138657 | 12/2006 |
| WO | WO 2006/138695 | 12/2006 |
| WO | WO 2006/138734 | 12/2006 |
| WO | WO 2007/022529 | 2/2007 |
| WO | WO 2007/028051 | 3/2007 |
| WO | WO 2007/058942 | 5/2007 |
| WO | WO 2007/074491 | 7/2007 |
| WO | WO 2007/095588 | 8/2007 |
| WO | WO 2007/113226 | 10/2007 |
| WO | WO 2007/145921 | 12/2007 |
| WO | WO 2007/149478 | 12/2007 |
| WO | WO 2008/005262 | 1/2008 |
| WO | WO 2008/005423 | 1/2008 |
| WO | WO 2008/005908 | 1/2008 |
| WO | WO 2008/008539 | 1/2008 |
| WO | WO 2008/011560 | 1/2008 |
| WO | WO 2008/027812 | 3/2008 |
| WO | WO 2008/037607 | 4/2008 |
| WO | WO 2008/045393 | 4/2008 |
| WO | WO 2008/056176 | 5/2008 |
| WO | WO 2008/064157 | 5/2008 |
| WO | WO 2008/065198 | 6/2008 |
| WO | WO 2008/113559 | 9/2008 |
| WO | WO 2008/125111 | 10/2008 |
| WO | WO 2008/130951 | 10/2008 |
| WO | WO 2008/141239 | 11/2008 |
| WO | WO 2008/154241 | 12/2008 |
| WO | WO 2008/156614 | 12/2008 |
| WO | WO 2008/157752 | 12/2008 |
| WO | WO 2009/010530 | 1/2009 |
| WO | WO 2009/017701 | 2/2009 |
| WO | WO 2009/017954 | 2/2009 |
| WO | WO 2009/023179 | 2/2009 |
| WO | WO 2009/045753 | 4/2009 |
| WO | WO 2009/047514 | 4/2009 |
| WO | WO 2009/047563 | 4/2009 |
| WO | WO 2009/085230 | 7/2009 |
| WO | WO 2009/085980 | 7/2009 |
| WO | WO 2009/091374 | 7/2009 |
| WO | WO 2009/114180 | 9/2009 |
| WO | WO 2009/114512 | 9/2009 |
| WO | WO 2009/128520 | 10/2009 |
| WO | WO 2010/010184 | 1/2010 |
| WO | WO 2010/010187 | 1/2010 |
| WO | WO 2010/010188 | 1/2010 |
| WO | WO 2010/010189 | 1/2010 |
| WO | WO 2010/019899 | 2/2010 |
| WO | WO 2010/033906 | 3/2010 |
| WO | WO 2010/036380 | 4/2010 |
| WO | WO 2010/043721 | 4/2010 |
| WO | WO 2010/048149 | 4/2010 |
| WO | WO 2010/064020 | 6/2010 |
| WO | WO 2010/084160 | 7/2010 |
| WO | WO 2010/088368 | 8/2010 |
| WO | WO 2010/091067 | 8/2010 |
| WO | WO 2010/104306 | 9/2010 |
| WO | WO 2010/108059 | 9/2010 |
| WO | WO 2010/113942 | 10/2010 |
| WO | WO 2010/119264 | 10/2010 |
| WO | WO 2010/136438 | 12/2010 |
| WO | WO 2010/144571 | 12/2010 |
| WO | WO 2010/151711 | 12/2010 |
| WO | WO 2011/022439 | 2/2011 |

(56) References Cited

FOREIGN PATENT DOCUMENTS

| | | |
|---|---|---|
| WO | WO 2011/033265 | 3/2011 |
| WO | WO 2011/035941 | 3/2011 |
| WO | WO 2011/042217 | 4/2011 |
| WO | WO 2011/050245 | 4/2011 |
| WO | WO 2011/089400 | 7/2011 |
| WO | WO 2011/097607 | 8/2011 |
| WO | WO 2011/106105 | 9/2011 |
| WO | WO 2011/106106 | 9/2011 |
| WO | WO 2011/112766 | 9/2011 |
| WO | WO 2011/113606 | 9/2011 |
| WO | WO 2011/113862 | 9/2011 |
| WO | WO 2011/121137 | 10/2011 |
| WO | WO 2011/131576 | 10/2011 |
| WO | WO 2011/131697 | 10/2011 |
| WO | WO 2011/141713 | 11/2011 |
| WO | WO 2011/143365 | 11/2011 |
| WO | WO 2011/160548 | 12/2011 |
| WO | WO 2012/003392 | 1/2012 |
| WO | WO 2012/007345 | 1/2012 |
| WO | WO 2012/013727 | 2/2012 |
| WO | WO 2012/013728 | 2/2012 |
| WO | WO 2012/016133 | 2/2012 |
| WO | WO 2012/034116 | 3/2012 |
| WO | WO 2012/042042 | 4/2012 |
| WO | WO 2012/047852 | 4/2012 |
| WO | WO 2012/052730 | 4/2012 |
| WO | WO 2012/052745 | 4/2012 |
| WO | WO 2012/054233 | 4/2012 |
| WO | WO 2012/071469 | 5/2012 |
| WO | WO 2012/072713 | 6/2012 |
| WO | WO 2012/080230 | 6/2012 |
| WO | WO 2012/080232 | 6/2012 |
| WO | WO 2012/080234 | 6/2012 |
| WO | WO 2012/080236 | 6/2012 |
| WO | WO 2012/080476 | 6/2012 |
| WO | WO 2012/080729 | 6/2012 |
| WO | WO 2012/088411 | 6/2012 |
| WO | WO 2012/088438 | 6/2012 |
| WO | WO 2012/100229 | 7/2012 |
| WO | WO 2012/107498 | 8/2012 |
| WO | WO 2012/107499 | 8/2012 |
| WO | WO 2012/116237 | 8/2012 |
| WO | WO 2012/129562 | 9/2012 |
| WO | WO 2012/135113 | 10/2012 |
| WO | WO 2012/147890 | 11/2012 |
| WO | WO 2012/156531 | 11/2012 |
| WO | WO 2012/156537 | 11/2012 |
| WO | WO 2012/176856 | 12/2012 |
| WO | WO 2012/177606 | 12/2012 |
| WO | WO 2013/010380 | 1/2013 |
| WO | WO 2013/025805 | 2/2013 |
| WO | WO 2013/033515 | 3/2013 |
| WO | WO 2013/033688 | 3/2013 |
| WO | WO 2013/053690 | 4/2013 |
| WO | WO 2013/057320 | 4/2013 |
| WO | WO 2013/057322 | 4/2013 |
| WO | WO 2013/074390 | 5/2013 |
| WO | WO 2013/085877 | 6/2013 |
| WO | WO 2013/131609 | 9/2013 |
| WO | WO 2013/147711 | 10/2013 |
| WO | WO 2014/002051 | 1/2014 |
| WO | WO 2014/009296 | 1/2014 |
| WO | WO 2014/058071 | 4/2014 |
| WO | WO 2014/078479 | 5/2014 |
| WO | WO 2014/084298 | 6/2014 |
| WO | WO 2014/085613 | 6/2014 |
| WO | WO 2014/086790 | 6/2014 |
| WO | WO 2014/127350 | 8/2014 |
| WO | WO 2014/138791 | 9/2014 |
| WO | WO 2014/164867 | 10/2014 |
| WO | WO 2014/194280 | 12/2014 |
| WO | WO 2014/205213 | 12/2014 |
| WO | WO 2013/022047 | 3/2015 |
| WO | WO 2015/031564 | 3/2015 |
| WO | WO 2015/089192 | 6/2015 |
| WO | WO 2015/156417 | 10/2015 |
| WO | WO 2015/181380 | 12/2015 |
| WO | WO 2016/007722 | 1/2016 |
| WO | WO 2016/007727 | 1/2016 |
| WO | WO 2016/007731 | 1/2016 |
| WO | WO 2016/007736 | 1/2016 |

OTHER PUBLICATIONS

Hackam, et al. JAMA, 296(14), 2006, 1731-1732.*
Guiles et al. "Preparation of triazolopyrimidine derivatives as P2T receptor antagonists," CA130:168386 (1999).
Improper Markush Fed. Reg. 76(27) p. 7612-75, slide 1, 64-67 (2011).
"LSD1 inhibitors of Lysine specific demethylase 1, a novel target in neurodegenerative disease," Powerpoint presentation, Oryzon, Feb. 2011, 42 pages.
Abdulla et al., "Natural Polyphenols Inhibit Lysine-Specific Demethylase-1 in vitro," Journal of Biochemical and Pharamcological Research, Mar. 2013, 1: 56-63.
Adamo et al., "LSD1 and pluripotency: a new player in the network," Cell Cycle, Oct. 2011, 10(19): 3215-6.
Adamo et al., "LSD1 regulates the balance between self-renewal and differentiation in human embryonic stem cells," Nat. Cell Biol, Jun. 2011, 13(6): 652-9.
Anand and Marmorstein, "Structure and mechanism of lysine-specific demethylase enzymes," J Biol Chem, Dec. 2007, 282(49): 35425-9.
Baron et al., "Molecular Mimicry and Ligand Recognition in Binding and Catalysis by the Histone Demethylase LSD1-CoREST Complex," Structure, Feb. 2011, 19: 212-220.
Bauer et al., "Reawakening fetal hemoglobin: prospects for new therapies for the β-globin disorders," Blood, Oct. 2012, 120(15): 3945-53.
Beck and Blanpain, "Unravelling cancer stem cell potential," Nat Rev Cancer, Oct. 2013, 13(10): 727-38.
Benelkebir et al., "Enantioselective synthesis of tranylcypromine analogues as lysine demethylase (LSD1) inhibitors," Bioorganic & Medicinal Chemistry, 2011, 19: 3709-3716.
Bennani-Baiti et al., "Lysine-specific demethylase 1 (LSD1/KDM1A/A0F2/BHC110) is expressed and is an epigenetic drug target in chondrosarcoma, Ewing's sarcoma, osteosarcoma, and rhabdomyosarcoma," Hum Pathol, Aug. 2012, 43(8): 1300-7.
Berge and Robiette, "Development of a Regioselective N-Methylation of (Benz)imidazoles Providing the More Sterically Hindered Isomer," The Journal of Organic Chemistry, 2013, A-D.
Berge et al., "Pharmaceutical salts," J Pharm Sci, 1977, 66(1): 1-19.
Binda et al., "Biochemical, Structural, and Biological Evaluation of Tranylcypromine Derivatives as Inhibitors of Histone Demethylases LSD1 and LSD2," J. Am. Chem. Soc., 2010, 132: 6827-6833.
Binda et al., "Molecular Insights into Human Monoamine Oxidase B Inhibition by the Glitazone Antidiabetes Drugs," ACS Med. Chem. Letter, 2012, 3: 39-42.
Blom et al., "Optimizing Preparative LC/MS Configurations and Methods for Parallel Synthesis Purification," J. Comb. Chem., 2003, 5(5): 670-683.
Blom et al., "Preparative LC-MS Purification: Improved Compound-Specific Method Optimization," J. Comb. Chem., 2004, 6(6): 874-883.
Blom, "Two-Pump at-Column-Dilution Configuration for Preparative Liquid Chomratography-Mass Spectrometry," J. Comb. Chem, 2002, 4(4): 295-301.
Cain, "AML takes LSD1," SciBX, Apr. 2012, 1-3.
Cao et al., "One-Pot Regiospecific Synthesis of Imidazo[1,2-a]pyridines: A Novel, Metal-Free, Three-Component Reaction for the Formation of C-N, C-O, and C-S Bonds," Org. Lett., 2013, A-D.
Chen and Flies, "Molecular mechanisms of T cell co-stimulation and co-inhibition," Nat Rev Immunol, Apr. 2013, 13(4): 227-42.
Chen et al., "Crystal structure of human histone lysine-specific demethylase 1 (LSD1)," Proc Natl Acad Sci USA, Sep. 2006, 103(38): 13956-61.

(56) References Cited

OTHER PUBLICATIONS

Chen et al., "Lysine-specific histone demethylase 1 (LSD1): A potential molecular target for tumor therapy," Crit Rev Eukaryot Gene Expre, 2012, 22(1): 53-9.
Cho et al., "Demethylation of RB regulator MYPT1 by histone demethylase LSD1 promotes cell cycle progression in cancer cells," Cancer Res., Feb. 2011, 71(3): 655-60.
Clevers, "The cancer stem cell: premises, promises and challenges," Nat Med., Mar. 2011, 17(3): 313-9.
Crea et al., "The emerging role of histone lysine demethylases in prostate cancer," Mol Cancer, Aug. 2012, 11:52.
Cui et al., "The LSD1 inhibitor RN-1 induces fetal hemoglobin synthesis and reduces disease pathology in sickle cell mice," Blood, 2015, 1-31.
Culhane and Cole, "LSD1 and the chemistry of histone demethylation," Current Opinion in Chemical Biology, 2007, 11: 561-568.
Culhane et al., "A Mechanism-Based Inactivator for Histone Demethylase LSD1," J. Am. Chem. Soc., 2006, 128: 4536-4537.
Culhane et al., "Comparative Analysis of Small Molecules and Histone Substrate Analogues as LSD1 Lysine Demethylase Inhibitors," J. Am. Chem. Soc., 2010, 132: 3164-3176.
Dancy et al., "Azalysine Analogues as Probes for Protein Lysine Deacetylation and Demethylation," J. Am. Chem. Soc., 2012, 5138-5148.
Dawson and Kouzarides, "Cancer epigenetics: from mechanism to therapy," Cell, Jul. 2012, 150(1): 12-27.
Dhanak, "Cracking the Code: The Promise of Epigenetics," ACS Med. Chem. Letter, 2012, 3: 521-523.
Dhudshia and Thadani, "Diastereoselective allylation and crotylation of N-unsubstituted imines derived from ketones," Chem. Commun., 33 pages.
Dhudshia et al., "Diastereoselective allylation and crotylation of N-unsubstituted imines derived from ketones," Chem Commun, 2005, 5551-5553.
Ding et al., "LSD1-mediated epigenetic modification contributes to proliferation and metastasis of colon cancer," Br J Cancer, Aug. 2013, 109(4): 994-1003.
Dulla et al., "Synthesis and evaluation of 3-amino/guanidine substituted phenyl oxazoles as a novel class of LSD1 inhibitors with anti-proliferative properties," The Royal Society of Chemistry, 2013, 1-25.
Ellsworth et al., "Reductions in log P Improved Protein Binding and Clearance Predictions Enabling the Prospective Design of Cannabinoid Receptor (CB1) Antagonists with Desired Pharmacokinetic Properties," J. Med. Chem., 2013, 56: 9586-9600.
Fiskus et al., "Pre-Clinical Efficacy of Combined Therapy with LSD1 Antagonist SP-2509 and Pan-Histone Deacetylase Inhibitor Against AML Blast Pregenitor Cells," 54th ASH Annual Meeting and Exposition, session 604, poster abstract, Dec. 2012, [retrieved on May 1, 2013]. Retrieved from the Internet at URL: https://ash.confex.com/ash/2012/webprogram/Paper53429.html, 2 pages.
Forneris et al., "LSD1: oxidative chemistry for multifaceted functions in chormatin regulation," Cell Press, Mar. 2008, 181-189.
Forneris, F., et al., *Structural basis of LSD1-CoREST selectivity in histone H3 recognition*. J Biol Chem, 2007. 282(28): p. 20070-4.
Ganesan, "Targeting Epigenetic Demethylation," University of East Anglia (School of Pharmacy), PowerPoint presentation, Presented from the World Epigenetics Summit, London, Jul. 24, 2012, 26 pages.
Ge et al., "Pd-Catalyzed α-Arylation of α,α-Difluoroketones with Aryl Bromides and Chlorides. A Route to Difluoromethylarenes," J. Am. Chem. Soc., 2014, A-D.
Gonzalez et al., "Selective and Potent Morpholinone Inhibitors of the MDM2-p53 Protein-Protein Interaction," J. Med. Chem., 2013, A-Q.
Gooden et al., "Facile synthesis of substituted trans-2-arylcyclopropylamine inhibitors of the human histone demethylase LSD1 and monoamine oxidases A and B," Bioorganic & Medicinal Chemistry Letters, 2008, 18: 3047-3051.
Greaves and Gribben, "The role of B7 family molecules in hematologic malignancy," Blood, Jan. 2013, 121(5): 734-44.
Gui et al., "C-H Methylation of Heteroarenes Inspired by Radical SAM Methyl Transferase," J. Am. Chem. Soc., 2014, A-D.
Hakimi et al., "A core-BRAF35 complex containing histone deacetylase mediates repression of neuronal-specific genes," Proc Natl Acad Sci USA, May 2002, 99(11): 7420-5.
Hamada et al., "Design, Synthesis, Enzyme-Inhibitory Activity, and Effect on Human Cancer Cells of a Novel Series of Jumonji Domain-Containing Protein 2 Histone Demethylase Inhibitors," J. Med. Chem., 2010, 52: 5629-5638.
Hamilton et al., "Comparison of a Direct and Indirect Method for Measuring Flavins-Assessing Flavin Status in Patients Receiving Total Parenteral Nutrition," The Open Clinical Chemistry Journal, 2009, 2: 42-48.
Han et al., "Synergistic re-activation of epigenetically silenced genes by combinatorial inhibition of DNMTs and LSD1 in cancer cells," pLoS One, Sep. 2013, 8(9): e75136.
Harris et al., "The histone demethylase KDM1A sustains the oncogenic potential of MLL-AF9 leukemia stem cells," Cancer Cell, Apr. 2012, 21(4): 473-87.
Hayami et al., "Overexpression of LSD1 contributes to human carcinogenesis through chromatin regulation in various cancers," Int J Cancer, Feb. 2011, 128(3): 574-86.
Hazeldine et al., "Low Molecular Weight Amidoximes that Act as Potent Inhibitors of Lysine-Specific Demethylase 1," J. Med. Chem., 2012, 55: 7378-7391.
Hesp et al., "Expedient Synthesis of α-Heteroaryl Piperidines Using a Pd-Catalyzed Suzuki Cross-Coupling—Reduction Sequence," Org. Lett., 2013, A-C.
Hicken et al., "Discovery of a Novel Class of Imidazo[1,2-a]Pyridines with Potent PDGFR Activity and Oral Bioavailability," ACS Med. Chem. Lett., 2013, A-F.
Hitchin et al., "Development and evaluation of selective, reversible LSD1 inhibitors derived from fragments," Med. Chem. Commun., 2013, 4: 1513-1522.
Hoffmann et al., "The role of histone demethylases in cancer therapy," Molecular Oncology, 2012, 6: 683-703.
Hou and Yu, "Structural insights into histone lysine demethylation," Current Opinion in Structural Biology, 2010, 20: 739-748.
Hruschka et al., "Fluorinated phenylcyclopropylamines. Part 5: Effects of electron-withdrawing or -donating aryl substituents on the inhibition of monoamine oxidases A and B by 2-aryl-2-fluoro-cyclopropylamines," Bioorganic & Medicinal Chemistry, 2008, 16: 7148-7166.
Huang et al., "p53 is regulated by the lysine demethylase LSD1," Nature, Sep. 2007, 449(7158): 105-8.
Huang et al., "Rhodium(III)-Catalyzed Direct Selective C(5)-H Oxidative Annulations of 2-Substituted Imidazoles and Alkynes by Double C-H Activation," Organic Letters, Feb. 2013, 15(8): 1878-1881.
International Search Report and Written Opinion in International Application No. PCT/US2015/015635, dated May 8, 2015, 10 pages.
International Search Report and Written Opinion in International Application No. PCT/US2015/015663, dated May 6, 2015, 10 pages.
International Search Report and Written Opinion in International Application No. PCT/US2015/015706, dated May 6, 2015, 16 pages.
International Search Report and Written Opinion in International Application No. PCT/US2015/015600, dated May 18, 2015, 9 pages.
International Search Report and Written Opinion in International Application No. PCT/US2015/039734, dated Sep. 18, 2015, 14 pages.
International Search Report and Written Opinion in International Application No. PCT/US2015/039724, dated Sep. 15, 2015, 14 pages.
International Search Report and Written Opinion in International Application No. PCT/US2015/039718, dated Sep. 15, 2015, 13 pages.

(56) References Cited

OTHER PUBLICATIONS

Jalluri, Drug Analysis Table, LSD1 KDM1a Cortellis Update, retrieved on May 6, 2013, 3 pages.

Kahl et al., "Androgen Receptor Coactivators Lysine-Specific Histone Demethylase 1 and Four and a Half LIM Domain Protein 2 Predict Risk of Prostate Cancer Recurrence," Cancer Res., 2006, 66(23): 11341-7.

Kakizawa et al., "Histone H3 peptide based LSD1-selective inhibitors," Bioorganic & Medicinal Chemistry Letters, 2015, 25: 1925-1928.

Karytinos et al., "A novel mammalian flavin-dependent histone demethylase," J Biol Chem, Jan. 2009, 284(26): 17775-82.

Kelly and Lipshutz, "Chemoselective Reductions of Nitroaromatics in Water at Room Temperature," Org. Lett., 2013, A-D.

Kettle et al., "Diverse Heterocyclic Scaffolds as Allosteric Inhibitors of AKT," Journal of Medicinal Chemistry, Mar. 2012, 55(3): 1261-1273.

Khan et al., "An Overview of Phenylcyclopropylamine Derivatives: Biochemical and Biological Significance and Recent Developments," Medicinal Research Reviews, 2012, 874-910.

Khoury et al., "Efficient Assembly of Iminodicarboxamides by a "Truly" Four-Component Reaction," Angew. Chem. Int. Ed., 2012, 51: 10280-10283.

Kinzel et al., "Identification of MK-5710 ((8aS)-8a-methyl-1,3-dioxo-2-[(1S,2R)-2-phenylcyclo-propyl]-N-(1-phenyl-1H-pyrazol-5-yl)hexahydro-imidazo[1,5-a]pyrazine-7(1H)-carboxamide), a potent smoothened antagonist for use in Hedgehog pathway dependent malignancies, part 2," Bioorg Med Chem Lett, Aug. 2011, 21(15): 4429-35.

Kjer-Nielsen et al., "MR1 presents microbial vitamin B metabolites to MAIT cells," Nature, Nov. 2012, 491: 717-725.

Kong et al., "Immunohistochemical expression of RBP2 and LSD1 in papillary thyroid carcinoma," Rom J Morphol Embryol, 2013, 54(3): 499-503.

Konovalov and Garcia-Bassets, "Analysis of the levels of lysine-specific demethylase 1 (LSD1) mRNA in human ovarian tumors and the effects of chemical LSD1 inhibitors in ovarian cancer cell lines," J Ovarian Res, Oct. 2013, 6(1): 75.

Kontaki and Talianidis, "Lysine methylation regulates E2F1-induced cell death," Mol Cell, Jul. 2010, 39(1): 152-60.

Kooistra and Helin, "Molecular mechanisms and potential functions of histone demethylases," Nat Rev Mol Cell Biol, Apr. 2012, 13(5): 297-311.

Kutz et al., "3,5-Diamino-1,2,4-triazoles as a novel scaffold for potent, reversible LSD1 (KDM1A) inhibitors," Med. Chem. Commun., 2014, 5: 1863-1870.

Lan et al., "Recognition of unmethylated histone H3 lysine 4 links BHC80 to LSD1-mediated gene repression," Nature, 2007, 718-723.

Larsen and Hartwig, "Iridium-Catalyzed C-H Borylation of Heteroarenes: Scope, Regioselectivity, Application to Late-Stage Functionalization, and Mechanism," J. Am. Chem. Soc., 2013, A-M.

Lee et al., "Functional interplay between histone demethylase and deacetylase enzymes," Mol Cell Biol, Sep. 2006, 26(17): 6395-402.

Liang et al., "A Novel Selective LSD1/KDM1A Inhibitor Epigenetically Blocks Herpes Simplex Virus Lytic Replication and Reactivation from Latency," mBio, 2013, 4(1): 1-9.

Liang et al., "Inhibition of the histone demethylase LSD1 blocks alpha-herpesvirus lytic replication and reactivation from latency," Nat Med., Nov. 2009, 15(11): 1312-7.

Liang et al., "Targeting the JMJD2 histone demethylases to epigenetically control herpesvirus infection and reactivation from latency," Sci Transl Med., Jan. 2013, 5(167): 167ra5.

Lim et al., "Lysine-specific demethylase 1 (LSD1) is highly expressed in ER-negative breast cancers and a biomarker predicting aggressive biology," Carcinogenesis, Mar. 2010, 31(3): 512-20.

Liu and Nefzi, "Solid-Phase Synthesis of N-Substituted Pyrrolidinone-Tethered N-Substituted Piperidines via Ugi Reaction," J. Comb. Chem., 2010, 12: 566-570.

Lund and van Lohuizen, "Epigenetics and cancer," Genes Dev., Oct. 2004, 18(19): 2315-35.

Lv et al., "Over-Expression of LSD1 Promotes Proliferation, Migration and Invasion in Non-Small Cell Lung Cancer," PLoS One, Apr. 2012, 7(4): 1-8, e35065.

Lynch et al., "CD86 expression as a surrogate cellular biomarker for pharmacological inhibition of the histone demethylase lysine-specific demethylase 1," Anal Biochem, Nov. 2013, 442(1): 104-6.

Lynch et al., "LSD1 Inhibition: A therapeutic strategy in cancer?," Expert Opinion on Therapeutic Targets, 2012, 16(12): 1239-1249.

Merck KGaA, "Product comparison—EMD4Biosciences," Comparison of LSD1 inhibitors, EMD Millipore USA, retrieved on May 6, 2013, 3 pages.

Metzger et al., "LSD1 demethylates repressive histone marks to promote androgen-receptor-dependent transcription," Nature, Sep. 2005, 437(7057): 436-9.

Mimasu et al., "Structurally Designed trans-2-Phenylcyclopropylamine Derivatives Potently Inhibit Histone Demethylase LSD1/KDM1," Biochemistry, 2010, 49: 6494-6503.

Moon et al., "Copper-Catalyzed Chan-Lam Coupling between Sulfonyl Azides and Boronic Acids at Room Temperature," Org. Lett., 2013, A-D.

Moormann et al., "Potential Antisecretory Antidiarrheals. 2. $\alpha_2$-Adrenergic 2-[(Aryloxy)alkyl]imidazolines," American Chemical Society, 1990, 33: 614-626.

Mosammaparast and Shi, "Reversal of histone methylation: biochemical and molecular mechanisms of histone demethylases," Annu Rev Biochem, 2010, 79: 155-79.

Mulder et al., "Development of a Safe and Economical Synthesis of Methyl 6-Chloro-5-(trifluoromethyl)nicotinate: Trifluoromethylation on Kilogram Scale," Org. Process Res. Dev., 2013, 940-945.

Neelamegam et al., "Brain-penetrant LSD1 inhibitors can block memory consolidation," Supplementary Data, 24 pages.

Neelamegam et al., "Brain-Penetrant LSD1 Inhibitors Can Block Memory Consolidation," ACS Chem. Neurosci., 2012, 3:120-128.

Ogasawara et al., "Lysine-Specific Demethylase 1-Selective Inactivators: Protein-Targeted Drug Delivery Mechanism," Angew. Chem. Int. Ed., 2013, 52: 8620-8624.

Ogasawara et al., "Lysine-Specific Demethylase 1-Selective Inactivators: Protein-Targeted Drug Delivery Mechanism," Supporting Information.

Patani et al., "Bioisosterism: A Rational Approach in Drug Design," Chemical Reviews, 1996, 96: 3147-3176.

Pitt "Heteroaromatic Rings of the Future" J. Med. Chem. 2009, 52, 2952-2963.

Portela and Esteller, "Epigenetic modifications and human disease," Nat Biotechnol, Oct. 2010, 28(10): 1057-68.

Potts et al., "The mass spectra of somes-triazolo[4,3-a]pyrazines," Organic Mass Spectrometry, Jun. 1971, 5(6): 663-674.

Pozharskii et. al. Heterocycles in Life and Society Wiley, 1997, pp. 1-6.

*Remington's Pharmaceutical Sciences*, 17$^{th}$ Ed., (Mack Publishing Company, Easton, 1985), p. 1418.

Roberston et al., "Expanding the Druggable Space of the LSD1/CoREST Epigenetic Target: New Potential Binding Regions for Drug-Like Molecules, Peptides, Protein Partners, and Chromatin," PLOS, Jul. 2013, 9(7): 1-10.

Rostom et al., "A facile synthesis of some 3-cyano-1,4,6-trisubstituted-2(1)-pyridinones and their biological evaluation as anticancer agents," Medicinal Chemistry Research, Oct. 2010, 20(8): 1260-1272.

Rotilli and Mai, "Targeting Histone Demethylases: A New Avenue for the Fight against Cancer," Genes and Cancer, 2011, 2(6): 663-679.

Sakane et al., "Activation of HIV transcription by the viral Tat protein requires a demethylation step mediated by lysine-specific demethylase 1 (LSD1/KDM1)," PLoS Pathog., Aug. 2011, 7(8):e1002184.

Salarius Pharmaceuticals (Non confidential pharmaceutical package), Oncology Epigenetic Therapy Sp-2528, an Inhibitor of Lysine-Specific Demethylase 1 (LSD1), Jan. 2012, 28 pages.

(56) References Cited

OTHER PUBLICATIONS

Samann et al., "Full Functionalization of the Imidazole Scaffold by Selective Metalation and Sulfoxide/Magnesium Exchange," Angew. Chem. Int. Ed., 2013, 52: 1-6.
Sankaran and Orkin, "The switch from fetal to adult hemoglobin," Cold Spring Harb Perspect Med., Jan. 2013, 3(1): a011643.
Sareddy et al., "KDM1 is a novel therapeutic target for the treatment of gliomas," Oncotarget, Jan. 2013, 4(1): 18-28.
Schenk et al., "Inhibition of the LSD1 (KDM1A) demethylase reactivates the all-trans-retinoic acid differentiation pathway in acute myeloid leukemia," Nat Med, Mar. 2012, 18(4): 605-11.
Schmitt et al., "Nonpeptidic Propargylamines as Inhibitors of Lysine Specific Demethylase 1 (LSD1) with Cellular Activity," J. Med. Chem., 2013, A-I.
Schulte et al., "Lysine-Specific Demethylase 1 Is Strongly Expressed in Poorly Differentiated Neuroblastoma: Implications for Therapy," Cancer Res, 2009, 69(5): 2065-71.
Senecal et al., "A General, Practical Palladium-Catalyzed Cyanation of (Hetero) Aryl Chlorides and Bromides," Angew. Chem. Int. Ed., 2013, 52: 1-6.
Serce et al., "Elecated expression of LSD1 (Lysine-specific demethylase 1) during tumour progression from re-invasive to invasive ductal carcinoma of the breast," BMC Clin Pathol, Aug. 2012, 12:13.
Sharma et al., "(Bis)urea and (Bis)thiourea Inhibitors of Lysine-Specific Demethylase 1 as Epigenetic Modulators," J. Med. Chem., 2010, 53: 5197-5212.
Shen and Laird, "Interplay between the cancer genome and epigenome," Cell, Mar. 2013, 153(1): 38-55.
Shi et al., "Histone demethylation mediated by the nuclear amine oxidase homolog LSD1," Cell, Dec. 2004, 119(7): 941-53.
Shi et al., "Lysine-specific demethylase 1 is a therapeutic target for fetal hemoglobin induction," Nat Med, Mar. 2013, 19(3): 291-4.
Shi et al., "Regulation of LSD1 Histone Demethylase Activity by Its Associated Factors," Molecular Cell, Sep. 2005, 19: 857-864.
Singh et al., "Inhibition of LSD1 sensitizes gliobastoma cells to histone deacetylase inhibitors," Neuro Oncol, Aug. 2011, 13(8): 894-903.
Son et al., "Structure of human monoamine oxidase A at 2.2-A resolution: The control of opening the entry for substrates/inhibitors," PNAS, Apr. 2008, 105(15): 5739-5744.
Stavropoulos et al., "Crystal structure and mechanism of human lysine-specific demethylase-1," Nat Struct Mol Biol, Jul. 2006, 13(7): 626-32.
Search Report, May 30, 2014, 6 pages.
Search Report, May 30, 2014, 109 pages.
Search Report, Jun. 3, 2014, 7 pages.
Suikki et al., "Genetic alterations and changes in expression of histone demethylases in prostate cancer," Prostate, Jun. 2010, 70(8): 889-96.
Sun et al., "Histone demethylase LSD1 regulates neural stem cell proliferation," Mol Cell Biol, Apr. 2010, 30(8): 1997-2005.
Suzuki and Miyata, "Lysine Demethylases Inhibitors," J. Med. Chem., 2011, 54: 8236-8250.
Szewczuk et al., "Mechanistic Analysis of a Suicide Inactivator of Histone Demethylase LSD1," Biochemistry, 2007, 46: 6892-6902.
Szostak et al., "Highly Chemoselective Reduction of Amides (Primary, Secondary, Tertiary) to Alcohols using $SmI_2$/Amine/$H_2O$ under Mild Conditions," J. Am. Chem. Soc., 2013, A-D.
Theisen et al., "Reversible inhibition of lysine specific demethylase 1 is a novel anti-tumor strategy for poorly differentiated endometrial carcinoma," BMC Cancer, 2014, 14:752 1-12.
Tortorici et al., "Protein Recognition by Short Peptide Reversible Inhibitors of the Chromatin-Modifying LSD1/CoREST Lysine Demethylase," ACS Chem. Biol., 2013, 8(8): 1677-1682.
Ueda and Nagasawa, "Facile Synthesis of 1,2,4-Triazoles via a Copper-Catalyzed Tandem Addition—Oxidative Cyclization," J. Am. Chem. Soc., 2009, 131: 15080-15081.
Ueda et al., "Identification of Cell-Active Lysine Specific Demethylase 1-Selective Inhibitors," J. Am. Chem. Soc., 2009, 131: 17536-17537.
Vianello et al., "Synthesis, biological activity and mechanistic insights of 1-substituted cyclopropylamine derivatives: A novel class of irreversible inhibitors of histone demethylase KDM1A," European Journal of Medicinal Chemistry, 2014, 86: 352-363.
Wakefield, Basil "Fluorinated Pharamceuticals" Innovations in Pharamceutical Technology 2003, 74: 76-78, Online "http://web.archive.org/web/20030905122408/http://www.iptonline.com/articles/public/IPTFOUR74NP.pdf". (accessed via Wayback machine Nov. 20, 2009 showing web availability as of Sep. 2003).
Waldmann and Schneider, "Targeting histone modifications—epigenetics in cancer," Curr Opin Cell Biol, Apr. 2013, 25(2): 184-9.
Wang et al., "Novel Histone Demethylase LSD1 Inhibitors Selectively Target Cancer Cells with Pluripotent Stem Cell Properties," Cancer Res, Dec. 2011, 7238-7249.
Wang et al., "The lysine demethylase LSD1 (KDM1) is required for maintenance of global DNA methylation," Nat Genet, Jan. 2009, 41(1): 125-9.
Wen et al., "Triptolide induces cell-cycle arrest and apoptosis of human multiple myeloma cells in vitro via altering expression of histone demethylase LSD1 and JMJD2B," Acta Pharmacologica Sinica, 2012, 33: 109-119.
Wengryniuk et al., "Regioselective Bromination of Fused Heterocyclic N-Oxides," American Chemical Society, 2013, 15(4): 792-795.
Willmann et al., "Impairment of prostate cancer cell growth by a selective and reversible lysine-specific demethylase 1 inhibitor," Int. J. Cancer, 2012, 131: 2704-2709.
Xu et al., "Corepressor-dependent silencing of fetal hemoglobin expression by BCL11A," Proc Natl Acad Sci USA, Apr. 2013, 110(16): 6518-23.
Yang et al., "Reversible methylation of promoter-bound STAT3 by histone-modifying enzymes," Proc Natl Acad Sci USA, Dec. 2010, 107(50): 21499-504.
Yang et al., "Structural Basis for the Inhibition of the LSD1 Histone Demethylase by the Antidepressant trans-2-Phenylcyclopropylamine," Biochemistry, 2007, 46: 8058-8065.
Yang et al., "Structural basis of histone demethylation by LSD1 revealed by suicide inactivation," Nature Structural & Molecular Biology, Jun. 2007, 14(6): 535-539.
Yoshida et al., "Fluorinated Phenylcyclopropylamines. 1. Synthesis and Effect of Fluorine Substitution at the Cyclopropane Ring on Inhibition of Microbial Tyramine Oxidase," J. Med. Chem., 2004, 47: 1796-1806.
You et al., "CoREST is an integral component of the CoREST-human histone deacetylase complex," Proc Natl Acad Sci USA, Feb. 2001, 98(4): 1454-8.
Yu et al., "Energetic factos determining the binding of type I inhibitors to c-Met kinase: experimental studies and quantum mechanical calculations," Acta Pharmacologica Sinica, Nov. 2013, 34(11): 1475-1783.
Yu et al., "High expression of lysine-specific demethylase 1 correlates with poor prognosis of patients with esophageal squamous cell carcinoma," Biochem Biophys Res Commun, Jul. 2013, 437(2): 192-8.
Zhang et al., "Pluripotent stem cell protein Sox2 confers sensitivity to LSD1 inhibition in cancer cells," Cell Rep, Oct. 2013, 5(2): 445-57.
Zheng et al., "A Systematic Review of Histone Lysine-Specific Demethylase 1 and Its Inhibitors," 2015, 1-40.
Carey, FA. Organic Chemistry 6th Ed. McGraw Hill. 2006, chapter 1, p. 9.
Hackam et al., JAMA, 296(14), 2006, 1731-1732.
International Preliminary Report on Patentability in International Application No. PCT/US2015/015600, dated Aug. 25, 2016, 7 pages.
International Preliminary Report on Patentability in International Application No. PCT/US2015/015635, dated Aug. 16, 2016, 8 pages.

(56) References Cited

OTHER PUBLICATIONS

International Preliminary Report on Patentability in International Application No. PCT/US2015/015663, dated Aug. 16, 2016, 7 pages.
International Preliminary Report on Patentability in International Application No. PCT/US2015/015706, dated Aug. 16, 2016, 10 pages.
International Preliminary Report on Patentability in International Application No. PCT/US2015/039734, dated Jan. 10, 2017, 10 pages.
International Preliminary Report on Patentability in International Application No. PCT/US2015/039706, dated Jan. 10, 2017, 10 pages.
International Preliminary Report on Patentability in International Application No. PCT/US2015/039724, dated Jan. 10, 2017, 10 pages.
International Preliminary Report on Patentability in International Application No. PCT/US2015/039718, dated Jan. 10, 2017, 9 pages.
International Search Report and Written Opinion in International Application No. PCT/US2016/025550, dated Aug. 30, 2016, 12 pages.
International Search Report and Written Opinion in International Application No. PCT/US2016/046497, dated Oct. 21, 2016, 13 pages.
International Search Report and Written Opinion in International Application No. PCT/US2015/039706, dated Sep. 16, 2015, 12 pages.
Jordan, V.C. Nature Reviews: Drug Discovery, 2, 2003, 205.
Kocienski, PJ. et al. Protecting Groups. Thieme. 2005, p. 52.
Kuroyanagi et al., "Novel anti fungal agents: Triazolopyridines as inhibitors of beta-1,6-glucan synthesis," Bioorgan IC & Medicinal Chemistry, Aug. 2010, 18(16):5845-5854.
Kuroyanagi et al., "1,3-Benzoxazole-4-carbonitrile as a novel antifungal scaffold of beta-1,6-glucan synthesis inhibitors," Bioorganic & Medicinal Chemistry, Nov. 2010, 18(21):7593-7606.
Zhu et al., "Preparation of imidazolidin-2-imines and their analogs as aspartyl protease inhibitors for treating various diseases," CA149: 307842 (2008).

\* cited by examiner

SUBSTITUTED IMIDAZO[1,2-A]PYRAZINES AS LSD1 INHIBITORS

FIELD OF THE INVENTION

The present invention is directed to imidazo[1,2-a]pyrazine derivatives which are LSD1 inhibitors useful in the treatment of diseases such as cancer.

BACKGROUND OF THE INVENTION

Epigenetic modifications can impact genetic variation but, when dysregulated, can also contribute to the development of various diseases (Portela, A. and M. Esteller, *Epigenetic modifications and human disease*. Nat Biotechnol, 2010. 28(10): p. 1057-68; Lund, A. H. and M. van Lohuizen, *Epigenetics and cancer*. Genes Dev, 2004. 18(19): p. 2315-35). Recently, in depth cancer genomics studies have discovered many epigenetic regulatory genes are often mutated or their own expression is abnormal in a variety of cancers (Dawson, M. A. and T. Kouzarides, *Cancer epigenetics: from mechanism to therapy*. Cell, 2012. 150(1): p. 12-27; Waldmann, T. and R. Schneider, *Targeting histone modifications—epigenetics in cancer*. Curr Opin Cell Biol, 2013. 25(2): p. 184-9; Shen, H. and P. W. Laird, *Interplay between the cancer genome and epigenome*. Cell, 2013. 153(1): p. 38-55). This implies epigenetic regulators function as cancer drivers or are permissive for tumorigenesis or disease progression. Therefore, deregulated epigenetic regulators are attractive therapeutic targets.

One particular enzyme which is associated with human diseases is lysine specific demethylase-1 (LSD1), the first discovered histone demethylase (Shi, Y., et al., *Histone demethylation mediated by the nuclear amine oxidase homolog LSD1*. Cell, 2004. 119(7): p. 941-53). It consists of three major domains: the N-terminal SWIRM which functions in nucleosome targeting, the tower domain which is involved in protein-protein interaction, such as transcriptional co-repressor, co-repressor of RE1-silencing transcription factor (CoREST), and lastly the C terminal catalytic domain whose sequence and structure share homology with the flavin adenine dinucleotide (FAD)-dependent monoamine oxidases (i.e., MAO-A and MAO-B) (Forneris, F., et al., *Structural basis of LSD1-CoREST selectivity in histone H3 recognition*. J Biol Chem, 2007. 282(28): p. 20070-4; Anand, R. and R. Marmorstein, *Structure and mechanism of lysine-specific demethylase enzymes*. J Biol Chem, 2007. 282(49): p. 35425-9; Stavropoulos, P., G. Blobel, and A. Hoelz, *Crystal structure and mechanism of human lysine-specific demethylase-1*. Nat Struct Mol Biol, 2006. 13(7): p. 626-32; Chen, Y., et al., *Crystal structure of human histone lysine-specific demethylase 1 (LSD1)*. Proc Natl Acad Sci USA, 2006. 103(38): p. 13956-61). LSD1 also shares a fair degree of homology with another lysine specific demethylase (LSD2) (Karytinos, A., et al., *A novel mammalian flavin-dependent histone demethylase*. J Biol Chem, 2009. 284(26): p. 17775-82). Although the biochemical mechanism of action is conserved in two isoforms, the substrate specificities are thought to be distinct with relatively small overlap. The enzymatic reactions of LSD1 and LSD2 are dependent on the redox process of FAD and the requirement of a protonated nitrogen in the methylated lysine is thought to limit the activity of LSD1/2 to mono- and di-methylated lysines at the position of 4 or 9 of histone 3 (H3K4 or H3K9). These mechanisms make LSD1/2 distinct from other histone demethylase families (i.e. Jumonji domain containing family) that can demethylate mono-, di-, and tri-methylated lysines through alpha-ketoglutarate dependent reactions (Kooistra, S. M. and K. Helin, *Molecular mechanisms and potential functions of histone demethylases*. Nat Rev Mol Cell Biol, 2012. 13(5): p. 297-311; Mosammaparast, N. and Y. Shi, *Reversal of histone methylation: biochemical and molecular mechanisms of histone demethylases*. Annu Rev Biochem, 2010. 79: p. 155-79).

Methylated histone marks on H3K4 and H3K9 are generally coupled with transcriptional activation and repression, respectively. As part of corepressor complexes (e.g., CoREST), LSD1 has been reported to demethylate H3K4 and repress transcription, whereas LSD1, in nuclear hormone receptor complex (e.g., androgen receptor), may demethylate H3K9 to activate gene expression (Metzger, E., et al., *LSD1 demethylates repressive histone marks to promote androgen-receptor-dependent transcription*. Nature, 2005. 437(7057): p. 436-9; Kahl, P., et al., *Androgen receptor coactivators lysine-specific histone demethylase 1 and four and a half LIM domain protein 2 predict risk of prostate cancer recurrence*. Cancer Res, 2006. 66(23): p. 11341-7). This suggests the substrate specificity of LSD1 can be determined by associated factors, thereby regulating alternative gene expressions in a context dependent manner. In addition to histone proteins, LSD1 may demethylate non-histone proteins. These include p53 (Huang, J., et al., *p53 is regulated by the lysine demethylase LSD1*. Nature, 2007. 449(7158): p. 105-8.), E2F (Kontaki, H. and I. Talianidis, *Lysine methylation regulates E2FJ-induced cell death*. Mol Cell, 2010. 39(1): p. 152-60), STAT3 (Yang, J., et al., *Reversible methylation of promoter-bound STAT3 by histone-modifying enzymes*. Proc Natl Acad Sci USA, 2010. 107(50): p. 21499-504), Tat (Sakane, N., et al., *Activation of HIV transcription by the viral Tat protein requires a demethylation step mediated by lysine-specific demethylase 1 (LSD1/KDM1)*. PLoS Pathog, 2011. 7(8): p. e1002184), and myosin phosphatase target subunit 1 (MYPT1) (Cho, H. S., et al., *Demethylation of $R^B$ regulator MYPT1 by histone demethylase LSD1 promotes cell cycle progression in cancer cells*. Cancer Res, 2011. 71(3): p. 655-60). The lists of non-histone substrates are growing with technical advances in functional proteomics studies. These suggest additional oncogenic roles of LSD1 beyond regulating chromatin remodeling. LSD1 also associates with other epigenetic regulators, such as DNA methyltransferase 1 (DNMT1) (Wang, J., et al., *The lysine demethylase LSD1 (KDM1) is required for maintenance of global DNA methylation*. Nat Genet, 2009. 41(1): p. 125-9) and histone deacetylases (HDACs) complexes (Hakimi, M. A., et al., *A core-BRAF35 complex containing histone deacetylase mediates repression of neuronal-specific genes*. Proc Natl Acad Sci USA, 2002. 99(11): p. 7420-5; Lee, M. G., et al., *Functional interplay between histone demethylase and deacetylase enzymes*. Mol Cell Biol, 2006. 26(17): p. 6395-402; You, A., et al., *CoREST is an integral component of the CoREST-human histone deacetylase complex*. Proc Natl Acad Sci USA, 2001. 98(4): p. 1454-8). These associations augment the activities of DNMT or HDACs. LSD1 inhibitors may therefore potentiate the effects of HDAC or DNMT inhibitors. Indeed, preclinical studies have shown such potential already (Singh, M. M., et al., *Inhibition of LSD1 sensitizes glioblastoma cells to histone deacetylase inhibitors*. Neuro Oncol, 2011. 13(8): p. 894-903; Han, H., et al., *Synergistic re-activation of epigenetically silenced genes by combinatorial inhibition of DNMTs and LSD1 in cancer cells*. PLoS One, 2013. 8(9): p. e75136).

LSD1 has been reported to contribute to a variety of biological processes, including cell proliferation, epithelialmesenchymal transition (EMT), and stem cell biology (both embryonic stem cells and cancer stem cells) or self-renewal and cellular transformation of somatic cells (Chen, Y., et al., *Lysine-specific histone demethylase 1 (LSD1): A potential molecular target for tumor therapy*. Crit Rev Eukaryot Gene Expr, 2012. 22(1): p. 53-9; Sun, G., et al., *Histone demethylase LSD1 regulates neural stem cell proliferation*. Mol Cell Biol, 2010. 30(8): p. 1997-2005; Adamo, A., M. J. Barrero, and J. C. Izpisua Belmonte, *LSD1 and pluripotency: a new player in the network*. Cell Cycle, 2011. 10(19): p. 3215-6; Adamo, A., et al., *LSD1 regulates the balance between self-renewal and differentiation in human embryonic stem cells*. Nat Cell Biol, 2011. 13(6): p. 652-9). In particular, cancer stem cells or cancer initiating cells have some pluripotent stem cell properties that contribute to the heterogeneity of cancer cells. This feature may render cancer cells more resistant to conventional therapies, such as chemotherapy or radiotherapy, and then develop recurrence after treatment (Clevers, H., *The cancer stem cell: premises, promises and challenges*. Nat Med, 2011. 17(3): p. 313-9; Beck, B. and C. Blanpain, *Unravelling cancer stem cell potential*. Nat Rev Cancer, 2013. 13(10): p. 727-38). LSD1 was reported to maintain an undifferentiated tumor initiating or cancer stem cell phenotype in a spectrum of cancers (Zhang, X., et al., *Pluripotent Stem Cell Protein Sox2 Confers Sensitivity to LSD1 Inhibition in Cancer Cells*. Cell Rep, 2013. 5(2): p. 445-57; Wang, J., et al., *Novel histone demethylase LSD1 inhibitors selectively target cancer cells with pluripotent stem cell properties*. Cancer Res, 2011. 71(23): p. 7238-49). Acute myeloid leukemias (AMLs) are an example of neoplastic cells that retain some of their less differentiated stem cell like phenotype or leukemia stem cell (LSC) potential. Analysis of AML cells including gene expression arrays and chromatin immunoprecipitation with next generation sequencing (ChIP-Seq) revealed that LSD1 may regulate a subset of genes involved in multiple oncogenic programs to maintain LSC (Harris, W. J., et al., *The histone demethylase KDM1A sustains the oncogenic potential of MLL-AF9 leukemia stem cells*. Cancer Cell, 2012. 21(4): p. 473-87; Schenk, T., et al., *Inhibition of the LSD1 (KDM1A) demethylase reactivates the all-trans-retinoic acid differentiation pathway in acute myeloid leukemia*. Nat Med, 2012. 18(4): p. 605-11). These findings suggest potential therapeutic benefit of LSD1 inhibitors targeting cancers having stem cell properties, such as AMLs.

Overexpression of LSD1 is frequently observed in many types of cancers, including bladder cancer, NSCLC, breast carcinomas, ovary cancer, glioma, colorectal cancer, sarcoma including chondrosarcoma, Ewing's sarcoma, osteosarcoma, and rhabdomyosarcoma, neuroblastoma, prostate cancer, esophageal squamous cell carcinoma, and papillary thyroid carcinoma. Notably, studies found over-expression of LSD1 was significantly associated with clinically aggressive cancers, for example, recurrent prostate cancer, NSCLC, glioma, breast, colon cancer, ovary cancer, esophageal squamous cell carcinoma, and neuroblastoma. In these studies, either knockdown of LSD1 expression or treatment with small molecular inhibitors of LSD1 resulted in decreased cancer cell proliferation and/or induction of apoptosis. See, e.g., Hayami, S., et al., *Overexpression of LSD1 contributes to human carcinogenesis through chromatin regulation in various cancers*. Int J Cancer, 2011. 128(3): p. 574-86; Lv, T., et al., *Over-expression of LSD1 promotes proliferation, migration and invasion in non-small cell lung cancer*. PLoS One, 2012. 7(4): p. e35065; Serce, N., et al., *Elevated expression of LSD1 (Lysine-specific demethylase 1) during tumour progression from pre-invasive to invasive ductal carcinoma of the breast*. BMC Clin Pathol, 2012. 12: p. 13; Lim, S., et al., *Lysine-specific demethylase 1 (LSD1) is highly expressed in ER-negative breast cancers and a biomarker predicting aggressive biology*. Carcinogenesis, 2010. 31(3): p. 512-20; Konovalov, S. and I. Garcia-Bassets, *Analysis of the levels of lysine-specific demethylase 1 (LSD1) mRNA in human ovarian tumors and the effects of chemical LSD1 inhibitors in ovarian cancer cell lines*. J Ovarian Res, 2013. 6(1): p. 75; Sareddy, G. R., et al., *KDM1 is a novel therapeutic target for the treatment of gliomas*. Oncotarget, 2013. 4(1): p. 18-28; Ding, J., et al., *LSD1-mediated epigenetic modification contributes to proliferation and metastasis of colon cancer*. Br J Cancer, 2013. 109(4): p. 994-1003; Bennani-Baiti, I. M., et al., *Lysine-specific demethylase 1 (LSD1/KDM1A/AOF2/BHC110) is expressed and is an epigenetic drug target in chondrosarcoma, Ewing's sarcoma, osteosarcoma, and rhabdomyosarcoma*. Hum Pathol, 2012. 43(8): p. 1300-7; Schulte, J. H., et al., *Lysine-specific demethylase 1 is strongly expressed in poorly differentiated neuroblastoma: implications for therapy*. Cancer Res, 2009. 69(5): p. 2065-71; Crea, F., et al., *The emerging role of histone lysine demethylases in prostate cancer*. Mol Cancer, 2012. 11: p. 52; Suikki, H. E., et al., *Genetic alterations and changes in expression of histone demethylases in prostate cancer*. Prostate, 2010. 70(8): p. 889-98; Yu, Y., et al., *High expression of lysine-specific demethylase 1 correlates with poor prognosis of patients with esophageal squamous cell carcinoma*. Biochem Biophys Res Commun, 2013. 437(2): p. 192-8; Kong, L., et al., *Immunohistochemical expression of RBP2 and LSD1 in papillary thyroid carcinoma*. Rom J Morphol Embryol, 2013. 54(3): p. 499-503.

Recently, the induction of CD86 expression by inhibiting LSD1 activity was reported (Lynch, J. T., et al., *CD86 expression as a surrogate cellular biomarker for pharmacological inhibition of the histone demethylase lysine-specific demethylase 1*. Anal Biochem, 2013. 442(1): p. 104-6). CD86 expression is a marker of maturation of dendritic cells (DCs) which are involved in antitumor immune response. Notably, CD86 functions as a co-stimulatory factor to activate T cell proliferation (Greaves, P. and J. G. Gribben, *The role of B7 family molecules in hematologic malignancy*. Blood, 2013. 121(5): p. 734-44; Chen, L. and D. B. Flies, *Molecular mechanisms of T cell co-stimulation and co-inhibition*. Nat Rev Immunol, 2013. 13(4): p. 227-42).

In addition to playing a role in cancer, LSD1 activity has also been associated with viral pathogenesis. Particularly, LSD1 activity appears to be linked with viral replications and expressions of viral genes. For example, LSD1 functions as a co-activator to induce gene expression from the viral immediate early genes of various type of herpes virus including herpes simplex virus (HSV), varicella zoster virus (VZV), and β-herpesvirus human cytomegalovirus (Liang, Y., et al., *Targeting the JMJD2 histone demethylases to epigenetically control herpesvirus infection and reactivation from latency*. Sci Transl Med, 2013. 5(167): p. 167ra5; Liang, Y., et al., *Inhibition of the histone demethylase LSD1 blocks alpha-herpesvirus lytic replication and reactivation from latency*. Nat Med, 2009. 15(11): p. 1312-7). In this setting, a LSD1 inhibitor showed antiviral activity by blocking viral replication and altering virus associated gene expression.

Recent studies have also shown that the inhibition of LSD1 by either genetic depletion or pharmacological intervention increased fetal globin gene expression in erythroid cells (Shi, L., et al., *Lysine-specific demethylase 1 is a therapeutic target for fetal hemoglobin induction*. Nat Med, 2013. 19(3): p. 291-4; Xu, J., et al., *Corepressor-dependent silencing of fetal hemoglobin expression by BCL11A*. Proc Natl Acad Sci USA, 2013. 110(16): p. 6518-23). Inducing fetal globin gene would be potentially therapeutically beneficial for the disease of β-globinopathies, including β-thalassemia and sickle cell disease where the production of normal β-globin, a component of adult hemoglobin, is impaired (Sankaran, V. G. and S. H. Orkin, *The switch from fetal to adult hemoglobin*. Cold Spring Harb Perspect Med, 2013. 3(1): p. a011643; Bauer, D. E., S. C. Kamran, and S. H. Orkin, *Reawakening fetal hemoglobin: prospects for new therapies for the beta-globin disorders*. Blood, 2012. 120 (15): p. 2945-53). Moreover, LSD1 inhibition may potentiate other clinically used therapies, such as hydroxyurea or azacitidine. These agents may act, at least in part, by increasing γ-globin gene expression through different mechanisms.

In summary, LSD1 contributes to tumor development by altering epigenetic marks on histones and non-histone proteins. Accumulating data have validated that either genetic depletion or pharmacological intervention of LSD1 normalizes altered gene expressions, thereby inducing differentiation programs into mature cell types, decreasing cell proliferation, and promoting apoptosis in cancer cells. Therefore, LSD1 inhibitors alone or in combination with established therapeutic drugs would be effective to treat the diseases associated with LSD1 activity.

SUMMARY OF THE INVENTION

The present invention is directed to, inter alia, a compound of Formula I:

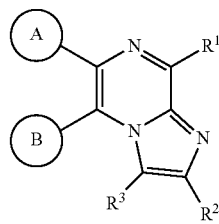

I or a pharmaceutically acceptable salt thereof, wherein constituent variables are defined herein.

The present invention is further directed to a pharmaceutical composition comprising a compound of Formula I and at least one pharmaceutically acceptable carrier.

The present invention is further directed to a method of inhibiting LSD1 comprising contacting the LSD1 with a compound of Formula I.

The present invention is further directed to a method of treating an LSD1-mediated disease in a patient comprising administering to the patient a therapeutically effective amount of a compound of Formula I.

DETAILED DESCRIPTION

The present invention provides, inter alia, LSD1-inhibiting compounds such as a compound of Formula I:

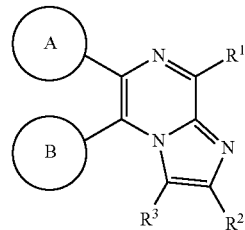

I or a pharmaceutically acceptable salt thereof, wherein:

Ring A is $C_{6-10}$ aryl or 5-10 membered heteroaryl comprising (or having) carbon and 1, 2, 3, or 4 heteroatoms selected from N, O, and S, wherein said $C_{6-10}$ aryl and 5-10 membered heteroaryl are each optionally substituted by 1, 2, 3, or 4 substituents independently selected from $R^A$;

Ring B is $C_{6-10}$ aryl; 5-10 membered heteroaryl comprising (or having) carbon and 1, 2, 3 or 4 heteroatoms selected from N, O, and S; $C_{3-10}$ cycloalkyl; or 4-10 membered heterocycloalkyl comprising (or having) carbon and 1, 2, 3 or 4 heteroatoms selected from N, O, and S; wherein said $C_{6-10}$ aryl, 5-10 membered heteroaryl, $C_{3-10}$ cycloalkyl, and 4-10 membered heterocycloalkyl are each optionally substituted by 1, 2, 3, or 4 substituents independently selected from $R^B$;

$R^1$ is halo, $C_{1-6}$ alkyl, $C_{2-6}$ alkenyl, $C_{2-6}$ alkynyl, $C_{1-6}$ haloalkyl, $Cy^1$, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})NR^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, or $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $Cy^1$, halo, CN, OH, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

$R^2$ and $R^3$ are each independently selected from H, halo, $C_{1-6}$ alkyl, $C_{2-6}$ alkenyl, $C_{2-6}$ alkynyl, $C_{1-6}$ haloalkyl, $Cy^2$, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1, 2, or 3 substituents independently selected from $Cy^2$, halo, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

each $R^A$ is independently selected from halo, $C_{1-6}$ alkyl, $C_{2-6}$ alkenyl, $C_{2-6}$ alkynyl, $C_{1-6}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$, wherein said $C_{1-6}$ alkyl, $C_{2-6}$ alkenyl, and $C_{2-6}$ alkynyl are each optionally substituted by 1, 2, or 3, substituents independently selected from halo, $C_{1-6}$ haloalkyl, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, C(=NR$^{e4}$)R$^{b4}$, C(=NR$^{e4}$)NR$^{c4}$R$^{d4}$, NR$^{c4}$C(=NR$^{e4}$)NR$^{c4}$R$^{d4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, and S(O)$_2$NR$^{c4}$R$^{d4}$;

each R$^B$ is independently selected from Cy$^3$, halo, $C_{1-6}$ alkyl, $C_{2-6}$ alkenyl, $C_{2-6}$ alkynyl, $C_{1-6}$ haloalkyl, CN, NO$_2$, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)OR$^{a5}$, NR$^{c5}$C(O)NR$^{c5}$R$^{d5}$, C(=NR$^{e5}$)R$^{b5}$, C(=NR$^{e5}$)NR$^{c5}$R$^{d5}$, NR$^{c5}$C(=NR$^{e5}$)NR$^{c5}$R$^{d5}$, NR$^{c5}$S(O)R$^{b5}$, NR$^{c5}$S(O)$_2$R$^{b5}$, NR$^{c5}$S(O)$_2$NR$^{c5}$R$^{d5}$, S(O)R$^{b5}$, S(O)NR$^{c5}$R$^{d5}$, S(O)$_2$R$^{b5}$, and S(O)$_2$NR$^{c5}$R$^{d5}$, wherein said $C_{1-6}$ alkyl, $C_{2-6}$ alkenyl, and $C_{2-6}$ alkynyl are each optionally substituted by 1, 2, or 3 substituents independently selected from Cy$^3$, halo, $C_{1-6}$ haloalkyl, CN, NO$_2$, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)OR$^{a5}$, NR$^{c5}$C(O)NR$^{c5}$R$^{d5}$, C(=NR$^{e5}$)R$^{b5}$, C(=NR$^{e5}$)NR$^{c5}$R$^{d5}$, NR$^{c5}$C(=NR$^{e5}$) NR$^{c5}$R$^{d5}$, NR$^{c5}$S(O)R$^{b5}$, NR$^{c5}$S(O)$_2$R$^{b5}$, NR$^{c5}$S(O)$_2$ NR$^{c5}$R$^{d5}$, S(O)R$^{b5}$, S(O)NR$^{c5}$R$^{d5}$, S(O)$_2$R$^{b5}$, and S(O)$_2$ NR$^{c5}$R$^{d5}$;

each Cy$^1$, Cy$^2$, Cy$^3$, and Cy$^4$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, or 4 substituents independently selected from R$^{Cy}$;

each R$^{Cy}$ is independently selected from halo, $C_{1-4}$ alkyl, $C_{1-4}$ haloalkyl, $C_{1-4}$ cyanoalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-4}$ alkyl-, $C_{3-7}$ cycloalkyl-$C_{1-4}$ alkyl-, (5-6 membered heteroaryl)-$C_{1-4}$ alkyl-, and (4-7 membered heterocycloalkyl)-$C_{1-4}$ alkyl-, CN, NO$_2$, OR$^{a6}$, SR$^{a6}$, C(O)R$^{b6}$, C(O)NR$^{c6}$R$^{d6}$, C(O)OR$^{a6}$, OC(O)R$^{b6}$, OC(O)NR$^{c6}$R$^{d6}$, C(=NR$^{e6}$)NR$^{c6}$R$^{d6}$, NR$^{c6}$C(=NR$^{e6}$) NR$^{c6}$R$^{d6}$, NR$^{c6}$R$^{d6}$, NR$^{c6}$C(O)R$^{b6}$, NR$^{c6}$C(O)OR$^{a6}$, NR$^{c6}$C(O)NR$^{c6}$R$^{d6}$, NR$^{c6}$S(O)R$^{b6}$, NR$^{c6}$S(O)$_2$R$^{b6}$, NR$^{c6}$S(O)$_2$NR$^{c6}$R$^{d6}$, S(O)R$^{b6}$, S(O)NR$^{c6}$R$^{d6}$, S(O)$_2$R$^{b6}$, and S(O)$_2$NR$^{c6}$R$^{d6}$, wherein said $C_{1-4}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-4}$ alkyl-, $C_{3-7}$ cycloalkyl-$C_{1-4}$ alkyl-, (5-6 membered heteroaryl)-$C_{1-4}$ alkyl-, and (4-7 membered heterocycloalkyl)-$C_{1-4}$ alkyl- are each optionally substituted by 1, 2, or 3 substituents independently selected from $C_{1-6}$ alkyl, $C_{1-4}$ haloalkyl, $C_{1-6}$ cyanoalkyl, halo, CN, NO$_2$, OR$^{a6}$, SR$^{a6}$, C(O)R$^{b6}$, C(O)NR$^{c6}$R$^{d6}$, C(O)OR$^{a6}$, OC(O)R$^{b6}$, OC(O)NR$^{c6}$R$^{d6}$, C(=NR$^{e6}$)NR$^{c6}$R$^{d6}$, NR$^{c6}$C(=NR$^{e6}$)NR$^{c6}$R$^{d6}$, NR$^{c6}$R$^{d6}$, NR$^{c6}$C(O)R$^{b6}$, NR$^{c6}$C(O)OR$^{a6}$, NR$^{c6}$C(O)NR$^{c6}$R$^{d6}$, NR$^{c6}$S(O)R$^{b6}$, NR$^{c6}$S(O)$_2$R$^{b6}$, NR$^{c6}$S(O)$_2$NR$^{c6}$R$^{d6}$, S(O)R$^{b6}$, S(O)NR$^{c6}$R$^{d6}$, S(O)$_2$R$^{b6}$, and S(O)$_2$NR$^{c6}$R$^{d6}$;

each R$^{a1}$ is independently selected from $C_{1-6}$ alkyl, $C_{2-6}$ alkenyl, $C_{2-6}$ alkynyl, and Cy$^4$; wherein said $C_{1-6}$ alkyl, $C_{2-6}$ alkenyl, and $C_{2-6}$ alkynyl are each optionally substituted with 1, 2, or 3 substituents independently selected from Cy$^4$, halo, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, C(=NR$^{e3}$)R$^{b3}$, C(=NR$^{e3}$)NR$^{c3}$R$^{d3}$, NR$^{c3}$C(=NR$^{e3}$)NR$^{c3}$R$^{d3}$, NR$^{c3}$S(O) R$^{b3}$, NR$^{c3}$S(O)$_2$R$^{b3}$, NR$^{c3}$S(O)$_2$NR$^{c3}$R$^{d3}$, S(O)R$^{b3}$, S(O) NR$^{c3}$R$^{d3}$, S(O)$_2$R$^{b3}$, and S(O)$_2$NR$^{c3}$R$^{d3}$;

each R$^{b1}$, R$^{c1}$, and R$^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, OR$^{a7}$, SR$^{a7}$, C(O)R$^{b7}$, C(O)NR$^{c7}$R$^{d7}$, C(O)OR$^{a7}$, OC(O)R$^{b7}$, OC(O)NR$^{c7}$R$^{d7}$, NR$^{c7}$R$^{d7}$, NR$^{c7}$C(O)R$^{b7}$, NR$^{c7}$C(O)NR$^{c7}$R$^{d7}$, NR$^{c7}$C(O)OR$^{a7}$, C(=NR$^{e7}$)NR$^{c7}$R$^{d7}$, NR$^{c7}$C(=NR$^{e7}$)NR$^{c7}$R$^{d7}$, S(O)R$^{b7}$, S(O)NR$^{c7}$R$^{d7}$, S(O)$_2$R$^{b7}$, NR$^{c7}$S(O)$_2$R$^{b7}$, NR$^{c7}$S(O)$_2$ NR$^{c7}$R$^{d7}$, and S(O)$_2$NR$^{c7}$R$^{d7}$;

or any R$^{c1}$ and R$^{d1}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, OR$^{a7}$, SR$^{a7}$, C(O)R$^{b7}$, C(O)NR$^{c7}$R$^{d7}$, C(O)OR$^{a7}$, OC(O)R$^{b7}$, OC(O) NR$^{c7}$R$^{d7}$, NR$^{c7}$R$^{d7}$, NR$^{c7}$C(O)R$^{b7}$, NR$^{c7}$C(O)NR$^{c7}$R$^{d7}$, NR$^{c7}$C(O)OR$^{a7}$, C(=NR$^{e7}$)NR$^{c7}$R$^{d7}$, NR$^{c7}$C(=NR$^{e7}$) NR$^{c7}$R$^{d7}$, S(O)R$^{b7}$, S(O)NR$^{c7}$R$^{d7}$, S(O)$_2$R$^{b7}$, NR$^{c7}$S(O)$_2$ R$^{b7}$, NR$^{c7}$S(O)$_2$NR$^{c7}$R$^{d7}$, and S(O)$_2$NR$^{c7}$R$^{d7}$, wherein said $C_{1-6}$ alkyl, $C_{3-7}$ cycloalkyl, 4-7 membered heterocycloalkyl, $C_{6-10}$ aryl, and 5-6 membered heteroaryl are each optionally substituted by 1, 2, or 3 substituents independently selected from halo, $C_{1-4}$ alkyl, $C_{1-4}$ haloalkyl, $C_{1-4}$ cyanoalkyl, CN, OR$^{a7}$, SR$^{a7}$, C(O)R$^{b7}$, C(O)NR$^{c7}$R$^{d7}$, C(O)OR$^{a7}$, OC(O) R$^{b7}$, OC(O)NR$^{c7}$R$^{d7}$, NR$^{c7}$R$^{d7}$, NR$^{c7}$C(O)R$^{b7}$, NR$^{c7}$C(O) NR$^{c7}$R$^{d7}$, NR$^{c7}$C(O)OR$^{a7}$, C(=NR$^{e7}$)NR$^{c7}$R$^{d7}$, NR$^{c7}$C (=NR$^{e7}$)NR$^{c7}$R$^{d7}$, S(O)R$^{b7}$, S(O)NR$^{c7}$R$^{d7}$, S(O)$_2$R$^{b7}$, NR$^{c7}$S(O)$_2$R$^{b7}$, NR$^{c7}$S(O)$_2$NR$^{c7}$R$^{d7}$, and S(O)$_2$NR$^{c7}$R$^{d7}$;

each R$^{a2}$, R$^{b2}$, R$^{c2}$, and R$^{d2}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, OR$^{a7}$, SR$^{a7}$, C(O)R$^{b7}$, C(O) NR$^{c7}$R$^{d7}$, C(O)OR$^{a7}$, OC(O)R$^{b7}$, OC(O)NR$^{c7}$R$^{d7}$, NR$^{c7}$R$^{d7}$, NR$^{c7}$C(O)R$^{b7}$, NR$^{c7}$C(O)NR$^{c7}$R$^{d7}$, NR$^{c7}$C(O)OR$^{a7}$, C(=NR$^{e7}$)NR$^{c7}$R$^{d7}$, NR$^{c7}$C(=NR$^{e7}$)NR$^{c7}$R$^{d7}$, S(O)R$^{b7}$, S(O)NR$^{c7}$R$^{d7}$, S(O)$_2$R$^{b7}$, NR$^{c7}$S(O)$_2$R$^{b7}$, NR$^{c7}$S(O)$_2$ NR$^{c7}$R$^{d7}$, and S(O)$_2$NR$^{c7}$R$^{d7}$;

or any R$^{c2}$ and R$^{d2}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, phenyl, 5-6 membered heteroaryl, $C_{1-6}$ haloalkyl, halo, CN, OR$^{a7}$, SR$^{a7}$, C(O)R$^{b7}$, C(O)NR$^{c7}$R$^{d7}$, C(O)OR$^{a7}$, OC(O)R$^{b7}$, OC(O) NR$^{c7}$R$^{d7}$, NR$^{c7}$R$^{d7}$, NR$^{c7}$C(O)R$^{b7}$, NR$^{c7}$C(O)NR$^{c7}$R$^{d7}$, NR$^{c7}$C(O)OR$^{a7}$, C(=NR$^{e7}$)NR$^{c7}$R$^{d7}$, NR$^{c7}$C(=NR$^{e7}$) NR$^{c7}$R$^{d7}$, S(O)R$^{b7}$, S(O)NR$^{c7}$R$^{d7}$, S(O)$_2$R$^{b7}$, NR$^{c7}$S(O)$_2$ R$^{b7}$, NR$^{c7}$S(O)$_2$NR$^{c7}$R$^{d7}$, and S(O)$_2$NR$^{c7}$R$^{d7}$, wherein said $C_{1-6}$ alkyl, $C_{3-7}$ cycloalkyl, 4-7 membered heterocycloalkyl, phenyl, and 5-6 membered heteroaryl are each optionally substituted by 1, 2, or 3 substituents independently selected from halo, $C_{1-4}$ alkyl, $C_{1-4}$ haloalkyl, $C_{1-4}$ cyanoalkyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c7}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

each $R^{a3}$, $R^{b3}$, $R^{c3}$, and $R^{d3}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c7}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

or any $R^{c3}$ and $R^{d3}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, phenyl, 5-6 membered heteroaryl, $C_{1-6}$ haloalkyl, halo, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c7}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$, wherein said $C_{1-6}$ alkyl, $C_{3-7}$ cycloalkyl, 4-7 membered heterocycloalkyl, phenyl, and 5-6 membered heteroaryl are each optionally substituted by 1, 2, or 3 substituents independently selected from halo, $C_{1-4}$ alkyl, $C_{1-4}$ haloalkyl, $C_{1-4}$ cyanoalkyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c7}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

each $R^{a4}$, $R^{b4}$, $R^{c4}$, and $R^{d4}$ is independently selected from H, $C_{1-6}$ alkyl, $C_{1-4}$ haloalkyl, $C_{2-6}$ alkenyl, and $C_{2-6}$ alkynyl, wherein said $C_{1-6}$ alkyl, $C_{2-6}$ alkenyl, and $C_{2-6}$ alkynyl are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c7}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

or any $R^{c4}$ and $R^{d4}$ together with the N atom to which they are attached form a 4-, 5-, 6-, or 7-membered heterocycloalkyl group optionally substituted with 1, 2, or 3 substituents independently selected from $C_{1-6}$ alkyl, $C_{1-6}$ haloalkyl, halo, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c7}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

each $R^{a5}$, $R^{b5}$, $R^{c5}$, and $R^{d5}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c7}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

or any $R^{c5}$ and $R^{d5}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c7}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$, wherein said $C_{1-6}$ alkyl, $C_{3-7}$ cycloalkyl, 4-7 membered heterocycloalkyl, $C_{6-10}$ aryl, and 5-6 membered heteroaryl are each optionally substituted by 1, 2, or 3 substituents independently selected from halo, $C_{1-4}$ alkyl, $C_{1-4}$ haloalkyl, $C_{1-4}$ cyanoalkyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c7}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

each $R^{a6}$, $R^{b6}$, $R^{c6}$, and $R^{d6}$ is independently selected from H, $C_{1-6}$ alkyl, $C_{1-4}$ haloalkyl, $C_{2-6}$ alkenyl, and $C_{2-6}$ alkynyl, wherein said $C_{1-6}$ alkyl, $C_{2-6}$ alkenyl, and $C_{2-6}$ alkynyl are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c7}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

or any $R^{c6}$ and $R^{d6}$ together with the N atom to which they are attached form a 4-, 5-, 6-, or 7-membered heterocycloalkyl group optionally substituted with 1, 2, or 3 substituents independently selected from $C_{1-6}$ alkyl, $C_{1-6}$ haloalkyl, halo, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c7}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

each $R^{a7}$, $R^{b7}$, $R^{c7}$, and $R^{d7}$ is independently selected from H, $C_{1-4}$ alkyl, $C_{1-4}$ haloalkyl, $C_{2-4}$ alkenyl, and $C_{2-4}$ alkynyl, wherein said $C_{1-4}$ alkyl, $C_{2-4}$ alkenyl, and $C_{2-4}$ alkynyl are each optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy; and each $R^{e1}$, $R^{e2}$, $R^{e3}$, $R^{e4}$, $R^{e5}$, $R^{e6}$, and $R^{e7}$ is independently selected from H, $C_{1-4}$ alkyl, and CN.

In some embodiments:

Ring A is phenyl optionally substituted by 1, 2, or 3 substituents independently selected from $R^A$;

Ring B is phenyl or 5-6 membered heteroaryl comprising (or having) carbon and 1 or 2 heteroatoms selected from N; wherein said phenyl or 5-6 membered heteroaryl is optionally substituted by 1, or 2 substituents independently selected from $R^B$;

$R^1$ is halo, $C_{1-6}$ alkyl, $C_{2-6}$ alkenyl, $C_{2-6}$ alkynyl, $C_{1-6}$ haloalkyl, $Cy^1$, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, or $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $Cy^1$, halo, CN, OH, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

$R^2$ is H, halo, $C_{1-6}$ alkyl, $C_{2-6}$ alkenyl, $C_{2-6}$ alkynyl, $C_{1-6}$ haloalkyl, $Cy^2$, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, or $S(O)_2NR^{c2}R^{d2}$; wherein said $C_{1-6}$ alkyl, $C_{2-6}$ alkenyl, and $C_{2-6}$ alkynyl are each optionally substituted with 1, 2, or 3 substituents independently selected from $Cy^2$, halo, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

$R^3$ is H;

each $R^A$ is independently selected from halo, $C_{1-6}$ alkyl, $C_{2-6}$ alkenyl, $C_{2-6}$ alkynyl, $C_{1-6}$ haloalkyl, CN, $OR^{a4}$, $SR^{a4}$, $C(O)R^{b4}$, $C(O)NR^{c4}R^{d4}$, $NR^{c4}R^{d4}$, $NR^{c4}C(O)R^{b4}$, $NR^{c4}S(O)_2R^{b4}$, $S(O)R^{b4}$, $S(O)NR^{c4}R^{d4}$, $S(O)_2R^{b4}$, and $S(O)_2NR^{c4}R^{d4}$, wherein said $C_{1-6}$ alkyl, $C_{2-6}$ alkenyl, and $C_{2-6}$ alkynyl are each optionally substituted by 1, 2, or 3, substituents independently selected from halo, $C_{1-6}$ haloalkyl, CN, $OR^{a4}$, $SR^{a4}$, $C(O)R^{b4}$, $C(O)NR^{c4}R^{d4}$, $NR^{c4}R^{d4}$, $NR^{c4}C(O)R^{b4}$, $NR^{c4}S(O)_2R^{b4}$, $S(O)R^{b4}$, $S(O)NR^{c4}R^{d4}$, $S(O)_2R^{b4}$, and $S(O)_2NR^{c4}R^{d4}$;

each $R^B$ is independently selected from $Cy^3$, halo, $C_{1-6}$ alkyl, $C_{2-6}$ alkenyl, $C_{2-6}$ alkynyl, $C_{1-6}$ haloalkyl, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$, wherein said $C_{1-6}$ alkyl, $C_{2-6}$ alkenyl, and $C_{2-6}$ alkynyl are each optionally substituted by 1, 2, or 3 substituents independently selected from $Cy^3$, halo, $C_{1-6}$ alkyl, $C_{2-6}$ alkenyl, $C_{2-6}$ alkynyl, $C_{1-6}$ haloalkyl, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$;

each $Cy^1$, $Cy^2$, $Cy^3$, and $Cy^4$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, or 4 substituents independently selected from $R^{Cy}$;

each $R^{Cy}$ is selected from halo, $C_{1-4}$ alkyl, $C_{1-4}$ haloalkyl, $C_{1-4}$ cyanoalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-4}$ alkyl-, $C_{3-7}$ cycloalkyl-$C_{1-4}$ alkyl-, (5-6 membered heteroaryl)-$C_{1-4}$ alkyl-, and (4-7 membered heterocycloalkyl)-$C_{1-4}$ alkyl-, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $NR^{c6}C(O)NR^{c6}R^{d6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, and $S(O)_2NR^{c6}R^{d6}$, wherein said $C_{1-4}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-4}$ alkyl-, $C_{3-7}$ cycloalkyl-$C_{1-4}$ alkyl-, (5-6 membered heteroaryl)-$C_{1-4}$ alkyl-, and (4-7 membered heterocycloalkyl)-$C_{1-4}$ alkyl- are each optionally substituted by 1, 2, or 3 substituents independently selected from $C_{1-6}$ alkyl, $C_{1-4}$ haloalkyl, $C_{1-6}$ cyanoalkyl, halo, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $NR^{c6}C(O)NR^{c6}R^{d6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, and $S(O)_2NR^{c6}R^{d6}$;

each $R^{a1}$ is independently selected from $C_{1-6}$ alkyl, $C_{2-6}$ alkenyl, $C_{2-6}$ alkynyl, and $Cy^4$; wherein said $C_{1-6}$ alkyl, $C_{2-6}$ alkenyl, and $C_{2-6}$ alkynyl are each optionally substituted with 1, 2, or 3 substituents independently selected from $Cy^4$, halo, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

each $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

or any $R^{c1}$ and $R^{d1}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c7}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$, wherein said $C_{1-6}$ alkyl, $C_{3-7}$ cycloalkyl, 4-7 membered heterocycloalkyl, $C_{6-10}$ aryl, and 5-6 membered heteroaryl are each optionally substituted by 1, 2, or 3 substituents independently selected from halo, $C_{1-4}$ alkyl, $C_{1-4}$ haloalkyl, $C_{1-4}$ cyanoalkyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c7}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

each $R^{a2}$, $R^{b2}$, $R^{c2}$, and $R^{d2}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

each $R^{a3}$, $R^{b3}$, $R^{c3}$, and $R^{d3}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

each $R^{a4}$, $R^{b4}$, $R^{c4}$, and $R^{d4}$ is independently selected from H and $C_{1-3}$ alkyl;

each $R^{a5}$, $R^{b5}$, $R^{c5}$, and $R^{d5}$ is independently selected from H or $C_{1-3}$ alkyl;

each $R^{a6}$, $R^{b6}$, $R^{c6}$, and $R^{d6}$ is independently selected from H or $C_{1-3}$ alkyl; and each $R^{a7}$, $R^{b7}$, $R^{c7}$, and $R^{d7}$ is independently selected from H or $C_{1-3}$ alkyl.

In some embodiments:

Ring A is phenyl optionally substituted by 1, 2, or 3 substituents independently selected from $R^A$;

Ring B is phenyl, pyridyl, or pyrimidinyl, each optionally substituted by 1 or 2 substituents independently selected from $R^B$;

$R^1$ is halo, $C_{1-3}$ alkyl, $Cy^1$, $OR^{a1}$, $SR^{a1}$, $C(O)NR^{c1}R^{d1}$, $NR^{c1}R^{d1}$, $NR^{c1}C(O)R^{b1}$, or $NR^{c1}C(O)NR^{c1}R^{d1}$; wherein said $C_{1-3}$ alkyl is optionally substituted with 1, 2, or 3 substituents independently selected from $Cy^1$, halo, CN, OH, $OR^{a1}$, $C(O)NR^{c1}R^{d1}$, $NR^{c1}R^{d1}$, and $NR^{c1}C(O)R^{b1}$;

$R^2$ is H, halo, $C_{1-3}$ alkyl, $C_{1-3}$ haloalkyl, $Cy^2$, $C(O)NR^{c2}R^{d2}$, $NR^{c2}R^{d2}$, or $NR^{c2}C(O)R^{b2}$; wherein said $C_{1-3}$ alkyl is optionally substituted with 1, 2, or 3 substituents independently selected from $Cy^2$, halo, CN, $OR^{a2}$, $C(O)NR^{c2}R^{d2}$, $NR^{c2}R^{d2}$, and $NR^{c2}C(O)R^{b2}$;

$R^3$ is H;

each $R^A$ is independently selected from halo, $C_{1-6}$ alkyl, $C_{2-6}$ alkenyl, $C_{2-6}$ alkynyl, $C_{1-6}$ haloalkyl, CN, $OR^{a4}$, $SR^{a4}$, $C(O)R^{b4}$, $C(O)NR^{c4}R^{d4}$, $NR^{c4}R^{d4}$, $NR^{c4}C(O)R^{b4}$, $NR^{c4}S(O)_2R^{b4}$, $S(O)R^{b4}$, $S(O)NR^{c4}R^{d4}$, $S(O)_2R^{b4}$, and $S(O)_2NR^{c4}R^{d4}$, wherein said $C_{1-6}$ alkyl, $C_{2-6}$ alkenyl, and $C_{2-6}$ alkynyl are each optionally substituted by 1, 2, or 3, substituents independently selected from halo, $C_{1-6}$ haloalkyl, CN, $OR^{a4}$, $SR^{a4}$, $C(O)R^{b4}$, $C(O)NR^{c4}R^{d4}$, $NR^{c4}R^{d4}$, $NR^{c4}C(O)R^{b4}$, $NR^{c4}S(O)_2R^{b4}$, $S(O)R^{b4}$, $S(O)NR^{c4}R^{d4}$, $S(O)_2R^{b4}$, and $S(O)_2NR^{c4}R^{d4}$;

each $R^B$ is independently selected from $Cy^3$, halo, $C_{1-6}$ alkyl, $C_{1-6}$ haloalkyl, CN, $OR^{a5}$, $C(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)_2R^{b5}$, $NR^{c5}S(O)_2R^{b5}$, and $NR^{c5}S(O)_2NR^{c5}R^{d5}$, wherein said $C_{1-6}$ alkyl is optionally substituted by 1, 2, or 3 substituents independently selected from $Cy^3$, halo, $C_{1-6}$ haloalkyl, CN, $OR^{a5}$, $C(O)NR^{c5}R^{d5}$, $NR^{c5}R^{d5}$, and $NR^{c5}C(O)R^{b5}$;

each $Cy^1$, $Cy^2$, $Cy^3$, and $Cy^4$ is independently selected from phenyl, cyclopropyl, azetidine, piperidine, pyrrolidine, diazapane, and diazaspirononane, each of which is optionally substituted with 1 or 2 substituents independently selected from $R^{Cy}$;

each $R^{Cy}$ is independently selected from halo, $C_{1-4}$ alkyl, $C_{1-4}$ haloalkyl, $C_{1-4}$ cyanoalkyl, CN, $OR^{a6}$, and $NR^{c6}R^{d6}$;

each $R^{a1}$ is independently selected from $C_{1-3}$ alkyl and $Cy^4$; wherein said $C_{1-3}$ alkyl is optionally substituted with 1, 2, or 3 substituents independently selected from $Cy^4$, halo, CN, and $OR^{a3}$, and $NR^{c3}R^{d3}$;

each $R^{b1}$, $R^{c1}$ and $R^{d1}$ is independently selected from H, $C_{1-3}$ alkyl, $C_{1-3}$ haloalkyl, phenyl, cyclopropyl, cyclobutyl, cyclopentyl, cyclohexyl, pyridine, pyrimidine, azetidine, piperidine, pyrrolidine, thiazolyl, phenyl-$C_{1-2}$ alkyl-, cyclopropyl-$C_{1-2}$ alkyl-, cyclobutyl-$C_{1-2}$ alkyl-, cyclopentyl-$C_{1-2}$ alkyl-, cyclohexyl-$C_{1-2}$ alkyl-, pyridine-$C_{1-2}$ alkyl-, pyrimidine-$C_{1-2}$ alkyl-, azetidine-$C_{1-2}$ alkyl-, piperidine-$C_{1-2}$ alkyl-, pyrrolidine-$C_{1-2}$ alkyl-, and thiazolyl-$C_{1-2}$ alkyl-, wherein said $C_{1-3}$ alkyl, $C_{1-3}$ haloalkyl, phenyl, cyclopropyl, cyclobutyl, cyclopentyl, cyclohexyl, pyridine, pyrimidine, azetidine, piperidine, pyrrolidine, thiazolyl, phenyl-$C_{1-2}$ alkyl-, cyclopropyl-$C_{1-2}$ alkyl-, cyclobutyl-$C_{1-2}$ alkyl-, cyclopentyl-$C_{1-2}$ alkyl-, cyclohexyl-$C_{1-2}$ alkyl-, pyridine-$C_{1-2}$ alkyl-, pyrimidine-$C_{1-2}$ alkyl-, azetidine-$C_{1-2}$ alkyl-, piperidine-$C_{1-2}$ alkyl-, pyrrolidine-$C_{1-2}$ alkyl-, and thiazolyl-$C_{1-2}$ alkyl- are each optionally substituted with 1, 2, or 3 substituents independently selected from $C_{1-3}$ alkyl, $C_{1-3}$ haloalkyl, halo, CN, $OR^{a7}$, and $NR^{c7}R^{d7}$;

or any $R^{c1}$ and $R^{d1}$ together with the N atom to which they are attached form a 4-, 5-, 6-, or 7-membered heterocycloalkyl group optionally substituted with $NR^{c7}R^{d7}$;

each $R^{a2}$, $R^{b2}$, $R^{c2}$, and $R^{d2}$ is independently selected from H, $C_{1-3}$ alkyl, $C_{1-3}$ haloalkyl, phenyl, cyclopropyl, cyclobutyl, cyclopropyl-$C_{1-2}$ alkyl-, cyclobutyl-$C_{1-2}$ alkyl-, pyridine, pyrimidine, isoxazole, azetidine, piperidine, and pyrrolidine, wherein said $C_{1-3}$ alkyl, $C_{1-3}$ haloalkyl, phenyl, cyclopropyl, cyclobutyl, cyclopropyl-$C_{1-2}$ alkyl-, cyclobutyl-$C_{1-2}$ alkyl-, pyridine, pyrimidine, isoxazole, azetidine, piperidine, and pyrrolidine are each optionally substituted with 1 or 2 substituents independently selected from $C_{1-4}$ alkyl, $C_{1-4}$ haloalkyl, $C_{1-4}$ cyanoalkyl, halo, CN, $OR^{a7}$, and $NR^{c7}R^{d7}$;

each $R^{a3}$, $R^{b3}$, $R^{c3}$, and $R^{d3}$ is independently selected from H, $C_{1-3}$ alkyl, $C_{1-3}$ haloalkyl, phenyl, cyclopropyl, cyclobutyl, cyclopropyl-$C_{1-2}$ alkyl-, cyclobutyl-$C_{1-2}$ alkyl-, pyridine, pyrimidine, isoxazole, azetidine, piperidine, and pyrrolidine, wherein said $C_{1-3}$ alkyl, $C_{1-3}$ haloalkyl, phenyl, cyclopropyl, cyclobutyl, cyclopropyl-$C_{1-2}$ alkyl-, cyclobutyl-$C_{1-2}$ alkyl-, pyridine, pyrimidine, isoxazole, azetidine, piperidine, and pyrrolidine are each optionally substituted with 1 or 2 substituents independently selected from $C_{1-4}$ alkyl, $C_{1-4}$ haloalkyl, $C_{1-4}$ cyanoalkyl, halo, CN, $OR^{a7}$, and $NR^{c7}R^{d7}$;

each $R^{a4}$, $R^{b4}$, $R^{c4}$, and $R^{d4}$ is independently selected from H and $C_{1-3}$ alkyl;

each $R^{a5}$, $R^{b5}$, $R^{c5}$, and $R^{d5}$ is independently selected from H or $C_{1-3}$ alkyl;

each $R^{a6}$, $R^{b6}$, $R^{c6}$, and $R^{d6}$ is independently selected from H or $C_{1-3}$ alkyl; and each $R^{a7}$, $R^{b7}$, $R^{c7}$, and $R^{d7}$ is independently selected from H or $C_{1-3}$ alkyl.

In some embodiments, the compound is other than 5,6-diphenylimidazo[1,2-a]pyrazin-8-ol or a tautomer thereof.

In some embodiments, Ring A is phenyl optionally substituted by 1, 2, 3, or 4 substituents independently selected from $R^A$.

In some embodiments, Ring A is phenyl substituted by one $R^A$.

In some embodiments, Ring A is phenyl substituted by CN.

In some embodiments, Ring B is phenyl, $C_{3-10}$ cycloalkyl, 4-10 membered heterocycloalkyl, or 5-6 membered heteroaryl, each optionally substituted by 1, 2, 3, or 4 substituents independently selected from $R^B$.

In some embodiments, Ring B is phenyl or 5-6 membered heteroaryl, each optionally substituted by 1, 2, 3, or 4 substituents independently selected from $R^B$.

In some embodiments, Ring B is phenyl, pyridyl, 3-oxo-3,4-dihydro-2H-1,4-benzoxazinyl, 2,3-dihydro-1,4-benzodioxinyl, pyrrolo[2,3-b]pyridinyl, pyrazolo[3,4-b]pyridinyl, 1,3-benzothiazolyl, 2-oxo-2,3-dihydro-1,3-benzoxazolyl, indazolyl, 2-oxo-2,3-dihydro[1,3]oxazolo[4,5-b]pyridinyl, 2,3-dihydro-1H-indenyl, 2-oxo-2,3-dihydro-1H-indolyl, quinoxalinyl, 2-oxo-1,2,3,4-tetrahydroquinolinyl, benzimidazolyl, 3-oxo-3,4-dihydro-2H-pyrido[3,2-b][1,4]oxazinyl, 2-oxo-2,3-dihydro-1H-pyrrolo[2,3-b]pyridinyl, or pyrimidinyl, each optionally substituted by 1, 2, 3, or 4 substituents independently selected from $R^B$.

In some embodiments, Ring B is phenyl, pyridyl, or pyrimidinyl, each optionally substituted by 1, 2, 3, or 4 substituents independently selected from $R^B$.

In some embodiments, Ring B is phenyl, pyridyl, 3-oxo-3,4-dihydro-2H-1,4-benzoxazinyl, 2,3-dihydro-1,4-benzodioxinyl, pyrrolo[2,3-b]pyridinyl, pyrazolo[3,4-b]pyridinyl, 1,3-benzothiazolyl, 2-oxo-2,3-dihydro-1,3-benzoxazolyl, indazolyl, 2-oxo-2,3-dihydro[1,3]oxazolo[4,5-b]pyridinyl, 2,3-dihydro-1H-indenyl, 2-oxo-2,3-dihydro-1H-indolyl, quinoxalinyl, 2-oxo-1,2,3,4-tetrahydroquinolinyl, benzimidazolyl, 3-oxo-3,4-dihydro-2H-pyrido[3,2-b][1,4]oxazinyl, 2-oxo-2,3-dihydro-1H-pyrrolo[2,3-b]pyridinyl, or pyrimidinyl, each optionally substituted by 1, 2, 3, or 4 substituents independently selected from $Cy^3$, halo, $C_{1-6}$ alkyl, $C_{1-6}$ haloalkyl, $OR^{a5}$, CN, $NR^{c5}C(O)OR^{a5}$, and $NR^{c5}R^{d5}$.

In some embodiments, Ring B is phenyl, pyridyl, or pyrimidinyl, each optionally substituted by one substituent selected from $Cy^3$, halo, $C_{1-6}$ alkyl, $C_{1-6}$ haloalkyl, $OR^{a5}$, and $NR^{c5}R^{d5}$.

In some embodiments, Ring B is phenyl, pyridyl, 3-oxo-3,4-dihydro-2H-1,4-benzoxazinyl, 2,3-dihydro-1,4-benzodioxinyl, pyrrolo[2,3-b]pyridinyl, pyrazolo[3,4-b]pyridinyl, 1,3-benzothiazolyl, 2-oxo-2,3-dihydro-1,3-benzoxazolyl, indazolyl, 2-oxo-2,3-dihydro[1,3]oxazolo[4,5-b]pyridinyl, 2,3-dihydro-1H-indenyl, 2-oxo-2,3-dihydro-1H-indolyl, quinoxalinyl, 2-oxo-1,2,3,4-tetrahydroquinolinyl, benzimidazolyl, 3-oxo-3,4-dihydro-2H-pyrido[3,2-b][1,4]oxazinyl, 2-oxo-2,3-dihydro-1H-pyrrolo[2,3-b]pyridinyl, or pyrimidinyl, each optionally selected from chloro, methyl, trifluoromethyl, piperidinyl, methoxy, ethyl, 2-oxopyrrolidinyl, methyl(tetrahydrofuran-2-ylmethyl)amino, fluoro, 2-oxo-1,3-oxazolidinyl, amino, cyano, hydroxymethyl, (4-(methylsulfonyl)piperazin-1-yl)methyl, hydroxyl, morpholin-4-ylmethyl, $(CH_3O)(C=O)N(CH_3)$, $(CH_3O)(C=O)N(CH_3)$-methyl, 1-hydroxyethyl, cyanomethyl, 3-methyl-2-oxoimidazolidinyl or dimethylamino.

In some embodiments, Ring B is phenyl, pyridyl, or pyrimidinyl, each optionally substituted by chloro, methyl, trifluoromethyl, piperidinyl, methoxy, or dimethylamino.

In some embodiments, Ring B is phenyl substituted by methyl.

In some embodiments, $R^1$ is $C_{1-6}$ alkyl, $Cy^1$, $OR^{a1}$, $SR^{a1}$, $C(O)NR^{c1}R^{d1}$, $NR^{c1}R^{d1}$, $NR^{c1}C(O)R^{b1}$, or $NR^{c1}C(O)NR^{c1}R^{d1}$ wherein said $C_{1-6}$ alkyl is optionally substituted with 1, 2, or 3 substituents independently selected from $Cy^1$, halo, CN, OH, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

In some embodiments, $R^1$ is $C_{1-6}$ alkyl, $Cy^1$, $OR^{a1}$, $SR^{a1}$, $C(O)NR^{c1}R^{d1}$, $NR^{c1}R^{d1}$, $NR^{c1}C(O)R^{b1}$, or $NR^{c1}C(O)NR^{c1}R^{d1}$, wherein said $C_{1-6}$ alkyl is optionally substituted with $Cy^1$, OH, or $OR^{a1}$.

In some embodiments, $R^1$ is $OR^{a1}$.

In some embodiments, $R^1$ is $C_{1-6}$ alkyl substituted with 1 or 2 substituents independently selected from $Cy^1$ or $OR^{a1}$.

In some embodiments, $R^1$ is $Cy^1$ optionally substituted with 1 or 2 substituents independently selected from $C_{1-4}$ alkyl or $NR^{c6}R^{d6}$.

In some embodiments, $R^1$ is pyrrolidin-3-ylmethoxy, 2-pyrrolidin-3-ylethyl, [pyrrolidin-3-yloxy]methyl, [3-(dimethylamino)pyrrolidin-1-yl]methyl, [3-(dimethylamino)pyrrolidin-1-yl]ethyl, (1-methylpyrrolidin-3-yl)oxy, 3-(dimethylamino)propoxy, piperidin-3-ylmethoxy, [1,methylpyrrolidin-3-yl]methoxy, [1-methylpiperidin-3-yl]methoxy, [pyrrolidin-3-ylmethyl]thio, 4-(dimethylamino)piperidin-1-yl, 3-(dimethylamino)propyl](methyl)amino, [2-(1-methylpyrrolidin-2-yl)ethyl]amino, (1-methylpiperidin-4-yl)amino, 4-methyl-1,4-diazepan-1-yl, 2,7-diazaspiro[4.4]non-2-yl, 2,7-diazaspiro[3.5]non-7-yl, 3-(dimethylamino)-N-methylpyrrolidine, [2-(2-amino-1,3-thiazol-4-yl)ethyl]amino, azetidin-3-ylmethylaminocarbonyl, 3-(dimethylamino)piperidin-1-yl, [1-(2-hydroxyethyl)piperidin-3-yl]methoxy, [1-(2-cyanoethyl)piperidin-3-yl]methoxy, [1-ethylpiperidin-3-yl]methoxy, or 1-methylazetidin-3-ylaminocarbonyl.

In some embodiments, $R^1$ is pyrrolidin-3-ylmethoxy, 2-pyrrolidin-3-ylethyl, [pyrrolidin-3-yloxy]methyl, [3-(dimethylamino)pyrrolidin-1-yl]methyl, [3-(dimethylamino)pyrrolidin-1-yl]ethyl, (1-methylpyrrolidin-3-yl)oxy, 3-(dimethylamino)propoxy, piperidin-3-ylmethoxy, [1,methylpyrrolidin-3-yl]methoxy, [1-methylpiperidin-3-yl]methoxy, [pyrrolidin-3-ylmethyl]thio, 4-(dimethylamino)piperidin-1-yl, 3-(dimethylamino)propyl](methyl)amino, [2-(1-methylpyrrolidin-2-yl)ethyl]amino, (1-methylpiperidin-4-yl)amino, 4-methyl-1,4-diazepan-1-yl, 2,7-diazaspiro[4.4]non-2-yl, 2,7-diazaspiro[3.5]non-7-yl, 3-(dimethylamino)-N-methylpyrrolidine, [2-(2-amino-1,3-thiazol-4-yl)ethyl]amino, azetidin-3-ylmethylaminocarbonyl, or 1-methylazetidin-3-ylaminocarbonyl.

In some embodiments, $R^{a1}$ is independently selected from $C_{1-6}$ alkyl, $C_{2-6}$ alkenyl, $C_{2-6}$ alkynyl, and $Cy^4$; wherein said $C_{1-6}$ alkyl, $C_{2-6}$ alkenyl, and $C_{2-6}$ alkynyl are each optionally substituted with 1, 2, or 3 substituents independently selected from $Cy^4$, halo, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$.

In some embodiments, $R^{a1}$ is $C_{1-6}$ alkyl optionally substituted with 1 or 2 substituents independently selected from $Cy^4$ and $NR^{c3}R^{d3}$.

In some embodiments, $R^{a1}$ is $C_{1-3}$ alkyl optionally substituted with pyrrolidinyl, piperidinyl, or dimethylamino, wherein said pyrrolidinyl and piperidinyl are each optionally substituted with 1, 2, or 3 substituents independently selected from methyl, ethyl, cyanoethyl, and hydroxyethyl.

In some embodiments, $R^2$ is H, $C_{1-6}$ alkyl, $C_{1-6}$ haloalkyl, $Cy^2$, or $C(O)NR^{c2}R^{d2}$, wherein said $C_{1-6}$ alkyl is optionally substituted with 1, 2, or 3 substituents independently selected from $Cy^2$, halo, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$.

In some embodiments, $R^2$ is H, $C_{1-6}$ alkyl, $C_{1-6}$ haloalkyl, $Cy^2$, or $C(O)NR^{c2}R^{d2}$, wherein said $C_{1-6}$ alkyl is optionally substituted with 1 or 2 substituents independently selected from $Cy^2$, CN, $OR^{a2}$, and $NR^{c2}R^{d2}$.

In some embodiments, $R^2$ is H, methyl, trifluoromethyl, 4-methylphenyl, cyanomethyl, methylaminocarbonyl, dimethylaminocarbonyl, cyclopropylaminocarbonyl, 1-methylazetidin-3-ylaminocarbonyl, hydroxymethyl, azetidin-1-ylmethyl, cyclopropylmethylaminomethyl, (isoxazol-3-ylamino)methyl, dimethylaminomethyl, or dimethylaminoethyl.

In some embodiments, $R^2$ is H.
In some embodiments, $R^3$ is H.
In some embodiments, $R^A$ is CN.
In some embodiments, $R^B$ is independently selected from $Cy^3$, halo, $C_{1-6}$ alkyl, $C_{1-6}$ haloalkyl, CN, $NR^{c5}C(O)OR^{a5}$, $NR^{c5}R^{d5}$ and $OR^{a5}$.

In some embodiments, $R^B$ is independently selected from $Cy^3$, halo, $C_{1-6}$ alkyl, $C_{1-6}$ haloalkyl, and $OR^{a5}$.

In some embodiments, $R^B$ is $C_{1-6}$ alkyl.

In some embodiments, $R^B$ is methyl, chloro, trifluoromethyl, piperidinyl, methoxy, ethyl, 2-oxopyrrolidinyl, methyl (tetrahydrofuran-2-ylmethyl)amino, fluoro, 2-oxo-1,3-oxazolidinyl, amino, cyano, hydroxymethyl, (4-(methylsulfonyl)piperazin-1-yl)methyl, hydroxyl, morpholin-4-ylmethyl, $(CH_3O)(C=O)N(CH_3)$, $(CH_3O)(C=O)N(CH_3)$-methyl, 1-hydroxyethyl, cyanomethyl, 3-methyl-2-oxoimidazolidinyl or dimethylamino.

In some embodiments, $R^B$ is methyl.
In some embodiments, $Cy^1$ is independently selected from 5-10 membered heteroaryl and 4-10 membered heterocycloalkyl, each of which is optionally substituted with 1, 2, 3, or 4 substituents independently selected from $R^{Cy}$.

In some embodiments, $Cy^1$ is independently selected from 5-10 membered heteroaryl and 4-10 membered heterocycloalkyl, each of which is optionally substituted with 1 or 2 substituents independently selected from $C_{1-4}$ alkyl and $NR^{c6}R^{d6}$.

In some embodiments, $Cy^1$ is 4-10 membered heterocycloalkyl, each of which is optionally substituted with 1, 2, 3, or 4 substituents independently selected from $R^{Cy}$.

In some embodiments, $Cy^1$ is azetidine, piperidine, pyrrolidine, diazapane, or diazaspirononane, each optionally substituted with 1 or 2 substituents independently selected from $R^{Cy}$.

In some embodiments, the compounds of the invention have Formula II:

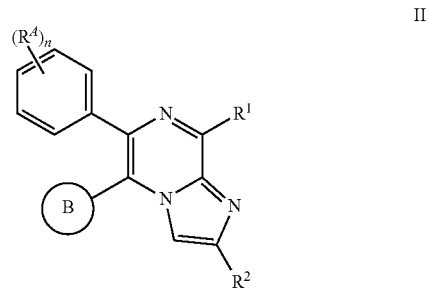

wherein n is 0, 1, 2, 3, or 4.

In some embodiments, the compounds of the invention have Formula IIa:

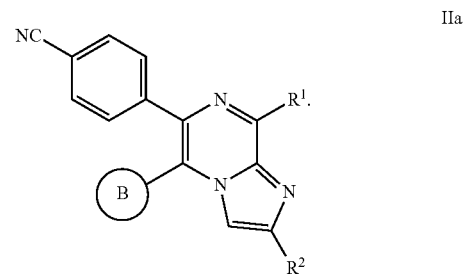

In some embodiments, where the compound of the invention has Formula II or IIa, the group:

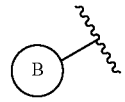

is selected from any one of Formulae (B-1) to (B-15):

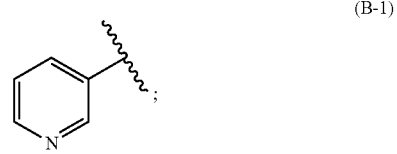

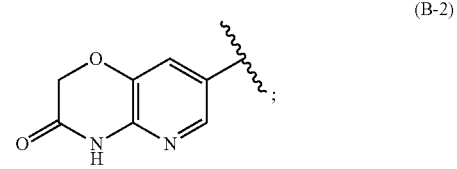

(B-3) 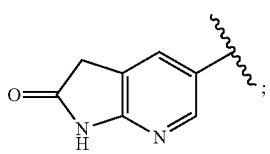
(B-4) 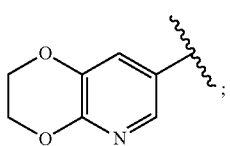
(B-5) 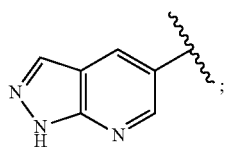
(B-6) 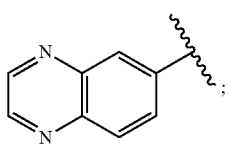
(B-7) 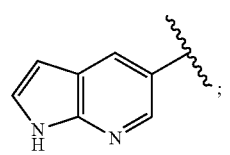
(B-8) 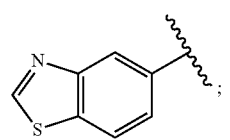
(B-9) 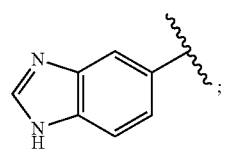
(B-10) 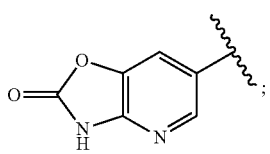
(B-11) 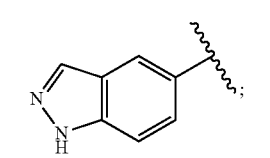
(B-12) 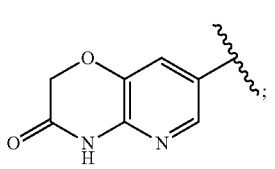
(B-13) 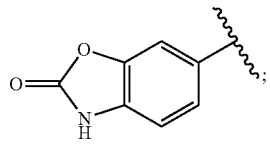
(B-14) 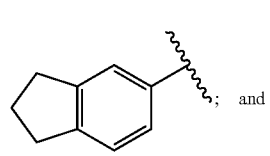; and
(B-15) 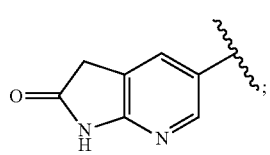
wherein any one of the groups of Formulae (B-1) to (B-15) is optionally substituted with 1, 2, 3, or 4 substituents independently selected from $R^B$.
In some embodiments, the compounds of the invention have Formula III:
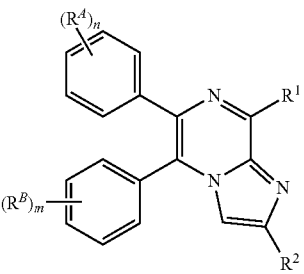
III
wherein n is 0, 1, 2, 3, or 4 and wherein m is 0, 1, 2, 3, or 4.
In some embodiments, the compounds of the invention have Formula IV:
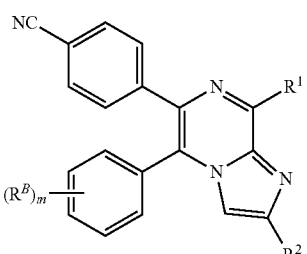
IV
wherein m is 0, 1, 2, 3, or 4.

In some embodiments, the compounds of the invention have Formula V:

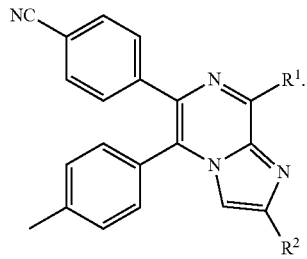

V

In some embodiments, the compounds of the invention have Formula VI:

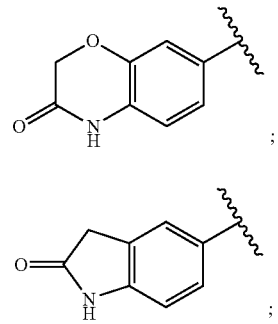

VI

In some embodiments, the compounds of the invention have Formula VII:

VII

In some embodiments, where the compound of the invention has Formula VII, the group:

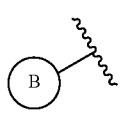

is selected from any one of Formulae (B-1a) to (B-15a):

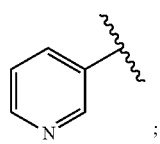

(B-1a)

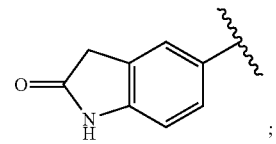

(B-2a)

(B-3a)

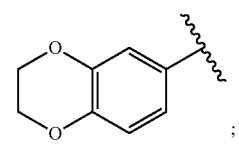

(B-4a)

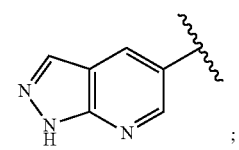

(B-5a)

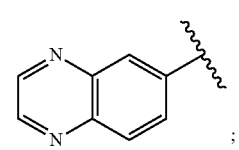

(B-6a)

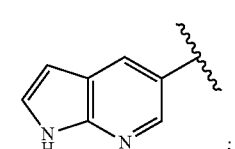

(B-7a)

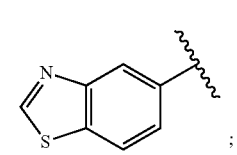

(B-8a)

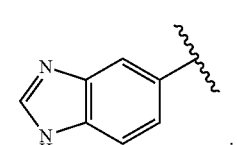

(B-9a)

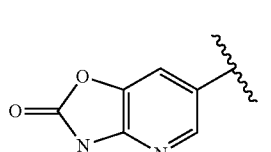

(B-10a)

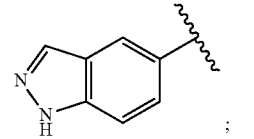

(B-11a)

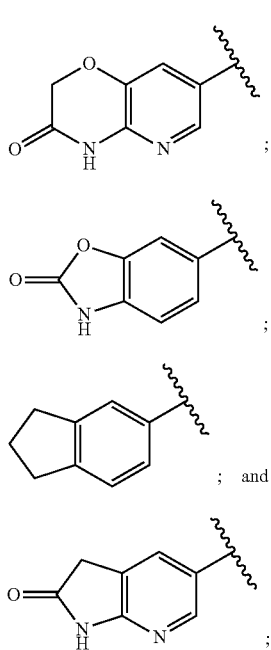

wherein any one of the groups of Formulae (B-1a) to (B-15a) is optionally substituted with 1, 2, 3, or 4 substituents independently selected from $R^B$.

In some embodiments, n is 0, 1, or 2.
In some embodiments, n is 1.
In some embodiments, m is 0, 1, or 2.
In some embodiments, m is 1.

It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, the phrase "optionally substituted" means unsubstituted or substituted. As used herein, the term "substituted" means that a hydrogen atom is removed and replaced by a monovalent substituent, or two hydrogen atoms are replaced with a divalent substituent like a terminal oxo group. It is to be understood that substitution at a given atom is limited by valency.

Throughout the definitions, the term "$C_{i-j}$" indicates a range which includes the endpoints, wherein i and j are integers and indicate the number of carbons. Examples include $C_{1-4}$, $C_{1-6}$, and the like.

The term "z-membered" (where z is an integer) typically describes the number of ring-forming atoms in a moiety where the number of ring-forming atoms is z. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the term "$C_{i-j}$ alkyl," employed alone or in combination with other terms, refers to a saturated hydrocarbon group that may be straight-chain or branched, having i to j carbons. In some embodiments, the alkyl group contains from 1 to 6 carbon atoms or from 1 to 4 carbon atoms, or from 1 to 3 carbon atoms. Examples of alkyl moieties include, but are not limited to, chemical groups such as methyl, ethyl, n-propyl, isopropyl, n-butyl, s-butyl, and t-butyl.

As used herein, the term "$C_{i-j}$ alkoxy," employed alone or in combination with other terms, refers to a group of formula —O-alkyl, wherein the alkyl group has i to j carbons. Example alkoxy groups include methoxy, ethoxy, and propoxy (e.g., n-propoxy and isopropoxy). In some embodiments, the alkyl group has 1 to 3 carbon atoms.

As used herein, "$C_{i-j}$ alkenyl," employed alone or in combination with other terms, refers to an unsaturated hydrocarbon group having one or more double carbon-carbon bonds and having i to j carbons. In some embodiments, the alkenyl moiety contains 2 to 6 or 2 to 4 carbon atoms. Example alkenyl groups include, but are not limited to, ethenyl, n-propenyl, isopropenyl, n-butenyl, sec-butenyl, and the like.

As used herein, "$C_{i-j}$ alkynyl," employed alone or in combination with other terms, refers to an unsaturated hydrocarbon group having one or more triple carbon-carbon bonds and having i to j carbons. Example alkynyl groups include, but are not limited to, ethynyl, propyn-1-yl, propyn-2-yl, and the like. In some embodiments, the alkynyl moiety contains 2 to 6 or 2 to 4 carbon atoms.

As used herein, the term "$C_{i-j}$ alkylamino," employed alone or in combination with other terms, refers to a group of formula —NH(alkyl), wherein the alkyl group has i to j carbon atoms. In some embodiments, the alkyl group has 1 to 6 or 1 to 4 carbon atoms. In some embodiments, the alkylamino group is —NH($C_{1-4}$ alkyl) such as, for example, methylamino, ethylamino, or propylamino.

As used herein, the term "di-$C_{i-j}$-alkylamino," employed alone or in combination with other terms, refers to a group of formula —N(alkyl)$_2$, wherein each of the two alkyl groups has, independently, i to j carbon atoms. In some embodiments, each alkyl group independently has 1 to 6 or 1 to 4 carbon atoms. In some embodiments, the dialkylamino group is —N($C_{1-4}$ alkyl)$_2$ such as, for example, dimethylamino or diethylamino.

As used herein, the term "$C_{i-j}$ alkylthio," employed alone or in combination with other terms, refers to a group of formula —S-alkyl, wherein the alkyl group has i to j carbon atoms. In some embodiments, the alkyl group has 1 to 6 or 1 to 4 carbon atoms. In some embodiments, the alkylthio group is $C_{1-4}$ alkylthio such as, for example, methylthio or ethylthio.

As used herein, the term "amino," employed alone or in combination with other terms, refers to a group of formula —NH$_2$.

As used herein, the term "aryl," employed alone or in combination with other terms, refers to a monocyclic or polycyclic (e.g., having 2, 3 or 4 fused rings) aromatic hydrocarbon, such as, but not limited to, phenyl, 1-naphthyl, 2-naphthyl, anthracenyl, phenanthrenyl, and the like. In some embodiments, aryl is $C_{6-10}$ aryl. In some embodiments, the aryl group is a naphthalene ring or phenyl ring. In some embodiments, the aryl group is phenyl.

As used herein, the term "aryl-$C_{i-j}$ alkyl," employed alone or in combination with other terms, refers to an alkyl group substituted by an aryl group. An example of a aryl-$C_{i-j}$ alkyl group is benzyl.

As used herein, the term "carbonyl", employed alone or in combination with other terms, refers to a —C(O)— group.

As used herein, the term "$C_{i-j}$ cycloalkyl," employed alone or in combination with other terms, refers to a non-aromatic cyclic hydrocarbon moiety having i to j ring-forming carbon atoms, which may optionally contain one or more alkenylene groups as part of the ring structure. Cycloalkyl groups can include mono- or polycyclic (e.g., having 2, 3 or 4 fused rings) ring systems. Also included in the definition of cycloalkyl are moieties that have one or more aromatic rings fused (i.e., having a bond in common with) to the cycloalkyl ring, for example, benzo derivatives of cyclopentane, cyclopentene, cyclohexane, and the like. One or more ring-forming carbon atoms of a cycloalkyl group can be oxidized to form carbonyl linkages. In some embodiments, cycloalkyl is $C_{3-10}$ cycloalkyl, $C_{3-7}$ cycloalkyl, or $C_{5-6}$ cycloalkyl. Exemplary cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. Further exemplary cycloalkyl groups include cyclopropyl, cyclobutyl, cyclopentyl, and cyclohexyl.

As used herein, the term "$C_{i-j}$ cycloalkyl-$C_{i-j}$ alkyl," employed alone or in combination with other terms, refers to an alkyl group substituted by a cycloalkyl group. An example of a cycloalkyl-$C_{i-j}$ alkyl group is cyclopropylmethyl.

As used herein, "$C_{i-j}$ haloalkoxy," employed alone or in combination with other terms, refers to a group of formula —O-haloalkyl having i to j carbon atoms. An example haloalkoxy group is $OCF_3$. An additional example haloalkoxy group is $OCHF_2$. In some embodiments, the haloalkoxy group is fluorinated only. In some embodiments, the alkyl group has 1 to 6 or 1 to 4 carbon atoms. In some embodiments, the haloalkoxy group is $C_{1-4}$ haloalkoxy.

As used herein, the term "halo," employed alone or in combination with other terms, refers to a halogen atom selected from F, Cl, I or Br. In some embodiments, "halo" refers to a halogen atom selected from F, Cl, or Br. In some embodiments, the halo substituent is F.

As used herein, the term "C haloalkyl," employed alone or in combination with other terms, refers to an alkyl group having from one halogen atom to 2s+1 halogen atoms which may be the same or different, where "s" is the number of carbon atoms in the alkyl group, wherein the alkyl group has i to j carbon atoms. In some embodiments, the haloalkyl group is fluorinated only. In some embodiments, the haloalkyl group is fluoromethyl, difluoromethyl, or trifluoromethyl. In some embodiments, the haloalkyl group is trifluoromethyl. In some embodiments, the alkyl group has 1 to 6 or 1 to 4 carbon atoms.

As used herein, the term "heteroaryl," employed alone or in combination with other terms, refers to a monocyclic or polycyclic (e.g., having 2, 3 or 4 fused rings) aromatic heterocylic moiety, having one or more heteroatom ring members selected from nitrogen, sulfur and oxygen. In some embodiments, the heteroaryl group has 1, 2, 3, or 4 heteroatom ring members. In some embodiments, the heteroaryl group has 1, 2, or 3 heteroatom ring members. In some embodiments, the heteroaryl group has 1 or 2 heteroatom ring members. In some embodiments, the heteroaryl group has 1 heteroatom ring member. In some embodiments, the heteroaryl group is 5- to 10-membered or 5- to 6-membered. In some embodiments, the heteroaryl group is 5-membered. In some embodiments, the heteroaryl group is 6-membered. When the heteroaryl group contains more than one heteroatom ring member, the heteroatoms may be the same or different. The nitrogen atoms in the ring(s) of the heteroaryl group can be oxidized to form N-oxides. Example heteroaryl groups include, but are not limited to, pyridine, pyrimidine, pyrazine, pyridazine, pyrrole, pyrazole, azolyl, oxazole, isoxazole, thiazole, isothiazole, imidazole, furan, thiophene, triazole, tetrazole, thiadiazole, quinoline, isoquinoline, indole, benzothiophene, benzofuran, benzisoxazole, imidazo[1,2-b]thiazole, purine, triazine, and the like.

A 5-membered heteroaryl is a heteroaryl group having five ring-forming atoms wherein one or more of the ring-forming atoms are independently selected from N, O, and S. In some embodiments, the 5-membered heteroaryl group has 1, 2, 3, or 4 heteroatom ring members. In some embodiments, the 5-membered heteroaryl group has 1, 2, or 3 heteroatom ring members. In some embodiments, the 5-membered heteroaryl group has 1 or 2 heteroatom ring members. In some embodiments, the 5-membered heteroaryl group has 1 heteroatom ring member. Example ring-forming members include CH, N, NH, O, and S. Example five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A 6-membered heteroaryl is a heteroaryl group having six ring-forming atoms wherein one or more of the ring-forming atoms is N. In some embodiments, the 6-membered heteroaryl group has 1, 2, or 3 heteroatom ring members. In some embodiments, the 6-membered heteroaryl group has 1 or 2 heteroatom ring members. In some embodiments, the 6-membered heteroaryl group has 1 heteroatom ring member. Example ring-forming members include CH and N. Example six-membered ring heteroaryls are pyridyl, pyrazinyl, pyrimidinyl, triazinyl, and pyridazinyl.

As used herein, the term "heteroaryl-$C_{i-j}$ alkyl," employed alone or in combination with other terms, refers to an alkyl group substituted by a heteroaryl group. An example of a heteroaryl-$C_{i-j}$ alkyl group is pyridylmethyl.

As used herein, the term "heterocycloalkyl," employed alone or in combination with other terms, refers to non-aromatic heterocyclic ring system, which may optionally contain one or more unsaturations as part of the ring structure, and which has at least one heteroatom ring member independently selected from nitrogen, sulfur and oxygen. In some embodiments, the heterocycloalkyl group has 1, 2, 3, or 4 heteroatom ring members. In some embodiments, the heterocycloalkyl group has 1, 2, or 3 heteroatom ring members. In some embodiments, the heterocycloalkyl group has 1 or 2 heteroatom ring members. In some embodiments, the heterocycloalkyl group has 1 heteroatom ring member. When the heterocycloalkyl group contains more than one heteroatom in the ring, the heteroatoms may be the same or different. Example ring-forming members include CH, $CH_2$, C(O), N, NH, O, S, S(O), and $S(O)_2$. Heterocycloalkyl groups can include mono- or polycyclic (e.g., having 2, 3 or 4 fused rings) ring systems, including spiro systems. Also included in the definition of heterocycloalkyl are moieties that have one or more aromatic rings fused (i.e., having a bond in common with) to the non-aromatic ring, for example, 1,2,3,4-tetrahydro-quinoline, dihydrobenzofuran and the like. The carbon atoms or heteroatoms in the ring(s) of the heterocycloalkyl group can be oxidized to form a carbonyl, sulfinyl, or sulfonyl group (or other oxidized linkage) or a nitrogen atom can be quaternized. In some embodiments, the heterocycloalkyl is 5- to 10-membered, 4- to 10-membered, 4- to 7-membered, 5-membered, or 6-membered. Examples of heterocycloalkyl groups include 1,2,3,4-tetrahydro-quinoline, dihydrobenzofuran, azetidine, azepane, pyrrolidine, piperidine, piperazine, morpholine, thiomorpholine, and pyran. In further embodiments, the heterocycloalkyl group is azetidine, piperidine, pyrrolidine, diazapane, or diazaspirononane.

As used herein, the term "heterocycloalkyl-$C_{i-j}$ alkyl," employed alone or in combination with other terms, refers to an alkyl group substituted by a heterocycloalkyl group. An example of a heterocycloalkyl-$C_{i-j}$ alkyl group is pyrrolidinylmethyl.

The compounds described herein can be asymmetric (e.g., having one or more stereocenters). All stereoisomers, such as enantiomers and diastereoisomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

When the compounds of the invention contain a chiral center, the compounds can be any of the possible stereoisomers. In compounds with a single chiral center, the stereochemistry of the chiral center can be (R) or (S). In compounds with two chiral centers, the stereochemistry of the chiral centers can each be independently (R) or (S) so the configuration of the chiral centers can be (R) and (R), (R) and (S); (S) and (R), or (S) and (S). In compounds with three chiral centers, the stereochemistry each of the three chiral centers can each be independently (R) or (S) so the configuration of the chiral centers can be (R), (R) and (R); (R), (R) and (S); (R), (S) and (R); (R), (S) and (S); (S), (R) and (R); (S), (R) and (S); (S), (S) and (R); or (S), (S) and (S).

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereoisomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

All compounds, and pharmaceutically acceptable salts thereof, can be found together with other substances such as water and solvents (e.g., hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in a compound of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences*, 17$^{th}$ Ed., (Mack Publishing Company, Easton, 1985), p. 1418, Berge et al., *J. Pharm. Sci.*, 1977, 66(1), 1-19, and in Stahl et al., *Handbook of Pharmaceutical Salts: Properties, Selection, and Use*, (Wiley, 2002).

The following abbreviations may be used herein: AcOH (acetic acid); Ac$_2$O (acetic anhydride); aq. (aqueous); atm. (atmosphere(s)); Boc (t-butoxycarbonyl); BOP ((benzotriazol-1-yloxy)tris(dimethylamino)phosphonium hexafluorophosphate); br (broad); Cbz (carboxybenzyl); calc. (calculated); d (doublet); dd (doublet of doublets); DBU (1,8-diazabicyclo[5.4.0]undec-7-ene); DCM (dichloromethane); DIAD (N,N'-diisopropyl azidodicarboxylate); DIEA (N,N-diisopropylethylamine); DIPEA (N, N-diisopropylethylamine); DMF (N, N-dimethylformamide); Et (ethyl); EtOAc (ethyl acetate); g (gram(s)); h (hour(s)); HATU (N,N,N',N'-tetramethyl-O-(7-azabenzotriazol-1-yl)uronium hexafluorophosphate); HCl (hydrochloric acid); HPLC (high performance liquid chromatography); Hz (hertz); IPA (isopropyl alcohol); J (coupling constant); LCMS (liquid chromatography-mass spectrometry); m (multiplet); M (molar); mCPBA (3-chloroperoxybenzoic acid); MS (Mass spectrometry); Me (methyl); MeCN (acetonitrile); MeOH (methanol); mg (milligram(s)); min. (minutes(s)); mL (milliliter(s)); mmol (millimole(s)); N (normal); nM (nanomolar); NMP (N-methylpyrrolidinone); NMR (nuclear magnetic resonance spectroscopy); OTf (trifluoromethanesulfonate); Ph (phenyl); pM (picomolar); RP-HPLC (reverse phase high performance liquid chromatography); s (singlet); t (triplet or tertiary); TBS (tert-butyldimethylsilyl); tert (tertiary); tt (triplet of triplets); TFA (trifluoroacetic acid); THF (tetrahydrofuran); µg (microgram (s)); µL (microliter(s)); µM (micromolar); wt % (weight percent).

Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in P. G. M. Wuts and T. W. Greene, *Protective Groups in Organic Synthesis*, 4$^{th}$ Ed., Wiley & Sons, Inc., New York (2006), which is incorporated herein by reference in its entirety. Protecting groups in the synthetic schemes are typically represented by "PG."

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("*Preparative LC-MS Purification: Improved Compound Specific Method Optimization*" Karl F. Blom, Brian Glass, Richard Sparks, Andrew P. Combs *J. Combi. Chem.* 2004, 6(6), 874-883, which is incorporated herein by reference in its entirety) and normal phase silica chromatography.

Compound of formula 11 can be prepared via the synthetic route outlined in Scheme 1. The commercially available starting material 1 can undergo Suzuki coupling with the boronic acid or ester of formula 2 (R is, e.g., H or C$_{1-6}$ alkyl) under standard Suzuki conditions (e.g., in the presence of a palladium catalyst and a base such as potassium carbonate) to afford compound 3.

The chloride in compound 3 can be coupled to compound of formula 4, in which M is a boronic acid, boronic ester or an appropriately substituted metal [e.g., M is B(OR)$_2$, Sn(alkyl)$_4$, or Zn-Hal], under standard Suzuki coupling conditions (e.g., in the presence of a palladium catalyst and a suitable base) or standard Stille coupling conditions (e.g., in the presence of a palladium catalyst), or standard Negishi coupling conditions (e.g., in the presence of a palladium catalyst) to give the derivative of formula 5.

Alternatively, compound 4 can be a cyclic amine (where M is H and attached to a ring-forming nitrogen atom in Ring B) and the coupling of compound 4 to compound 3 can be achieved by direct SNAr displacement of the chloride in compound 3 by the amine in compound 4 in the presence of a suitable base such diisopropylethylamine at elevated temperature. The coupling of arylchloride 3 with the cyclic amine 4 can also be performed under Buchwald amination conditions (e.g., in the presence of a palladium catalyst and a base such as sodium tert-butoxide).

Bromination of compound 5 can be performed under standard conditions [e.g., in the presence of N-bromosuccinimide (NBS)] to give compound 6. Installation of R$^1$ group can be achieved by SNAr displacement of the bromide in compound 6 with R$^1$-M (wherein R$^1$-M is an alcohol or an amine, e.g., M is H which is attached to an oxygen or nitrogen atom in R$^1$) in the presence of a suitable base such as sodium hydride, sodium hydroxide, potassium carbonate or diisopropylethylamine at elevated temperature. The coupling of compound 6 with R$^1$-M can also be performed under standard Suzuki conditions (when M is boronic acid or ester), or standard Stille coupling conditions [when M is Sn(alkyl)$_4$], or standard Negishi coupling conditions (when M is Zn-Hal) to give compound of formula 7.

Condensation of compound 7 with ketone derivatives of formula 8 (X is a leaving group such as Cl or Br) at elevated temperature can generate the bicyclic compound of formula 9, which can be brominated with a suitable reagent such as NBS to give compound 10. Finally, installation of substituent R$^3$ can be achieved by coupling of bromide 10 with R$^3$-M under standard cross coupling conditions, such as Suzuki coupling conditions (when M is boronic acid or ester), or Negishi coupling conditions (when M is Zn-Hal) or Stille coupling conditions [when M is Sn(alkyl)$_4$] to give compounds of formula 11.

Scheme 1

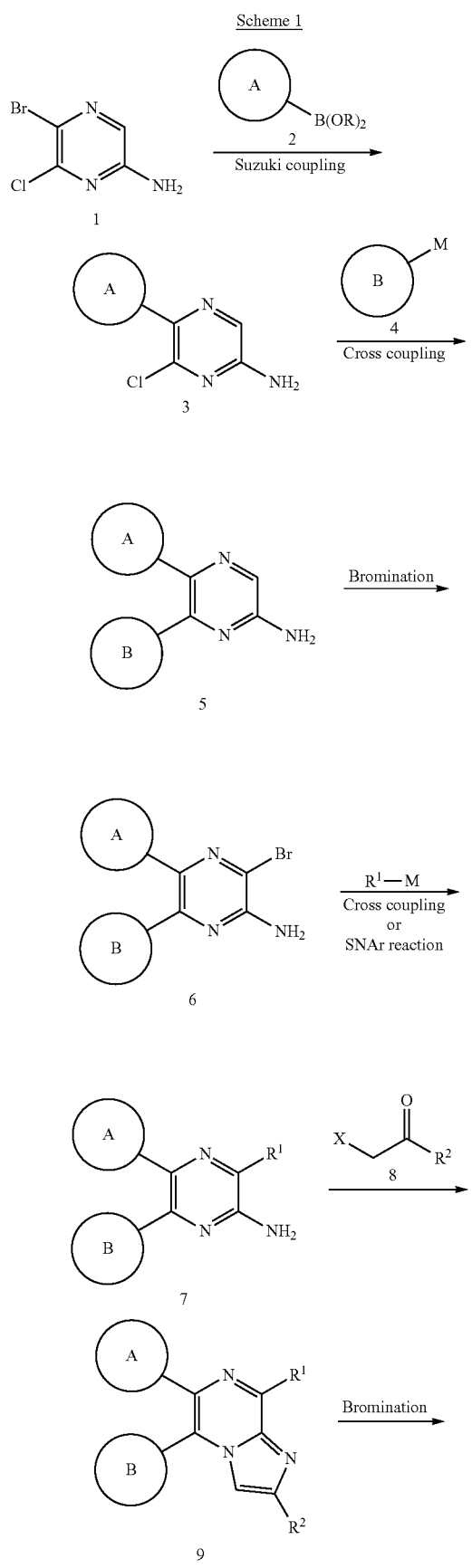

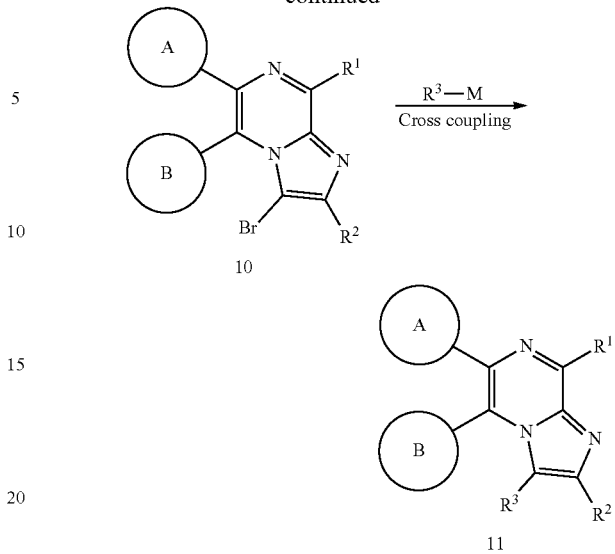

Methods of Use

Compounds of the invention are LSD1 inhibitors and, thus, are useful in treating diseases and disorders associated with activity of LSD1. For the uses described herein, any of the compounds of the invention, including any of the embodiments thereof, may be used.

In some embodiments, the compounds of the invention are selective for LSD1 over LSD2, meaning that the compounds bind to or inhibit LSD1 with greater affinity or potency, compared to LSD2. In general, selectivity can be at least about 5-fold, at least about 10-fold, at least about 20-fold, at least about 50-fold, at least about 100-fold, at least about 200-fold, at least about 500-fold or at least about 1000-fold.

As inhibitors of LSD1, the compounds of the invention are useful in treating LSD1-mediated diseases and disorders. The term "LSD1-mediated disease" or "LSD1-mediated disorder" refers to any disease or condition in which LSD1 plays a role, or where the disease or condition is associated with expression or activity of LSD1. The compounds of the invention can therefore be used to treat or lessen the severity of diseases and conditions where LSD1 is known to play a role.

Diseases and conditions treatable using the compounds of the invention include, generally cancers, inflammation, autoimmune diseases, viral induced pathogenesis, beta-globinopathies, and other diseases linked to LSD1 activity.

Cancers treatable using compounds according to the present invention include, for example, hematological cancers, sarcomas, lung cancers, gastrointestinal cancers, genitourinary tract cancers, liver cancers, bone cancers, nervous system cancers, gynecological cancers, and skin cancers.

Example hematological cancers include, for example, lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), essential thrombocytosis (ET)), myelodysplasia syndrome (MDS), and multiple myeloma.

Example sarcomas include, for example, chondrosarcoma, Ewing's sarcoma, osteosarcoma, rhabdomyosarcoma, angiosarcoma, fibrosarcoma, liposarcoma, myxoma, rhabdomyoma, fibroma, lipoma, harmatoma, and teratoma.

Example lung cancers include, for example, non-small cell lung cancer (NSCLC), bronchogenic carcinoma (squamous cell, undifferentiated small cell, undifferentiated large cell, adenocarcinoma), alveolar (bronchiolar) carcinoma, bronchial adenoma, chondromatous hamartoma, and mesothelioma.

Example gastrointestinal cancers include, for example, cancers of the esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer.

Example genitourinary tract cancers include, for example, cancers of the kidney (adenocarcinoma, Wilm's tumor [nephroblastoma]), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

Example liver cancers include, for example, hepatoma (hepatocellular carcinoma), cholangiocarcinoma, hepatoblastoma, angiosarcoma, hepatocellular adenoma, and hemangioma.

Example bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Example nervous system cancers include, for example, cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma multiform, oligodendroglioma, schwannoma, retinoblastoma, congenital tumors), and spinal cord (neurofibroma, meningioma, glioma, sarcoma), as well as neuroblastoma and Lhermitte-Duclos disease.

Example gynecological cancers include, for example, cancers of the uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosathecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Example skin cancers include, for example, melanoma, basal cell carcinoma, squamous cell carcinoma, Kaposi's sarcoma, moles dysplastic nevi, lipoma, angioma, dermatofibroma, and keloids.

The compounds of the invention can further be used to treat cancer types where LSD1 may be overexpressed including, for example, breast, prostate, head and neck, laryngeal, oral, and thyroid cancers (e.g., papillary thyroid carcinoma).

The compounds of the invention can further be used to treat genetic disorders such as Cowden syndrome and Bannayan-Zonana syndrome.

The compounds of the invention can further be used to treat viral diseases such as herpes simplex virus (HSV), varicella zoster virus (VZV), human cytomegalovirus, hepatitis B virus (HBV), and adenovirus.

The compounds of the invention can further be used to treat beta-globinopathies including, for example, beta-thalassemia and sickle cell anemia.

As used herein, the term "contacting" refers to the bringing together of indicated moieties in an in vitro system or an in vivo system. For example, "contacting" a LSD1 protein with a compound of the invention includes the administration of a compound of the present invention to an individual or patient, such as a human, having a LSD1 protein, as well as, for example, introducing a compound of the invention into a sample containing a cellular or purified preparation containing the LSD1 protein.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to inhibiting the disease; for example, inhibiting a disease, condition or disorder in an individual who is experiencing or displaying the pathology or symptomatology of the disease, condition or disorder (i.e., arresting further development of the pathology and/or symptomatology) or ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used herein, the term "preventing" or "prevention" refers to preventing the disease; for example, preventing a disease, condition or disorder in an individual who may be predisposed to the disease, condition or disorder but does not yet experience or display the pathology or symptomatology of the disease.

Combination Therapies

The compounds of the invention can be used in combination treatments where the compound of the invention is administered in conjunction with other treatments such as the administration of one or more additional therapeutic agents. The additional therapeutic agents are typically those which are normally used to treat the particular condition to be treated. The additional therapeutic agents can include, e.g., chemotherapeutics, anti-inflammatory agents, steroids, immunosuppressants, as well as Bcr-Abl, Flt-3, RAF, FAK, JAK, PIM, PI3K inhibitors for treatment of LSD1-mediated diseases, disorders or conditions. The one or more additional pharmaceutical agents can be administered to a patient simultaneously or sequentially.

In some embodiments, the compounds of the invention can be used in combination with a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, e.g., vorinostat.

For treating cancer and other proliferative diseases, the compounds of the invention can be used in combination with chemotherapeutic agents, agonists or antagonists of nuclear receptors, or other anti-proliferative agents. The compounds of the invention can also be used in combination with medical therapy such as surgery or radiotherapy, e.g., gamma-radiation, neutron beam radiotherapy, electron beam radiotherapy, proton therapy, brachytherapy, and systemic radioactive isotopes. Examples of suitable chemotherapeutic agents include any of: abarelix, aldesleukin, alemtuzumab, alitretinoin, allopurinol, altretamine, anastrozole, arsenic trioxide, asparaginase, azacitidine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, and zoledronate.

For treating cancer and other proliferative diseases, the compounds of the invention can be used in combination with ruxolitinib.

For treating autoimmune or inflammatory conditions, the compound of the invention can be administered in combination with a corticosteroid such as triamcinolone, dexamethasone, fluocinolone, cortisone, prednisolone, or flumetholone.

For treating autoimmune or inflammatory conditions, the compound of the invention can be administered in combination with an immune suppressant such as fluocinolone acetonide (Retisert®), rimexolone (AL-2178, Vexol, Alcon), or cyclosporine (Restasis®).

For treating autoimmune or inflammatory conditions, the compound of the invention can be administered in combination with one or more additional agents selected from Dehydrex™ (Holles Labs), Civamide (Opko), sodium hyaluronate (Vismed, Lantibio/TR$^B$ Chemedia), cyclosporine (ST-603, Sirion Therapeutics), ARG101(T) (testosterone, Argentis), AGR1012(P) (Argentis), ecabet sodium (Senju-Ista), gefarnate (Santen), 15-(s)-hydroxyeicosatetraenoic acid (15(S)-HETE), cevilemine, doxycycline (ALTY-0501, Alacrity), minocycline, iDestrin™ (NP50301, Nascent Pharmaceuticals), cyclosporine A (Nova22007, Novagali), oxytetracycline (Duramycin, MOLI1901, Lantibio), CF101 (2S,3S,4R,5R)-3,4-dihydroxy-5-[6-[(3-iodophenyl)methylamino]purin-9-yl]-N-methyl-oxolane-2-carbamyl, Can-Fite Biopharma), voclosporin (LX212 or LX214, Lux Biosciences), ARG103 (Agentis), RX-10045 (synthetic resolvin analog, Resolvyx), DYN15 (Dyanmis Therapeutics), rivoglitazone (DE011, Daiichi Sanko), TB4 (RegeneRx), OPH-01 (Ophtalmis Monaco), PCS101 (Pericor Science), REV1-31 (Evolutec), Lacritin (Senju), rebamipide (Otsuka-Novartis), OT-551 (Othera), PAI-2 (University of Pennsylvania and Temple University), pilocarpine, tacrolimus, pimecrolimus (AMS981, Novartis), loteprednol etabonate, rituximab, diquafosol tetrasodium (INS365, Inspire), KLS-0611 (Kissei Pharmaceuticals), dehydroepiandrosterone, anakinra, efalizumab, mycophenolate sodium, etanercept (Embrel®), hydroxychloroquine, NGX267 (TorreyPines Therapeutics), or thalidomide.

For treating beta-thalassemia or sickle cell disease, the compound of the invention can be administered in combination with one or more additional agents such as Hydrea® (hydroxyurea).

In some embodiments, the compound of the invention can be administered in combination with one or more agents selected from an antibiotic, antiviral, antifungal, anesthetic, anti-inflammatory agents including steroidal and non-steroidal anti-inflammatories, and anti-allergic agents. Examples of suitable medicaments include aminoglycosides such as amikacin, gentamycin, tobramycin, streptomycin, netilmycin, and kanamycin; fluoroquinolones such as ciprofloxacin, norfloxacin, ofloxacin, trovafloxacin, lomefloxacin, levofloxacin, and enoxacin; naphthyridine; sulfonamides; polymyxin; chloramphenicol; neomycin; paramomycin; colistimethate; bacitracin; vancomycin; tetracyclines; rifampin and its derivatives ("rifampins"); cycloserine; beta-lactams; cephalosporins; amphotericins; fluconazole; flucytosine; natamycin; miconazole; ketoconazole; corticosteroids; diclofenac; flurbiprofen; ketorolac; suprofen; cromolyn; lodoxamide; levocabastin; naphazoline; antazoline; pheniramine; or azalide antibiotic.

Other examples of agents, one or more of which a provided compound may also be combined with include: a treatment for Alzheimer's Disease such as donepezil and rivastigmine; a treatment for Parkinson's Disease such as L-DOPA/carbidopa, entacapone, ropinirole, pramipexole, bromocriptine, pergolide, trihexyphenidyl, and amantadine; an agent for treating multiple sclerosis (MS) such as beta interferon (e.g., Avonex® and Rebif®), glatiramer acetate, and mitoxantrone; a treatment for asthma such as albuterol and montelukast; an agent for treating schizophrenia such as zyprexa, risperdal, seroquel, and haloperidol; an anti-inflammatory agent such as a corticosteroid, such as dexamethasone or prednisone, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor such as an acetylcholinesterase inhibitor, an MAO inhibitor, an interferon, an anti-convulsant, an ion channel blocker, riluzole, or an anti-Parkinson's agent; an agent for treating cardiovascular disease such as a beta-blocker, an ACE inhibitor, a diuretic, a nitrate, a calcium channel blocker, or a statin; an agent for treating liver disease such as a corticosteroid, cholestyramine, an interferon, and an anti-viral agent; an agent for treating blood disorders such as a corticosteroid, an anti-leukemic agent, or a growth factor; or an agent for treating immunodeficiency disorders such as gamma globulin.

Formulation, Dosage Forms and Administration

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1,000 mg (1 g), more usually about 100 mg to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed hereinabove.

Labeled Compounds and Assay Methods

Another aspect of the present invention relates to labeled compounds of the invention (radio-labeled, fluorescent-labeled, etc.) that would be useful not only in imaging techniques but also in assays, both in vitro and in vivo, for localizing and quantitating LSD1 in tissue samples, including human, and for identifying LSD1 ligands by inhibition binding of a labeled compound. Accordingly, the present invention includes LSD1 assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound.

It is to be understood that a "radio-labeled" or "labeled compound" is a compound that has incorporated at least one radionuclide. In some embodiments the radionuclide is selected from the group consisting of $^3$H, $^{14}$C, $^{125}$I, $^{35}$S and $^{82}$Br. In some embodiments, the compound incorporates 1, 2, or 3 deuterium atoms.

The present invention can further include synthetic methods for incorporating radio-isotopes into compounds of the invention. Synthetic methods for incorporating radio-isotopes into organic compounds are well known in the art, and an ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind LSD1 by monitoring its concentration variation when contacting with LSD1, through tracking of the labeling. For example, a test compound (labeled) can be evaluated for its ability to reduce binding of another compound which is known to bind to LSD1 (i.e., standard compound). Accordingly, the ability of a test compound to compete with the standard compound for binding to LSD1 directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples were found to be inhibitors of LSD1 as described below.

EXAMPLES

Experimental procedures for compounds of the invention are provided below. Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Haque, A. Combs, *J. Combi. Chem.*, 5, 670 (2003); and "Preparative LC-MS Purification: Improved Compound Specific Method Optimization", K. Blom, B. Glass, R. Sparks, A. Combs, *J. Combi. Chem.*, 6, 874-883 (2004). The compounds separated were typically subjected to analytical liquid chromatography mass spectrometry (LCMS) for purity check under the following conditions: Instrument; Agilent 1100 series, LC/MSD, Column: Waters Sunfire™ $C_{18}$ 5 μm particle size, 2.1×5.0 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 μm particle size, 19×100 mm column, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with the 30×100 mm column was 60 mL/minute.

pH=10 purifications: Waters XBridge $C_{18}$ 5 μm particle size, 19×100 mm column, eluting with mobile phase A: 0.15% $NH_4OH$ in water and mobile phase B: acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with 30×100 mm column was 60 mL/minute.

Example 1

4-{5-(4-methylphenyl)-8-[(3R)-pyrrolidin-3-yl-methoxy]imidazo[1,2-a]pyrazin-6-yl}benzonitrile

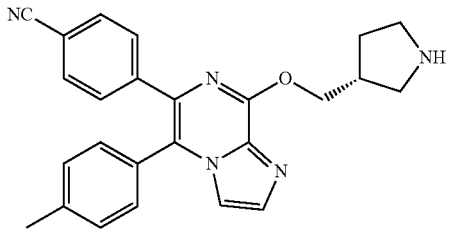 [SMILES: Cc1ccc(-c2c(-c3ccc(C#N)cc3)nc(OC[C@@H]3CCNC3)c3nccn23)cc1]

Step 1:
4-(5-amino-3-chloropyrazin-2-yl)benzonitrile

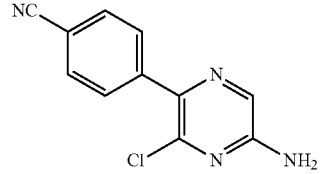 [SMILES: N#Cc1ccc(-c2ncc(N)nc2Cl)cc1]

A reaction vessel containing a mixture of 5-bromo-6-chloropyrazin-2-amine (1.04 g, 5.00 mmol), (4-cyanophenyl)boronic acid (0.882 g, 6.00 mmol), dichloro(bis{di-tert-butyl[4-(dimethylamino)phenyl]phosphoranyl})palladium (110 mg, 0.15 mmol), and sodium carbonate (1.06 g, 10.0 mmol) in 1,4-dioxane (12.0 mL) and water (2.0 mL) was evacuated then filled with nitrogen. The resulting mixture was stirred at 90° C. for 4 h then cooled to room temperature. The mixture was diluted with methylene chloride (15 mL) and water (5 mL). The precipitate was collected by filtration and washed with methyl t-butyl ether then dried to afford the desired product (1.05 g, 91%). LC-MS calculated for $C_{11}H_8ClN_4$ (M+H)$^+$: m/z=231.0. found 231.1.

Step 2: 4-[5-amino-3-(4-methylphenyl)pyrazin-2-yl]benzonitrile

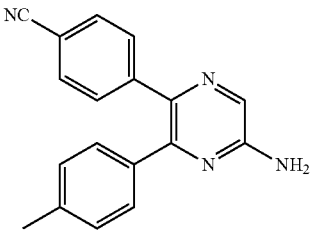 [SMILES: Cc1ccc(-c2nc(N)cnc2-c2ccc(C#N)cc2)cc1]

A reaction vessel containing a mixture of 4-(5-amino-3-chloropyrazin-2-yl)benzonitrile (1.15 g, 5.00 mmol), (4-methylphenyl)boronic acid (0.86 g, 6.4 mmol), sodium carbonate (1.06 g, 10.0 mmol) and [1,1'-bis(diphenylphosphino)ferrocene]dichloropalladium(II) complexed with dichloromethane (1:1) (0.20 g, 0.25 mmol) in 1,4-dioxane (20.0 mL) and water (4.0 mL) was evacuated then refilled with nitrogen. The resulting mixture was stirred at 110° C. for 3 h then cooled to room temperature. The mixture was diluted with methylene chloride, washed with saturated NaHCO₃ aqueous solution, water and brine. The organic layer was dried over Na₂SO₄, filtered and concentrated under reduced pressure. The residue was treated with DCM/diethyl-ether (1:1). The precipitate was collected by filtration to afford the desired product (0.61 g). The filtrate was concentrated and the residue was purified by flash chromatography on a silica gel column eluting with 0 to 100% EtOAc/DCM to afford another batch of the product (0.60 g). LC-MS calculated for $C_{18}H_{15}N_4$ (M+H)⁺: m/z=287.1. found 287.1.

Step 3: 4-[5-amino-6-bromo-3-(4-methylphenyl)pyrazin-2-yl]benzonitrile

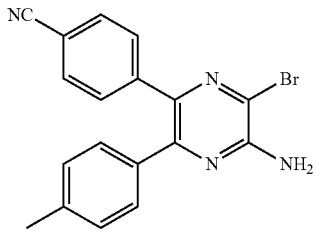 [SMILES: Cc1ccc(-c2nc(N)c(Br)nc2-c2ccc(C#N)cc2)cc1]

To a solution of 4-[5-amino-3-(4-methylphenyl)pyrazin-2-yl]benzonitrile (2.40 g, 8.38 mmol) in tetrahydrofuran (36 mL) at 0° C. was added N-bromosuccinimide (1.64 g, 9.22 mmol). The resulting mixture was stirred at 0° C. for 1 h then warmed to room temperature. The mixture was diluted with methylene chloride, washed with saturated NaHCO₃ aqueous solution, water, and brine. The organic layer was dried over Na₂SO₄, filtered and concentrated. The residue was purified on a silica gel column eluting with 0 to 60% EtOAc/DCM to give the desired product (2.8 g, 92%). LC-MS calculated for $C_{18}H_{14}BrN_4$ (M+H)⁺: m/z=365.0. found 365.0.

Step 4: tert-butyl (3R)-3-({[3-amino-6-(4-cyanophenyl)-5-(4-methylphenyl)pyrazin-2-yl]oxy}methyl)pyrrolidine-1-carboxylate

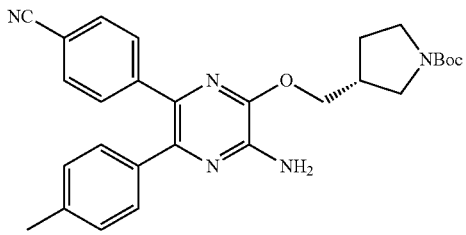 [SMILES: Cc1ccc(-c2nc(N)c(OC[C@@H]3CCN(C(=O)OC(C)(C)C)C3)nc2-c2ccc(C#N)cc2)cc1]

To a solution of tert-butyl (3R)-3-(hydroxymethyl)pyrrolidine-1-carboxylate (2.06 g, 10.2 mmol) in tetrahydrofuran (25 mL) at room temperature was added NaH (60 wt. % in mineral oil, 413 mg, 17.2 mmol). The resulting mixture was stirred at room temperature for 30 min then 4-[5-amino-6-bromo-3-(4-methylphenyl)pyrazin-2-yl]benzonitrile (1.50 g, 4.10 mmol) was added. The reaction mixture was stirred at 85° C. for 15 h then cooled to room temperature. The mixture was quenched with saturated NaHCO₃ aqueous solution and extracted with EtOAc. The combined organic layers were dried over Na₂SO₄, and concentrated. The residue was purified on a silica gel column eluting with 10 to 40% EtOAc/DCM to give the product as a yellow solid. LC-MS calculated for $C_{24}H_{24}N_5O_3$ (M-tBu+2H)⁺: m/z=430.2. found 430.1.

Step 5: 4-{5-(4-methylphenyl)-8-[(3R)-pyrrolidin-3-ylmethoxy]imidazo[1,2-a]pyrazin-6-yl}benzonitrile A mixture of tert-butyl (3R)-3-({[3-amino-6-(4-cyanophenyl)-5-(4-methylphenyl)pyrazin-2-yl]oxy}methyl)pyrrolidine-1-carboxylate (87.5 g, 0.180 mmol) and chloroacetaldehyde (50 wt. % in water, 1.0 mL, 7.5 mmol) in isopropyl alcohol (3.0 mL) was heated to 105° C. and stirred for 1.5 h. The reaction mixture was cooled to room temperature then purified by prep HPLC (pH=2, acetonitrile/water+TFA) to give the desired product as the TFA salt. LC-MS calculated for $C_{25}H_{24}N_5O$ (M+H)⁺: m/z=410.2. found 410.2. ¹H NMR (500 MHz, CD₃OD) δ 7.76 (br, 1H), 7.62-7.54 (m, 5H), 7.37 (d, J=8.0 Hz, 2H), 7.31 (d, J=8.0 Hz, 2H), 4.76-4.68 (m, 2H), 3.64-3.52 (m, 2H), 3.46-3.33 (m, 2H), 3.12-3.02 (m, 1H), 2.44 (s, 3H), 2.41-2.33 (m, 1H), 2.16-2.06 (m, 1H).

Example 2

4-[5-(4-methylphenyl)-8-(2-pyrrolidin-3-ylethyl)imidazo[1,2-a]pyrazin-6-yl]benzonitrile

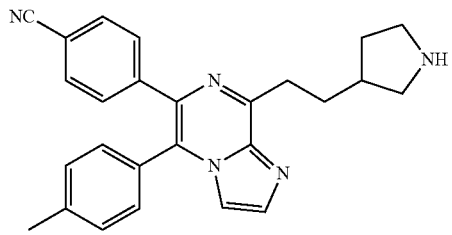 [SMILES: Cc1ccc(-c2c(-c3ccc(C#N)cc3)nc(CCC3CCNC3)c3nccn23)cc1]

Step 1: 4-[8-chloro-5-(4-methylphenyl)imidazo[1,2-a]pyrazin-6-yl]benzonitrile

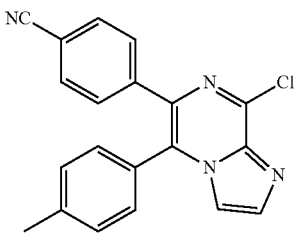 [SMILES: Cc1ccc(-c2c(-c3ccc(C#N)cc3)nc(Cl)c3nccn23)cc1]

A mixture of 4-[5-amino-6-bromo-3-(4-methylphenyl)pyrazin-2-yl]benzonitrile (Example 1, step 3, 2.80 g, 7.67 mmol) and chloroacetaldehyde (50 wt. % in water, 12 mL, 90. mmol) in isopropyl alcohol (40 mL) was heated to 105° C. and stirred for 1.5 h. The reaction mixture was cooled to room temperature then concentrated. The residue was dissolved in ethyl acetate, washed with saturated NaHCO₃ aqueous solution, water and brine. The organic layer was dried over Na₂SO₄, filtered and concentrated under reduced pressure. The residue was purified by flash chromatography on a silica gel column eluting with 0 to 70% EtOAc/Hexanes to afford the desired product (2.4 g, 91%). LC-MS calculated for $C_{20}H_{14}ClN_4$ (M+H)$^+$: m/z=345.1. found 345.0.

Step 2: tert-butyl 3-ethynylpyrrolidine-1-carboxylate

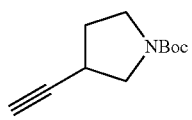

To a solution of tert-butyl 3-formylpyrrolidine-1-carboxylate (580 mg, 2.91 mmol) in methanol (15 mL) at room temperature was added potassium carbonate (1.00 g, 7.28 mmol) and dimethyl (1-diazo-2-oxopropyl)phosphonate (839 mg, 4.37 mmol). The resulting mixture was stirred at room temperature for 3 h then passed through a short pad of celite and concentrated. The residue was purified on a silica gel column eluting with 0 to 50% EtOAc/Hexanes to give the product as a colorless oil which solidified upon standing in fridge to give a white solid (374 mg, 66%).

Step 3: tert-butyl 3-{[6-(4-cyanophenyl)-5-(4-methylphenyl)imidazo[1,2-a]pyrazin-8-yl]ethynyl}pyrrolidine-1-carboxylate

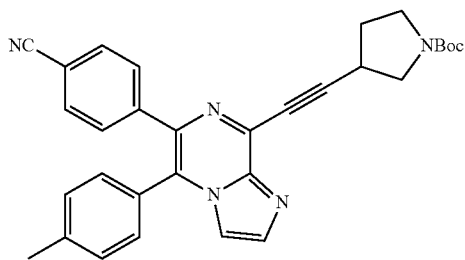 [SMILES: Cc1ccc(-c2c(-c3ccc(C#N)cc3)nc(C#CC3CCN(C(=O)OC(C)(C)C)C3)c3nccn23)cc1]

A reaction vessel containing a mixture of 4-[8-chloro-5-(4-methylphenyl)imidazo[1,2-a]pyrazin-6-yl]benzonitrile (30.0 g, 0.0870 mmol), tert-butyl 3-ethynylpyrrolidine-1-carboxylate (34 mg, 0.17 mmol), copper(I) iodide (5 mg, 0.03 mmol) and dichloro[bis(triphenylphosphoranyl)]palladium (3 mg, 0.004 mmol) in triethylamine (0.5 mL, 4 mmol) was evacuated then refilled with nitrogen. The resulting mixture was stirred at 95° C. overnight. The mixture was then cooled to room temperature, diluted with $CH_2Cl_2$, filtered and concentrated. The residue was purified on a silica gel column eluting with 0 to 20% EtOAc/DCM to give the desired product (35 mg, 81%). LC-MS calculated for $C_{31}H_{30}N_5O_2$ (M+H)$^+$: m/z=504.2. found 504.2.

Step 4: 4-[5-(4-methylphenyl)-8-(2-pyrrolidin-3-ylethyl)imidazo[1,2-a]pyrazin-6-yl]benzonitrile A mixture of tert-butyl 3-{[6-(4-cyanophenyl)-5-(4-methylphenyl)imidazo[1,2-a]pyrazin-8-yl]ethynyl}pyrrolidine-1-carboxylate (29 mg, 0.057 mmol) and Pd (10 wt % on carbon, 20 mg) in methanol (2.0 mL) and ethyl acetate (2.0 mL) was stirred under a balloon of hydrogen for 6 h at room temperature. The reaction mixture was filtered and the filtrate was concentrated. The residue was dissolved in $CH_2Cl_2$ (1 mL) and then TFA (0.5 mL) was added. The resulting mixture was stirred at room temperature for 30 min then concentrated. The residue was purified by prep-HPLC (pH=2, acetonitrile/water+TFA) to give the desired product as the TFA salt. LC-MS calculated for $C_{26}H_{26}N_5$ (M+H)$^+$: m/z=408.2. found 408.2.

Example 3

4-(5-(4-methylphenyl)-8-{[(3R)-pyrrolidin-3-yloxy]methyl}imidazo[1,2-a]pyrazin-6-yl)benzonitrile

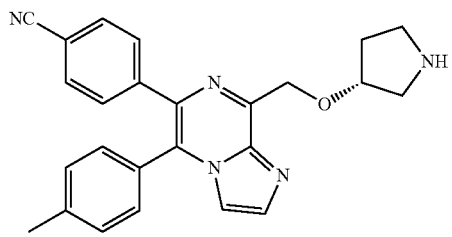 [SMILES: Cc1ccc(-c2c(-c3ccc(C#N)cc3)nc(CO[C@@H]3CCNC3)c3nccn23)cc1]

Step 1: 4-[5-(4-methylphenyl)-8-vinylimidazo[1,2-a]pyrazin-6-yl]benzonitrile

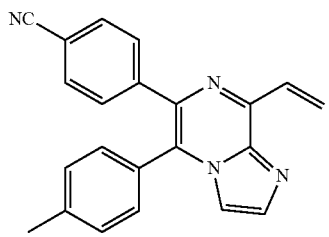 [SMILES: C=Cc1nc(-c2ccc(C#N)cc2)c(-c2ccc(C)cc2)n2ccnc12]

A mixture of 4-[8-chloro-5-(4-methylphenyl)imidazo[1,2-a]pyrazin-6-yl]benzonitrile (Example 2, Step 1, 120 mg, 0.35 mmol), 4,4,5,5-tetramethyl-2-vinyl-1,3,2-dioxaborolane (86 mg, 0.56 mmol), sodium carbonate (74 mg, 0.70 mmol) and [1,1'-bis(diphenylphosphino)ferrocene]dichloropalladium(II) complexed with dichloromethane (1:1) (28 mg, 0.035 mmol) in 1,4-dioxane (3 mL)/water (0.3 mL) was evacuated then refilled with nitrogen. The resulting mixture was heated to 110° C. and stirred for 3 h. The mixture was cooled to room temperature then diluted with methylene chloride, washed with saturated $NaHCO_3$, water and brine. The organic layer was dried over $Na_2SO_4$, filtered and concentrated. The residue was purified on a silica gel column eluting with 0 to 40% EtOAc/Hexanes to give the desired product. LC-MS calculated for $C_{22}H_{17}N_4$ (M+H)$^+$: m/z=337.1. found 337.1.

Step 2: 4-[8-formyl-5-(4-methylphenyl)imidazo[1,2-a]pyrazin-6-yl]benzonitrile

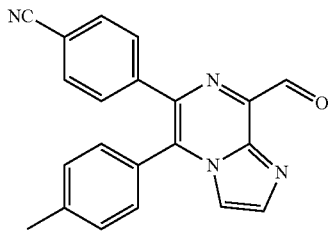 [SMILES: Cc1ccc(-c2c(-c3ccc(C#N)cc3)nc(C=O)c3nccn23)cc1]

To a mixture of 4-[5-(4-methylphenyl)-8-vinylimidazo[1,2-a]pyrazin-6-yl]benzonitrile (80.0 g, 0.238 mmol) and sodium periodate (240 mg, 1.1 mmol) in tetrahydrofuran (3.0 mL) and water (0.3 mL) was added osmium tetraoxide (4 wt. % in water, 0.44 mL, 0.071 mmol). The resulting mixture was heated to 70° C. and stirred for 2 h. The mixture was cooled to room temperature then diluted with methylene chloride, washed with saturated NaHCO$_3$ aqueous solution, water and brine. The organic layer was dried over Na$_2$SO$_4$, filtered and concentrated. The residue was purified on a silica gel column eluting with 0 to 10% EtOAc/DCM to give the desired product. LC-MS calculated for $C_{21}H_{15}N_4O$ (M+H)$^+$: m/z=339.1. found 339.1.

Step 3: 4-[8-(hydroxymethyl)-5-(4-methylphenyl)imidazo[1,2-a]pyrazin-6-yl]benzonitrile

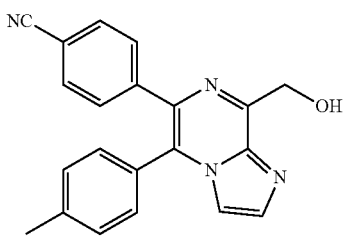 [SMILES: Cc1ccc(-c2c(-c3ccc(C#N)cc3)nc(CO)c3nccn23)cc1]

To a solution of 4-[8-formyl-5-(4-methylphenyl)imidazo[1,2-a]pyrazin-6-yl]benzonitrile (0.080 g, 0.24 mmol) in methanol (2 mL) at 0° C. was added sodium tetrahydroborate (18 mg, 0.47 mmol). The resulting mixture was warmed to room temperature and stirred for 30 min. The mixture was then diluted with methylene chloride, washed with saturated NaHCO$_3$ aqueous solution, water and brine. The organic layer dried over Na$_2$SO$_4$, filtered and concentrated. The residue was used in the next step without further purification. LC-MS calculated for $C_{21}H_{17}N_4O$ (M+H)$^+$: m/z=341.1. found 341.1.

Step 4: [6-(4-cyanophenyl)-5-(4-methylphenyl)imidazo[1,2-a]pyrazin-8-yl]methyl methanesulfonate

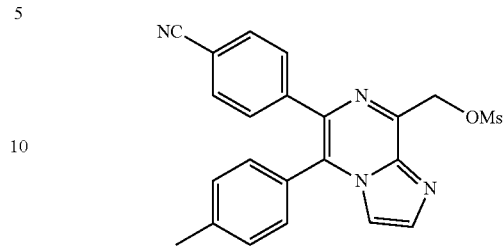

To a solution of 4-[8-(hydroxymethyl)-5-(4-methylphenyl)imidazo[1,2-a]pyrazin-6-yl]benzonitrile (80.0 g, 0.235 mmol) and N,N-diisopropylethylamine (0.091 g, 0.70 mmol) in methylene chloride (1.0 mL) at 0° C. was added methanesulfonyl chloride (0.040 g, 0.35 mmol). The resulting mixture was stirred at 0° C. for 1 h then diluted with methylene chloride, washed with saturated NaHCO$_3$ aqueous solution, water and brine. The organic layer was dried over Na$_2$SO$_4$, filtered and concentrated. The residue was used in the next step without further purification. LC-MS calculated for $C_{22}H_{19}N_4O_3S$ (M+H)$^+$: m/z=419.1. found 419.0.

Step 5: 4-(5-(4-methylphenyl)-8-{[(3R)-pyrrolidin-3-yloxy]methyl}imidazo[1,2-a]pyrazin-6-yl)benzonitrile To a solution of tert-butyl (3R)-3-hydroxypyrrolidine-1-carboxylate (27 mg, 0.14 mmol) in tetrahydrofuran (0.5 mL) was added sodium hydride (3.4 g, 0.14 mmol). The resulting mixture was stirred at room temperature for 1 h then a solution of [6-(4-cyanophenyl)-5-(4-methylphenyl)imidazo[1,2-a]pyrazin-8-yl]methyl methanesulfonate (10.0 g, 0.0239 mmol) in tetrahydrofuran (0.5 mL) was added. The mixture was then stirred at 50° C. overnight. The mixture was cooled to room temperature, diluted with methylene chloride, washed with water and brine. The organic layer was dried over Na$_2$SO$_4$, filtered and concentrated. The residue was dissolved in CH$_2$Cl$_2$ (0.5 mL) then HCl (4N in 1,4-dioxane, 0.8 mL) was added. The mixture was stirred at room temperature for 30 min then concentrated. The residue was dissolved in MeOH and purified by prep-HPLC (pH=2, acetonitrile/water+TFA) to give the desired product as the TFA salt. LC-MS calculated for $C_{25}H_{24}N_5O$ (M+H)$^+$: m/z=410.2. found 410.2.

Example 4

4-[8-{[(3S)-3-(dimethylamino)pyrrolidin-yl]methyl}-5-(4-methylphenyl)imidazo[1,2-a]pyrazin-6-yl]benzonitrile

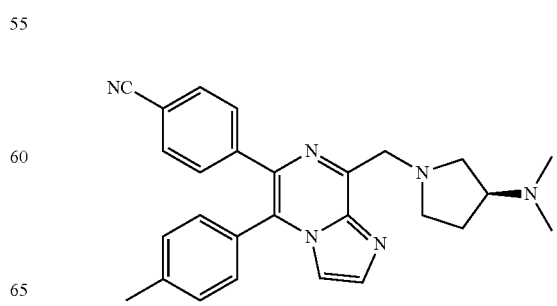

To a solution of 4-[8-formyl-5-(4-methylphenyl)imidazo[1,2-a]pyrazin-6-yl]benzonitrile (Example 3, Step 2: 10 mg, 0.03 mmol) and (3S)—N,N-dimethylpyrrolidin-3-amine (10 mg, 0.09 mmol) in methylene chloride (1 mL) was added acetic acid (10 μL). The resulting mixture was stirred at room temperature for 1 h then sodium triacetoxyborohydride (20 mg, 0.09 mmol) was added. The mixture was stirred at room temperature overnight then diluted with methylene chloride, washed with saturated NaHCO$_3$ solution, water and brine. The organic layer was dried over Na$_2$SO$_4$ and concentrated. The residue was dissolved in acetonitrile then purified by prep-HPLC (pH=2, acetonitrile/water+TFA) to give the desired product as the TFA salt. LC-MS calculated for C$_{27}$H$_{29}$N$_6$ (M+H)$^+$: m/z=437.2. found 437.3.

Example 5

4-[8-{[(3R)-3-(dimethylamino)pyrrolidin-1-yl]methyl}-5-(4-methylphenyl)imidazo[1,2-a]pyrazin-6-yl]benzonitrile

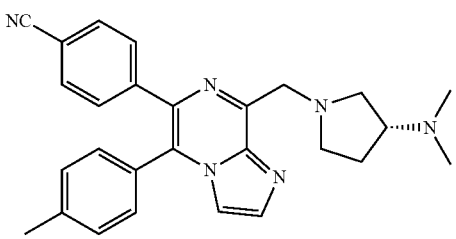

This compound was prepared using procedures analogous to those for Example 4 with (3R)—N,N-dimethylpyrrolidin-3-amine replacing (3S)—N,N-dimethylpyrrolidin-3-amine. The product was purified by prep-HPLC (pH=2, acetonitrile/water+TFA) to give the compound as the TFA salt. LC-MS calculated for C$_{27}$H$_{29}$N$_6$ (M+H)$^+$: m/z=437.2. found 437.2.

Example 6

4-[8-{2-[(3R)-3-(dimethylamino)pyrrolidin-1-yl]ethyl}-5-(4-methylphenyl)imidazo[1,2-a]pyrazin-6-yl]benzonitrile

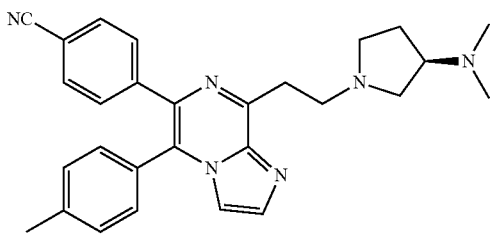

To a mixture of 4-[5-(4-methylphenyl)-8-vinylimidazo[1,2-a]pyrazin-6-yl]benzonitrile (Example 3, Step 1: 8.0 mg, 0.024 mmol) and (3R)—N,N-dimethylpyrrolidin-3-amine (4.1 mg, 0.036 mmol) in acetonitrile (0.5 mL) was added 1,8-diazabicyclo[5.4.0]undec-7-ene (5.3 μL, 0.036 mmol). The resulting mixture was heated to 65° C. and stirred overnight. The mixture was then cooled to room temperature and purified by prep-HPLC (pH=2, acetonitrile/water+TFA) to give the desired product as the TFA salt. LC-MS calculated for C$_{28}$H$_{31}$N$_6$ (M+H)$^+$: m/z=451.3. found 451.3.

Example 7

4-{5-(4-methylphenyl)-8-[(1-methylpyrrolidin-3-yl)oxy]imidazo[1,2-a]pyrazin-6-yl}benzonitrile

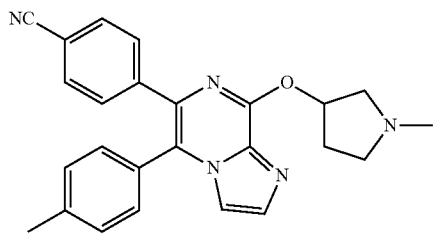

To a solution of 1-methyl-3-pyrrolidinol (12. mg, 0.12 mmol) in DMF (0.5 mL) was added sodium hydride (60 wt. % in mineral oil, 9.6 g, 0.24 mmol). The mixture was stirred at room temperature for 20 min then a solution of 4-[8-chloro-5-(4-methylphenyl)imidazo[1,2-a]pyrazin-6-yl]benzonitrile (Example 2, Step 1: 20.7 mg, 0.060 mmol) in DMF (0.5 mL) was added. The reaction mixture was heated to 80° C. and stirred for 1 h. The mixture was cooled to room temperature then diluted with methanol and purified by prep-HPLC (pH=10, acetonitrile/water+NH$_4$OH) to afford the desired product. LC-MS calculated for C$_{25}$H$_{24}$N$_5$O (M+H)$^+$: m/z=410.2. found 410.2.

Example 8

4-[8-[3-(dimethylamino)propoxy]-5-(4-methylphenyl)imidazo[1,2-a]pyrazin-6-yl]benzonitrile

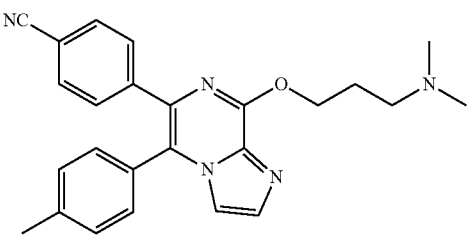

This compound was prepared using procedures analogous to those for Example 7 with 3-(dimethylamino)-1-propanol replacing 1-methyl-3-pyrrolidinol. The product was purified by prep-HPLC (pH=10, acetonitrile/water+NH$_4$OH) to afford the desired compound. LC-MS calculated for C$_{25}$H$_{26}$N$_5$O (M+H)$^+$: m/z=412.2. found 412.2.

Example 9

4-{5-(4-methylphenyl)-8-[(3R)-piperidin-3-yl-methoxy]imidazo[1,2-a]pyrazin-6-yl}benzonitrile

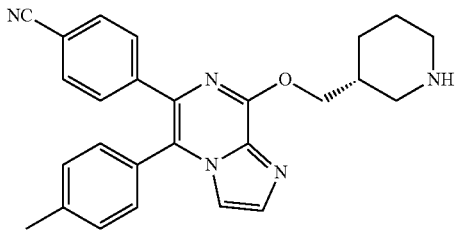 [SMILES: Cc1ccc(-c2c(-c3ccc(C#N)cc3)nc(OC[C@@H]3CCCNC3)c3nccn23)cc1]

Step 1: tert-butyl (3R)-3-({[6-(4-cyanophenyl)-5-(4-methylphenyl)imidazo[1,2-a]pyrazin-8-yl]oxy}methyl)piperidine-1-carboxylate

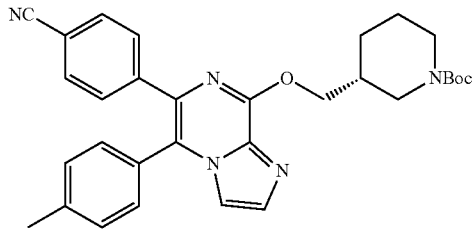

This compound was prepared using procedures analogous to those for Example 7 with tert-butyl (3R)-3-(hydroxymethyl)piperidine-1-carboxylate replacing 1-methyl-3-pyrrolidinol. The product was purified by prep-HPLC (pH=10, acetonitrile/water+NH$_4$OH) to afford the desired compound. LC-MS calculated for $C_{31}H_{34}N_5O_3$ (M+H)$^+$: m/z=524.3. found 524.2.

Step 2: 4-{5-(4-methylphenyl)-8-[(3R)-piperidin-3-ylmethoxy]imidazo[1,2-a]pyrazin-6-yl}benzonitrile The product from Step 1 was dissolved in TFA/DCM (0.5 mL, 1:1) and stirred at room temperature for 1 h. The reaction mixture was concentrated and the residue was dissolved in methanol then purified by prep-HPLC (pH=2, acetonitrile/water+TFA) to afford the desired product as the TFA salt. LC-MS calculated for $C_{26}H_{26}N_5O$ (M+H)$^+$: m/z=424.2. found 424.2.

Example 10

4-{5-(4-methylphenyl)-8-[(3S)-piperidin-3-yl-methoxy]imidazo[1,2-a]pyrazin-6-yl}benzonitrile

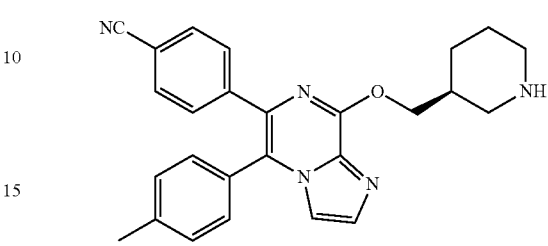

This compound was prepared using procedures analogous to those for Example 9 with tert-butyl (3S)-3-(hydroxymethyl)piperidine-1-carboxylate replacing tert-butyl (3R)-3-(hydroxymethyl)piperidine-1-carboxylate in Step 1. The product was purified by prep-HPLC (pH=2, acetonitrile/water+TFA) to afford the desired product as the TFA salt. LC-MS calculated for $C_{26}H_{26}N_5O$ (M+H)$^+$: m/z=424.2. found 424.2.

Example 11

4-(5-(4-methylphenyl)-8-{[(3R)-1-methylpyrrolidin-3-yl]methoxy}imidazo[1,2-a]pyrazin-6-yl)benzonitrile To a solution of 4-{5-(4-methylphenyl)-8-[(3R)-pyrrolidin-3-ylmethoxy]imidazo[1,2-a]pyrazin-6-yl}benzonitrile (Example 1: 40.0 mg, 0.0977 mmol) in methylene chloride (3 mL) was added formaldehyde (37 wt. % in water, 73 μL, 0.98 mmol), followed by acetic acid (33 μL, 0.59 mmol). The resulting mixture was stirred at room temperature for 3 h then sodium triacetoxyborohydride (120 mg, 0.59 mmol) was added. The reaction mixture was stirred at room temperature for 2 h then diluted with DCM and washed with saturated NaHCO$_3$ solution, water and brine. The organic layer was dried over Na$_2$SO$_4$ and concentrated. The residue was purified by prep-HPLC (pH=2, acetonitrile/water+TFA) to give the desired product as the TFA salt. LC-MS calculated for $C_{26}H_{26}N_5O$ (M+H)$^+$: m/z=424.2. found 424.2.

Example 12

4-(5-(4-methylphenyl)-8-{[(3R)-1-methylpiperidin-3-yl]methoxy}imidazo[1,2-a]pyrazin-6-yl)benzonitrile

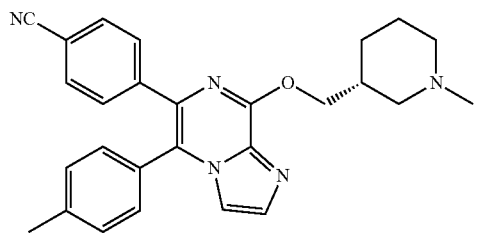

This compound was prepared using procedures analogous to those for Example 11 with 4-{5-(4-methylphenyl)-8-[(3R)-piperidin-3-ylmethoxy]imidazo[1,2-a]pyrazin-6-yl}benzonitrile replacing 4-{5-(4-methylphenyl)-8-[(3R)-pyrrolidin-3-ylmethoxy]imidazo[1,2-a]pyrazin-6-yl}benzonitrile. The product was purified by prep HPLC (pH=2, acetonitrile/water+TFA) to give the compound as the TFA salt. LC-MS calculated for $C_{27}H_{28}N_5O$ $(M+H)^+$: m/z=438.2. found 438.2.

Example 13

4-(5-(4-methylphenyl)-8-{[(3R)-pyrrolidin-3-ylmethyl]thio}imidazo[1,2-a]pyrazin-6-yl)benzonitrile

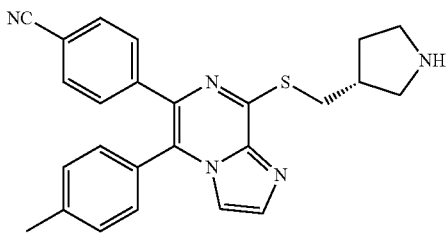

This compound was prepared using procedures analogous to those for Example 9 with tert-butyl (3R)-3-(mercaptomethyl)pyrrolidine-1-carboxylate replacing tert-butyl (3R)-3-(hydroxymethyl)piperidine-1-carboxylate in Step 1. The product was purified by prep-HPLC (pH=2, acetonitrile/water+TFA) to afford the desired product as the TFA salt. LC-MS calculated for $C_{25}H_{24}N_5S$ $(M+H)^+$: m/z=426.2. found 426.2.

Example 14

4-[8-[4-(dimethylamino)piperidin-1-yl]-5-(4-methylphenyl)imidazo[1,2-a]pyrazin-6-yl]benzonitrile

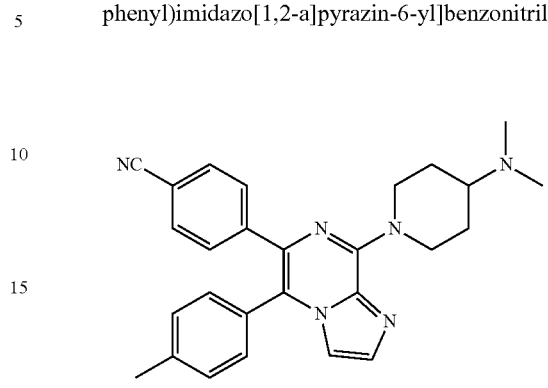

A mixture of 4-[8-chloro-5-(4-methylphenyl)imidazo[1,2-a]pyrazin-6-yl]benzonitrile (Example 2, Step 1: 20.7 mg, 0.060 mmol), N,N-dimethylpiperidin-4-amine (11.5 mg, 0.090 mmol), and N,N-diisopropylethylamine (20.9 μL, 0.12 mmol) in N-methyl-2-pyrrolidone (0.5 mL) was heated to 180° C. and stirred for 1 h. The mixture was then cooled to room temperature, diluted with methanol and purified by prep-HPLC (pH=10, acetonitrile/water+NH$_4$OH) to afford the desired product. LC-MS calculated for $C_{27}H_{29}N_6$ $(M+H)^+$: m/z=437.2. found 437.2.

Example 15

4-[8-[[3-(dimethylamino)propyl](methyl)amino]-5-(4-methylphenyl)imidazo[1,2-a]pyrazin-6-yl]benzonitrile

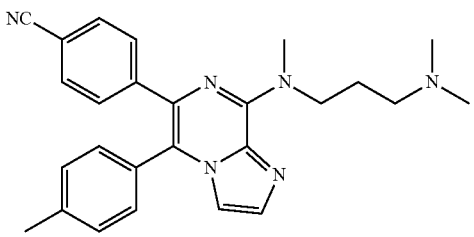

This compound was prepared using procedures analogous to those for Example 14 with N,N,N'-trimethylpropane-1,3-diamine replacing N,N-dimethylpiperidin-4-amine. The product was purified by prep-HPLC (pH=10, acetonitrile/water+NH$_4$OH) to afford the desired compound. LC-MS calculated for $C_{26}H_{29}N_6$ $(M+H)^+$: m/z=425.2. found 425.2.

Example 16

4-(5-(4-methylphenyl)-8-{[2-(1-methylpyrrolidin-2-yl)ethyl]amino}imidazo[1,2-a]pyrazin-6-yl)benzonitrile

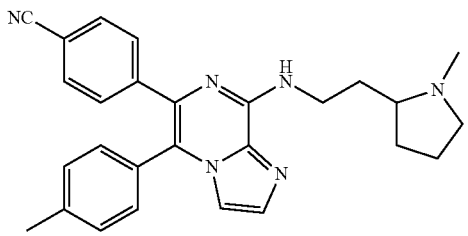 [SMILES: Cc1ccc(-c2c(-c3ccc(C#N)cc3)nc(NCCC3CCCN3C)c3nccn23)cc1]

This compound was prepared using procedures analogous to those for Example 14 with 2-(1-methylpyrrolidin-2-yl)ethanamine replacing N,N-dimethylpiperidin-4-amine. The product was purified by prep-HPLC (pH=10, acetonitrile/water+NH$_4$OH) to afford the desired compound. LC-MS calculated for $C_{27}H_{29}N_6$ (M+H)$^+$: m/z=437.2. found 437.2.

Example 17

4-{5-(4-methylphenyl)-8-[(1-methylpiperidin-4-yl)amino]imidazo[1,2-a]pyrazin-6-yl}benzonitrile

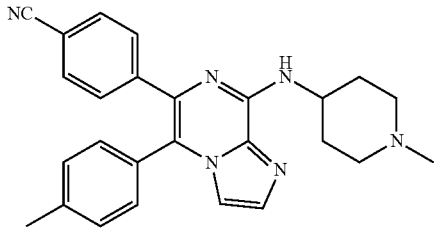

This compound was prepared using procedures analogous to those for Example 14 with 1-methylpiperidin-4-amine replacing N,N-dimethylpiperidin-4-amine. The product was purified by prep-HPLC (pH=10, acetonitrile/water+NH$_4$OH) to afford the desired compound. LC-MS calculated for $C_{26}H_{27}N_6$ (M+H)$^+$: m/z=423.2. found 423.2.

Example 18

4-[8-(4-methyl-1,4-diazepan-1-yl)-5-(4-methylphenyl)imidazo[1,2-a]pyrazin-6-yl]benzonitrile

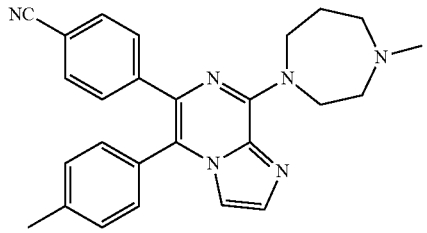

This compound was prepared using procedures analogous to those for Example 14 with 1-methyl-1,4-diazepane replacing N,N-dimethylpiperidin-4-amine. The product was purified by prep-HPLC (pH=10, acetonitrile/water+NH$_4$OH) to afford the desired compound. LC-MS calculated for $C_{26}H_{27}N_6$ (M+H)$^+$: m/z=423.2. found 423.2.

Example 19

4-[8-(2,7-diazaspiro[4.4]non-2-yl)-5-(4-methylphenyl)imidazo[1,2-a]pyrazin-6-yl]benzonitrile

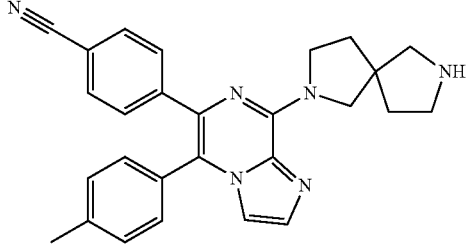 [SMILES: Cc1ccc(-c2c(-c3ccc(C#N)cc3)nc(N3CCC4(CCNC4)C3)c3nccn23)cc1]

This compound was prepared using procedures analogous to those for Example 14 with 2,7-diazaspiro[4.4]nonane replacing N,N-dimethylpiperidin-4-amine. The product was purified by prep-HPLC (pH=10, acetonitrile/water+NH$_4$OH) to afford the desired compound. LC-MS calculated for $C_{27}H_{27}N_6$ (M+H)$^+$: m/z=435.2. found 435.2.

Example 20

4-[8-(2,7-diazaspiro[3.5]non-7-yl)-5-(4-methylphenyl)imidazo[1,2-a]pyrazin-6-yl]benzonitrile

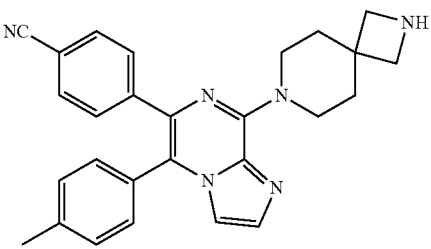 [SMILES: Cc1ccc(-c2c(-c3ccc(C#N)cc3)nc(N3CCC4(CC3)CNC4)c3nccn23)cc1]

This compound was prepared using procedures analogous to those for Example 14 with tert-butyl 2,7-diazaspiro[3.5]nonane-2-carboxylate replacing N,N-dimethylpiperidin-4-amine. The product was purified by prep-HPLC (pH=10, acetonitrile/water+NH$_4$OH) to afford the desired compound. LC-MS calculated for $C_{27}H_{27}N_6$ (M+H)$^+$: m/z=435.2. found 435.2.

Example 21

(3R)—N-[6-(4-cyanophenyl)-5-(4-methylphenyl)imidazo[1,2-a]pyrazin-8-yl]-3-(dimethylamino)-N-methylpyrrolidine-1-carboxamide

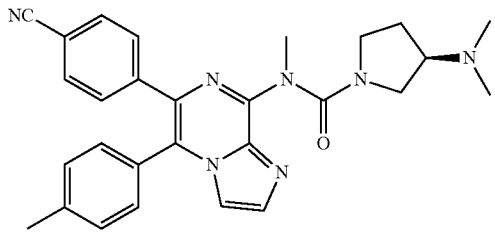

Step 1: 4-[8-(methylamino)-5-(4-methylphenyl)imidazo[1,2-a]pyrazin-6-yl]benzonitrile

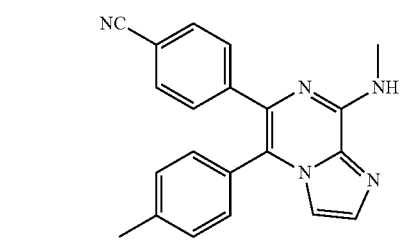

A mixture of 4-[8-chloro-5-(4-methylphenyl)imidazo[1,2-a]pyrazin-6-yl]benzonitrile (Example 2, Step 1, 40.0 mg, 0.116 mmol) and methylamine (8.0 M in methanol, 1.93 mL, 15.5 mmol) was stirred at 100° C. overnight. The mixture was then cooled to room temperature and concentrated. The residue was purified on a silica gel column eluting with 0 to 10% MeOH/DCM to afford the desired product (30 mg, 76%). LC-MS calculated for $C_{21}H_{18}N_5$ (M+H)$^+$: m/z=340.2. found 340.1.

Step 2: (3R)—N-[6-(4-cyanophenyl)-5-(4-methylphenyl)imidazo[1,2-a]pyrazin-8-yl]-3-(dimethylamino)-N-methylpyrrolidine-1-carboxamide To a solution of 4-[8-(methylamino)-5-(4-methylphenyl)imidazo[1,2-a]pyrazin-6-yl]benzonitrile (15.0 g, 0.0442 mmol) and N,N-diisopropylethylamine (30.0 μL, 0.172 mmol) in THF (1 mL) was added triphosgene (15.0 g, 0.0505 mmol). The mixture was stirred at room temperature for 1 h then the volatiles were removed under vacuum. The residue was dissolved in acetonitrile (1 mL) then (3R)—N,N-dimethylpyrrolidin-3-amine (8.4 μL, 0.066 mmol) and N,N-diisopropylethylamine (30 μL) were added. The mixture was stirred at room temperature overnight then purified by prep-HPLC (pH=10, acetonitrile/water+NH$_4$OH) to afford the desired product. LC-MS calculated for $C_{28}H_{30}N_7O$ (M+H)$^+$: m/z=480.3. found 480.2.

Example 22

(3S)—N-[6-(4-cyanophenyl)-5-(4-methylphenyl)imidazo[1,2-a]pyrazin-8-yl]-3-(dimethylamino)-N-methylpyrrolidine-1-carboxamide

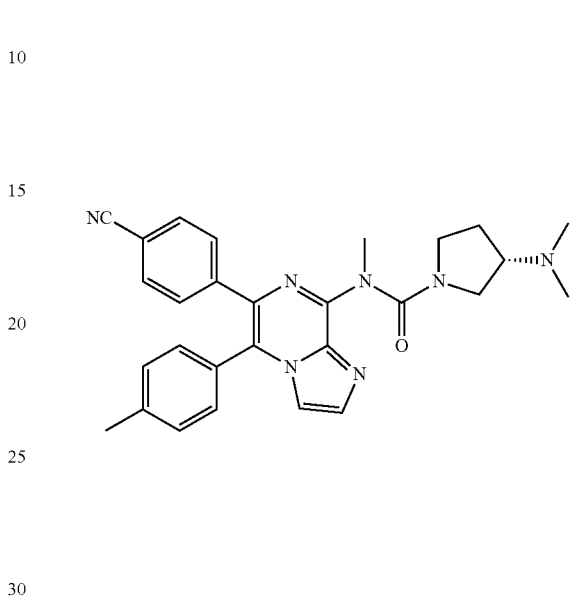

This compound was prepared using procedures analogous to those for Example 21 with (3S)—N,N-dimethylpyrrolidin-3-amine replacing (3R)—N,N-dimethylpyrrolidin-3-amine. The product was purified with prep-HPLC (pH=10, acetonitrile/water+NH$_4$OH) to afford the desired product. LC-MS calculated for $C_{28}H_{30}N_7O$ (M+H)$^+$: m/z=480.3. found 480.2.

Example 23

4-[8-{[2-(2-amino-1,3-thiazol-4-yl)ethyl]amino}-5-(4-methylphenyl)imidazo[1,2-a]pyrazin-6-yl]benzonitrile

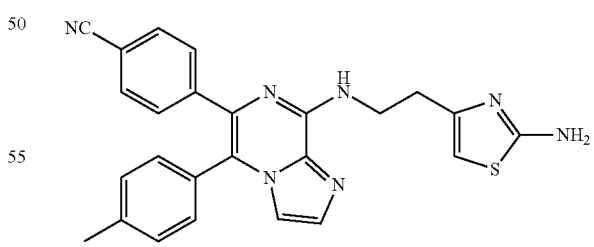

This compound was prepared using procedures analogous to those for Example 14 with 4-(2-aminoethyl)-1,3-thiazol-2-amine replacing N,N-dimethylpiperidin-4-amine. The product was purified by prep-HPLC (pH=2, acetonitrile/water+TFA) to afford the desired compound as the TFA salt. LC-MS calculated for $C_{25}H_{22}N_7S$ (M+H)$^+$: m/z=452.2. found 452.2.

Example 24

N-(azetidin-3-ylmethyl)-6-(4-cyanophenyl)-5-(4-methylphenyl)imidazo[1,2-a]pyrazine-8-carboxamide

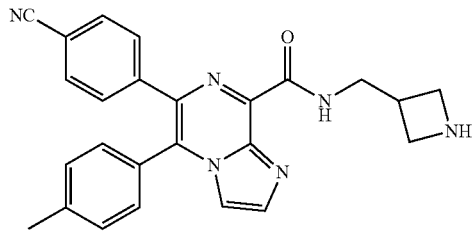 [SMILES: Cc1ccc(-c2c(-c3ccc(C#N)cc3)nc(C(=O)NCC3CNC3)c3nccn23)cc1]

Step 1: methyl 3-amino-6-(4-cyanophenyl)-5-(4-methylphenyl)pyrazine-2-carboxylate

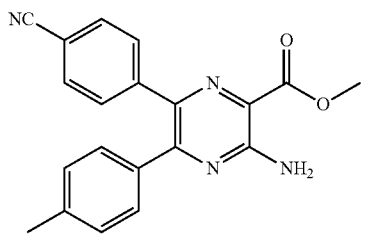

A mixture of methyl 3-amino-5,6-dichloropyrazine-2-carboxylate (1.00 g, 4.50 mmol), (4-methylphenyl)boronic acid (0.612 g, 4.50 mmol), sodium carbonate (0.955 g, 9.01 mmol) and [1,1'-bis(diphenylphosphino)ferrocene]dichloropalladium(II) complexed with dichloromethane (1:1) (0.18 g, 0.22 mmol) in 1,4-dioxane (18 mL) and water (2 mL) was evacuated then refilled with nitrogen. The resulting mixture was stirred at 90° C. for 2 h. The mixture was cooled to room temperature then (4-cyanophenyl)boronic acid (0.66 g, 4.50 mmol) was added, followed by another portion of [1,1'-bis(diphenylphosphino)ferrocene]dichloro-palladium(II) complexed with dichloromethane (1:1) (0.2 g, 0.2 mmol). The vessel containing the mixture was evacuated then refilled with nitrogen and stirred at 90° C. for additional 2 h. The reaction mixture was cooled to room temperature and diluted with methylene chloride, washed with water and brine. The organic layer was dried over $Na_2SO_4$, filtered and concentrated under reduced pressure. The residue was purified on a silica gel column eluting with 0 to 25% EtOAc/DCM to give the desired product (1.2 g, 77%). LC-MS calculated for $C_{20}H_{17}N_4O_2$ $(M+H)^+$: m/z=345.1. found 345.1.

Step 2: 6-(4-cyanophenyl)-5-(4-methylphenyl)imidazo[1,2-a]pyrazine-8-carboxylic acid

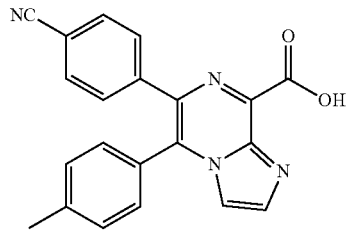 [SMILES: Cc1ccc(-c2c(-c3ccc(C#N)cc3)nc(C(=O)O)c3nccn23)cc1]

To a mixture of methyl 3-amino-6-(4-cyanophenyl)-5-(4-methylphenyl)pyrazine-2-carboxylate (0.410 g, 1.19 mmol) in isopropyl alcohol (5 mL) was added chloroacetaldehyde (50 wt. % in water, 1.9 mL, 14 mmol). The mixture was stirred at 105° C. for 1.5 h then cooled to room temperature and concentrated. The residue was dissolved in ethyl acetate, washed with saturated $NaHCO_3$ aqueous solution, water and brine. The organic layer was dried over $Na_2SO_4$, filtered and concentrated under reduced pressure. The residue was purified by flash chromatography on a silica gel column eluting with 0 to 70% EtOAc/Hexane to afford the desired intermediate (0.35 g). To a solution of the above intermediate in tetrahydrofuran (3 mL)/water (3 mL) was added lithium hydroxide, monohydrate (0.25 g, 5.95 mmol). The resulting mixture was stirred at room temperature overnight then acidified with 1N HCl and extracted with DCM/IPA (2:1). The combined extracts were dried over $Na_2SO_4$, filtered and concentrated under reduced pressure to afford the desired product (0.336 g, 80%), which was used in the next step without further purification. LC-MS calculated for $C_{21}H_{15}N_4O_2$ $(M+H)^+$: m/z=355.1. found 355.1.

Step 3: tert-butyl 3-[(([6-(4-cyanophenyl)-5-(4-methylphenyl)imidazo[1,2-a]pyrazin-8-yl]carbonyl}amino)methyl]azetidine-1-carboxylate

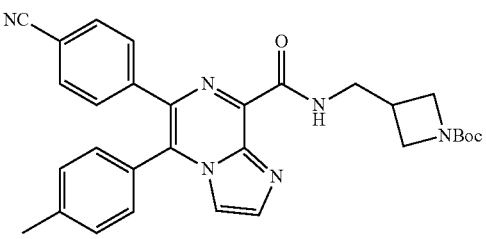 [SMILES: Cc1ccc(-c2c(-c3ccc(C#N)cc3)nc(C(=O)NCC3CN(C(=O)OC(C)(C)C)C3)c3nccn23)cc1]

To a solution of 6-(4-cyanophenyl)-5-(4-methylphenyl)imidazo[1,2-a]pyrazine-8-carboxylic acid (8.0 g, 0.022 mmol) and tert-butyl 3-(aminomethyl)azetidine-1-carboxylate (8.41 g, 0.0452 mmol) in N,N-dimethylformamide (0.5 mL) was added N,N-diisopropylethylamine (16 µL, 0.094 mmol), followed by N,N,N',N'-tetramethyl-O-(7-azabenzotriazol-1-yl)uronium hexafluorophosphate (8.6 g, 0.022 mmol). The resulting mixture was stirred at room temperature for 1 h then diluted with EtOAc and washed with water and brine. The organic layer was dried over $Na_2SO_4$ and concentrated. The residue was used in the next step without further purification. LC-MS calculated for $C_{30}H_{31}N_6O_3$ $(M+H)^+$: m/z=523.2. found 523.2.

Step 4: N-(azetidin-3-ylmethyl)-6-(4-cyanophenyl)-5-(4-methylphenyl)imidazo[1,2-a]pyrazine-8-carboxamide The crude product from Step 3 was dissolve in DCM (1 mL) then TFA (0.5 mL) was added. The resulting mixture was stirred at room temperature for 1 h then concentrated. The residue was dissolved in acetonitrile then purified by prep HPLC (pH=2, acetonitrile/water+TFA) to give the desired product as the TFA salt. LC-MS calculated for $C_{25}H_{23}N_6O$ (M+H)$^+$: m/z=423.2. found 423.2.

Example 25

6-(4-cyanophenyl)-N-(1-methylazetidin-3-yl)-5-(4-methylphenyl)imidazo[1,2-a]pyrazine-8-carboxamide

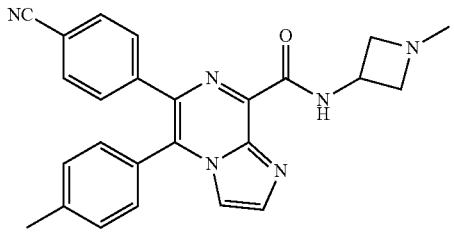

To a solution of 6-(4-cyanophenyl)-5-(4-methylphenyl)imidazo[1,2-a]pyrazine-8-carboxylic acid (Example 24, Step 2, 10.0 mg, 0.028 mmol) and 1-methylazetidin-3-amine (4.9 mg, 0.056 mmol) in N,N-dimethylformamide (0.5 mL) was added N,N-diisopropylethylamine (20 µL, 0.12 mmol), followed by N,N,N',N'-tetramethyl-O-(7-azabenzotriazol-1-yl)uronium hexafluorophosphate (11 mg, 0.028 mmol). The resulting mixture was stirred at room temperature for 1 h then purified by prep HPLC (pH=2, acetonitrile/water+TFA) to give the desired product as the TFA salt. LC-MS calculated for $C_{25}H_{23}N_6O$ (M+H)$^+$: m/z=423.2. found 423.2.

Example 26

4-{(5-phenyl)-8-[(3R)-pyrrolidin-3-ylmethoxy]imidazo[1,2-a]pyrazin-6-yl}benzonitrile

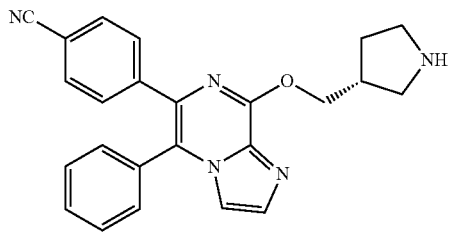 [SMILES: N#Cc1ccc(-c2nc(OC[C@@H]3CCNC3)c3nccn3c2-c2ccccc2)cc1]

Step 1: tert-butyl (3R)-3-{[(3-amino-6-bromo-5-chloropyrazin-2-yl)oxy]methyl}pyrrolidine-1-carboxylate

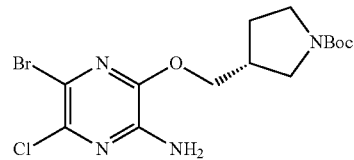

To a solution of 3,5-dibromo-6-chloropyrazin-2-amine (600.0 g, 2.088 mmol) in 1,4-dioxane (5 mL) was added sodium hydroxide (110 mg, 2.7 mmol), followed by tert-butyl (3R)-3-(hydroxymethyl)pyrrolidine-1-carboxylate (550 mg, 2.7 mmol). The resulting mixture was heated to 70° C. and stirred overnight. The reaction mixture was cooled to room temperature and concentrated. The residue was purified on a silica gel column eluting with 0 to 20% EtOAc/DCM to give the desired product (330 mg, 39%). LC-MS calculated for $C_{10}H_{13}BrClN_4O_3$ (M-$^t$Bu+2H)$^+$: m/z=351.0. found 351.0. $^1$H NMR (500 MHz, DMSO) δ 7.00 (br, 2H), 4.27-4.11 (m, 2H), 3.54-3.47 (m, 1H), 3.38-3.31 (m, 1H), 3.26-3.16 (m, 1H), 3.11-3.02 (m, 1H), 2.65-2.51 (m, 1H), 2.05-1.94 (m, 1H), 1.79-1.66 (m, 1H), 1.38 (s, 9H).

Step 2: tert-butyl (3R)-3-({[3-amino-5-chloro-6-(4-cyanophenyl)pyrazin-2-yl]oxy}methyl)pyrrolidine-1-carboxylate

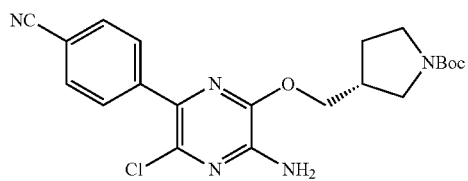 [SMILES: CC(C)(C)OC(=O)N1CC[C@@H](COc2nc(-c3ccc(C#N)cc3)c(Cl)nc2N)C1]

A reaction vessel containing a mixture of tert-butyl (3R)-3-{[(3-amino-6-bromo-5-chloropyrazin-2-yl)oxy]methyl}pyrrolidine-1-carboxylate (660 mg, 1.6 mmol), (4-cyanophenyl)boronic acid (285 mg, 1.94 mmol), dichloro(bis{di-tert-butyl[4-(dimethylamino)phenyl]phosphoranyl})palladium (60 mg, 0.08 mmol) and sodium carbonate (340 mg, 3.2 mmol) in 1,4-dioxane (10 mL) and water (1 mL) was evacuated then refilled with nitrogen. The resulting mixture was heated to 90° C. and stirred overnight. The reaction mixture was cooled to room temperature then diluted with EtOAc and washed with water and brine. The organic layer was dried over $Na_2SO_4$ and concentrated. The residue was purified on a silica gel column eluting with 0 to 30% EtOAc/DCM to give the desired product (590 mg, 85%). LC-MS calculated for $C_{16}H_{17}ClN_5O$ (M-Boc+2H)$^+$: m/z=330.1. found 330.2.

Step 3: 4-{5-chloro-8-[(3R)-pyrrolidin-3-yl-methoxy]imidazo[1,2-a]pyrazin-6-yl}benzonitrile

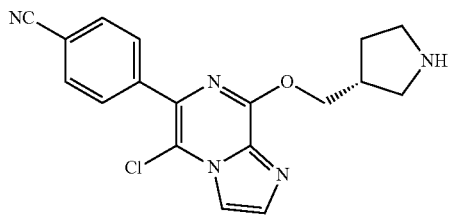 [SMILES: N#Cc1ccc(-c2nc(OC[C@@H]3CCNC3)c3nccn3c2Cl)cc1]

A mixture of tert-butyl (3R)-3-({[3-amino-5-chloro-6-(4-cyanophenyl)pyrazin-2-yl]oxy}methyl)pyrrolidine-1-carboxylate (456 mg, 1.06 mmol) and chloroacetaldehyde (50 wt. % in water, 1.2 mL, 9.0 mmol) in ethanol (7 mL) was heated to 95° C. and stirred overnight. The reaction mixture was then cooled to room temperature and concentrate. The residue was dissolved in DCM/IPA (2:1) then washed with saturated NaHCO$_3$ aqueous solution, dried over Na$_2$SO$_4$ and concentrated. The residue was triturated with hexanes then filtered and dried to give the desired product. LC-MS calculated for C$_{18}$H$_{17}$ClN$_5$O (M+H)$^+$: m/z=354.1. found 354.1.

Step 4: 4-{(5-phenyl)-8-[(3R)-pyrrolidin-3-yl-methoxy]imidazo[1,2-a]pyrazin-6-yl}benzonitrile A mixture of 4-{5-chloro-8-[(3R)-pyrrolidin-3-yl-methoxy]imidazo[1,2-a]pyrazin-6-yl}benzonitrile (20.0 g, 0.0565 mmol), phenylboronic acid (14 mg, 0.11 mmol), [1,1'-bis(di-cyclohexylphosphino)ferrocene]-dichloropalladium(II) (2 mg, 0.003 mmol), sodium carbonate (12 mg, 0.11 mmol) in tert-butyl alcohol (1.0 mL)/water (0.5 mL) was evacuated then refilled with nitrogen. The resulting mixture was heated to 90° C. and stirred for 2 h. The mixture was cooled to room temperature then purified by prep-HPLC (pH=2, acetonitrile/water+TFA) to give the desired product as the TFA salt. LC-MS calculated for C$_{24}$H$_{22}$N$_5$O (M+H)$^+$: m/z=396.2. found 396.1.

Example 27

4-{5-(4-chlorophenyl)-8-[(3R)-pyrrolidin-3-yl-methoxy]imidazo[1,2-a]pyrazin-6-yl}benzonitrile

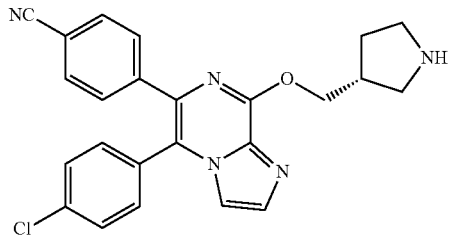 [SMILES: N#Cc1ccc(-c2nc(OC[C@@H]3CCNC3)c3nccn3c2-c2ccc(Cl)cc2)cc1]

This compound was prepared using procedures analogous to those for Example 26, Step 4 with (4-chlorophenyl)boronic acid replacing phenylboronic acid. The product was purified by prep-HPLC (pH=2, acetonitrile/water+TFA) to give the compound as the TFA salt. LC-MS calculated for C$_{24}$H$_{21}$ClN$_5$O (M+H)$^+$: m/z=430.1. found 430.1.

Example 28

4-{8-[(3R)-pyrrolidin-3-ylmethoxy]-5-[4-(trifluoromethyl)phenyl]imidazo[1,2-a]pyrazin-6-yl}benzonitrile

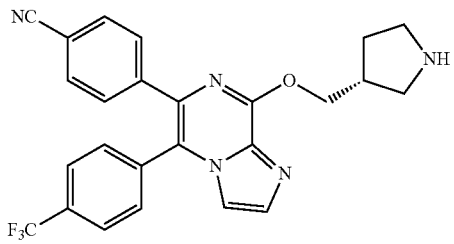 [SMILES: N#Cc1ccc(-c2nc(OC[C@@H]3CCNC3)c3nccn3c2-c2ccc(C(F)(F)F)cc2)cc1]

This compound was prepared using procedures analogous to those for Example 26, Step 4 with (4-trifluoromethylphenyl)boronic acid replacing phenylboronic acid. The product was purified by prep-HPLC (pH=2, acetonitrile/water+TFA) to give the compound as the TFA salt. LC-MS calculated for C$_{25}$H$_{21}$F$_3$N$_5$O (M+H)$^+$: m/z=464.2. found 464.1.

Example 29

4-{5-(4-piperidin-1-ylphenyl)-8-[(3R)-pyrrolidin-3-ylmethoxy]imidazo[1,2-a]pyrazin-6-yl}benzonitrile

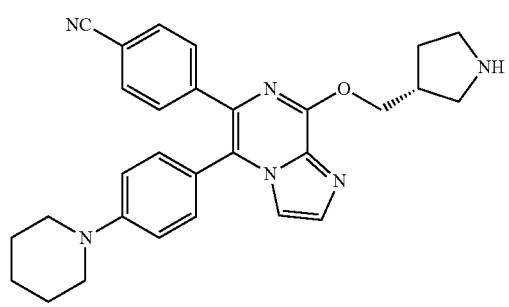 [SMILES: N#Cc1ccc(-c2nc(OC[C@@H]3CCNC3)c3nccn3c2-c2ccc(N3CCCCC3)cc2)cc1]

This compound was prepared using procedures analogous to those for Example 26, Step 4 with 1-[4-(4,4,5,5-tetramethyl-1,3,2-dioxaborolan-2-yl)phenyl]piperidine (Alfa Aesar, cat #H51922) replacing phenylboronic acid. The product was purified by prep-HPLC (pH=2, acetonitrile/water+TFA) to give the compound as the TFA salt. LC-MS calculated for C$_{29}$H$_{31}$N$_6$O (M+H)$^+$: m/z=479.3. found 479.2.

Example 30

4-{5-(4-methoxyphenyl)-8-[(3R)-pyrrolidin-3-yl-methoxy]imidazo[1,2-a]pyrazin-6-yl}benzonitrile

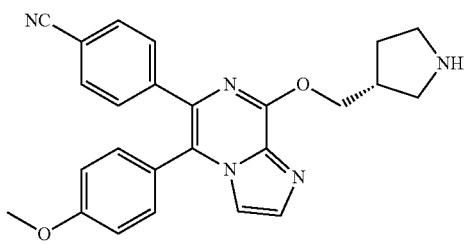 [SMILES: COc1ccc(-c2c(-c3ccc(C#N)cc3)nc(OC[C@@H]3CCNC3)c3nccn23)cc1]

This compound was prepared using procedures analogous to those for Example 26, Step 4 with 4-methoxyphenylboronic acid replacing phenylboronic acid. The product was purified by prep-HPLC (pH=2, acetonitrile/water+TFA) to give the compound as the TFA salt. LC-MS calculated for $C_{25}H_{24}N_5O_2$ (M+H)$^+$: m/z=426.2. found 426.1.

Example 31

4-{5-[2-(dimethylamino)pyrimidin-5-yl]-8-[(3R)-pyrrolidin-3-ylmethoxy]imidazo[1,2-a]pyrazin-6-yl}benzonitrile

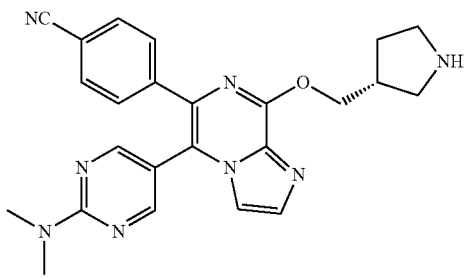 [SMILES: CN(C)c1ncc(-c2c(-c3ccc(C#N)cc3)nc(OC[C@@H]3CCNC3)c3nccn23)cn1]

This compound was prepared using procedures analogous to those for Example 26, Step 4 with 2-dimethylamino-pyrimidine-5-boronic acid pinacol ester (Frontier, cat #D1773) replacing phenylboronic acid. The product was purified by prep-HPLC (pH=2, acetonitrile/water+TFA) to give the compound as the TFA salt. LC-MS calculated for $C_{24}H_{25}N_8O$ (M+H)$^+$: m/z=441.2. found 441.2.

Example 32

4-(5-[6-(dimethylamino)pyridin-3-yl]-8-{[(3R)-1-methylpyrrolidin-3-yl]methoxy}imidazo[1,2-a]pyrazin-6-yl)benzonitrile

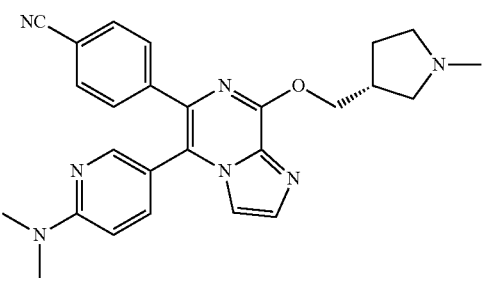

Step 1: 4-(5-chloro-8-{[(3R)-1-methylpyrrolidin-3-yl]methoxy}imidazo[1,2-a]pyrazin-6-yl)benzonitrile

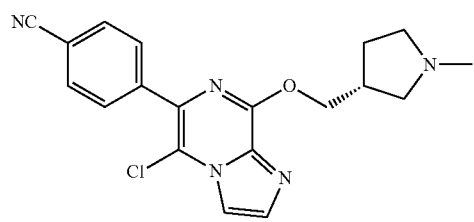 [SMILES: CN1CC[C@@H](COc2nc(-c3ccc(C#N)cc3)c(Cl)n3ccnc23)C1]

To a solution of 4-{5-chloro-8-[(3R)-pyrrolidin-3-yl-methoxy]imidazo[1,2-a]pyrazin-6-yl}benzonitrile (Example 26, Step 3, 215 mg, 0.608 mmol) in methylene chloride (10 mL) was added formaldehyde (37 wt. % in water, 452 µL, 6.08 mmol). The resulting mixture was stirred at room temperature for 30 min then sodium triacetoxyborohydride (390 mg, 1.8 mmol). The mixture was stirred at room temperature overnight then diluted with DCM and washed with saturated NaHCO$_3$ aqueous solution, water and brine. The organic layer was dried over Na$_2$SO$_4$ and concentrated. The residue was used in the next step without further purification. LC-MS calculated for $C_{19}H_{19}ClN_5O$ (M+H)$^+$: m/z=368.1. found 368.1.

Step 2: 4-(5-[6-(dimethylamino)pyridin-3-yl]-8-{[(3R)-1-methylpyrrolidin-3-yl]methoxy}imidazo[1,2-a]pyrazin-6-yl)benzonitrile A mixture of 4-(5-chloro-8-{[(3R)-1-methylpyrrolidin-3-yl]methoxy}imidazo[1,2-a]pyrazin-6-yl)benzonitrile (20. mg, 0.054 mmol), 6-(dimethylamino)pyridine-3-boronic acid (Combi-Blocks, cat #FA-2296: 19 mg, 0.11 mmol), [1,1'-bis(di-cyclohexylphosphino)ferrocene]-dichloropalladium(II) (2 mg, 0.003 mmol), sodium carbonate (12 mg, 0.11 mmol) in tert-butyl alcohol (0.5 mL)/water (0.5 mL) was evacuated then filled with nitrogen. The resulting mixture was heated to 100° C. and stirred for 2 h. The mixture was cooled to room temperature then diluted with MeOH and purified by prep-HPLC (pH=2, acetonitrile/water+TFA) to give the desired product as the TFA salt. LC-MS calculated for $C_{26}H_{28}N_7O$ (M+H)$^+$: m/z=454.2. found 454.2.

Example 33

4-{2-methyl-5-(4-methylphenyl)-8-[(3R)-pyrrolidin-3-ylmethoxy]imidazo[1,2-a]pyrazin-6-yl}benzonitrile

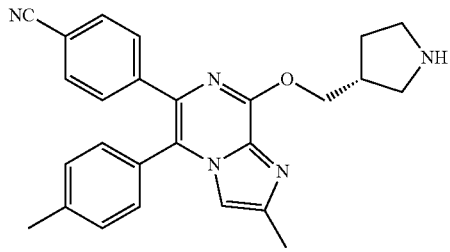 [SMILES: Cc1ccc(-c2c(-c3ccc(C#N)cc3)nc(OC[C@@H]3CCNC3)c3nc(C)cn23)cc1]

A mixture of tert-butyl (3R)-3-({[3-amino-6-(4-cyanophenyl)-5-(4-methylphenyl)pyrazin-2-yl]oxy}methyl)pyrrolidine-1-carboxylate (Example 1, Step 4: 20 mg, 0.04 mmol) and chloroacetone (82.0 µL, 1.03 mmol) in isopropyl alcohol (1.0 mL) was stirred at 105° C. overnight at which time LC-MS indicated the reaction was not complete. The reaction mixture was then heated to 130° C. and stirred for 1 h. The mixture was cooled to room temperature then purified by prep-HPLC (pH=10, acetonitrile/water+NH$_4$OH) to give the desired product. LC-MS calculated for C$_{26}$H$_{26}$N$_5$O (M+H)$^+$: m/z=424.2. found 424.2.

Example 34

4-[5-(4-methylphenyl)-8-[(3R)-pyrrolidin-3-ylmethoxy]-2-(trifluoromethyl)imidazo[1,2-a]pyrazin-6-yl]benzonitrile

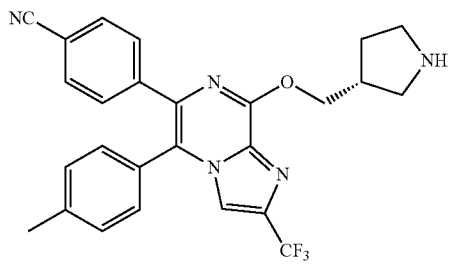 [SMILES: Cc1ccc(-c2c(-c3ccc(C#N)cc3)nc(OC[C@@H]3CCNC3)c3nc(C(F)(F)F)cn23)cc1]

A mixture of tert-butyl (3R)-3-({[3-amino-6-(4-cyanophenyl)-5-(4-methylphenyl)pyrazin-2-yl]oxy}methyl)pyrrolidine-1-carboxylate (Example 1, Step 4: 35.0 mg, 0.0721 mmol), sodium carbonate (38.2 g, 0.360 mmol) and 3-bromo-1,1,1-trifluoroacetone (74.84 µL, 0.7208 mmol) in isopropyl alcohol (1.5 mL) was stirred at 155° C. for 15 min. The reaction mixture was then cooled to room temperature, filtered and concentrated. The residue was purified by prep-HPLC (pH=2, acetonitrile/water+TFA) to give the desired product as the TFA salt. LC-MS calculated for C$_{26}$H$_{23}$F$_3$N$_5$O (M+H)$^+$: m/z=478.2. found 478.1.

Example 35

4-{2,5-bis(4-methylphenyl)-8-[(3R)-pyrrolidin-3-ylmethoxy]imidazo[1,2-a]pyrazin-6-yl}benzonitrile

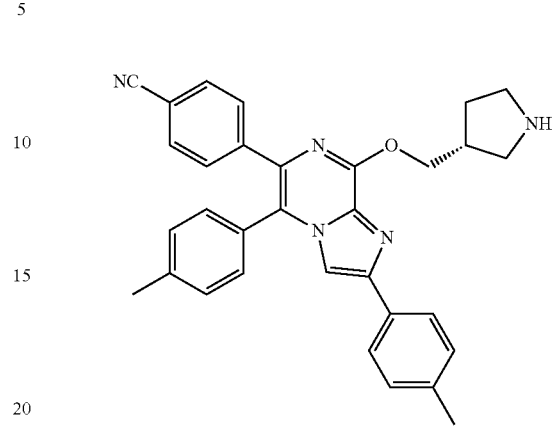

A mixture of tert-butyl (3R)-3-({[3-amino-6-(4-cyanophenyl)-5-(4-methylphenyl)pyrazin-2-yl]oxy}methyl)pyrrolidine-1-carboxylate (Example 1, Step 4: 30.0 mg, 0.0618 mmol), sodium carbonate (65.48 g, 0.6178 mmol) and 2-bromo-1-(4-methylphenyl)-ethanone (65.8 g, 0.309 mmol) in isopropyl alcohol (1.5 mL) was stirred at 155° C. for 3 h. The reaction mixture was then cooled to room temperature, filtered and concentrated. The residue was dissolved in methylene chloride (1.5 mL) then trifluoroacetic acid (0.5 mL) was added. The reaction mixture was stirred at room temperature for 1 h and concentrated. The crude material was then purified by prep-HPLC (pH=2, acetonitrile/water+TFA) to give the desired product as the TFA salt. LC-MS calculated for C$_{32}$H$_{30}$N$_5$O (M+H)$^+$: m/z=500.2. found 500.3.

Example 36

4-{2-(cyanomethyl)-5-(4-methylphenyl)-8-[(3R)-pyrrolidin-3-ylmethoxy]imidazo[1,2-a]pyrazin-6-yl}benzonitrile

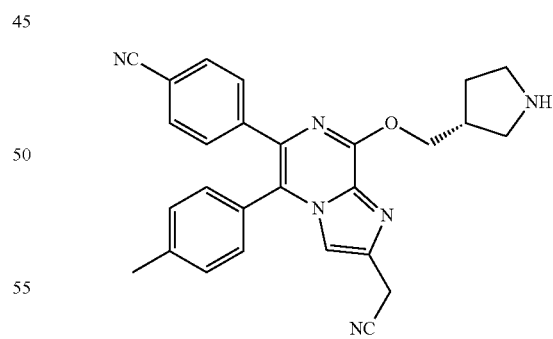

A mixture of tert-butyl (3R)-3-({[3-amino-6-(4-cyanophenyl)-5-(4-methylphenyl)pyrazin-2-yl]oxy}methyl)pyrrolidine-1-carboxylate (50.0 g, 0.103 mmol), disodium hydrogen phosphate (146 mg, 1.03 mmol) and 1,3-dichloro-2-propanone (130.7 mg, 1.030 mmol) in isopropyl alcohol (1.5 mL) was stirred at 110° C. for 4.5 h then cooled to room temperature, filtered and concentrated. The residue was dissolved in N,N-dimethylformamide (1.5 mL) then sodium cyanide (50.4 g, 1.03 mmol) was added. The resulting mixture was stirred at 65° C. for 30 min then cooled to room temperature and diluted with EtOAc, washed with saturated NaHCO$_3$ aqueous solution, water and brine. The organic layer was dried over Na$_2$SO$_4$ and concentrated. The residue was dissolved in methylene chloride (1.5 mL) then trifluoroacetic acid (1.0 mL) was added. The reaction mixture was stirred at room temperature for 1 h then concentrated. The crude material was purified by prep-HPLC (pH=2, acetonitrile/water+TFA) to give the desired product as the TFA salt. LC-MS calculated for C$_{27}$H$_{25}$N$_6$O (M+H)$^+$: m/z=449.2. found 449.3.

Example 37

6-(4-cyanophenyl)-N-methyl-5-(4-methylphenyl)-8-[(3R)-pyrrolidin-3-ylmethoxy]imidazo-[1,2-a]pyrazine-2-carboxamide

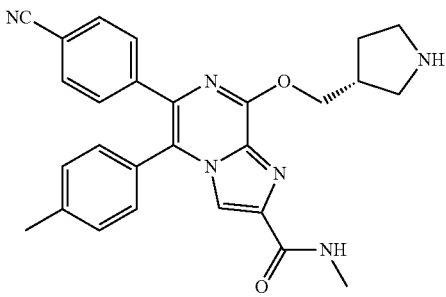 [SMILES: CNC(=O)c1cn2c(-c3ccc(C)cc3)c(-c3ccc(C#N)cc3)nc(OC[C@@H]3CCNC3)c2n1]

Step 1: 8-{[(3R)-1-(tert-butoxycarbonyl)pyrrolidin-3-yl]methoxy}-6-(4-cyanophenyl)-5-(4-methylphenyl)imidazo[1,2-a]pyrazine-2-carboxylic acid

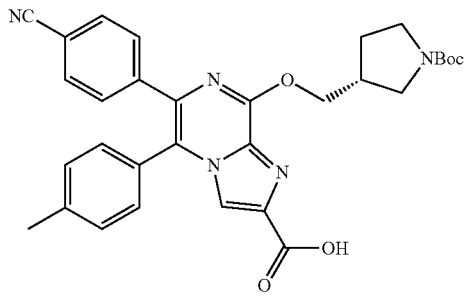 [SMILES: Cc1ccc(-c2c(-c3ccc(C#N)cc3)nc(OC[C@@H]3CCN(C(=O)OC(C)(C)C)C3)c3nc(C(=O)O)cn23)cc1]

A mixture of tert-butyl (3R)-3-({[3-amino-6-(4-cyanophenyl)-5-(4-methylphenyl)pyrazin-2-yl]oxy}methyl)pyrrolidine-1-carboxylate (150.0 g, 0.3089 mmol), disodium hydrogen phosphate (439 mg, 3.09 mmol) and ethyl bromopyruvate (387.6 μL, 3.089 mmol) in isopropyl alcohol (3.0 mL) was stirred at 95° C. for 2 h then cooled to room temperature, filtered and concentrated. The residue was purified on a silica gel column to give the desired intermediate. To a solution of the above intermediate in methanol (2.5 mL) and water (1.5 mL) was added sodium hydroxide (62 mg, 1.5 mmol). The resulting mixture was stirred at 55° C. for 2 h then cooled to room temperature and acidified to pH 1-3 with 1 M HCl. The mixture was extracted with EtOAc. The organic layer was dried over Na$_2$SO$_4$, and concentrated to give the desired product, which was used in the next step without further purification. LC-MS calculated for C$_{31}$H$_{32}$N$_5$O$_5$ (M+H)$^+$: m/z=554.2. found 554.1.

Step 2: 6-(4-cyanophenyl)-N-methyl-5-(4-methylphenyl)-8-[(3R)-pyrrolidin-3-ylmethoxy]imidazo[1,2-a]pyrazine-2-carboxamide To a mixture of 8-{[(3R)-1-(tert-butoxycarbonyl)pyrrolidin-3-yl]methoxy}-6-(4-cyanophenyl)-5-(4-methylphenyl)imidazo[1,2-a]pyrazine-2-carboxylic acid (35.0 mg, 0.0632 mmol), benzotriazol-1-yloxytris(dimethylamino)phosphonium hexafluorophosphate (55.9 mg, 0.126 mmol), and triethylamine (44.0 μL, 0.316 mmol) in methylene chloride (1.5 mL) was added methylamine (2M in THF, 158 μL, 0.316 mmol). The reaction mixture was stirred at room temperature for 2 h then concentrated. The residue was dissolved in methylene chloride (1.5 mL) then trifluoroacetic acid (1.0 mL) was added. The mixture was stirred at room temperature for 1 h then concentrated. The residue was purified by prep-HPLC (pH=2, acetonitrile/water+TFA) to give the desired product as the TFA salt. LC-MS calculated for C$_{27}$H$_{27}$N$_6$O$_2$ (M+H)$^+$: m/z=467.2. found 467.1.

Example 38

6-(4-cyanophenyl)-N,N-dimethyl-5-(4-methylphenyl)-8-[(3R)-pyrrolidin-3-ylmethoxy]imidazo[1,2-a]pyrazine-2-carboxamide

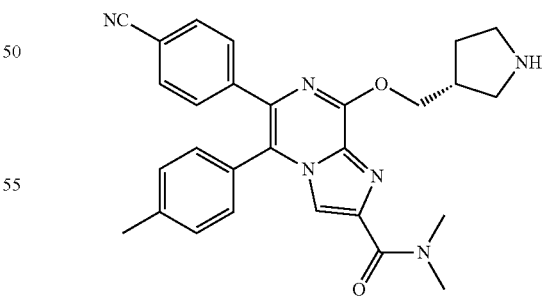

This compound was prepared using procedures analogous to those for Example 37 with dimethylamine (2M in THF) replacing methylamine in Step 2. The product was purified by prep-HPLC (pH=2, acetonitrile/water+TFA) to give the desired product as the TFA salt. LC-MS calculated for C$_{28}$H$_{29}$N$_6$O$_2$ (M+H)$^+$: m/z=481.2. found 481.2.

Example 39

6-(4-cyanophenyl)-N-cyclopropyl-5-(4-methylphenyl)-8-[(3R)-pyrrolidin-3-ylmethoxy]imidazo[1,2-a]pyrazine-2-carboxamide

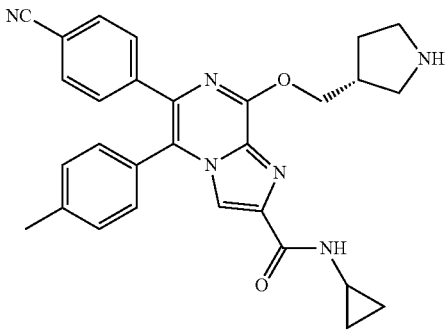 [SMILES: Cc1ccc(-c2c(-c3ccc(C#N)cc3)nc(OC[C@@H]3CCNC3)c3nc(C(=O)NC4CC4)cn23)cc1]

This compound was prepared using procedures analogous to those for Example 37 with cyclopropylamine replacing methylamine in Step 2. The product was purified by prep-HPLC (pH=2, acetonitrile/water+TFA) to give the desired product as the TFA salt. LC-MS calculated for $C_{29}H_{29}N_6O_2$ (M+H)$^+$: m/z=493.2. found 493.1.

Example 40

6-(4-cyanophenyl)-N-(1-methylazetidin-3-yl)-5-(4-methylphenyl)-8-[(3R)-pyrrolidin-3-ylmethoxy]imidazo[1,2-a]pyrazine-2-carboxamide

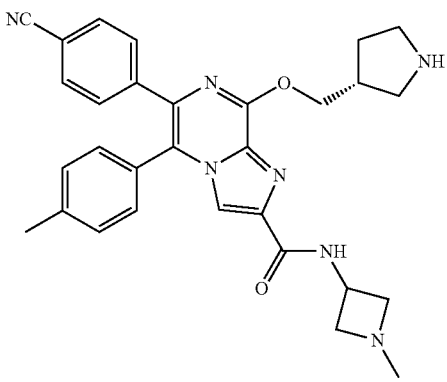 [SMILES: Cc1ccc(-c2c(-c3ccc(C#N)cc3)nc(OC[C@@H]3CCNC3)c3nc(C(=O)NC4CN(C)C4)cn23)cc1]

This compound was prepared using procedures analogous to those for Example 37 with 1-methylazetidin-3-amine replacing methylamine in Step 2. The product was purified by prep-HPLC (pH=2, acetonitrile/water+TFA) to give the desired product as the TFA salt. LC-MS calculated for $C_{30}H_{32}N_7O_2$ (M+H)$^+$: m/z=522.3. found 522.2.

Example 41

4-{2-(hydroxymethyl)-5-(4-methylphenyl)-8-[(3R)-pyrrolidin-3-ylmethoxy]imidazo[1,2-a]pyrazin-6-yl}benzonitrile

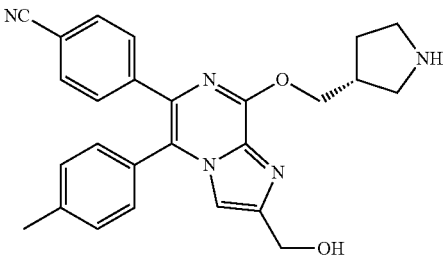 [SMILES: Cc1ccc(-c2c(-c3ccc(C#N)cc3)nc(OC[C@@H]3CCNC3)c3nc(CO)cn23)cc1]

Step 1: tert-butyl (3R)-3-({[6-(4-cyanophenyl)-2-(hydroxymethyl)-5-(4-methylphenyl)imidazo[1,2-a]pyrazin-8-yl]oxy}methyl)pyrrolidine-1-carboxylate

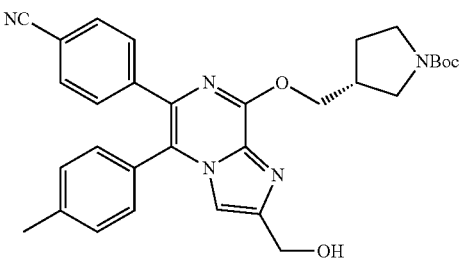 [SMILES: Cc1ccc(-c2c(-c3ccc(C#N)cc3)nc(OC[C@@H]3CCN(C(=O)OC(C)(C)C)C3)c3nc(CO)cn23)cc1]

To a solution of 8-{[(3R)-1-(tert-butoxycarbonyl)pyrrolidin-3-yl]methoxy}-6-(4-cyanophenyl)-5-(4-methylphenyl) imidazo[1,2-a]pyrazine-2-carboxylic acid (Example 37, Step 1: 190 mg, 0.34 mmol) in tetrahydrofuran (3.0 mL) at 0° C. was added 4-methylmorpholine (56 μL, 0.51 mmol) and isobutyl chloroformate (66 μL, 0.51 mmol). The reaction mixture was stirred at 0° C. for 30 min and then the resulting solid was filtered off and washed with 1.5 mL of THF. To the filtrate at 0° C. was added a solution of sodium tetrahydroborate (26 mg, 0.68 mmol) in water (0.5 mL). The reaction mixture was warmed to room temperature and stirred for 15 min. The mixture was then quenched with saturated NaHCO$_3$ aqueous solution and extracted with EtOAc. The combined organic layers were dried over Na$_2$SO$_4$ and concentrated. The residue was purified on a silica gel column to give the desired product. LC-MS calculated for $C_{31}H_{34}N_5O_4$ (M+H)$^+$: m/z=540.3. found 540.2.

Step 2: 4-{2-(hydroxymethyl)-5-(4-methylphenyl)-8-[(3R)-pyrrolidin-3-ylmethoxy]imidazo[1,2-a]pyrazin-6-yl}benzonitrile To a solution of tert-butyl (3R)-3-({[6-(4-cyanophenyl)-2-(hydroxymethyl)-5-(4-methylphenyl)imidazo[1,2-a]pyrazin-8-yl]oxy}methyl)pyrrolidine-1-carboxylate (30 mg) in DCM (1 mL) was added TFA (0.5 mL). The resulting mixture was stirred at room temperature for 1 h then concentrated. The residue was purified by prep-HPLC (pH=2, acetonitrile/water+TFA) to give the desired product as the TFA salt. LC-MS calculated for $C_{26}H_{26}N_5O_2$ (M+H)$^+$: m/z=440.2. found 440.1.

Example 42

4-{2-[(dimethylamino)methyl]-5-(4-methylphenyl)-8-[(3R)-pyrrolidin-3-ylmethoxy]imidazo[1,2-a]pyrazin-6-yl}benzonitrile

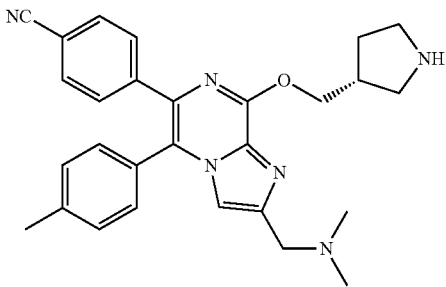 [SMILES: Cc1ccc(-c2c(-c3ccc(C#N)cc3)nc(OC[C@@H]3CCNC3)c3nc(CN(C)C)cn23)cc1]

Step 1: tert-butyl (3R)-3-({[6-(4-cyanophenyl)-2-formyl-5-(4-methylphenyl)imidazo[1,2-a]pyrazin-8-yl]oxy}methyl)pyrrolidine-1-carboxylate

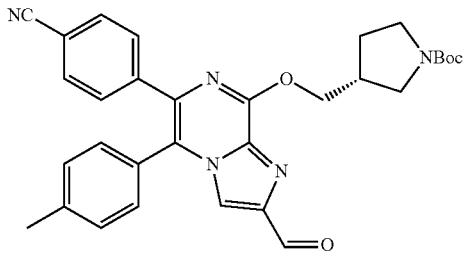 [SMILES: Cc1ccc(-c2c(-c3ccc(C#N)cc3)nc(OC[C@@H]3CCN(C(=O)OC(C)(C)C)C3)c3nc(C=O)cn23)cc1]

To a solution of tert-butyl (3R)-3-({[6-(4-cyanophenyl)-2-(hydroxymethyl)-5-(4-methylphenyl)imidazo[1,2-a]pyrazin-8-yl]oxy}methyl)pyrrolidine-1-carboxylate (Example 41, Step 1: 122 mg, 0.226 mmol) in methylene chloride (3.0 mL) was added sodium bicarbonate (57 mg, 0.68 mmol) and Dess-Martin periodinane (140 mg, 0.34 mmol). The resulting mixture was then stirred at room temperature overnight. The mixture was loaded directly into a silica gel column eluting with 0 to 50% EtOAc/DCM to give the desired product. LC-MS calculated for $C_{31}H_{32}N_5O_4$ (M+H)$^+$: m/z=538.2. found 538.1.

Step 2: 4-{2-[(dimethylamino)methyl]-5-(4-methylphenyl)-8-[(3R)-pyrrolidin-3-ylmethoxy]imidazo[1,2-a]pyrazin-6-yl}benzonitrile To a solution of tert-butyl (3R)-3-({[6-(4-cyanophenyl)-2-formyl-5-(4-methylphenyl)imidazo[1,2-a]pyrazin-8-yl]oxy}methyl)pyrrolidine-1-carboxylate (30.0 mg, 0.0558 mmol) and dimethylamine (2M in THF, 140 µL, 0.28 mmol) in methylene chloride (1.5 mL) was added acetic acid (16 µL, 0.28 mmol). The resulting mixture was stirred at room temperature for 3 h then sodium triacetoxyborohydride (59 mg, 0.28 mmol) was added. The reaction mixture was stirred at room temperature overnight then diluted with DCM and washed with saturated NaHCO$_3$ aqueous solution, water and brine. The organic layer was dried over Na$_2$SO$_4$ and concentrated. The residue was dissolved in DCM (1 mL) then trifluoroacetic acid (0.5 mL) was added. The resulting mixture was stirred at room temperature for 1 h and concentrated. The crude material was purified by prep-HPLC (pH=2, acetonitrile/water+TFA) to give the desired product as the TFA salt. LC-MS calculated for $C_{28}H_{31}N_6O$ (M+H)$^+$: m/z=467.3. found 467.2. $^1$H NMR (500 MHz, DMSO) δ 10.12 (br, 1H), 9.01 (br, 2H), 7.76-7.72 (m, 2H), 7.69 (s, 1H), 7.54-7.50 (m, 2H), 7.38-7.32 (m, 4H), 4.65-4.53 (m, 2H), 4.39 (s, 2H), 3.48-3.38 (m, 1H), 3.36-3.28 (m, 1H), 3.27-3.17 (m, 1H), 3.14-3.05 (m, 1H), 2.96-2.85 (m, 1H), 2.75 (s, 6H), 2.38 (s, 3H), 2.21-2.11 (m, 1H), 1.90-1.76 (m, 1H).

Example 43

4-{2-(azetidin-1-ylmethyl)-5-(4-methylphenyl)-8-[(3R)-pyrrolidin-3-ylmethoxy]imidazo[1,2-a]pyrazin-6-yl}benzonitrile

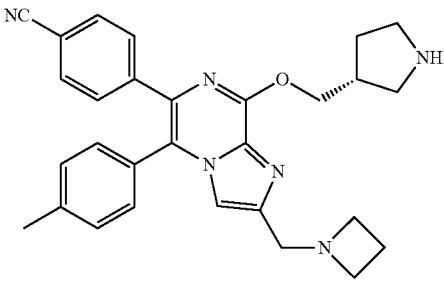 [SMILES: Cc1ccc(-c2c(-c3ccc(C#N)cc3)nc(OC[C@@H]3CCNC3)c3nc(CN4CCC4)cn23)cc1]

This compound was prepared using procedures analogous to those for Example 42 with azetidine hydrochloride replacing dimethylamine in Step 2. The product was purified by prep-HPLC (pH=2, acetonitrile/water+TFA) to give the compound as the TFA salt. LC-MS calculated for $C_{29}H_{31}N_6O$ (M+H)$^+$: m/z=479.3. found 479.2.

Example 44

4-{2-{[(cyclopropylmethyl)amino]methyl}-5-(4-methylphenyl)-8-[(3R)-pyrrolidin-3-ylmethoxy]imidazo[1,2-a]pyrazin-6-yl}benzonitrile

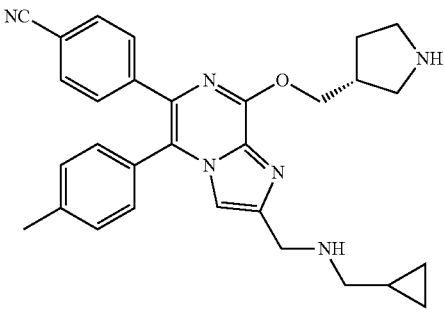 [SMILES: Cc1ccc(-c2c(-c3ccc(C#N)cc3)nc(OC[C@@H]3CCNC3)c3nc(CNCC4CC4)cn23)cc1]

This compound was prepared using procedures analogous to those for Example 42 with cyclopropylmethylamine replacing dimethylamine in Step 2. The product was purified by prep-HPLC (pH=2, acetonitrile/water+TFA) to give the compound as the TFA salt. LC-MS calculated for $C_{30}H_{33}N_6O$ (M+H)$^+$: m/z=493.3. found 493.2.

Example 45

4-{2-[(isoxazol-3-ylamino)methyl]-5-(4-methylphenyl)-8-[(3R)-pyrrolidin-3-ylmethoxy]imidazo[1,2-a]pyrazin-6-yl}benzonitrile

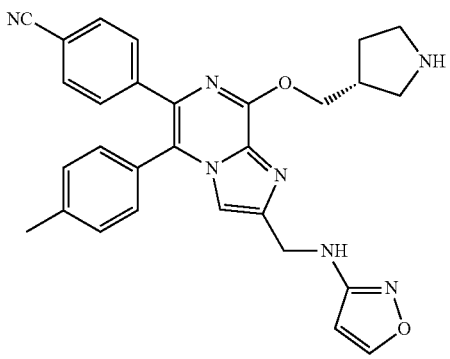 [SMILES: Cc1ccc(-c2c(-c3ccc(C#N)cc3)nc(OC[C@@H]3CCNC3)c3nc(CNc4ccon4)cn23)cc1]

This compound was prepared using procedures analogous to those for Example 42 with isoxazol-3-amine replacing dimethylamine in Step 2. The product was purified by prep-HPLC (pH=2, acetonitrile/water+TFA) to give the compound as the TFA salt. LC-MS calculated for $C_{29}H_{28}N_7O_2$ (M+H)$^+$: m/z=506.2. found 506.2.

Example 46

4-(2-[(dimethylamino)methyl]-5-(4-methylphenyl)-8-{[(3R)-1-methylpyrrolidin-3-yl]methoxy}imidazo[1,2-a]pyrazin-6-yl)benzonitrile

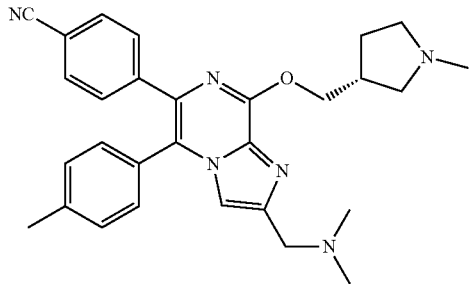

To a solution of 4-{2-[(dimethylamino)methyl]-5-(4-methylphenyl)-8-[(3R)-pyrrolidin-3-ylmethoxy]imidazo[1,2-a]pyrazin-6-yl}benzonitrile (Example 42: 10 mg, 0.02 mmol) in 1,2-dichloroethane (1.5 mL) was added formaldehyde (37 wt. % in water, 21 μL, 0.29 mmol), followed by acetic acid (10 μL, 0.2 mmol). The resulting mixture was stirred at room temperature for 3 h, followed by the addition of sodium triacetoxyborohydride (40 mg, 0.2 mmol). The mixture was stirred at room temperature for another 2 h and concentrated. The resulting residue was purified by prep-HPLC (pH=2, acetonitrile/water+TFA) to give the compound as the TFA salt. LC-MS calculated for $C_{29}H_{33}N_6O$ (M+H)$^+$: m/z=481.3. found 481.2.

Example 47

4-{2-[2-(dimethylamino)ethyl]-5-(4-methylphenyl)-8-[(3R)-pyrrolidin-3-ylmethoxy]imidazo[1,2-a]pyrazin-6-yl}benzonitrile

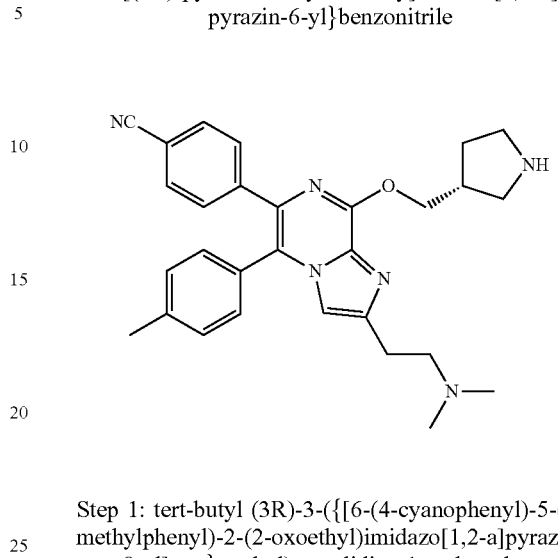

Step 1: tert-butyl (3R)-3-({[6-(4-cyanophenyl)-5-(4-methylphenyl)-2-(2-oxoethyl)imidazo[1,2-a]pyrazin-8-yl]oxy}methyl)pyrrolidine-1-carboxylate

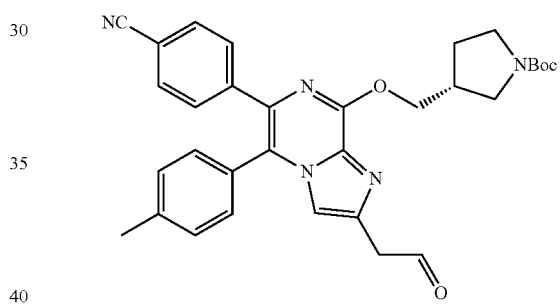

To a solution of chloro(methoxymethyl)triphenylphosphorane (255 mg, 0.744 mmol) in tetrahydrofuran (3.5 mL) at −78° C. was added 0.5 M potassium bis(trimethylsilyl)amide in toluene (1.30 mL, 0.65 mmol). The resulting mixture was stirred at 0° C. for 30 min, and then a solution of tert-butyl (3R)-3-({[6-(4-cyanophenyl)-2-formyl-5-(4-methylphenyl)imidazo[1,2-a]pyrazin-8-yl]oxy}methyl)pyrrolidine-1-carboxylate (Example 42, Step 1: 100 mg, 0.2 mmol) in tetrahydrofuran (1.5 mL) was added. The reaction mixture was warmed to room temperature and stirred overnight then quenched with saturated NaHCO$_3$ aqueous solution, and extracted with EtOAc. The combined extracts were dried over Na$_2$SO$_4$ and concentrated. The crude material was purified on a silica gel column to give the desired intermediate. To a solution of the above intermediate in tetrahydrofuran (3.0 mL) and water (0.3 mL) at 0° C. was added mercury(II) acetate (178 mg, 0.558 mmol). The reaction mixture was warmed to room temperature and stirred for 3 h then quenched by saturated solution of KI. The resulting mixture was stirred at room temperature for 1 h then extracted with EtOAc. The combined extracts were dried over Na$_2$SO$_4$ and concentrated. The crude material was purified on a silica gel column to give the desired product. LC-MS calculated for $C_{32}H_{34}N_5O_4$ (M+H)$^+$: m/z=552.3. found 552.2.

Step 2: 4-{2-[2-(dimethylamino)ethyl]-5-(4-methyl-phenyl)-8-[(3R)-pyrrolidin-3-ylmethoxy]imidazo[1,2-a]pyrazin-6-yl}benzonitrile To a solution of tert-butyl (3R)-3-({[6-(4-cyanophenyl)-5-(4-methylphenyl)-2-(2-oxoethyl)imidazo[1,2-a]pyrazin-8-yl]oxy}methyl)pyrrolidine-1-carboxylate (20 mg, 0.04 mmol) and dimethylamine (2M in THF, 90 µL, 0. 18 mmol) in methylene chloride (1.5 mL) was added acetic acid (10 µL, 0.18 mmol). The resulting mixture was stirred at room temperature for 1 h then sodium triacetoxyborohydride (23 mg, 0.11 mmol) was added. The mixture was stirred at room temperature overnight then diluted with DCM and washed with saturated NaHCO$_3$ solution, water and brine. The organic layer was dried over Na$_2$SO$_4$ and concentrated. The residue was dissolved in DCM (1 mL) then TFA (0.5 mL) was added. The resulting mixture was stirred at room temperature for 1 h then concentrated. The residue was purified by prep-HPLC (pH=2, acetonitrile/water+TFA) to give the desired product as the TFA salt. LC-MS calculated for C$_{29}$H$_{33}$N$_6$O (M+H)$^+$: m/z=481.3. found 481.4.

Example 48

4-{8-{[(3R)-1-methylpiperidin-3-yl]methoxy}-5-[6-(2-oxopyrrolidin-1-yl)pyridin-3-yl]imidazo[1,2-a]pyrazin-6-yl}benzonitrile

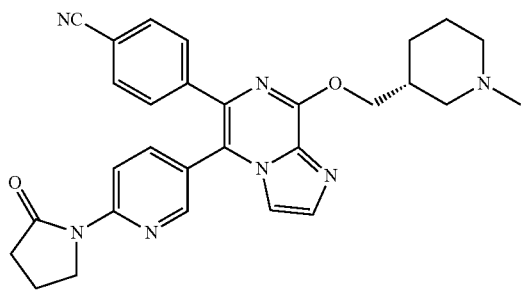 [SMILES: CN1CCC[C@@H](COc2nc(-c3ccc(C#N)cc3)c(-c3ccc(N4CCCC4=O)nc3)n3ccnc23)C1]

Step 1:
5-bromo-6-chloro-3-methoxypyrazin-2-amine

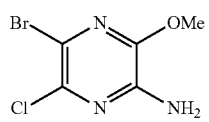 [SMILES: COc1nc(Br)c(Cl)nc1N]

Sodium methoxide (25 wt % in methanol, 60 mL, 300 mmol) was added to a solution of 3,5-dibromo-6-chloropyrazin-2-amine (Combi-Blocks, cat #ST-4448: 6.0 g, 21 mmol) in methanol (60 mL). The resulting mixture was stirred at 85° C. for 1.5 h then cooled to room temperature and concentrated to remove most of the methanol. The residue was poured into water and the precipitate was collected via filtration and washed with water then dried to give the desired product (4.0 g, 80%), which was used in the next step without further purification. LC-MS calculated for C$_5$H$_6$BrClN$_3$O (M+H)$^+$: m/z=237.9. found 237.9.

Step 2:
6-bromo-5-chloro-8-methoxyimidazo[1,2-a]pyrazine

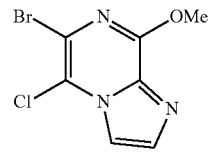 [SMILES: COc1nc(Br)c(Cl)n2ccnc12]

Chloroacetaldehyde (50 wt % in water, 17.7 mL, 140 mmol) was added to a mixture of 5-bromo-6-chloro-3-methoxypyrazin-2-amine (3.33 g, 14.0 mmol) in isopropyl alcohol (56 mL). The resulting mixture was stirred at 95° C. overnight then cooled to room temperature and concentrated. The residue was dissolved in DCM then washed with saturated NaHCO$_3$ aqueous solution, water and brine. The organic layer was dried over Na$_2$SO$_4$, filtered and concentrated. The residue was purified by flash chromatography on a silica gel column eluting with 0 to 50% EtOAc/Hexanes to give the desired product (2.4 g, 66%). LC-MS calculated for C$_7$H$_6$BrClN$_3$O (M+H)$^+$: m/z=261.9. found 261.9.

Step 3: 4-(5-chloro-8-methoxyimidazo[1,2-a]pyrazin-6-yl)benzonitrile

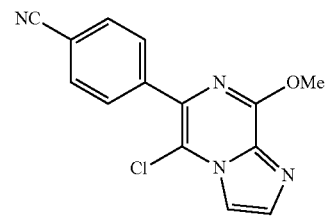 [SMILES: COc1nc(-c2ccc(C#N)cc2)c(Cl)n2ccnc12]

A mixture of 6-bromo-5-chloro-8-methoxyimidazo[1,2-a]pyrazine (1.1 g, 4.2 mmol), (4-cyanophenyl)boronic acid (800. mg, 5.45 mmol), tetrakis(triphenylphosphine)palladium(0) (300 mg, 0.2 mmol) and potassium phosphate (2.7 g, 12 mmol) in 1,4-dioxane (20 mL) and water (2.0 mL) was purged with nitrogen then stirred at 90° C. overnight. The reaction mixture was cooled to room temperature then filtered and concentrated. The residue was purified by flash chromatography on a silica gel column eluting with 0 to 20% EtOAc/DCM to give the desired product (960 mg, 80%). LC-MS calculated for C$_{14}$H$_{10}$ClN$_4$O (M+H)$^+$: m/z=285.1. found 285.1.

Step 4: 4-(5-chloro-8-hydroxyimidazo[1,2-a]pyrazin-6-yl)benzonitrile

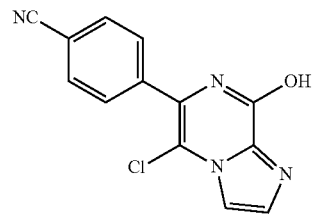 [SMILES: N#Cc1ccc(-c2nc(O)c3nccn3c2Cl)cc1]

To a solution of 4-(5-chloro-8-methoxyimidazo[1,2-a]pyrazin-6-yl)benzonitrile (1.30 g, 4.57 mmol) and sodium iodide (3.4 g, 23 mmol) in acetonitrile (10 mL) was added chlorotrimethylsilane (2.900 mL, 23 mmol). The resulting reaction mixture was stirred at 65° C. for 3 h then cooled to room temperature. The reaction mixture was quenched with addition of a few drops of water then diluted with DCM. The precipitate was collected via filtration then dried to give the desired product as a yellow solid, which was used in the next step without further purification. LC-MS calculated for $C_{13}H_8ClN_4O$ (M+H)$^+$: m/z=271.0. found 271.0.

Step 5: tert-butyl (3R)-3-({[5-chloro-6-(4-cyanophenyl)imidazo[1,2-a]pyrazin-8-yl]oxy}methyl)piperidine-1-carboxylate

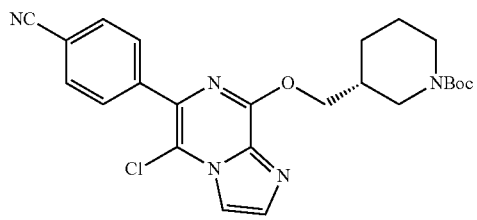

To a solution of 4-(5-chloro-8-hydroxyimidazo[1,2-a]pyrazin-6-yl)benzonitrile (1.45 g, 5.36 mmol), tert-butyl (3R)-3-(hydroxymethyl)piperidine-1-carboxylate (Synnovator, cat #PB00890: 2.3 g, 11 mmol) and triphenylphosphine (2.8 g, 11 mmol) in tetrahydrofuran (36 mL) at 0° C. was added diisopropyl azodicarboxylate (2.1 mL, 11 mmol) dropwise. The reaction mixture was allowed to warm to room temperature and stirred overnight then concentrated. The residue was purified by flash chromatography on a silica gel column eluting with 0 to 25% EtOAc/DCM to give the desired product (1.95 g, 78%). LC-MS calculated for $C_{24}H_{27}ClN_5O_3$ (M+H)$^+$: m/z=468.2. found 468.1.

Step 6: 4-{5-chloro-8-[(3R)-piperidin-3-ylmethoxy]imidazo[1,2-a]pyrazin-6-yl}benzonitrile

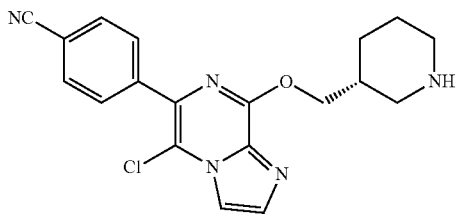 [SMILES: N#Cc1ccc(-c2nc(OC[C@@H]3CCCNC3)c3nccn3c2Cl)cc1]

To a solution of tert-butyl (3R)-3-({[5-chloro-6-(4-cyanophenyl)imidazo[1,2-a]pyrazin-8-yl]oxy}methyl)piperidine-1-carboxylate (1.0 g, 2.2 mmol) in methylene chloride (3.3 mL) was added trifluoroacetic acid (3.3 mL). The resulting mixture was stirred at room temperature for 1 h then concentrated. The residue was dissolved in DCM then washed with saturated NaHCO$_3$ aqueous solution, water and brine. The organic layer was dried over Na$_2$SO$_4$, filtered and concentrated. The residue was used in the next step without further purification. LC-MS calculated for $C_{19}H_{19}ClN_5O$ (M+H)$^+$: m/z=368.1. found 368.1.

Step 7: 4-(5-chloro-8-{[(3R)-1-methylpiperidin-3-yl]methoxy}imidazo[1,2-a]pyrazin-6-yl)benzonitrile

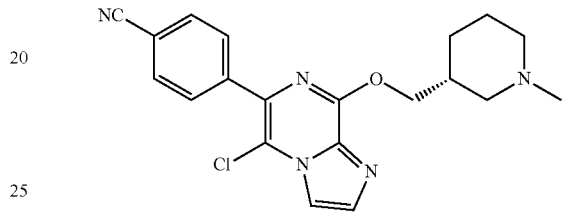

To the solution of the crude product from Step 6 in DCM (5 mL) was added formaldehyde (37 wt % in water, 120 μL, 4.4 mmol). The resulting mixture was stirred at room temperature for 30 min, then sodium triacetoxyborohydride (930 mg, 4.4 mmol) was added. The reaction mixture was stirred at room temperature for 2 h then diluted with DCM, washed with saturated NaHCO3 aqueous solution, water and brine. The organic layer was dried over Na$_2$SO$_4$, filtered and concentrated. The residue was purified by flash chromatography on a silica gel column eluting with 0 to 30% MeOH/DCM to give the desired product (420 mg). LC-MS calculated for $C_{20}H_{21}ClN_5O$ (M+H)$^+$: m/z=382.1. found 382.1.
$^1$H NMR (400 MHz, CD$_3$OD) δ 8.23 (d, J=1.2 Hz, 1H), 8.03 (d, J=8.5 Hz, 2H), 7.91-7.82 (m, 3H), 4.63 (dd, J=11.0, 4.5 Hz, 1H), 4.47 (dd, J=11.0, 7.0 Hz, 1H), 3.81 (d, J=12.0 Hz, 1H), 3.55 (d, J=10.7 Hz, 1H), 3.13-2.80 (m, 5H), 2.45 (m, 1H), 2.18-1.75 (m, 3H), 1.54 (m, 1H).

Step 8: 4-{8-{[(3R)-1-methylpiperidin-3-yl]methoxy}-5-[6-(2-oxopyrrolidin-1-yl)pyridin-3-yl]imidazo[1,2-a]pyrazin-6-yl}benzonitrile A mixture of 4-(5-chloro-8-{[(3R)-1-methylpiperidin-3-yl]methoxy}imidazo[1,2-a]pyrazin-6-yl)benzonitrile (47. mg, 0.12 mmol), potassium phosphate (78 mg, 0.37 mmol), dichloro[1,1'-bis(dicyclohexylphosphino)ferrocene]palladium(II) (9.3 g, 0.012 mmol), 1-[5-(4,4,5,5-tetramethyl-1,3,2-dioxaborolan-2-yl)pyridin-2-yl]pyrrolidin-2-one (JPM2 Pharma, cat #JPM2-00-744: 42 mg, 0.15 mmol) in 1,4-dioxane (3 mL) and water (1 mL) was purged with nitrogen then stirred at 90° C. for 3 h. The reaction mixture was cooled to room temperature then extracted with DCM. The combined extracts were concentrated and the residue was purified by flash chromatography on a silica gel column eluting with 0 to 30% MeOH/DCM to give the desired product, which was further purification by prep-HPLC (pH=10, acetonitrile/water+NH$_4$OH) to give the desired product. LC-MS calculated for $C_{29}H_{30}N_7O_2$ (M+H)$^+$: m/z=508.2. found 508.2.

Example 49

4-(5-(4-methyl-3-oxo-3,4-dihydro-2H-1,4-benzoxazin-7-yl)-8-{[(3R)-1-methylpiperidin-3-yl]methoxy}imidazo[1,2-a]pyrazin-6-yl)benzonitrile

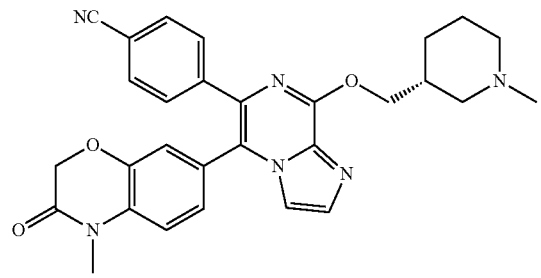 [SMILES: CN1CCC[C@@H](COc2nc(-c3ccc(C#N)cc3)c(-c3ccc4c(c3)OCC(=O)N4C)n3ccnc23)C1]

Step 1: 4-methyl-7-(4,4,5,5-tetramethyl-1,3,2-dioxaborolan-2-yl)-2H-1,4-benzoxazin-3(4H)-one

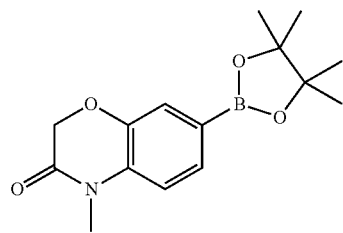 [SMILES: CN1C(=O)COc2cc(B3OC(C)(C)C(C)(C)O3)ccc21]

A mixture of 7-(4,4,5,5-tetramethyl-1,3,2-dioxaborolan-2-yl)-2H-1,4-benzoxazin-3(4H)-one (Combi-Blocks, cat #FM-4852: 0.54 g, 2.0 mmol), methyl iodide (0.18 mL, 2.9 mmol) and potassium carbonate (0.81 g, 5.9 mmol) in N,N-dimethylformamide (8 mL) was stirred at room temperature for 3 hours. The reaction mixture was diluted with EtOAc then washed with water and brine. The organic layer was dried over $Na_2SO_4$ and concentrated. The residue was used in the next step without further purification. LC-MS calculated for $C_{15}H_{21}BNO_4$ $(M+H)^+$: m/z=290.2. found 290.1.

Step 2: 4-(5-(4-methyl-3-oxo-3,4-dihydro-2H-1,4-benzoxazin-7-yl)-8-{[(3R)-1-methylpiperidin-3-yl]methoxy}imidazo[1,2-a]pyrazin-6-yl)benzonitrile The title compound was prepared using similar procedures as described for Example 48, Step 8 with 4-methyl-7-(4,4,5,5-tetramethyl-1,3,2-dioxaborolan-2-yl)-2H-1,4-benzoxazin-3(4H)-one replacing 1-[5-(4,4,5,5-tetramethyl-1,3,2-dioxaborolan-2-yl)pyridin-2-yl]pyrrolidin-2-one. The reaction mixture was purified by prep-HPLC (pH=10, acetonitrile/water+$NH_4OH$) to give the desired product. LC-MS calculated for $C_{29}H_{29}N_6O_3$ $(M+H)^+$: m/z=509.2. found 509.2. $^1H$ NMR (500 MHz, DMSO) δ 7.76-7.72 (m, 2H), 7.65 (d, J=1.2 Hz, 1H), 7.56-7.50 (m, 3H), 7.26 (d, J=8.4 Hz, 1H), 7.18 (d, J=1.9 Hz, 1H), 7.09 (dd, J=8.3, 1.9 Hz, 1H), 4.71 (s, 2H), 4.50-4.35 (m, 2H), 3.30 (s, 3H), 2.96-2.84 (m, 1H), 2.75-2.63 (m, 1H), 2.27-2.11 (m, 4H), 2.06-1.87 (m, 2H), 1.81-1.72 (m, 1H), 1.71-1.63 (m, 1H), 1.58-1.47 (m, 1H), 1.22-1.09 (m, 1H).

Example 50

4-(5-(2,3-dihydro-1,4-benzodioxin-6-yl)-8-{[(3R)-1-methylpiperidin-3-yl]methoxy}imidazo[1,2-a]pyrazin-6-yl)benzonitrile

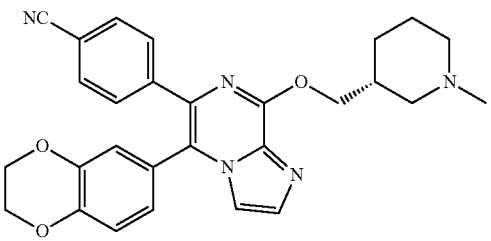 [SMILES: CN1CCC[C@@H](COc2nc(-c3ccc(C#N)cc3)c(-c3ccc4c(c3)OCCO4)n3ccnc23)C1]

The title compound was prepared using similar procedures as described for Example 48, Step 8 with 2,3-dihydro-1,4-benzodioxin-6-ylboronic acid (Aldrich, cat #635995) replacing 1-[5-(4,4,5,5-tetramethyl-1,3,2-dioxaborolan-2-yl)pyridin-2-yl]pyrrolidin-2-one. The reaction mixture was purified by prep-HPLC (pH=2, acetonitrile/water+TFA) to give the desired product as the TFA salt. LC-MS calculated for $C_{28}H_{28}N_5O_3$ $(M+H)^+$: m/z=482.2. found 482.2.

Example 51

4-(5-[6-(dimethylamino)pyridin-3-yl]-8-{[(3R)-1-methylpiperidin-3-yl]methoxy}imidazo[1,2-a]pyrazin-6-yl)benzonitrile

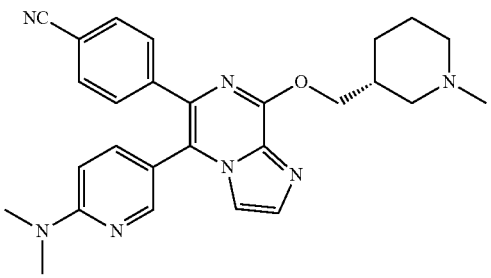

The title compound was prepared using similar procedures as described for Example 48, Step 8 with 6-(dimethylamino)pyridine-3-boronic acid (Ark Pharm, cat #AK-27114) replacing 1-[5-(4,4,5,5-tetramethyl-1,3,2-dioxaborolan-2-yl)pyridin-2-yl]pyrrolidin-2-one. The reaction mixture was purified by prep-HPLC (pH=2, acetonitrile/water+TFA) to give the desired product as the TFA salt. LC-MS calculated for $C_{27}H_{30}N_7O$ $(M+H)^+$: m/z=468.3. found 468.2.

Example 52

4-(8-{[(3R)-1-methylpiperidin-3-yl]methoxy}-5-{6-[methyl(tetrahydrofuran-2-ylmethyl)amino]pyridin-3-yl}imidazo[1,2-a]pyrazin-6-yl)benzonitrile

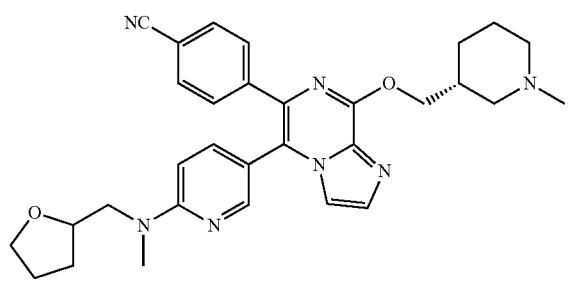 [SMILES: CN1CCC[C@@H](COc2nc(-c3ccc(C#N)cc3)c(-c3ccc(N(C)CC4CCCO4)nc3)n3ccnc23)C1]

Step 1: N-methyl-N-(tetrahydrofuran-2-ylmethyl)-5-(4,4,5,5-tetramethyl-1,3,2-dioxaborolan-2-yl)pyridin-2-amine

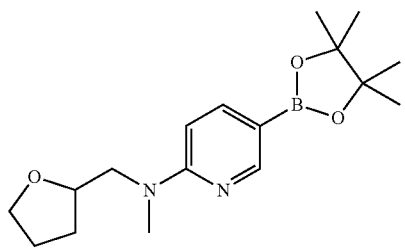 [SMILES: CN(CC1CCCO1)c1ccc(B2OC(C)(C)C(C)(C)O2)cn1]

The mixture of 2-chloro-5-(4,4,5,5-tetramethyl-1,3,2-dioxaborolan-2-yl)pyridine (Aldrich, cat #659843: 200 mg, 0.8 mmol), N-methyl-1-(tetrahydrofuran-2-yl)methanamine (ChemBridge, cat #4018249: 96 mg, 0.84 mmol) and triethylamine (240 µL, 1.7 mmol) in N,N-dimethylformamide (2 mL) was stirred at 140° C. for 2 h. The reaction mixture was cooled to room temperature then concentrated. The residue was purified by flash chromatography on a silica gel column eluting with 0 to 50% EtOAc/Hexanes to give the desired product. LC-MS calculated for $C_{17}H_{28}BN_2O_3$ $(M+H)^+$: m/z=319.2. found 319.2.

Step 2: 4-(8-{[(3R)-1-methylpiperidin-3-yl]methoxy}-5-{6-[methyl(tetrahydrofuran-2-ylmethyl)amino]pyridin-3-yl}imidazo[1,2-a]pyrazin-6-yl)benzonitrile The title compound was prepared using similar procedures as described for Example 48, Step 8 with N-methyl-N-(tetrahydrofuran-2-ylmethyl)-5-(4,4,5,5-tetramethyl-1,3,2-dioxaborolan-2-yl)pyridin-2-amine replacing 1-[5-(4,4,5,5-tetramethyl-1,3,2-dioxaborolan-2-yl)pyridin-2-yl]pyrrolidin-2-one. The reaction mixture was purified by prep-HPLC (pH=2, acetonitrile/water+TFA) to give the desired product as the TFA salt. LC-MS calculated for $C_{31}H_{36}N_7O_2$ $(M+H)^+$: m/z=538.3. found 538.3.

Example 53

4-[8-{[(3R)-1-methylpiperidin-3-yl]methoxy}-5-(1-methyl-1H-pyrrolo[2,3-b]pyridin-5-yl)imidazo[1,2-a]pyrazin-6-yl]benzonitrile

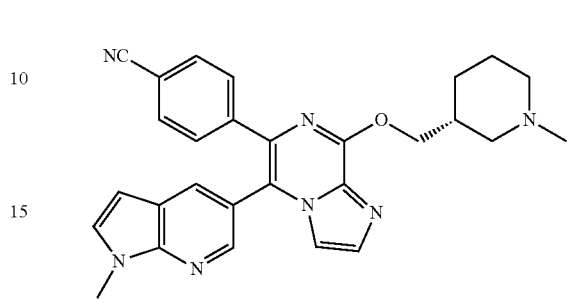

The title compound was prepared using similar procedures as described for Example 48, Step 8 with 1-methyl-5-(4,4,5,5-tetramethyl-1,3,2-dioxaborolan-2-yl)-1H-pyrrolo[2,3-b]pyridine (Combi-Blocks, cat #98552) replacing 1-[5-(4,4,5,5-tetramethyl-1,3,2-dioxaborolan-2-yl)pyridin-2-yl]pyrrolidin-2-one. The reaction mixture was purified by prep-HPLC (pH=2, acetonitrile/water+TFA) to give the desired product as the TFA salt. LC-MS calculated for $C_{28}H_{28}N_7O$ $(M+H)^+$: m/z=478.2. found 478.2.

Example 54

4-[8-{[(3R)-1-methylpiperidin-3-yl]methoxy}-5-(1-methyl-1H-pyrazolo[3,4-b]pyridin-5-yl)imidazo[1,2-a]pyrazin-6-yl]benzonitrile

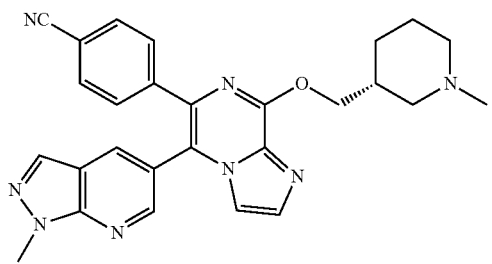 [SMILES: CN1CCC[C@@H](COc2nc(-c3ccc(C#N)cc3)c(-c3cnc4c(cnn4C)c3)n3ccnc23)C1]

The title compound was prepared using similar procedures as described for Example 48, Step 8 with 1-methyl-1H-pyrozolo[3,4-b]pyridine-5-boronic acid pinacol ester (Advanced ChemBlock, cat #I-9516) replacing 1-[5-(4,4,5,5-tetramethyl-1,3,2-dioxaborolan-2-yl)pyridin-2-yl]pyrrolidin-2-one. The reaction mixture was purified by prep-HPLC (pH=2, acetonitrile/water+TFA) to give the desired product as the TFA salt. LC-MS calculated for $C_{27}H_{28}N_8O$ $(M+H)^+$: m/z=479.2. found 479.2.

Example 55

4-(5-(1,3-benzothiazol-5-yl)-8-{[(3R)-1-methylpiperidin-3-yl]methoxy}imidazo[1,2-a]pyrazin-6-yl)benzonitrile

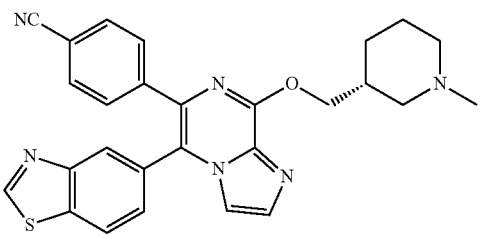 [SMILES: CN1CCC[C@@H](COc2nc(-c3ccc(C#N)cc3)c(-c3ccc4scnc4c3)n3ccnc23)C1]

The title compound was prepared using similar procedures as described for Example 48, Step 8 with 5-(4,4,5,5-tetramethyl-1,3,2-dioxaborolan-2-yl)-1,3-benzothiazole (Aldrich, cat #CDS008108) replacing 1-[5-(4,4,5,5-tetramethyl-1,3,2-dioxaborolan-2-yl)pyridin-2-yl]pyrrolidin-2-one. The reaction mixture was purified by prep-HPLC (pH=2, acetonitrile/water+TFA) to give the desired product as the TFA salt. LC-MS calculated for $C_{27}H_{25}N_6OS$ $(M+H)^+$: m/z=481.2. found 481.1.

Example 56

4-{8-{[(3S)-3-(dimethylamino)pyrrolidin-1-yl]methyl}-5-[6-(2-oxopyrrolidin-1-yl)pyridin-3-yl]imidazo[1,2-a]pyrazin-6-yl}benzonitrile

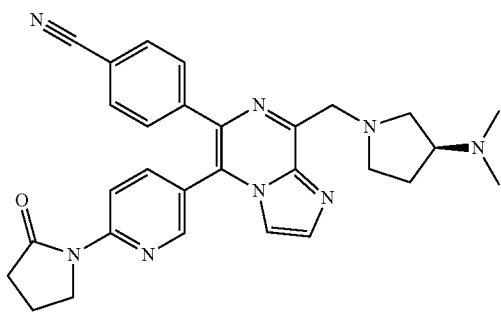 [SMILES: CN(C)[C@H]1CCN(Cc2nc(-c3ccc(C#N)cc3)c(-c3ccc(N4CCCC4=O)nc3)n3ccnc23)C1]

Step 1: 4-{8-methoxy-5-[6-(2-oxopyrrolidin-1-yl)pyridin-3-yl]imidazo[1,2-a]pyrazin-6-yl}benzonitrile

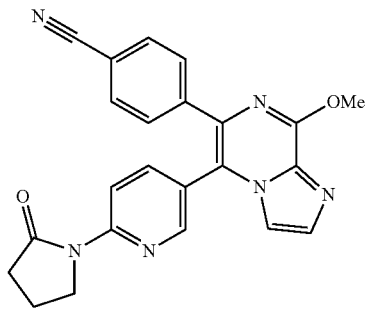 [SMILES: COc1nc(-c2ccc(C#N)cc2)c(-c2ccc(N3CCCC3=O)nc2)n2ccnc12]

The title compound was prepared using similar procedures as described for Example 48, Step 8 with 4-(5-chloro-8-methoxyimidazo[1,2-a]pyrazin-6-yl)benzonitrile (Example 48, Step 3) replacing 4-(5-chloro-8-{[(3R)-1-methylpiperidin-3-yl]methoxy}imidazo[1,2-a]pyrazin-6-yl)benzonitrile. After cooling to room temperature, the reaction mixture was concentrated and purified by column chromatography (gradient 0-90% EtOAc in hexanes) to give the desired product. LC-MS calculated for $C_{23}H_{19}N_6O_2$ $(M+H)^+$: m/z=411.2. found 411.1.

Step 2: 4-{8-hydroxy-5-[6-(2-oxopyrrolidin-1-yl)pyridin-3-yl]imidazo[1,2-a]pyrazin-6-yl}benzonitrile

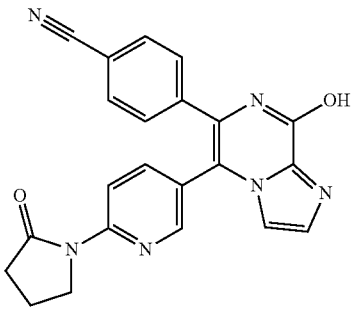 [SMILES: N#Cc1ccc(-c2nc(O)c3nccn3c2-c2ccc(N3CCCC3=O)nc2)cc1]

To a solution of 4-{8-methoxy-5-[6-(2-oxopyrrolidin-1-yl)pyridin-3-yl]imidazo[1,2-a]pyrazin-6-yl}benzonitrile (120 mg, 0.29 mmol) and sodium iodide (0.22 g, 1.5 mmol) in acetonitrile (0.6 mL) was added chlorotrimethylsilane (180 μL, 1.5 mmol). The resulting mixture was stirred at 65° C. for 3 h then cooled to room temperature. The reaction mixture was quenched with addition of a few drops of water then diluted with DCM. The precipitate was collected via filtration then dried to give the desired product as a yellow solid, which was used in the next step without further purification. LC-MS calculated for $C_{22}H_{17}N_6O_2$ $(M+H)^+$: m/z=397.1. found 397.1.

Step 3: 6-(4-cyanophenyl)-5-[6-(2-oxopyrrolidin-1-yl)pyridin-3-yl]imidazo[1,2-a]pyrazin-8-yl 4-methylbenzenesulfonate

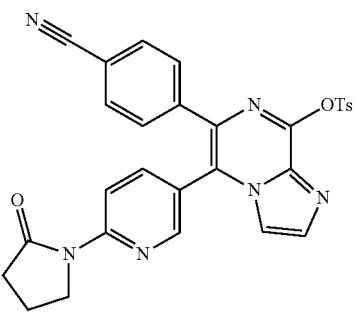 [SMILES: Cc1ccc(S(=O)(=O)Oc2nc(-c3ccc(C#N)cc3)c(-c3ccc(N4CCCC4=O)nc3)n3ccnc23)cc1]

To a solution of 4-{8-hydroxy-5-[6-(2-oxopyrrolidin-1-yl)pyridin-3-yl]imidazo[1,2-a]pyrazin-6-yl}benzonitrile (60 mg, 0.2 mmol) in methylene chloride (0.5 mL) was added triethyl amine (40 μL, 0.3 mmol) and 4-dimethylaminopyridine (4 mg, 0.03 mmol) followed by p-toluenesulfonyl chloride (38 mg, 0.20 mmol) at 0° C., then the resulting mixture was slowly warmed up and stirred at room temperature for 1 h. The reaction mixture was concentrated under reduced pressure and the residue was purified by flash chromatography on a silica gel column (gradient 0-90% EtOAc in hexanes) to afford the desired product. LC-MS calculated for $C_{29}H_{23}N_6O_4S$ (M+H)$^+$: m/z=551.2. found 551.1.

Step 4: 4-{5-[6-(2-oxopyrrolidin-1-yl)pyridin-3-yl]-8-vinylimidazo[1,2-a]pyrazin-6-yl}benzonitrile

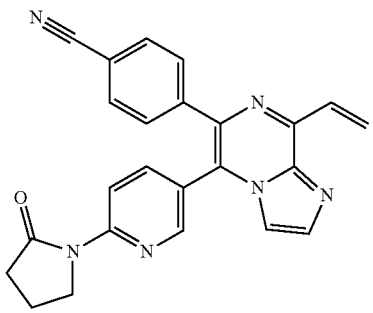 [SMILES: C=Cc1nc(-c2ccc(C#N)cc2)c(-c2ccc(N3CCCC3=O)nc2)n2ccnc12]

A degassed solution of 6-(4-cyanophenyl)-5-[6-(2-oxopyrrolidin-1-yl)pyridin-3-yl]imidazo[1,2-a]pyrazin-8-yl 4-methylbenzenesulfonate (50 mg, 0.09 mmol), 4,4,5,5-tetramethyl-2-vinyl-1,3,2-dioxaborolane (20 µL, 0.12 mmol), dichloro[1,1'-bis(dicyclohexylphosphino)ferrocene]palladium(II) (7 mg, 0.009 mmol), potassium phosphate (80 mg, 0.4 mmol) in a mixed solvent of 1,4-dioxane (6 mL) and water (1 mL) was heated at 90° C. in a sealed vial for 2 h. After cooling to room temperature, the mixture was concentrated and purified by flash chromatography on a silica gel column (gradient 0-80% EtOAc in hexanes) to afford the desired product. LC-MS calculated for $C_{24}H_{19}N_6O$ (M+H)$^+$: m/z=407.2. found 407.2.

Step 5: 4-{8-formyl-5-[6-(2-oxopyrrolidin-1-yl)pyridin-3-yl]imidazo[1,2-a]pyrazin-6-yl}benzonitrile

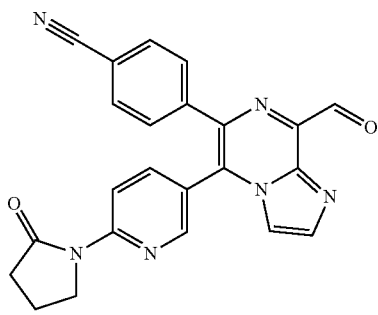 [SMILES: N#Cc1ccc(-c2nc(C=O)c3nccn3c2-c2ccc(N3CCCC3=O)nc2)cc1]

Osmium tetraoxide in water (0.16 M, 0.05 mL, 0.008 mmol) was added to a mixture of 4-{5-[6-(2-oxopyrrolidin-1-yl)pyridin-3-yl]-8-vinylimidazo[1,2-a]pyrazin-6-yl}benzonitrile (31 mg, 0.076 mmol), sodium metaperiodate (80 mg, 0.4 mmol) in tetrahydrofuran (0.8 mL) and water (0.1 mL). The resulting mixture was heated to 70° C. and stirred for 2 h. The mixture was cooled to room temperature then diluted with methylene chloride, washed with saturated NaHCO$_3$, water, brine then dried over Na$_2$SO$_4$. After filtration, the mixture was concentrated and the residue was used for next step without further purification. LC-MS calculated for $C_{23}H_{17}N_6O_2$ (M+H)$^+$: m/z=409.1. found 409.2.

Step 6: 4-{8-{[(3S)-3-(dimethylamino)pyrrolidin-1-yl]methyl}-5-[6-(2-oxopyrrolidin-1-yl)pyridin-3-yl]imidazo[1,2-a]pyrazin-6-yl}benzonitrile

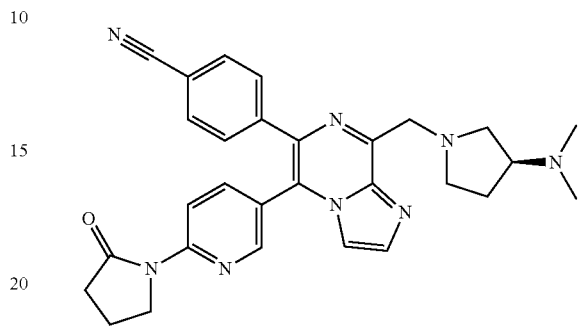

To a stirred solution of 4-{8-formyl-5-[6-(2-oxopyrrolidin-1-yl)pyridin-3-yl]imidazo[1,2-a]pyrazin-6-yl}benzonitrile (15 mg, 0.038 mmol) in methylene chloride (1 mL) was added (3S)—N,N-dimethylpyrrolidin-3-amine (Aldrich cat #656704, 10 µL, 0.08 mmol) and the mixture was stirred at room temperature for 10 min. Then sodium triacetoxyborohydride (20 mg, 0.1 mmol) was added to the reaction mixture and stirred for another 2 h. Then the reaction mixture was concentrated and purified by prep-HPLC (pH=2, acetonitrile/water+TFA) to give the desired product as the TFA salt. LC-MS calculated for $C_{29}H_{31}N_8O$ (M+H)$^+$: m/z=507.3. found 507.2.

Example 57

4-{8-[4-(dimethylamino)piperidin-1-yl]-5-[6-(2-oxopyrrolidin-1-yl)pyridin-3-yl]imidazo[1,2-a]pyrazin-6-yl}benzonitrile

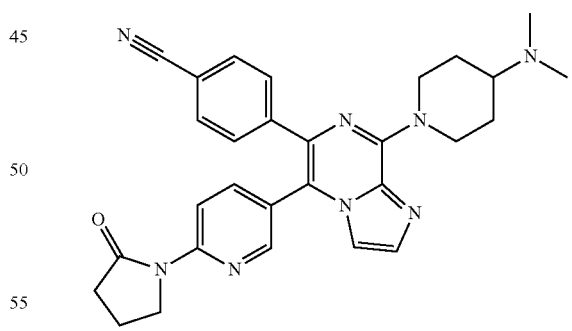

To a solution of 4-{8-hydroxy-5-[6-(2-oxopyrrolidin-1-yl)pyridin-3-yl]imidazo[1,2-a]pyrazin-6-yl}benzonitrile (Example 56, Step 2, 110 mg, 0.28 mmol) in methylene chloride (0.9 mL, 10 mmol) was added triethylamine (80 µL, 0.6 mmol) and 4-dimethylaminopyridine (7 mg, 0.06 mmol) followed by p-toluenesulfonyl chloride (69 mg, 0.36 mmol). The mixture was stirred at room temperature for 1 h. Then the reaction mixture was concentrated and the residue was treated with triethylamine (200 µL) and N,N-dimethylpiperidin-4-amine (Alfa Aesar cat #L20176, 80 µL). The resulting mixture was stirred at room temperature for 4 h. The reaction mixture was purified by prep-HPLC (pH=2, acetonitrile/water+TFA) to give the desired product as the TFA salt. LC-MS calculated for $C_{29}H_{31}N_5O$ (M+H)$^+$: m/z=507.3. found 507.3. $^1$H NMR (600 MHz, CD$_3$OD) δ 8.52 (d, J=8.7 Hz, 1H), 8.20 (d, J=1.8 Hz, 1H), 7.90 (dd, J=8.7, 2.4 Hz, 1H), 7.62-7.58 (m, 3H), 7.55-7.50 (m, 3H), 5.78-5.68 (m, 2H), 4.13-4.09 (m, 2H), 3.63-3.55 (m, 1H), 3.21-3.13 (m, 2H), 2.91 (s, 6H), 2.69 (t, J=8.1 Hz, 2H), 2.26-2.20 (m, 2H), 2.20-2.13 (m, 2H), 1.91-1.81 (m, 2H).

Example 58

4-[8-[4-(dimethylamino)piperidin-1-yl]-5-(1-methyl-1H-pyrazolo[3,4-b]pyridin-5-yl)imidazo[1,2-a]pyrazin-6-yl]benzonitrile

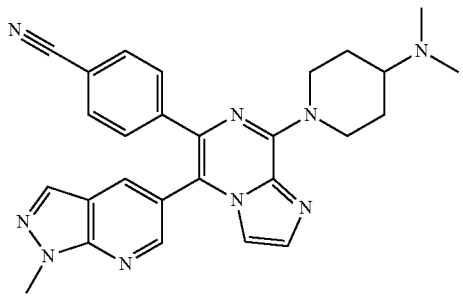 [SMILES: CN(C)C1CCN(c2nc(-c3ccc(C#N)cc3)c(-c3cnc4c(cnn4C)c3)n3ccnc23)CC1]

Step 1:
4-(5-amino-3-chloropyrazin-2-yl)benzonitrile

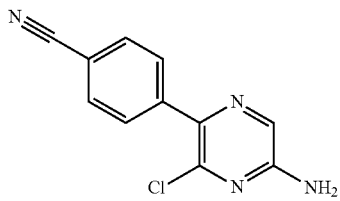 [SMILES: N#Cc1ccc(-c2ncc(N)nc2Cl)cc1]

Dichloro(bis {di-tert-butyl[4-(dimethylamino)phenyl]phosphoranyl})palladium (150 mg, 0.22 mmol) was added to a mixture of 5-bromo-6-chloropyrazin-2-amine (J&W, cat #65R0236: 1.51 g, 7.24 mmol), (4-cyanophenyl)boronic acid (1.08 g, 7.39 mmol), sodium carbonate (1.54 g, 14.5 mmol) in 1,4-dioxane (17.4 mL) and water (2.9 mL). The mixture was degassed with N$_2$ then stirred at 90° C. for 2 h in a sealed vial. After cooling, the reaction mixture was diluted with water (100 mL). The precipitate was collected by filtration and purified by column chromatography (gradient 0-100% EtOAc/Hexanes followed by 20% MeOH in EtOAc). LC-MS calculated for $C_{11}H_5ClN_4$ (M+H)$^+$: m/z=231.0. found 231.0.

Step 2: 4-(5-amino-6-bromo-3-chloropyrazin-2-yl)benzonitrile

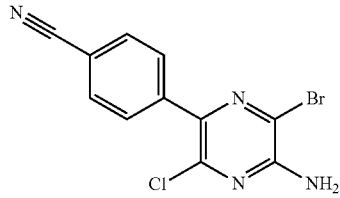 [SMILES: N#Cc1ccc(-c2nc(Br)c(N)nc2Cl)cc1]

N-Bromosuccinimide (620 mg, 3.5 mmol) in THF (2 mL) was added slowly to a solution of 4-(5-amino-3-chloropyrazin-2-yl)benzonitrile (0.73 g, 3.2 mmol) in N,N-dimethylformamide (12 mL) at 0° C. and then the reaction mixture was stirred at this temperature for 1 h. The mixture was diluted with saturated NaHCO$_3$ aqueous solution (50 mL) and the precipitate was collected via filtration then washed with water and dried under vacuum to afford the desired compound which was used in the next step without further purification. LC-MS calculated for $C_{11}H_7BrClN_4$ (M+H)$^+$: m/z=308.9. found 308.9.

Step 3. 4-(5,8-dichloroimidazo[1,2-a]pyrazin-6-yl)benzonitrile

Chloroacetaldehyde in water (2.4 mL, 18 mmol, 7.5 M) was added to a mixture of 4-(5-amino-6-bromo-3-chloropyrazin-2-yl)benzonitrile (0.8 g, 2 mmol) in isopropyl alcohol (6.3 mL) and the resulting mixture was stirred at 100° C. for 5 h. The mixture was cooled to room temperature then concentrated. The residue was dissolved in ethyl acetate then washed with saturated NaHCO$_3$, water and brine. The organic layer was dried over Na$_2$SO$_4$, filtered and concentrated under reduced pressure. The residue was purified by flash chromatography on a silica gel column eluting with 0 to 70% ethyl acetate in hexane to afford the desired product (610 mg, 80%). LC-MS calculated for $C_{13}H_7Cl_2N_4$ (M+H)$^+$: m/z=289.0. found 289.0.

Step 4: 4-(5-chloro-8-(4-(dimethylamino)piperidin-1-yl)imidazo[1,2-a]pyrazin-6-yl)benzonitrile

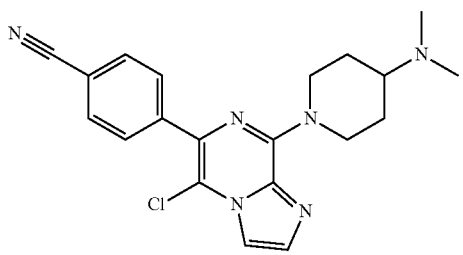 [SMILES: CN(C)C1CCN(c2nc(-c3ccc(C#N)cc3)c(Cl)n3ccnc23)CC1]

To a mixture of N,N-diisopropylethylamine (890 μL, 5.1 mmol) and 4-(5,8-dichloroimidazo[1,2-a]pyrazin-6-yl)benzonitrile (850 mg, 2.9 mmol) in acetonitrile (20 mL) was added N,N-dimethylpiperidin-4-amine (720 μL, 5.1 mmol). The reaction was stirred at room temperature for 30 min, then heated at 60° C. for 3 h. After cooling to room temperature, the reaction mixture was concentrated, and purified by column chromatography (gradient 0-60% MeOH in DCM) to afford the desired product (503 mg, 46%). LC-MS calculated for $C_{20}H_{22}ClN_6$ (M+H)$^+$: m/z=381.1. found 381.1. $^1$H NMR (400 MHz, CD$_3$OD) δ 8.07 (d, J=1.2 Hz, 1H), 8.00 (d, J=8.5 Hz, 2H), 7.84 (d, J=8.5 Hz, 2H), 7.71 (d, J=1.1 Hz, 1H), 5.77-5.61 (m, 2H), 3.65-3.50 (m, 1H), 3.14 (t, J=12.2 Hz, 2H), 2.90 (s, 6H), 2.27-2.11 (m, 2H), 1.90-1.73 (m, 2H).

Step 5: 4-[8-[4-(dimethylamino)piperidin-1-yl]-5-(1-methyl-1H-pyrazolo[3,4-b]pyridin-5-yl)imidazo[1,2-a]pyrazin-6-yl]benzonitrile A degassed solution of 4-{5-chloro-8-[4-(dimethylamino)piperidin-1-yl]imidazo[1,2-a]pyrazin-6-yl}benzonitrile (10 mg, 0.03 mmol), 1-methyl-5-(4,4,5,5-tetramethyl-1,3,2-dioxaborolan-2-yl)-1H-pyrazolo[3,4-b]pyridine (Advance ChemBlocks, cat #I-9516: 8.8 mg, 0.034 mmol), potassium phosphate (20 mg, 0.1 mmol) and dichloro[1,1'-bis(dicyclohexylphosphino)ferrocene]palladium(II) (2 mg, 0.003 mmol) in a mixed solvent of 1,4-dioxane (1 mL) and water (0.15 mL) was heated in a sealed vial at 90° C. for 2 h. After cooling to room temperature, the mixture was concentrated, diluted with MeOH, filtered then purified by prep-HPLC (pH=2, acetonitrile/water+TFA) to give the desired product as the TFA salt. LC-MS calculated for $C_{27}H_{28}N_9$ (M+H)$^+$: m/z=478.2. found 478.2.

Example 59

4-[8-[4-(dimethylamino)piperidin-1-yl]-5-(3-methyl-2-oxo-2,3-dihydro-1,3-benzoxazol-6-yl)imidazo[1,2-a]pyrazin-6-yl]benzonitrile

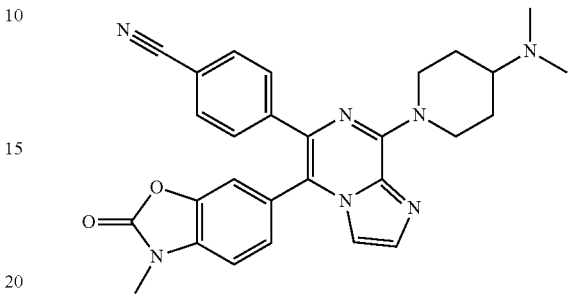

Step 1: 3-methyl-6-(4,4,5,5-tetramethyl-1,3,2-dioxaborolan-2-yl)-1,3-benzoxazol-2(3H)-one

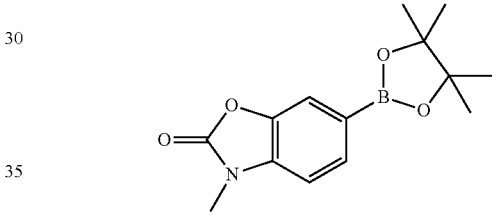

A mixture of 6-bromo-3-methyl-1,3-benzoxazol-2(3H)-one (Acros Organics, cat #43271: 0.5 g, 2 mmol), 4,4,5,5,4',4',5',5'-octamethyl-[2,2']bi[[1,3,2]dioxaborolanyl](0.84 g, 3.3 mmol), [1,1'-bis(diphenylphosphino)ferrocene]dichloropalladium(II) complex with dichloromethane (1:1) (90 mg, 0.1 mmol) and potassium acetate (0.64 g, 6.6 mmol) in 1,4-dioxane (20 mL) was degassed and heated at 90° C. overnight. After cooling to room temperature, the reaction mixture was concentrated. The residue was purified by flash column chromatography eluting with 0 to 25% AcOEt in Hexanes to give the desired product. LC-MS calculated for $C_{14}H_{19}BNO_4$ (M+H)$^+$: m/z=276.1. found 276.1.

Step 2: 4-[8-[4-(dimethylamino)piperidin-1-yl]-5-(3-methyl-2-oxo-2,3-dihydro-1,3-benzoxazol-6-yl)imidazo[1,2-a]pyrazin-6-yl]benzonitrile The title compound was prepared using similar procedures as described for Example 58, Step 5 with 3-methyl-6-(4,4,5,5-tetramethyl-1,3,2-dioxaborolan-2-yl)-1,3-benzoxazol-2(3H)-one replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{28}H_{28}N_7O_2$ (M+H)$^+$: m/z=494.2. found 494.2.

Example 60

4-[8-[4-(dimethylamino)piperidin-1-yl]-5-(4-methyl-3-oxo-3,4-dihydro-2H-1,4-benzoxazin-7-yl)imidazo[1,2-a]pyrazin-6-yl]benzonitrile

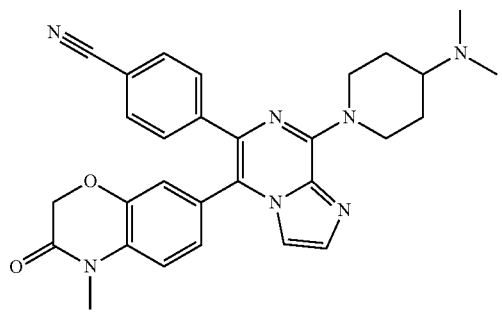 [SMILES: CN1C(=O)COc2cc(-c3c(-c4ccc(C#N)cc4)nc(N4CCC(N(C)C)CC4)c4nccn34)ccc21]

Step 1: 4-methyl-7-(4,4,5,5-tetramethyl-1,3,2-dioxaborolan-2-yl)-2H-1,4-benzoxazin-3(4H)-one

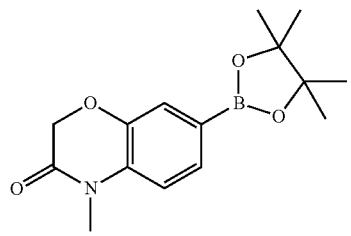 [SMILES: CN1C(=O)COc2cc(B3OC(C)(C)C(C)(C)O3)ccc21]

To a mixture of 7-(4,4,5,5-tetramethyl-1,3,2-dioxaborolan-2-yl)-2H-1,4-benzoxazin-3(4H)-one (Combi-Blocks, cat #FM-4852: 0.3 g, 1 mmol) and potassium carbonate (150 mg, 1.1 mmol) in acetone (5 mL) was added methyl iodide (0.20 mL, 3.3 mmol). The reaction mixture was stirred at 80° C. overnight then cooled to room temperature and concentrated. The residue was dissolved in EtOAc, washed with water and brine. The organic layer was dried over $Na_2SO_4$ and concentrated. The residue was used in the next step without further purification. LC-MS calculated for $C_{15}H_{21}BNO_4$ $(M+H)^+$: m/z=290.2. found 290.2.

Step 2: 4-[8-[4-(dimethylamino)piperidin-1-yl]-5-(4-methyl-3-oxo-3,4-dihydro-2H-1,4-benzoxazin-7-yl)imidazo[1,2-a]pyrazin-6-yl]benzonitrile The title compound was prepared using similar procedures as described for Example 58, Step 5 with 4-methyl-7-(4,4,5,5-tetramethyl-1,3,2-dioxaborolan-2-yl)-2H-1,4-benzoxazin-3(4H)-one replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{29}H_{30}N_7O_2$ $(M+H)^+$: m/z=508.2. found 508.2.

Example 61

4-[8-{[(3R)-1-ethylpiperidin-3-yl]methoxy}-5-(1-methyl-1H-pyrrolo[2,3-b]pyridin-5-yl)imidazo[1,2-a]pyrazin-6-yl]benzonitrile

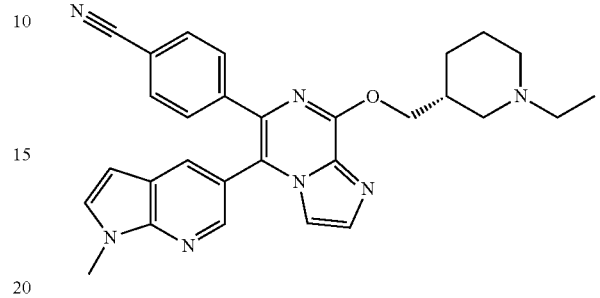

Step 1: 4-(5-chloro-8-{[(3R)-1-ethylpiperidin-3-yl]methoxy}imidazo[1,2-a]pyrazin-6-yl)benzonitrile

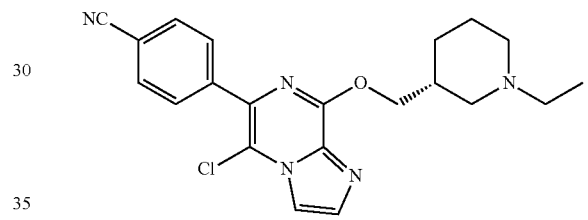

To a solution of tert-butyl (3R)-3-({[5-chloro-6-(4-cyanophenyl)imidazo[1,2-a]pyrazin-8-yl]oxy}methyl)piperidine-1-carboxylate (Example 48, Step 5: 20 mg, 0.03 mmol) in methylene chloride (52 μL) was added trifluoroacetic acid (52 μL). The mixture was stirred at room temperature for 1 h then concentrated. The residue was dissolved in methylene chloride (0.3 mL) then acetaldehyde (9 μL, 0.2 mmol) and sodium triacetoxyborohydride (10 mg, 0.07 mmol) were added subsequently to the reaction mixture. The mixture was allowed to stir for 2 h at room temperature. The mixture was concentrated and purified by flash chromatography eluting with 0 to 40% MeOH in DCM to give the desired product. LC-MS calculated for $C_{21}H_{23}ClN_5O$ $(M+H)^+$: m/z=396.2. found 396.1.

Step 2: 4-[8-{[(3R)-1-ethylpiperidin-3-yl]methoxy}-5-(1-methyl-1H-pyrrolo[2,3-b]pyridin-5-yl)imidazo[1,2-a]pyrazin-6-yl]benzonitrile The title compound was prepared using similar procedures as described for Example 53 with 4-(5-chloro-8-{[(3R)-1-ethylpiperidin-3-yl]methoxy}imidazo[1,2-a]pyrazin-6-yl)benzonitrile replacing 4-(5-chloro-8-{[(3R)-1-methylpiperidin-3-yl]methoxy}imidazo[1,2-a]pyrazin-6-yl)benzonitrile. The reaction mixture was purified by prep-HPLC (pH=2, acetonitrile/water+TFA) to give the desired product as the TFA salt. LC-MS calculated for $C_{29}H_{30}N_7O$ $(M+H)^+$: m/z=492.3. found 492.2.

Example 62

4-[8-[4-(dimethylamino)piperidin-1-yl]-5-(5-fluoro-3-methyl-2-oxo-2,3-dihydro-1,3-benzoxazol-6-yl)imidazo[1,2-a]pyrazin-6-yl]benzonitrile

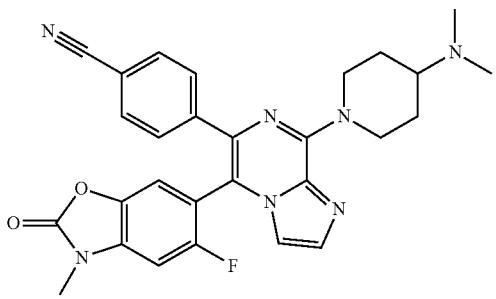 [SMILES: CN(C)C1CCN(c2nc(-c3ccc(C#N)cc3)c(-c3cc4oc(=O)n(C)c4cc3F)n3ccnc23)CC1]

Step 1: 6-bromo-5-fluoro-1,3-benzoxazol-2(3H)-one

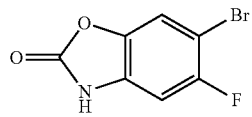 [SMILES: O=c1[nH]c2cc(F)c(Br)cc2o1]

To a mixture of 2-amino-5-bromo-4-fluorophenol (0.3 g, 1 mmol) [Synquest Labs, cat #4656-B-15] and triethylamine (1.0 mL, 7.3 mmol) in tetrahydrofuran (20 mL) at 0° C. was added triphosgene (0.52 g, 1.7 mmol). The mixture was stirred for 1 h, then 1.0 M sodium hydroxide in water (2.9 mL, 2.9 mmol) was added to the reaction mixture. The mixture was stirred at room temperature for another hour then diluted with EtOAc, washed with water and brine. The organic layer was dried over $Na_2SO_4$ and the solvents were removed under reduced pressure. The residue was used for next step directly without purification.

Step 2: 6-bromo-5-fluoro-3-methyl-1,3-benzoxazol-2(3H)-one

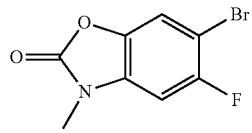

A mixture of 6-bromo-5-fluoro-1,3-benzoxazol-2(3H)-one (crude product from Step 1), potassium carbonate (0.4 g, 3 mmol) and methyl iodide (0.2 mL, 3 mmol) in acetone (5 mL) was heated at 80° C. overnight. The reaction mixture was cooled to room temperature then concentrated. The residue was dissolved in EtOAc then washed with water and brine. The organic layer was dried over $Na_2SO_4$, filtered then concentrated. The residue was purified by flash chromatography on a silica gel column eluting with 0 to 25% EtOAc in Hexanes. LC-MS calculated for $C_8H_6BrFNO_2$ $(M+H)^+$: m/z=246.0. found 245.9.

Step 3: 5-fluoro-3-methyl-6-(4,4,5,5-tetramethyl-1,3,2-dioxaborolan-2-yl)-1,3-benzoxazol-2(3H)-one

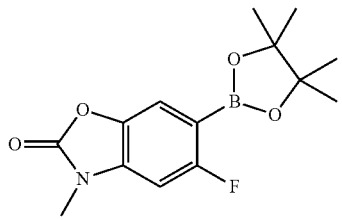 [SMILES: Cn1c(=O)oc2cc(B3OC(C)(C)C(C)(C)O3)c(F)cc21]

A mixture of 6-bromo-5-fluoro-3-methylbenzo[d]oxazol-2(3H)-one (290 mg, 1.2 mmol), 4,4,5,5,4',4',5',5'-octamethyl-[2,2']bi[[1,3,2]dioxaborolanyl](450 mg, 1.8 mmol), [1,1'-bis(diphenylphosphino)ferrocene]dichloropalladium (II) complexed with dichloromethane (1:1) (50 mg, 0.06 mmol), potassium acetate (350 mg, 3.5 mmol) in 1,4-dioxane (10 mL) was purged with nitrogen and heated at 90° C. for 5 h. After cooling to room temperature, the reaction mixture was concentrated and the residue was purified by column chromatography eluting with 0 to 30% EtOAc in hexanes to give the desired product. LC-MS calculated for $C_{14}H_{18}BFNO_4$ $(M+H)^+$: m/z=294.1. found 294.1.

Step 4: 4-[8-[4-(dimethylamino)piperidin-1-yl]-5-(5-fluoro-3-methyl-2-oxo-2,3-dihydro-1,3-benzoxazol-6-yl)imidazo[1,2-a]pyrazin-6-yl]benzonitrile The title compound was prepared using similar procedures as described for Example 58, Step 5 with 5-fluoro-3-methyl-6-(4,4,5,5-tetramethyl-1,3,2-dioxaborolan-2-yl)benzo[d]oxazol-2(3H)-one replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{28}H_{27}FN_7O_2$ $(M+H)^+$: m/z=512.2. found 512.2.

Example 63

4-[8-{[(3R)-1-ethylpiperidin-3-yl]methoxy}-5-(3-methyl-2-oxo-2,3-dihydro-1,3-benzoxazol-6-yl)imidazo[1,2-a]pyrazin-6-yl]benzonitrile

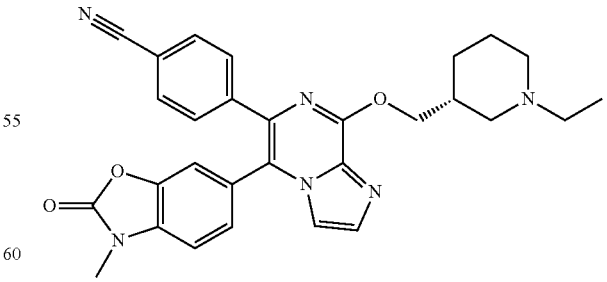

The title compound was prepared using similar procedures as described for Example 59, Step 2 with 4-(5-chloro-8-{[(3R)-1-ethylpiperidin-3-yl]methoxy}imidazo[1,2-a]pyrazin-6-yl)benzonitrile (Example 61, Step 1) replacing 4-(5-chloro-8-(4-(dimethylamino)piperidin-1-yl)imidazo[1, 2-a]pyrazin-6-yl)benzonitrile. The reaction mixture was purified by prep-HPLC (pH=2, acetonitrile/water+TFA) to give the desired product as the TFA salt. LC-MS calculated for $C_{29}H_{29}N_6O_3$ (M+H)$^+$: m/z=509.2. found 509.2.

Example 64

4-[8-{[(3R)-1-(2-cyanoethyl)piperidin-3-yl]methoxy}-5-(3-methyl-2-oxo-2,3-dihydro-1,3-benzoxazol-6-yl)imidazo[1,2-a]pyrazin-6-yl]benzonitrile

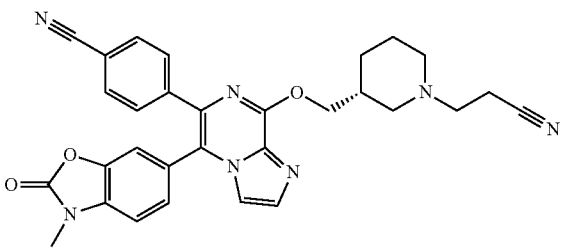 [SMILES: Cn1c(=O)oc2cc(-c3c(-c4ccc(C#N)cc4)nc(OC[C@@H]4CCCN(CCC#N)C4)c4nccn34)ccc21]

Step 1: 4-(5-chloro-8-{[(3R)-1-(2-cyanoethyl)piperidin-3-yl]ethoxy}imidazo[1,2-a]pyrazin-6-yl)benzonitrile

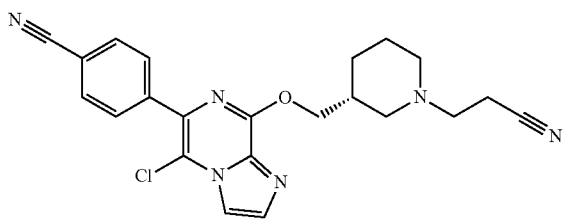 [SMILES: N#CCCN1CCC[C@@H](COc2nc(-c3ccc(C#N)cc3)c(Cl)n3ccnc23)C1]

To a solution of tert-butyl (3R)-3-({[5-chloro-6-(4-cyanophenyl)imidazo[1,2-a]pyrazin-8-yl]oxy}methyl)piperidine-1-carboxylate (Example 48, Step 5: 120 mg, 0.26 mmol) in methylene chloride (400 μL) was added trifluoroacetic acid (400 μL). The mixture was stirred at room temperature for 1 h. After concentration to remove most of the acid, 1,8-diazabicyclo[5.4.0]undec-7-ene (10 μL, 0.07 mmol) and 2-propenenitrile (800 μL, 10 mmol) were added to the resulting residue. Then the mixture was allowed to stir overnight at room temperature. The mixture was concentrated and purified by flash chromatograph on a silica gel column eluting with 0-60% EtOAc in Hexanes to give the desired product. LC-MS calculated for $C_{22}H_{22}ClN_6O$ (M+H)$^+$: m/z=421.2. found 421.2.

Step 2: 4-[8-{[(3R)-1-(2-cyanoethyl)piperidin-3-yl]methoxy}-5-(3-methyl-2-oxo-2,3-dihydro-1,3-benzoxazol-6-yl)imidazo[1,2-a]pyrazin-6-yl]benzonitrile A degassed solution of 4-(5-chloro-8-{[(3R)-1-(2-cyanoethyl)piperidin-3-yl]methoxy}imidazo[1,2-a]pyrazin-6-yl)benzonitrile (10 mg, 0.03 mmol), 3-methyl-6-(4,4,5,5-tetramethyl-1,3,2-dioxaborolan-2-yl)-1,3-benzoxazol-2(3H)-one (Example 59, Step 1: 9.4 mg, 0.034 mmol), potassium phosphate (20 mg, 0.1 mmol), dichloro[1,1'-bis(dicyclohexylphosphino)ferrocene]palladium(II) (2 mg, 0.003 mmol) in 1,4-dioxane (0.9 mL) and water (0.2 mL) was heated in a sealed vial at 90° C. for 2 h. After cooling to room temperature, the mixture was concentrated, diluted with MeOH and filtered. The filtrate was purified by prep-HPLC (pH=2, acetonitrile/water+TFA) to give the desired product as the TFA salt. LC-MS calculated for $C_{30}H_{28}N_7O_3$ (M+H)$^+$: m/z=534.2. found 534.2.

Example 65

4-[8-{[(3R)-1-(2-hydroxyethyl)piperidin-3-yl]methoxy}-5-(1-methyl-1H-indazol-5-yl)imidazo[1,2-a]pyrazin-6-yl]benzonitrile

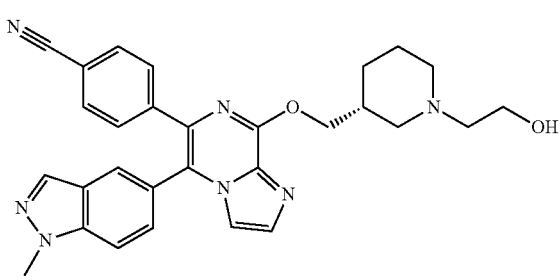 [SMILES: Cn1ncc2cc(-c3c(-c4ccc(C#N)cc4)nc(OC[C@@H]4CCCN(CCO)C4)c4nccn34)ccc21]

Step 1: 4-(5-chloro-8-{[(3R)-1-(2-hydroxyethyl)piperidin-3-yl]methoxy}imidazo[1,2-a]pyrazin-6-yl)benzonitrile

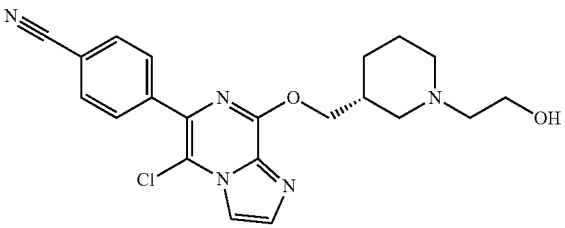 [SMILES: N#Cc1ccc(-c2nc(OC[C@@H]3CCCN(CCO)C3)c3nccn3c2Cl)cc1]

To a solution of tert-butyl (3R)-3-({[5-chloro-6-(4-cyanophenyl)imidazo[1,2-a]pyrazin-8-yl]oxy}methyl)piperidine-1-carboxylate (Example 48, Step 5: 200 mg, 0.4 mmol) in methylene chloride (660 μL) was added trifluoroacetic acid (660 μL). The mixture was stirred at room temperature for 1 h. Then the mixture was concentrated and the residue was mixed with triethylamine (1 mL) followed by addition of 2-bromoethanol (120 μL, 1.7 mmol). The resulting mixture was stirred at room temperature overnight and then concentrated in vacuo. The residue was purified by flash chromatography on a silica gel column eluting with 0 to 40% MeOH in DCM to give the desired product. LC-MS calculated for $C_{21}H_{23}ClN_5O_2$ (M+H)$^+$: m/z=412.2. found 412.1.

Step 2: 4-[8-{[(3R)-1-(2-hydroxyethyl)piperidin-3-yl]methoxy}-5-(1-methyl-H-indazol-5-yl)imidazo[1,2-a]pyrazin-6-yl]benzonitrile A mixture of 4-(5-chloro-8-{[(3R)-1-(2-hydroxyethyl)piperidin-3-yl]methoxy}imidazo[1,2-a]pyrazin-6-yl)benzonitrile (10 mg, 0.03 mmol), (1-methyl-1H-indazol-5-yl)boronic acid (6.0 g, 0.034 mmol), potassium phosphate (20 mg, 0.1 mmol) and dichloro[1,1'-bis(dicyclohexylphosphino)ferrocene]palladium(II) (2 mg, 0.003 mmol) in 1,4-dioxane (0.9 mL) and water (0.2 mL) was purged with nitrogen then stirred in a sealed vial at 90° C. for 2 h. After cooling to room temperature, the mixture was concentrated, diluted with MeOH and filtered. The filtrate was purified by prep-HPLC (pH=2, acetonitrile/water+TFA) to give the desired product as the TFA salt. LC-MS calculated for $C_{29}H_{30}N_7O_2$ (M+H)$^+$: m/z=508.2. found 508.2.

Example 66

4-[8-[4-(dimethylamino)piperidin-1-yl]-5-(3-methyl-2-oxo-2,3-dihydro[1,3]oxazolo[4,5-b]pyridin-6-yl)imidazo[1,2-a]pyrazin-6-yl]benzonitrile

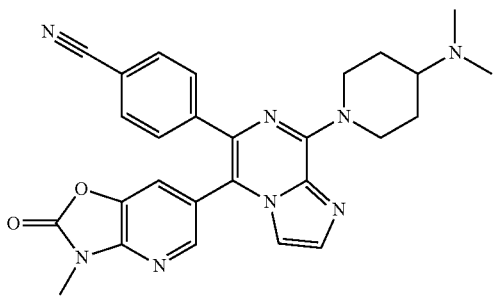 [SMILES: CN(C)C1CCN(c2nc(-c3ccc(C#N)cc3)c(-c3cnc4c(c3)oc(=O)n4C)n3ccnc23)CC1]

Step 1: 6-bromo-3-methyl-[1,3]oxazolo[4,5-b]pyridin-2(3H)-one

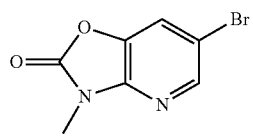

To a solution of 6-bromo[1,3]oxazolo[4,5-b]pyridin-2(3H)-one (Ark Pharm, cat #AK-24539: 0.394 g, 1.83 mmol) in N,N-dimethylformamide (5 mL) at −40° C. was added sodium hydride (60 wt % in mineral oil, 290 mg, 7.3 mmol). The resulting mixture was stirred at −40° C. for 1 hour then methyl iodide (1.14 mL, 18.3 mmol) was added dropwise. The reaction mixture was stirred at −40° C. for another 2 hours, then warmed to 0° C. and quenched by saturated NH$_4$Cl aqueous solution. The mixture was extracted with EtOAc, then DCM/iPrOH (2:1). The combined extracts were dried over Na$_2$SO$_4$, filtered and concentrated. The residue was used in the next step without further purification. LC-MS calculated for $C_7H_6BrN_2O_2$ (M+H)$^+$: m/z=229.0. found 229.0.

Step 2: 3-methyl-6-(4,4,5,5-tetramethyl-1,3,2-dioxaborolan-2-yl)[1,3]oxazolo[4,5-b]pyridin-2(3H)-one

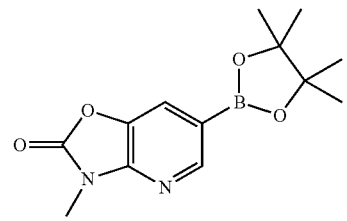 [SMILES: Cn1c(=O)oc2cc(B3OC(C)(C)C(C)(C)O3)cnc21]

A mixture of 6-bromo-3-methyl[1,3]oxazolo[4,5-b]pyridin-2(3H)-one (0.15 g, 0.66 mmol), 4,4,5,5,4',4',5',5'-octamethyl-[2,2']bi[[1,3,2]dioxaborolanyl](250 mg, 0.98 mmol), [1,1'-bis(diphenylphosphino)ferrocene]dichloropalladium(II) complex with dichloromethane (1:1) (30 mg, 0.03 mmol) and potassium acetate (190 mg, 2.0 mmol) in 1,4-dioxane (6 mL) was purged with nitrogen then heated at 90° C. overnight. After cooling to room temperature, the reaction mixture was concentrated. The crude material was purified by flash chromatography on a silica gel column eluting with 0 to 5% MeOH in DCM to give the desired product. LC-MS calculated for $C_{13}H_{18}BN_2O_4$ (M+H)$^+$: m/z=277.1. found 277.1.

Step 3: 4-[8-[4-(dimethylamino)piperidin-1-yl]-5-(3-methyl-2-oxo-2,3-dihydro[1,3]oxazolo[4,5-b]pyridin-6-yl)imidazo[1,2-a]pyrazin-6-yl]benzonitrile The title compound was prepared using similar procedures as described for Example 58, Step 5 with 3-methyl-6-(4,4,5,5-tetramethyl-1,3,2-dioxaborolan-2-yl)[1,3]oxazolo[4,5-b]pyridin-2(3H)-one replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{27}H_{27}N_8O_2$ (M+H)$^+$: m/z=495.2. found 495.2. $^1$H NMR (600 MHz, CD$_3$OD) δ 7.95 (d, J=1.7 Hz, 1H), 7.75 (d, J=1.7 Hz, 1H), 7.62-7.58 (m, 3H), 7.57-7.53 (m, 3H), 5.80-5.69 (m, 2H), 3.65-3.54 (m, 1H), 3.46 (s, 3H), 3.20-3.14 (m, 2H), 2.92 (s, 6H), 2.27-2.20 (m, 2H), 1.91-1.81 (m, 2H).

Example 67

4-{8-[4-(dimethylamino)piperidin-1-yl]-5-[6-(2-oxo-1,3-oxazolidin-3-yl)pyridin-3-yl]imidazo[1,2-a]pyrazin-6-yl}benzonitrile

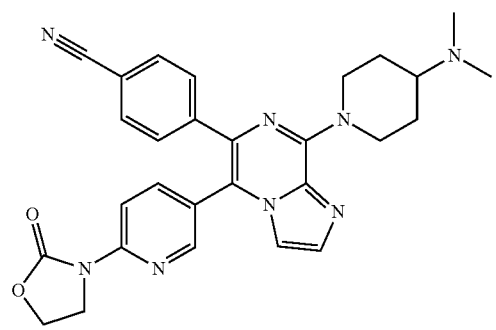 [SMILES: CN(C)C1CCN(c2nc(-c3ccc(C#N)cc3)c(-c3ccc(N4CCOC4=O)nc3)n3ccnc23)CC1]

Step 1:
3-(5-bromopyridin-2-yl)-1,3-oxazolidin-2-one

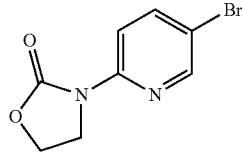 [SMILES: O=C1OCCN1c1ccc(Br)cn1]

To a solution of oxazolidin-2-one (183 mg, 2.10 mmol) in N,N-dimethylformamide (2.1 mL) at 0° C. was added sodium hydride (83.9 g, 2.10 mmol) in portions. The mixture was stirred for 30 min at room temperature then a solution of 5-bromo-2-fluoropyridine (Aldrich cat #520438, 0.216 mL, 2.10 mmol) in N,N-dimethylformamide (0.42 mL) was added dropwise. The resulting mixture was stirred overnight at room temperature then heated at 80° C. for 1.5 h. The reaction mixture was cooled to room temperature, quenched by methanol and water then extracted with dichloromethane. The combined extracts were dried over $Na_2SO_4$, filtered and concentrated. The residue was purified by flash chromatography on a silica column eluting with 0 to 50% ethyl acetate in hexanes to afford the desired product. LC-MS calculated for $C_8H_8BrN_2O_2$ $(M+H)^+$: m/z=243.0. found 243.0.

Step 2: 3-[5-(4,4,5,5-tetramethyl-1,3,2-dioxaborolan-2-yl)pyridin-2-yl]-1,3-oxazolidin-2-one

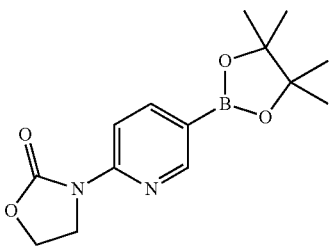 [SMILES: CC1(C)OB(c2ccc(N3CCOC3=O)nc2)OC1(C)C]

A mixture of 3-(5-bromopyridin-2-yl)-1,3-oxazolidin-2-one (240 mg, 1.0 mmol), 4,4,5,5,4',4',5',5'-octamethyl-[2,2']bi[[1,3,2]dioxaborolanyl](280 mg, 1.1 mmol), [1,1'-bis(diphenylphosphino)ferrocene]dichloropalladium(II) complex with dichloromethane (1:1) (88 mg, 0.11 mmol) and potassium acetate (300 mg, 3 mmol) in DMF (5 mL) was purged with nitrogen then heated at 70° C. overnight. After cooling to room temperature, the mixture was concentrated. The residue was dissolved in EtOAc then filtered. The filtrate was concentrated and the residue was purified by column chromatography eluting with 0-60% EtOAc in hexanes to give the desired product. LC-MS calculated for $C_{14}H_{20}BN_2O_4$ $(M+H)^+$: m/z=291.2. found 291.2.

Step 3: 4-{8-[4-(dimethylamino)piperidin-1-yl]-5-[6-(2-oxo-1,3-oxazolidin-3-yl)pyridin-3-yl]imidazo[1,2-a]pyrazin-6-yl}benzonitrile The title compound was prepared using similar procedures as described for Example 58, Step 5 with 3-(5-(4,4,5,5-tetramethyl-1,3,2-dioxaborolan-2-yl)pyridin-2-yl)oxazolidin-2-one replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{28}H_{29}N_8O_2$ $(M+H)^+$: m/z=509.2. found 509.2.

Example 68

4-{5-(3-amino-1-methyl-1H-indazol-5-yl)-8-[4-(dimethylamino)piperidin-1-yl]imidazo[1,2-a]pyrazin-6-yl}benzonitrile

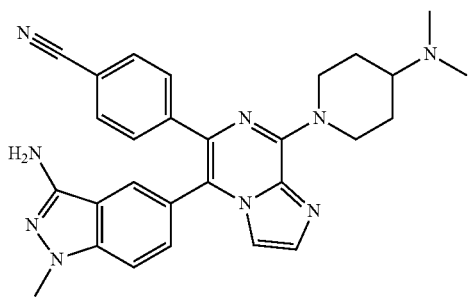 [SMILES: CN(C)C1CCN(c2nc(-c3ccc(C#N)cc3)c(-c3ccc4c(c3)c(N)nn4C)n3ccnc23)CC1]

The title compound was prepared using similar procedures as described for Example 58, Step 5 with 1-methyl-5-(4,4,5,5-tetramethyl-1,3,2-dioxaborolan-2-yl)-1H-indazol-3-amine (Combi-Blocks, cat #FF-5931) replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{28}H_{30}N_9$ $(M+H)^+$: m/z=492.3. found 492.2.

Example 69

5-(6-(4-cyanophenyl)-8-{[(3R)-1-methylpiperidin-3-yl]methoxy}imidazo[1,2-a]pyrazin-5-yl)-2-methylbenzonitrile

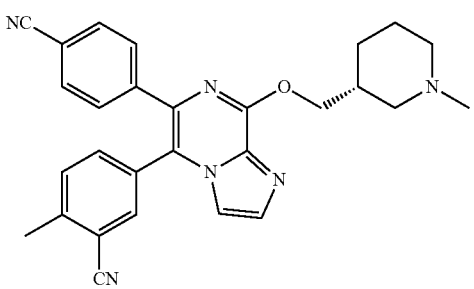

The title compound was prepared using similar procedures as described for Example 48, Step 8 with 2-methyl-5-(4,4,5,5-tetramethyl-1,3,2-dioxaborolan-2-yl)benzonitrile (Sigma-Aldrich, cat #CDS019666) replacing 1-[5-(4,4,5,5-tetramethyl-1,3,2-dioxaborolan-2-yl)pyridin-2-yl]pyrrolidin-2-one. The reaction mixture was purified by prep-HPLC (pH=2, acetonitrile/water+TFA) to give the desired product as the TFA salt. LC-MS calculated for $C_{28}H_{27}N_6O$ $(M+H)^+$: m/z=463.2. found 463.2.

Example 70

4-(5-[3-(hydroxymethyl)-4-methylphenyl]-8-{[(3R)-1-methylpiperidin-3-yl]methoxy}imidazo[1,2-a]pyrazin-6-yl)benzonitrile

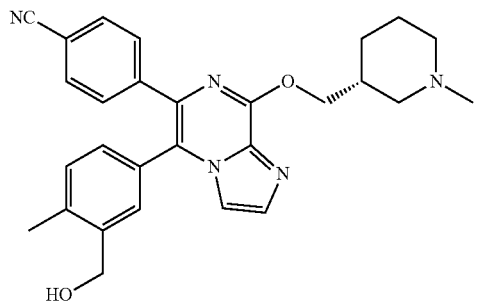

The title compound was prepared using similar procedures as described for Example 48, Step 8 with (2-methyl-5-(4,4,5,5-tetramethyl-1,3,2-dioxaborolan-2-yl)phenyl)methanol (Combi-Blocks, cat #FM-2080) replacing 1-[5-(4,4,5,5-tetramethyl-1,3,2-dioxaborolan-2-yl)pyridin-2-yl]pyrrolidin-2-one. The reaction mixture was purified by prep-HPLC (pH=2, acetonitrile/water+TFA) to give the desired product as the TFA salt. LC-MS calculated for $C_{28}H_{30}N_5O_2$ $(M+H)^+$: m/z=468.2. found 468.2.

Example 71

4-(5-(4-methyl-3-{[4-(methylsulfonyl)piperazin-1-yl]methyl}phenyl)-8-{[(3R)-1-methylpiperidin-3-yl]methoxy}imidazo[1,2-a]pyrazin-6-yl)benzonitrile

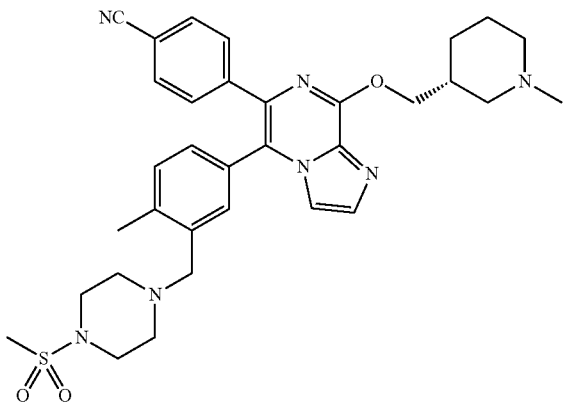

Step 1: 2-methyl-5-(4,4,5,5-tetramethyl-1,3,2-dioxaborolan-2-yl)benzaldehyde

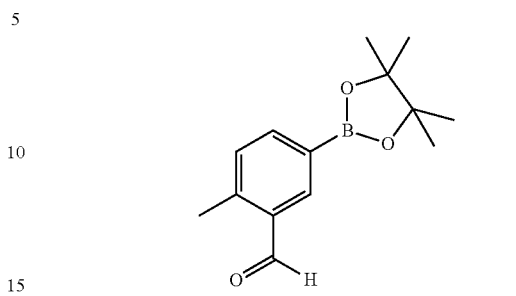

A stream of nitrogen gas was bubbled through a mixture of 5-bromo-2-methylbenzaldehyde (1550 mg, 7.79 mmol), 4,4,5,5,4',4',5',5'-octamethyl-[2,2']bi[[1,3,2]dioxaborolanyl] (2200 mg, 8.6 mmol), and potassium acetate (2300 mg, 23 mmol) in N,N-dimethylformamide (30 mL) for ~15 minutes. Then palladium acetate (90 mg, 0.4 mmol) was added, the vial was sealed, and the reaction was heated to 85° C. for 3 h. After cooling, the mixture was concentrated and the residue was partitioned between 75 mL of EtOAc and 75 mL water. The suspension was filtered through celite, the filter cake was washed with EtOAc, then the layers were separated. The organic phase was washed with water, brine, dried over sodium sulfate, and concentrated. The residue was purified by flash chromatography on a silica gel column eluting with 0 to 10% EtOAc/hexanes to give the desired compound (1025 mg, 54%). LC-MS calculated for $C_{14}H_{20}BO_3$ $(M+H)^+$: m/z=247.2. found 247.1.

Step 2: 1-(2-methyl-5-(4,4,5,5-tetramethyl-1,3,2-dioxaborolan-2-yl)benzyl)-4-(methylsulfonyl)piperazine

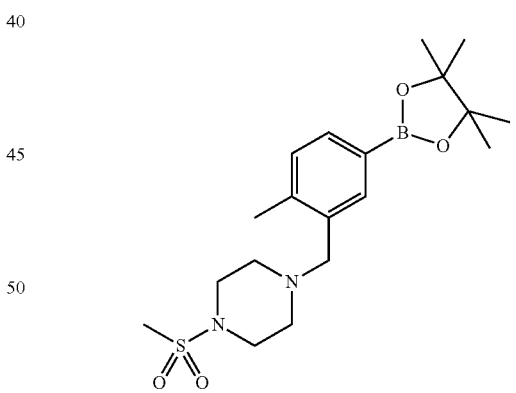

A solution of 2-methyl-5-(4,4,5,5-tetramethyl-1,3,2-dioxaborolan-2-yl)benzaldehyde (100 mg, 0.4 mmol), 1-(methylsulfonyl)piperazine (0.080 g, 0.49 mmol), and acetic acid (50 µL, 0.9 mmol) in methylene chloride (6 mL) was first stirred for 30 minutes, then sodium triacetoxyborohydride (260 mg, 1.2 mmol) was added and the reaction mixture was stirred at room temperature overnight. The mixture was diluted with methylene chloride, was with saturated NaHCO$_3$, water, and brine, dried over sodium sulfate, and concentrated. The residue was used in the next step without further purification. LC-MS calculated for $C_{19}H_{32}BN_2O_4S$ $(M+H)^+$: m/z=395.2. found 395.2.

Step 3: 4-(5-(4-methyl-3-{[4-(methylsulfonyl)piperazin-1-yl]methyl}phenyl)-8-{[(3R)-1-methylpiperidin-3-yl]methoxy}imidazo[1,2-a]pyrazin-6-yl)benzonitrile The title compound was prepared using similar procedures as described for Example 48, Step 8 with 1-(2-methyl-5-(4,4,5,5-tetramethyl-1,3,2-dioxaborolan-2-yl)benzyl)-4-(methylsulfonyl)piperazine replacing 1-[5-(4,4,5,5-tetramethyl-1,3,2-dioxaborolan-2-yl)pyridin-2-yl]pyrrolidin-2-one. The reaction mixture was purified by prep-HPLC (pH=2, acetonitrile/water+TFA) to give the desired product as the TFA salt. LC-MS calculated for $C_{33}H_{40}N_7O_3S$ $(M+H)^+$: m/z=614.3. found 614.3.

Example 72

4-(5-[4-(hydroxymethyl)-3-methylphenyl]-8-{[(3R)-1-methylpiperidin-3-yl]methoxy}imidazo[1,2-a]pyrazin-6-yl)benzonitrile

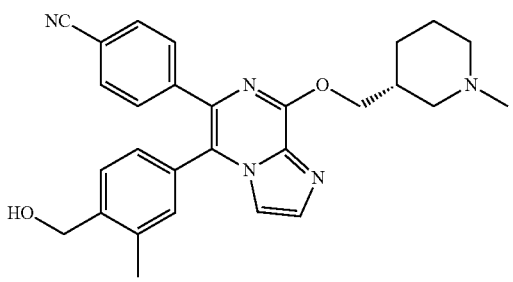

The title compound was prepared using similar procedures as described for Example 48, Step 8 with 4-hydroxymethyl-3-methylphenylboronic acid (Sigma-Aldrich, cat #005902) replacing 1-[5-(4,4,5,5-tetramethyl-1,3,2-dioxaborolan-2-yl)pyridin-2-yl]pyrrolidin-2-one. The reaction mixture was purified by prep-HPLC (pH=2, acetonitrile/water+TFA) to give the desired product as the TFA salt. LC-MS calculated for $C_{28}H_{30}N_5O_2$ $(M+H)^+$: m/z=468.2. found 468.2.

Example 73

4-(5-(3-hydroxy-2,3-dihydro-1H-inden-5-yl)-8-{[(3R)-1-methylpiperidin-3-yl]methoxy}imidazo[1,2-a]pyrazin-6-yl)benzonitrile

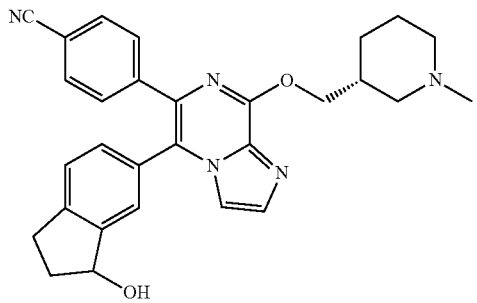 [SMILES: CN1CCC[C@@H](COc2nc(-c3ccc(C#N)cc3)c(-c3ccc4c(c3)C(O)CC4)n3ccnc23)C1]

Step 1: 6-bromo-2,3-dihydro-1H-inden-1-ol

To a solution of 6-bromoindan-1-one (Aldrich, cat #597147: 250 mg, 1.2 mmol) in methanol (3 mL) was added sodium tetrahydroborate (49 mg, 1.3 mmol) in 2 portions. The reaction mixture was stirred at room temperature for 2 h leading to complete conversion. The solvent was removed and the residue was partitioned between water and EtOAc. The EtOAc layer was washed with brine, dried over sodium sulfate, and the solvent was removed to obtain 6-bromoindan-1-ol (racemic, 240 mg, 95%) which was used in the next step without further purification. LC-MS calculated for $C_9H_8Br$ $(M+H-H_2O)^+$: m/z=195.0. found 195.0.

Step 2: 6-(4,4,5,5-tetramethyl-1,3,2-dioxaborolan-2-yl)-2,3-dihydro-1H-inden-1-ol

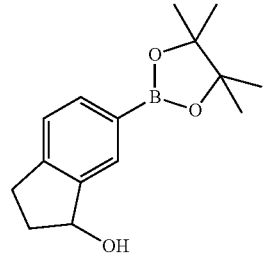 [SMILES: CC1(C)OB(c2ccc3c(c2)C(O)CC3)OC1(C)C]

A suspension of 6-bromoindan-1-ol (240 mg, 1.1 mmol), potassium acetate (550 mg, 5.6 mmol) and 4,4,5,5,4',4',5',5'-octamethyl-[2,2']bi[[1,3,2]dioxaborolanyl](430 mg, 1.7 mmol) in 1,4-doxane (3.3 mL) was first degassed with stream of nitrogen for ~5 min, then [1,1'-bis(diphenylphosphino)ferrocene]dichloropalladium(II), complex with dichloromethane (1:1) (92 mg, 0.11 mmol) was added and the mixture was heated to 90° C. overnight. The reaction mixture was then diluted with EtOAc, filtered through celite, and concentrated. The residue was purified by flash chromatography on a silica gel column eluting with 0 to 25% EtOAc/hexanes to provide the desired product (256 mg, 87%). LC-MS calculated for $C_{15}H_{20}BO_2$ $(M+H-H_2O)^+$: m/z=243.2. found 243.2.

Step 3: 4-(5-(3-hydroxy-2,3-dihydro-H-inden-5-yl)-8-{[(3R)-1-methylpiperidin-3-yl]methoxy}imidazo[1,2-a]pyrazin-6-yl)benzonitrile The title compound was prepared using similar procedures as described for Example 48, Step 8 with 6-(4,4,5,5-tetramethyl-1,3,2-dioxaborolan-2-yl)-2,3-dihydro-1H-inden-1-ol replacing 1-[5-(4,4,5,5-tetramethyl-1,3,2-dioxaborolan-2-yl)pyridin-2-yl]pyrrolidin-2-one. The reaction mixture was purified by prep-HPLC (pH=2, acetonitrile/water+TFA) to give the desired product (a mixture of two diastereomers) as the TFA salt. LC-MS calculated for $C_{29}H_{30}N_5O_2$ (M+H)$^+$: m/z=480.2. found 480.2.

Example 74

4-(5-[4-(hydroxymethyl)phenyl]-8-{[(3R)-1-methylpiperidin-3-yl]methoxy}imidazo[1,2-a]pyrazin-6-yl)benzonitrile

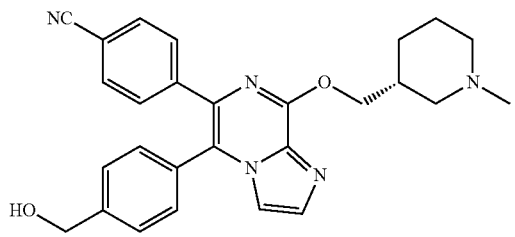 [SMILES: CN1CCC[C@@H](COc2nc(-c3ccc(C#N)cc3)c(-c3ccc(CO)cc3)n3ccnc23)C1]

The title compound was prepared using similar procedures as described for Example 48, Step 8 with 4-(hydroxymethyl)phenylboronic acid (Sigma-Aldrich, cat #512338) replacing 1-[5-(4,4,5,5-tetramethyl-1,3,2-dioxaborolan-2-yl)pyridin-2-yl]pyrrolidin-2-one. The reaction mixture was purified by prep-HPLC (pH=2, acetonitrile/water+TFA) to give the desired product as the TFA salt. LC-MS calculated for $C_{27}H_{28}N_5O_2$ (M+H)$^+$: m/z=454.2. found 454.2.

Example 75

4-{8-{[(3R)-1-methylpiperidin-3-yl]methoxy}-5-[4-(morpholin-4-ylmethyl)phenyl]imidazo[1,2-a]pyrazin-6-yl}benzonitrile

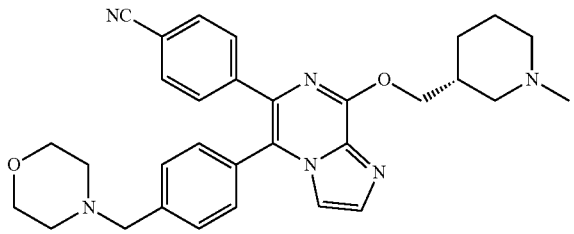 [SMILES: CN1CCC[C@@H](COc2nc(-c3ccc(C#N)cc3)c(-c3ccc(CN4CCOCC4)cc3)n3ccnc23)C1]

The title compound was prepared using similar procedures as described for Example 48, Step 8 with 4-(4-(4,4,5,5-tetramethyl-1,3,2-dioxaborolan-2-yl)benzyl)morpholine (Combi-Blocks, cat #PN-8855) replacing 1-[5-(4,4,5,5-tetramethyl-1,3,2-dioxaborolan-2-yl)pyridin-2-yl]pyrrolidin-2-one. The reaction mixture was purified by prep-HPLC (pH=2, acetonitrile/water+TFA) to give the desired product as the TFA salt. LC-MS calculated for $C_{31}H_{35}N_6O_2$ (M+H)$^+$: m/z=523.3. found 523.2.

Example 76 methyl [5-(6-(4-cyanophenyl)-8-{[(3R)-1-methylpiperidin-3-yl]methoxy}imidazo[1,2-a]pyrazin-5-yl)-2-methylphenyl]methylcarbamate

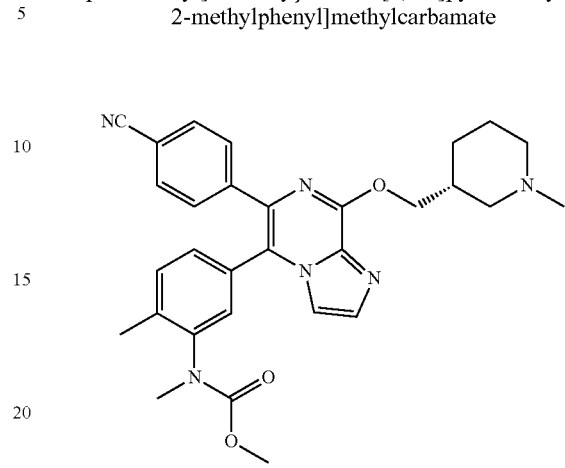

Step 1: methyl methyl(2-methyl-5-(4,4,5,5-tetramethyl-1,3,2-dioxaborolan-2-yl)phenyl) carbamate

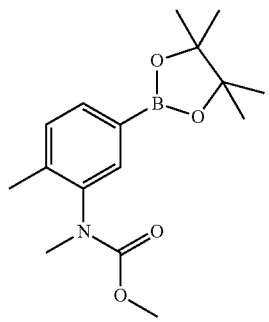

Methyl chloroformate (52 µL, 0.67 mmol) was added to a solution of N,2-dimethyl-5-(4,4,5,5-tetramethyl-1,3,2-dioxaborolan-2-yl)aniline (Combi-Blocks, cat #PN-1190: 110 mg, 0.45 mmol) and N,N-diisopropylethylamine (0.20 mL, 1.1 mmol) in methylene chloride (2.0 mL). The resulting mixture was stirred at room temperature for 2 h, then diluted with DCM, washed with 0.1 M HCl, dried over sodium sulfate, and concentrated. The product obtained was used in the next step without further purification. LC-MS calculated for $C_{16}H_{25}BNO_4$ (M+H)$^+$: m/z=306.2. found 306.2.

Step 2: methyl [5-(6-(4-cyanophenyl)-8-{[(3R)-1-methylpiperidin-3-yl]methoxy}imidazo[1,2-a]pyrazin-5-yl)-2-methylphenyl]methylcarbamate The title compound was prepared using similar procedures as described for Example 48, Step 8 with methyl methyl(2-methyl-5-(4,4,5,5-tetramethyl-1,3,2-dioxaborolan-2-yl)phenyl)carbamate replacing 1-[5-(4,4,5,5-tetramethyl-1,3,2-dioxaborolan-2-yl)pyridin-2-yl]pyrrolidin-2-one. The reaction mixture was purified by prep-HPLC (pH=2, acetonitrile/water+TFA) to give the desired product as the TFA salt. LC-MS calculated for $C_{30}H_{33}N_6O_3$ (M+H)$^+$: m/z=525.3. found 525.2.

Example 77 methyl [4-(6-(4-cyanophenyl)-8-{[(3R)-1-methylpiperidin-3-yl]methoxy}imidazo[1,2-a]pyrazin-5-yl)phenyl]methylcarbamate

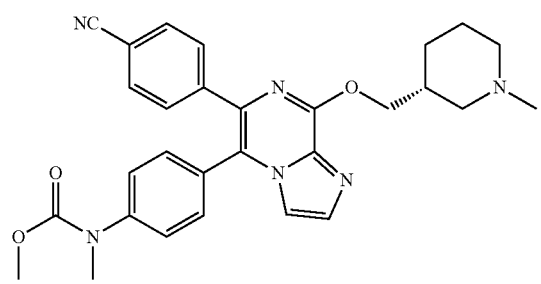 [SMILES: COC(=O)N(C)c1ccc(-c2c(-c3ccc(C#N)cc3)nc(OC[C@@H]3CCCN(C)C3)c3nccn23)cc1]

Step 1: methyl methyl(4-(4,4,5,5-tetramethyl-1,3,2-dioxaborolan-2-yl)phenyl)carbamate

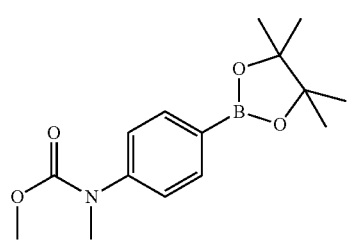 [SMILES: COC(=O)N(C)c1ccc(B2OC(C)(C)C(C)(C)O2)cc1]

The title compound was prepared using similar procedures as described for Example 76, Step 1 with N-methyl-4-(4,4,5,5-tetramethyl-1,3,2-dioxaborolan-2-yl)aniline (Combi-Blocks, cat #PN-8673) replacing N,2-dimethyl-5-(4,4,5,5-tetramethyl-1,3,2-dioxaborolan-2-yl)aniline. LC-MS calculated for $C_{15}H_{23}BNO_4$ (M+H)$^+$: m/z=292.2. found 292.2.

Step 2. methyl [4-(6-(4-cyanophenyl)-8-{[(3R)-1-methylpiperidin-3-yl]methoxy}imidazo[1,2-a]pyrazin-5-yl)phenyl]methylcarbamate The title compound was prepared using similar procedures as described for Example 48, Step 8 with methyl methyl(4-(4,4,5,5-tetramethyl-1,3,2-dioxaborolan-2-yl)phenyl)carbamate replacing 1-[5-(4,4,5,5-tetramethyl-1,3,2-dioxaborolan-2-yl)pyridin-2-yl]pyrrolidin-2-one. The reaction mixture was purified by prep-HPLC (pH=2, acetonitrile/water+TFA) to give the desired product as the TFA salt. LC-MS calculated for $C_{29}H_{31}N_6O_3$ (M+H)$^+$: m/z=511.2. found 511.2.

Example 78

4-(5-(2-hydroxy-2,3-dihydro-1H-inden-5-yl)-8-{[(3R)-1-methylpiperidin-3-yl]methoxy}imidazo[1,2-a]pyrazin-6-yl)benzonitrile

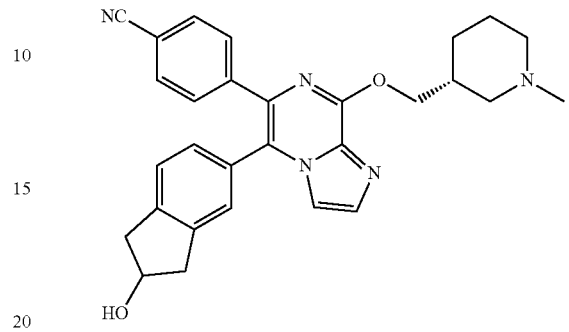

Step 1: 5-(4,4,5,5-tetramethyl-1,3,2-dioxaborolan-2-yl)-2,3-dihydro-1H-inden-2-ol

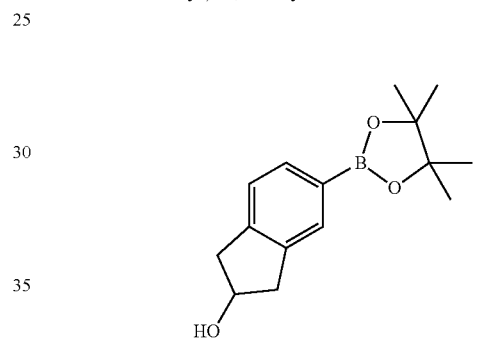

A suspension of 5-bromoindan-2-ol (Combi-Blocks, cat #QA3834: 114 mg, 0.535 mmol), potassium acetate (160 mg, 1.6 mmol) and 4,4,5,5,4',4',5',5'-octamethyl-[2,2']bi[[1,3,2]dioxaborolanyl](200 mg, 0.80 mmol) in 1,4-dioxane (2.4 mL) was first degassed with stream of nitrogen for ~5 min, then [1,1'-bis(diphenylphosphino)ferrocene]dichloropalladium(II), complex with dichloromethane (1:1) (20 mg, 0.03 mmol) was added and the mixture was heated to 100° C. overnight. The reaction mixture was cooled to room temperature, concentrated then diluted with 1:1 ethyl acetate/hexanes, filtered through celite, and concentrated. The residue obtained was purified by flash chromatography on a silica gel column eluting with 0 to 40% EtOAc/Hexanes to provide the desired intermediate in nearly quantitative yield.

Step 2: 4-(5-(2-hydroxy-2,3-dihydro-H-inden-5-yl)-8-{[(3R)-1-methylpiperidin-3-yl]methoxy}imidazo[1,2-a]pyrazin-6-yl)benzonitrile The title compound was prepared using similar procedures as described for Example 48, Step 8 with 5-(4,4,5,5-tetramethyl-1,3,2-dioxaborolan-2-yl)-2,3-dihydro-1H-inden-2-ol replacing 1-[5-(4,4,5,5-tetramethyl-1,3,2-dioxaborolan-2-yl)pyridin-2-yl]pyrrolidin-2-one. The reaction mixture was purified by prep-HPLC (pH=2, acetonitrile/water+TFA) to give the desired product as the TFA salt. LC-MS calculated for $C_{29}H_{30}N_5O_2$ (M+H)$^+$: m/z=480.2. found 480.2.

The above product, epimeric at the indanol stereocenter, was further purified using prep-HPLC on a column containing a chiral stationary phase (Phenomenex Lux Cellulose C-2, 5 μm, 21.2×250 mm) and eluting with 45% EtOH in hexane, to obtain the desired product as the free base.

Peak 1: $t_r$=10.1 min. LC-MS calculated for $C_{29}H_{30}N_5O_2$ (M+H)$^+$: m/z=480.2. found 480.3. $^1$H NMR (500 MHz, MeOD) δ 7.62 (m, 1H), 7.60-7.54 (m, 4H), 7.50 (m, 1H), 7.37 (d, J=7.6 Hz, 1H), 7.30 (s, 1H), 7.17 (d, J=7.5 Hz, 1H), 4.70-4.65 (m, 1H), 4.59 (dd, J=10.9, 5.7 Hz, 1H), 4.46 (dd, J=10.8, 7.3 Hz, 1H), 3.28-3.11 (m, 3H), 2.99-2.82 (m, 3H), 2.37-2.24 (m, 4H), 2.13-2.00 (m, 2H), 1.97-1.89 (m, 1H), 1.84-1.76 (m, 1H), 1.73-1.64 (m, 1H), 1.36-1.17 (m, 2H).

Peak 2: $t_r$=12.9 min. LC-MS calculated for $C_{29}H_{30}N_5O_2$ (M+H)$^+$: m/z=480.2. found 480.2. $^1$H NMR (600 MHz, MeOD) δ 7.62 (s, 1H), 7.60-7.54 (m, 4H), 7.53-7.47 (m, 1H), 7.37 (d, J=7.6 Hz, 1H), 7.30 (s, 1H), 7.17 (d, J=7.6 Hz, 1H), 4.70-4.65 (m, 1H), 4.59 (dd, J=10.8, 5.7 Hz, 1H), 4.46 (dd, J=10.8, 7.3 Hz, 1H), 3.28-3.13 (m, 3H), 2.97-2.83 (m, 3H), 2.36-2.29 (m, 4H), 2.12-2.03 (m, 2H), 1.96-1.90 (m, 1H), 1.83-1.76 (m, 1H), 1.72-1.63 (m, 1H), 1.30-1.20 (m, 1H).

Example 79

4-(5-(7-fluoro-3-hydroxy-2,3-dihydro-1H-inden-5-yl)-8-{[(3R)-1-methylpiperidin-3-yl]methoxy}imidazo[1,2-a]pyrazin-6-yl)benzonitrile

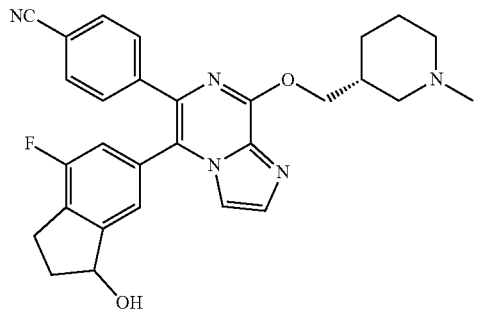 [SMILES: CN1CCC[C@@H](COc2nc(-c3ccc(C#N)cc3)c(-c3cc(F)c4c(c3)C(O)CC4)n3ccnc23)C1]

Step 1: 6-bromo-4-fluoro-2,3-dihydro-1H-inden-1-ol

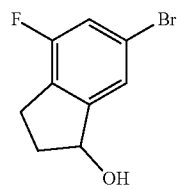

To a solution of 6-bromo-4-fluoroindan-1-one (Sigma-Aldrich, cat #775819: 120 mg, 0.54 mmol) in methanol (2 mL) was added sodium tetrahydroborate (22 mg, 0.60 mmol) in 2 portions. The reaction mixture was stirred at room temperature for 2 h leading to complete conversion. The solvent was removed and the residue partitioned between water and EtOAc. The EtOAc layer was washed with brine, dried over sodium sulfate, and the solvent was removed to the desired product (115 mg, 92%) which was used in the next step without further purification. LC-MS calculated for $C_9H_7BrF$ (M+H—$H_2O$)$^+$: m/z=213.0. found 213.0.

Step 2: 4-fluoro-6-(4,4,5,5-tetramethyl-1,3,2-dioxaborolan-2-yl)-2,3-dihydro-1H-inden-1-ol

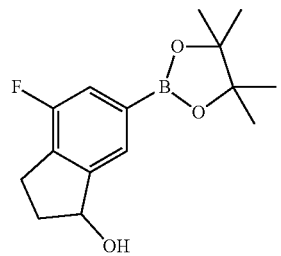 [SMILES: CC1(C)OB(c2cc(F)c3c(c2)C(O)CC3)OC1(C)C]

The title compound was prepared using similar procedures as described for Example 78, Step 1 with 6-bromo-4-fluoro-2,3-dihydro-1H-inden-1-ol replacing 5-bromoindan-2-ol. LC-MS calculated for $C_{15}H_{19}BFO_2$ (M+H—$H_2O$)$^+$: m/z=261.1. found 261.1.

Step 3: 4-(5-(7-fluoro-3-hydroxy-2,3-dihydro-1H-inden-5-yl)-8-{[(3R)-1-methylpiperidin-3-yl]methoxy}imidazo[1,2-a]pyrazin-6-yl)benzonitrile The title compound was prepared using similar procedures as described for Example 48, Step 8 with 4-fluoro-6-(4,4,5,5-tetramethyl-1,3,2-dioxaborolan-2-yl)-2,3-dihydro-1H-inden-1-ol replacing 1-[5-(4,4,5,5-tetramethyl-1,3,2-dioxaborolan-2-yl)pyridin-2-yl]pyrrolidin-2-one. The reaction mixture was purified by prep-HPLC (pH=2, acetonitrile/water+TFA) to give the desired product (a mixture of two diastereomers) as the TFA salt. LC-MS calculated for $C_{29}H_{29}FN_5O_2$ (M+H)$^+$: m/z=498.2. found 498.2.

Example 80

4-(5-(1-hydroxy-2,3-dihydro-1H-inden-5-yl)-8-{[(3R)-1-methylpiperidin-3-yl]methoxy}imidazo[1,2-a]pyrazin-6-yl)benzonitrile

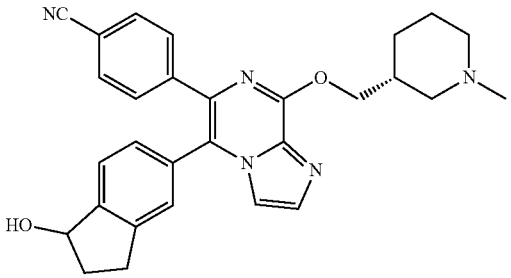 [SMILES: CN1CCC[C@@H](COc2nc(-c3ccc(C#N)cc3)c(-c3ccc4c(c3)CCC4O)n3ccnc23)C1]

Step 1: 5-(4,4,5,5-tetramethyl-1,3,2-dioxaborolan-2-yl)-2,3-dihydro-1H-inden-1-ol

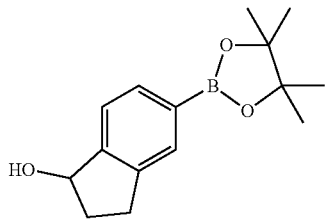 [SMILES: CC1(C)OB(c2ccc3c(c2)CCC3O)OC1(C)C]

The title compound was prepared using similar procedures as described for Example 78, Step 1 with 5-bromo-2,3-dihydro-1H-inden-1-ol (Aurum Pharmatech, cat #NE44343) replacing 5-bromoindan-2-ol. LC-MS calculated for $C_{15}H_{20}BO_2$ (M+H—$H_2O$)$^+$: m/z=243.2. found 243.2.

Step 2: 4-(5-(1-hydroxy-2,3-dihydro-H-inden-5-yl)-8-{[(3R)-1-methylpiperidin-3-yl]methoxy}imidazo[1,2-a]pyrazin-6-yl)benzonitrile The title compound was prepared using similar procedures as described for Example 48, Step 8 with 5-(4,4,5,5-tetramethyl-1,3,2-dioxaborolan-2-yl)-2,3-dihydro-1H-inden-1-ol replacing 1-[5-(4,4,5,5-tetramethyl-1,3,2-dioxaborolan-2-yl)pyridin-2-yl]pyrrolidin-2-one. The reaction mixture was purified by prep-HPLC (pH=2, acetonitrile/water+TFA) to give the desired product (a mixture of two diastereomers) as the TFA salt. LC-MS calculated for $C_{29}H_{30}N_5O_2$ (M+H)$^+$: m/z=480.2. found 480.2.

Example 81

4-(5-[3-fluoro-4-(hydroxymethyl)-5-methylphenyl]-8-{[(3R)-1-methylpiperidin-3-yl]methoxy}imidazo[1,2-a]pyrazin-6-yl)benzonitrile

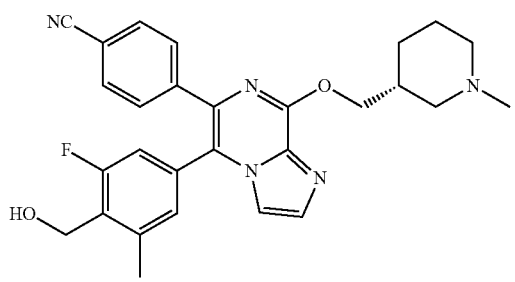 [SMILES: Cc1cc(-c2c(-c3ccc(C#N)cc3)nc(OC[C@@H]3CCCN(C)C3)c3nccn23)cc(F)c1CO]

Step 1: (4-bromo-2-fluoro-6-methylphenyl)methanol

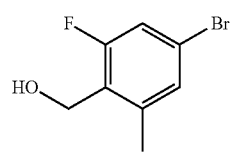

2.0 M Lithium tetrahydroborate in THF (0.92 mL, 1.8 mmol) was added to a solution of methyl 4-bromo-2-fluoro-6-methylbenzoate (AstaTech, cat #CL9030: 207 mg, 0.838 mmol) in tetrahydrofuran (1.0 mL). The solution was heated to reflux for 4 h, and then the mixture was cooled to room temperature, quenched with water, and extracted 3 times with EtOAc. The combined extracts were washed with brine, dried over sodium sulfate and concentrated. The residue was purified by flash chromatography on a silica gel column eluting with 3 to 30% EtOAc/hexanes to provide the desired compound (109 mg, 60%). LC-MS calculated for $C_8H_7BrF$ (M+H—$H_2O$)$^+$: m/z=201.0. found 201.0.

Step 2: (2-fluoro-6-methyl-4-(4,4,5,5-tetramethyl-1,3,2-dioxaborolan-2-yl)phenyl)methanol

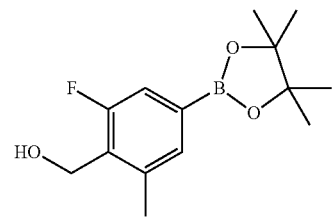 [SMILES: Cc1cc(B2OC(C)(C)C(C)(C)O2)cc(F)c1CO]

The title compound was prepared using similar procedures as described for Example 78, Step 1 with (4-bromo-2-fluoro-6-methylphenyl)methanol replacing 5-bromoindan-2-ol. LC-MS calculated for $C_{14}H_{19}BFO_2$ (M+H—$H_2O$)$^+$: m/z=249.1. found 249.1.

Step 3: 4-(5-[3-fluoro-4-(hydroxymethyl)-5-methylphenyl]-8-{[(3R)-1-methylpiperidin-3-yl]methoxy}imidazo[1,2-a]pyrazin-6-yl)benzonitrile The title compound was prepared using similar procedures as described for Example 48, Step 8 with (2-fluoro-6-methyl-4-(4,4,5,5-tetramethyl-1,3,2-dioxaborolan-2-yl)phenyl)methanol replacing 1-[5-(4,4,5,5-tetramethyl-1,3,2-dioxaborolan-2-yl)pyridin-2-yl]pyrrolidin-2-one. The reaction mixture was purified by prep-HPLC (pH=2, acetonitrile/water+TFA) to give the desired product as the TFA salt. LC-MS calculated for $C_{28}H_{29}FN_5O_2$ (M+H)$^+$: m/z=486.2. found 486.2.

Example 82

4-(5-[3-fluoro-4-(morpholin-4-ylmethyl)phenyl]-8-{[(3R)-1-methylpiperidin-3-yl]methoxy}imidazo[1,2-a]pyrazin-6-yl)benzonitrile

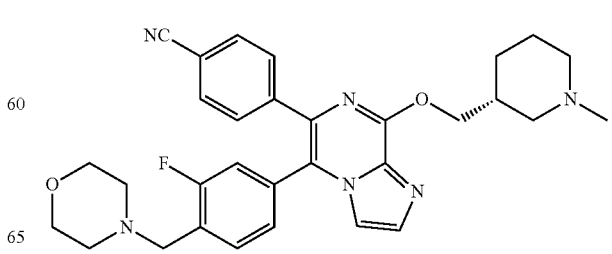

The title compound was prepared using similar procedures as described for Example 48, Step 8 with 4-(2-fluoro-4-(4,4,5,5-tetramethyl-1,3,2-dioxaborolan-2-yl)benzyl)morpholine (Combi-Blocks, cat #PN-8769) replacing 1-[5-(4,4,5,5-tetramethyl-1,3,2-dioxaborolan-2-yl)pyridin-2-yl]pyrrolidin-2-one. The reaction mixture was purified by prep-HPLC (pH=2, acetonitrile/water+TFA) to give the desired product as the TFA salt. LC-MS calculated for $C_{31}H_{34}FN_6O_2$ (M+H)$^+$: m/z=541.3. found 541.2.

Example 83

4-(5-[3,5-difluoro-4-(hydroxymethyl)phenyl]-8-{[(3R)-1-methylpiperidin-3-yl]methoxy}imidazo[1,2-a]pyrazin-6-yl)benzonitrile

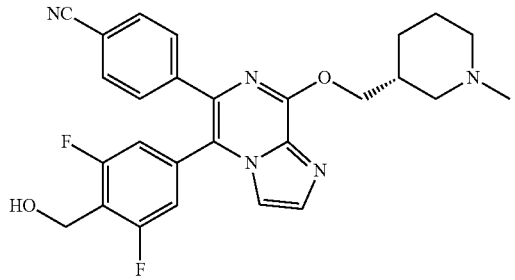 [SMILES: CN1CCC[C@@H](COc2nc(-c3ccc(C#N)cc3)c(-c3cc(F)c(CO)c(F)c3)n3ccnc23)C1]

The title compound was prepared using similar procedures as described for Example 48, Step 8 with 3,5-difluoro-4-(hydroxymethyl)phenylboronic acid (Combi-Blocks, cat #BB-8390) replacing 1-[5-(4,4,5,5-tetramethyl-1,3,2-dioxaborolan-2-yl)pyridin-2-yl]pyrrolidin-2-one. The reaction mixture was purified by prep-HPLC (pH=2, acetonitrile/water+TFA) to give the desired product as the TFA salt. LC-MS calculated for $C_{27}H_{26}F_2N_5O_2$ (M+H)$^+$: m/z=490.2. found 490.2.

Example 84

4-(5-(5-fluoro-6-methoxypyridin-3-yl)-8-{[(3R)-1-methylpiperidin-3-yl]methoxy}imidazo[1,2-a]pyrazin-6-yl)benzonitrile

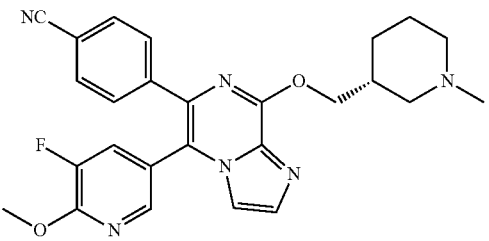

The title compound was prepared using similar procedures as described for Example 48, Step 8 with 5-fluoro-6-methoxypyridin-3-ylboronic acid (Combi-Blocks, cat #BB-84600) replacing 1-[5-(4,4,5,5-tetramethyl-1,3,2-dioxaborolan-2-yl)pyridin-2-yl]pyrrolidin-2-one. The reaction mixture was purified by prep-HPLC (pH=2, acetonitrile/water+TFA) to give the desired product as the TFA salt. LC-MS calculated for $C_{26}H_{26}FN_6O_2$ (M+H)$^+$: m/z=473.2. found 473.2.

Example 85 methyl [4-(6-(4-cyanophenyl)-8-{[(3R)-1-methylpiperidin-3-yl]methoxy}imidazo[1,2-a]pyrazin-5-yl)-2-fluorobenzyl]methylcarbamate

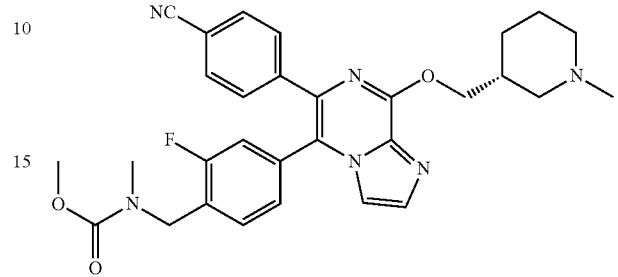

Step 1: 1-[2-fluoro-4-(4,4,5,5-tetramethyl-1,3,2-dioxaborolan-2-yl)phenyl]-N-methylmethanamine

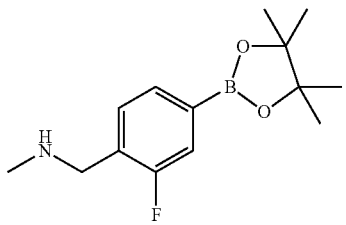

2.0 M Methylamine in THF (3 mL, 6 mmol) was added dropwise to a solution of 2-[4-(bromomethyl)-3-fluorophenyl]-4,4,5,5-tetramethyl-1,3,2-dioxaborolane (Combi-Blocks, cat #PN-5656: 200 mg, 0.6 mmol) in THF (10 mL) over 1 hour. After stirring for an additional 2 h, the reaction was concentrated and used without further purification. LC-MS calculated for $C_{14}H_{22}BFNO_2$ (M+H)$^+$: m/z=266.2. found 266.2.

Step 2: methyl [2-fluoro-4-(4,4,5,5-tetramethyl-1,3,2-dioxaborolan-2-yl)benzyl]methylcarbamate

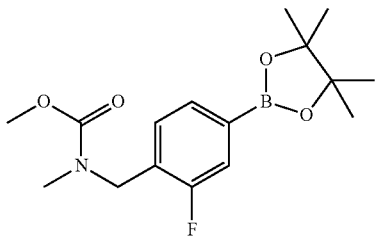

Methyl chloroformate (19 µL, 0.24 mmol), followed by N,N-diisopropylethylamine (0.056 mL, 0.32 mmol) were added to a solution of 1-[2-fluoro-4-(4,4,5,5-tetramethyl-1,3,2-dioxaborolan-2-yl)phenyl]-N-methylmethanamine (40 mg, 0.2 mmol) in methylene chloride (2.0 mL). After 2 h the reaction mixture was concentrated and used without further purification. LC-MS calculated for $C_{16}H_{24}BFNO_4$ (M+H)$^+$: m/z=324.2. found 324.2.

Step 3: methyl [4-(6-(4-cyanophenyl)-8-{[(3R)-1-methylpiperidin-3-yl]methoxy}imidazo[1,2-a]pyrazin-5-yl)-2-fluorobenzyl]methylcarbamate The title compound was prepared using similar procedures as described for Example 48, Step 8 with methyl 2-fluoro-4-(4,4,5,5-tetramethyl-1,3,2-dioxaborolan-2-yl)benzyl(methyl)carbamate replacing 1-[5-(4,4,5,5-tetramethyl-1,3,2-dioxaborolan-2-yl)pyridin-2-yl]pyrrolidin-2-one. The reaction mixture was purified by prep-HPLC (pH=2, acetonitrile/water+TFA) to give the desired product as the TFA salt. LC-MS calculated for $C_{30}H_{32}FN_6O_3$ (M+H)$^+$: m/z=543.3. found 543.2.

Example 86

4-(5-[4-(1-hydroxyethyl)-3-methylphenyl]-8-{[(3R)-1-methylpiperidin-3-yl]methoxy}imidazo[1,2-a]pyrazin-6-yl)benzonitrile

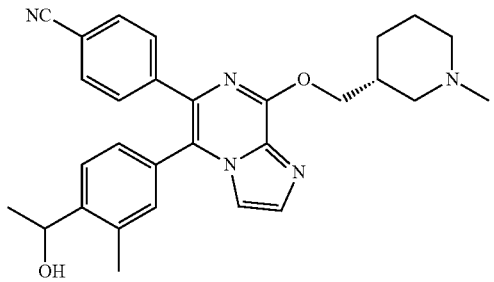 [SMILES: Cc1cc(-c2c(-c3ccc(C#N)cc3)nc(OC[C@@H]3CCCN(C)C3)c3nccn23)ccc1C(C)O]

Step 1: 1-(4-bromo-2-methylphenyl) ethanol

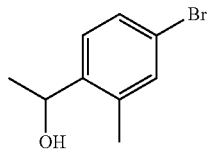

3.0 M methylmagnesium bromide in diethyl ether (2.7 mL, 8.2 mmol) was added over ~5 min to a solution of 4-bromo-2-methylbenzaldehyde (AstaTech, cat #BL005480: 325 mg, 1.63 mmol) in tetrahydrofuran (3.0 mL) at 0° C. The reaction mixture was allowed to warm to room temperature and stirred for 3 h, after which time saturated aqueous ammonium chloride was added carefully. The solution was then extracted 3 times with EtOAc, dried over sodium sulfate, and concentrated. The residue was purified by flash chromatography on silica gel eluting with 0 to 25% EtOAc/hexanes to afford the desired product (351 mg, 84%). LC-MS calculated for $C_9H_{10}Br$ (M+H—$H_2O$)$^+$: m/z=197.0. found 197.0.

Step 2: 1-(2-methyl-4-(4,4,5,5-tetramethyl-1,3,2-dioxaborolan-2-yl)phenyl) ethanol

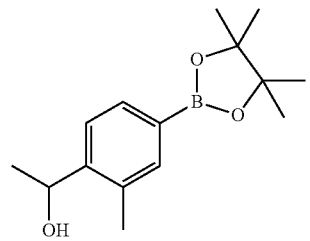 [SMILES: Cc1cc(B2OC(C)(C)C(C)(C)O2)ccc1C(C)O]

A suspension of 1-(4-bromo-2-methylphenyl)ethanol (296 mg, 1.38 mmol), potassium acetate (400 mg, 4.1 mmol) and 4,4,5,5,4',4',5',5'-octamethyl-[2,2']bi[[1,3,2]dioxaborolanyl](520 mg, 2.1 mmol) in 1,4-dioxane (6.3 mL) was purged with stream of nitrogen for ~5 min, then [1,1'-bis(diphenylphosphino)ferrocene]dichloropalladium(II), complex with dichloromethane (1:1) (60 mg, 0.07 mmol) was added and the mixture was heated at 100° C. overnight. The reaction mixture was then cooled to room temperature and concentrated. The residue was diluted with ethyl acetate, filtered through a pad of celite, and the filtrate was concentrated. The residue was purified by flash chromatography on a silica gel column eluting with 0 to 25% EtOAc/hexanes to afford the desired product (300 mg, 83%). LC-MS calculated for $C_{15}H_{22}BO_2$ (M+H—$H_2O$)$^+$: m/z=245.2. found 245.1.

Step 3: 4-(5-[4-(1-hydroxyethyl)-3-methylphenyl]-8-{[(3R)-1-methylpiperidin-3-yl]methoxy}imidazo[1,2-a]pyrazin-6-yl)benzonitrile The title compound was prepared using similar procedures as described for Example 48, Step 8 with 1-(2-methyl-4-(4,4,5,5-tetramethyl-1,3,2-dioxaborolan-2-yl)phenyl) ethanol replacing 1-[5-(4,4,5,5-tetramethyl-1,3,2-dioxaborolan-2-yl)pyridin-2-yl]pyrrolidin-2-one. The reaction mixture was purified by prep-HPLC (pH=2, acetonitrile/water+TFA) to give the desired product as the TFA salt. LC-MS calculated for $C_{29}H_{32}N_5O_2$ (M+H)$^+$: m/z=482.3. found 482.2.

Example 87

4-(5-[3-(1-hydroxyethyl)-4-methylphenyl]-8-{[(3R)-1-methylpiperidin-3-yl]methoxy}imidazo[1,2-a]pyrazin-6-yl)benzonitrile

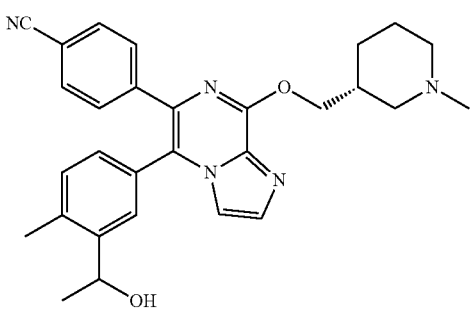

119

Step 1: 1-(5-bromo-2-methylphenyl)ethanol

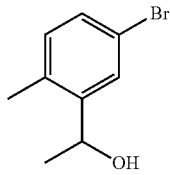

The title compound was prepared using similar procedures as described for Example 86, Step 1 with 5-bromo-2-methylbenzaldehyde (ArkPharm, cat #AK-36810) replacing 4-bromo-2-methylbenzaldehyde. LC-MS calculated for $C_9H_{10}Br$ $(M+H-H_2O)^+$: m/z=197.0. found 197.0.

Step 2: 1-(2-methyl-5-(4,4,5,5-tetramethyl-1,3,2-dioxaborolan-2-yl)phenyl)ethanol

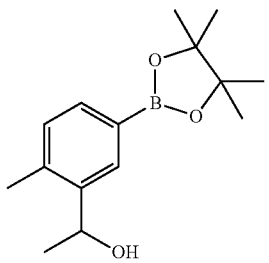

The title compound was prepared using similar procedures as described for Example 86, Step 2 with 1-(5-bromo-2-methylphenyl)ethanol replacing 1-(4-bromo-2-methylphenyl)ethanol. LC-MS calculated for $C_{15}H_{22}BO_2$ $(M+H-H_2O)^+$: m/z=245.2. found 245.2.

Step 3: 4-(5-[3-(1-hydroxyethyl)-4-methylphenyl]-8-{[(3R)-1-methylpiperidin-3-yl]methoxy}imidazo[1,2-a]pyrazin-6-yl)benzonitrile The title compound was prepared using similar procedures as described for Example 48, Step 8 with 1-(2-methyl-5-(4,4,5,5-tetramethyl-1,3,2-dioxaborolan-2-yl)phenyl)ethanol replacing 1-[5-(4,4,5,5-tetramethyl-1,3,2-dioxaborolan-2-yl)pyridin-2-yl]pyrrolidin-2-one. The reaction mixture was purified by prep-HPLC (pH=2, acetonitrile/water+TFA) to give the desired product as the TFA salt. LC-MS calculated for $C_{29}H_{32}N_5O_2$ $(M+H)^+$: m/z=482.3. found 482.2.

120

Example 88

4-(5-(7-fluoro-1-hydroxy-2,3-dihydro-1H-inden-5-yl)-8-{[(3R)-1-methylpiperidin-3-yl]methoxy}imidazo[1,2-a]pyrazin-6-yl)benzonitrile

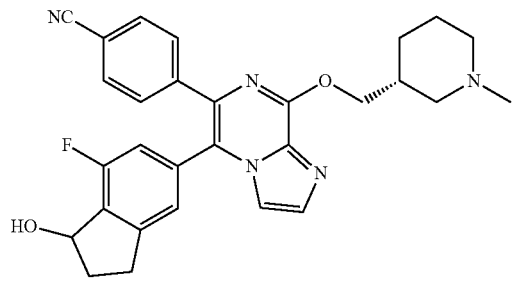 [SMILES: CN1CCC[C@@H](COc2nc(-c3ccc(C#N)cc3)c(-c3cc(F)c4c(c3)CCC4O)n3ccnc23)C1]

Step 1: 5-bromo-7-fluoro-2,3-dihydro-1H-inden-1-ol

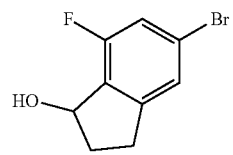 [SMILES: OC1CCc2cc(Br)cc(F)c21]

The title compound was prepared using similar procedures as described for Example 79, Step 1 with 5-bromo-7-fluoro-2,3-dihydro-1H-inden-1-one (AstaTech, cat #31063) replacing 6-bromo-4-fluoroindan-1-one. LC-MS calculated for $C_9H_7BrF$ $(M+H-H_2O)^+$: m/z=213.0. found 212.9.

Step 2: 7-fluoro-5-(4,4,5,5-tetramethyl-1,3,2-dioxaborolan-2-yl)-2,3-dihydro-1H-inden-1-ol

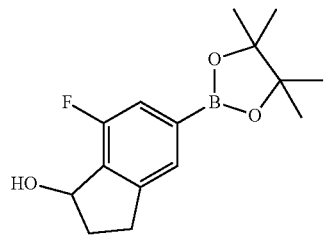 [SMILES: CC1(C)OB(c2cc(F)c3c(c2)CCC3O)OC1(C)C]

The title compound was prepared using similar procedures as described for Example 79, Step 2 with 5-bromo-7-fluoro-2,3-dihydro-1H-inden-1-ol replacing 6-bromo-4-fluoro-2,3-dihydro-1H-inden-1-ol. LC-MS calculated for $C_{15}H_{19}BFO_2$ $(M+H-H_2O)^+$: m/z=261.1. found 261.2.

Step 3: 4-(5-(7-fluoro-1-hydroxy-2,3-dihydro-H-inden-5-yl)-8-{[(3R)-1-methylpiperidin-3-yl]methoxy}imidazo[1,2-a]pyrazin-6-yl)benzonitrile The title compound was prepared using similar procedures as described for Example 48, Step 8 with 7-fluoro-5-(4,4,5,5-tetramethyl-1,3,2-dioxaborolan-2-yl)-2,3-dihydro- 1H-inden-1-ol replacing 1-[5-(4,4,5,5-tetramethyl-1,3,2-dioxaborolan-2-yl)pyridin-2-yl]pyrrolidin-2-one. The reaction mixture was purified by prep-HPLC (pH=2, acetonitrile/water+TFA) to give the desired product (a mixture of two diastereomers) as the TFA salt. LC-MS calculated for $C_{29}H_{29}FN_5O_2$ (M+H)$^+$: m/z=498.2. found 498.2.

Example 89

4-(5-[2-fluoro-4-(morpholin-4-ylmethyl)phenyl]-8-{[(3R)-1-methylpiperidin-3-yl]methoxy}imidazo[1,2-a]pyrazin-6-yl)benzonitrile

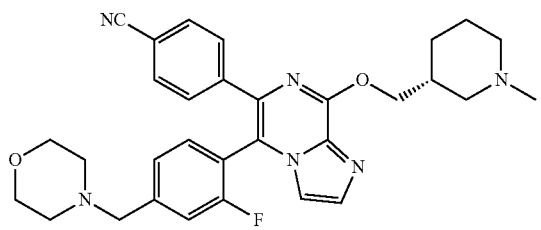 [SMILES: CN1CCC[C@@H](COc2nc(-c3ccc(C#N)cc3)c(-c3ccc(CN4CCOCC4)cc3F)n3ccnc23)C1]

The title compound was prepared using similar procedures as described for Example 48, Step 8 with 4-(3-fluoro-4-(4,4,5,5-tetramethyl-1,3,2-dioxaborolan-2-yl)benzyl)morpholine (Combi-Blocks, cat #PN-6786) replacing 1-[5-(4,4,5,5-tetramethyl-1,3,2-dioxaborolan-2-yl)pyridin-2-yl]pyrrolidin-2-one. The reaction mixture was purified by prep-HPLC (pH=2, acetonitrile/water+TFA) to give the desired product as the TFA salt. LC-MS calculated for $C_{31}H_{34}FN_6O_2$ (M+H)$^+$: m/z=541.3. found 541.2.

Example 90

4-(5-[2-(hydroxymethyl)-4-methylphenyl]-8-{[(3R)-1-methylpiperidin-3-yl]methoxy}imidazo[1,2-a]pyrazin-6-yl)benzonitrile

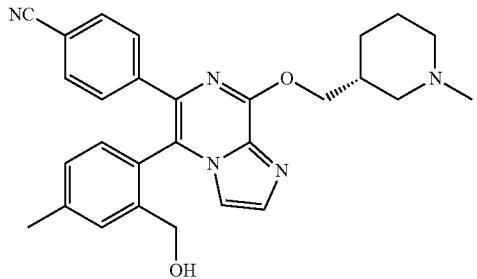

The title compound was prepared using similar procedures as described for Example 48, Step 8 with 2-(hydroxymethyl)-4-methylphenylboronic acid (Aurum PharmaTech, cat #Q-7538) replacing 1-[5-(4,4,5,5-tetramethyl-1,3,2-dioxaborolan-2-yl)pyridin-2-yl]pyrrolidin-2-one. The reaction mixture was purified by prep-HPLC (pH=2, acetonitrile/water+TFA) to give the desired product as the TFA salt. LC-MS calculated for $C_{28}H_{30}N_5O_2$ (M+H)$^+$: m/z=468.2. found 468.2.

Example 91

4-(5-[3-(cyanomethyl)-4-methylphenyl]-8-{[(3R)-1-methylpiperidin-3-yl]methoxy}imidazo[1,2-a]pyrazin-6-yl)benzonitrile

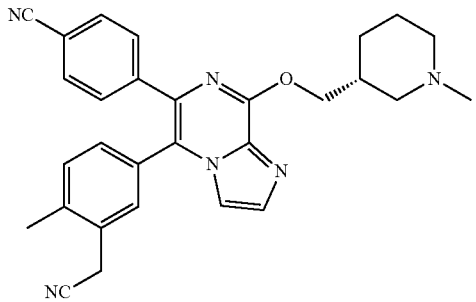

Step 1: 2-(2-methyl-5-(4,4,5,5-tetramethyl-1,3,2-dioxaborolan-2-yl)phenyl)acetonitrile

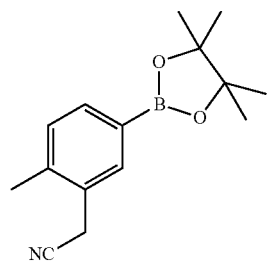

The title compound was prepared using similar procedures as described for Example 78, Step 1 with 2-(5-bromo-2-methylphenyl)acetonitrile (AstaTech, cat #CL9129) replacing 5-bromoindan-2-ol LC-MS calculated for $C_{15}H_{22}BNO_3$ (M+H$_2$O)$^+$: m/z=275.2. found 275.2.

Step 2: 4-(5-[3-(cyanomethyl)-4-methylphenyl]-8-{[(3R)-1-methylpiperidin-3-yl]methoxy}imidazo[1,2-a]pyrazin-6-yl)benzonitrile The title compound was prepared using similar procedures as described for Example 48, Step 8 with 2-(2-methyl-5-(4,4,5,5-tetramethyl-1,3,2-dioxaborolan-2-yl)phenyl)acetonitrile replacing 1-[5-(4,4,5,5-tetramethyl-1,3,2-dioxaborolan-2-yl)pyridin-2-yl]pyrrolidin-2-one. The reaction mixture was purified by prep-HPLC (pH=2, acetonitrile/water+TFA) to give the desired product as the TFA salt. LC-MS calculated for $C_{29}H_{29}N_6O$ (M+H)$^+$: m/z=477.2. found 477.2.

Example 92

4-[8-[4-(dimethylamino)piperidin-1-yl]-5-(5,6-dimethylpyridin-3-yl)imidazo[1,2-a]pyrazin-6-yl]benzonitrile

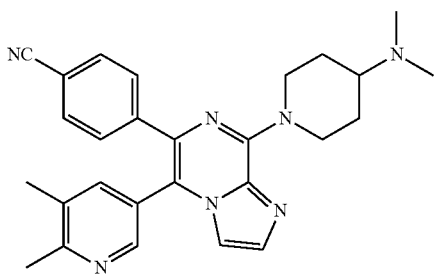

A degassed solution of 4-{5-chloro-8-[4-(dimethylamino)piperidin-1-yl]imidazo[1,2-a]pyrazin-6-yl}benzonitrile (Example 58, Step 4: 10 mg, 0.03 mmol), 2,3-dimethyl-5-(4,4,5,5-tetramethyl-1,3,2-dioxaborolan-2-yl)pyridine (Combi-Blocks, cat #FM-6236: 7.9 mg, 0.034 mmol), potassium phosphate (20 mg, 0.1 mmol), dichloro[1,1'-bis(dicyclohexylphosphino)ferrocene]palladium(II) (2 mg, 0.003 mmol) in 1,4-dioxane (1 mL) and water (0.15 mL) was heated at 90° C. for 2 h. The reaction mixture was cooled to room temperature and purified by prep-HPLC (pH=2, acetonitrile/water+TFA) to give the desired product as the TFA salt. LC-MS calculated for $C_{27}H_{30}N_7$ $(M+H)^+$: m/z=452.3. found 452.2.

Example 93

4-[8-[4-(dimethylamino)piperidin-1-yl]-5-(2-hydroxy-2,3-dihydro-1H-inden-5-yl)imidazo[1,2-a]pyrazin-6-yl]benzonitrile

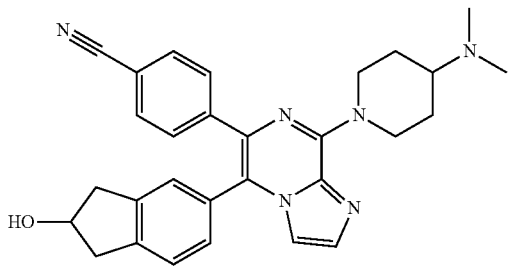 [SMILES: CN(C)C1CCN(c2nc(-c3ccc(C#N)cc3)c(-c3ccc4c(c3)CC(O)C4)n3ccnc23)CC1]

The title compound was prepared using similar procedures as described for Example 92 with 5-(4,4,5,5-tetramethyl-1,3,2-dioxaborolan-2-yl)-2,3-dihydro-1H-inden-2-ol (Example 78, Step 1) replacing 2,3-dimethyl-5-(4,4,5,5-tetramethyl-1,3,2-dioxaborolan-2-yl)pyridine. The reaction mixture was purified by prep-HPLC (pH=2, acetonitrile/water+TFA) to give the desired product (racemic) as the TFA salt. LC-MS calculated for $C_{29}H_{31}N_6O$ $(M+H)^+$: m/z=479.3. found 479.2.

Example 94

4-[8-[4-(dimethylamino)piperidin-1-yl]-5-(5-hydroxy-6-methylpyridin-3-yl)imidazo[1,2-a]pyrazin-6-yl]benzonitrile

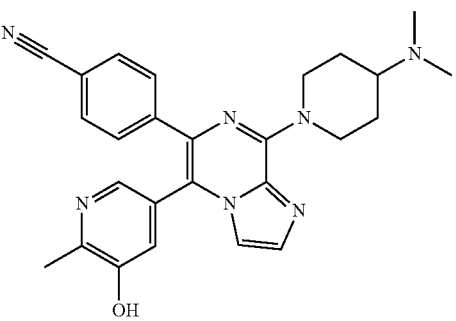 [SMILES: Cc1ncc(-c2c(-c3ccc(C#N)cc3)nc(N3CCC(N(C)C)CC3)c3nccn23)cc1O]

Step 1: 2-methyl-5-(4,4,5,5-tetramethyl-1,3,2-dioxaborolan-2-yl)pyridin-3-ol

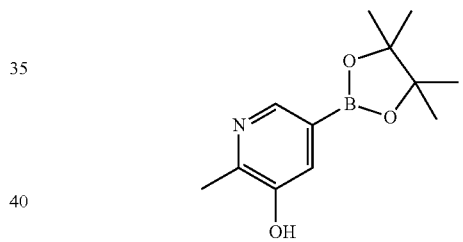

The title compound was prepared using similar procedures as described for Example 78, Step 1 with 5-bromo-2-methylpyridin-3-ol (Combi-Blocks, cat #QA-0238) replacing 5-bromoindan-2-ol LC-MS calculated for $C_{12}H_{19}BNO_3$ $(M+H)^+$: m/z=236.1. found 236.1.

Step 2: 4-[8-[4-(dimethylamino)piperidin-1-yl]-5-(5-hydroxy-6-methylpyridin-3-yl)imidazo[1,2-a]pyrazin-6-yl]benzonitrile The title compound was prepared using similar procedures as described for Example 92 with 2-methyl-5-(4,4,5,5-tetramethyl-1,3,2-dioxaborolan-2-yl)pyridin-3-ol replacing 2,3-dimethyl-5-(4,4,5,5-tetramethyl-1,3,2-dioxaborolan-2-yl)pyridine. The reaction mixture was purified by prep-HPLC (pH=2, acetonitrile/water+TFA) to give the desired product as the TFA salt. LC-MS calculated for $C_{26}H_{28}N_7O$ $(M+H)^+$: m/z=454.2. found 454.2.

Example 95

4-[8-[4-(dimethylamino)piperidin-1-yl]-5-(3-hydroxy-2,3-dihydro-1H-inden-5-yl)imidazo[1,2-a]pyrazin-6-yl]benzonitrile

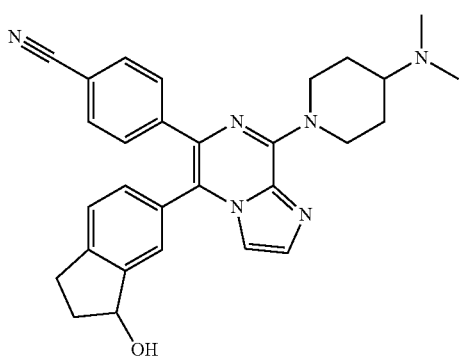 [SMILES: CN(C)C1CCN(c2nc(-c3ccc(C#N)cc3)c(-c3ccc4c(c3)C(O)CC4)n3ccnc23)CC1]

The title compound was prepared using similar procedures as described for Example 92 with 6-(4,4,5,5-tetramethyl-1,3,2-dioxaborolan-2-yl)-2,3-dihydro-1H-inden-1-ol (Example 73, Step 2) replacing 2,3-dimethyl-5-(4,4,5,5-tetramethyl-1,3,2-dioxaborolan-2-yl)pyridine. The reaction mixture was purified by prep-HPLC (pH=2, acetonitrile/water+TFA) to give the desired product (racemic) as the TFA salt. LC-MS calculated for $C_{29}H_{31}N_6O$ $(M+H)^+$: m/z=479.3. found 479.2.

Example 96

4-{8-[4-(dimethylamino)piperidin-1-yl]-5-[3-(hydroxymethyl)-4-methylphenyl]imidazo[1,2-a]pyrazin-6-yl}benzonitrile

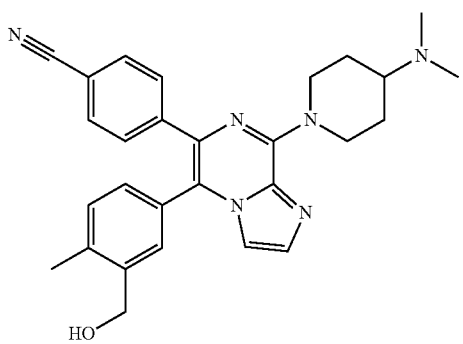 [SMILES: Cc1ccc(-c2c(-c3ccc(C#N)cc3)nc(N3CCC(N(C)C)CC3)c3nccn23)cc1CO]

The title compound was prepared using similar procedures as described for Example 92 with (2-methyl-5-(4,4,5,5-tetramethyl-1,3,2-dioxaborolan-2-yl)phenyl)methanol (Combi-Blocks, cat #FM-2080) replacing 2,3-dimethyl-5-(4,4,5,5-tetramethyl-1,3,2-dioxaborolan-2-yl)pyridine.

The reaction mixture was purified by prep-HPLC (pH=2, acetonitrile/water+TFA) to give the desired product as the TFA salt. LC-MS calculated for $C_{28}H_{31}N_6O$ $(M+H)^+$: m/z=467.3. found 467.2.

Example 97

4-{8-[4-(dimethylamino)piperidin-1-yl]-5-[3-fluoro-4-(hydroxymethyl)-5-methylphenyl]imidazo[1,2-a]pyrazin-6-yl}benzonitrile

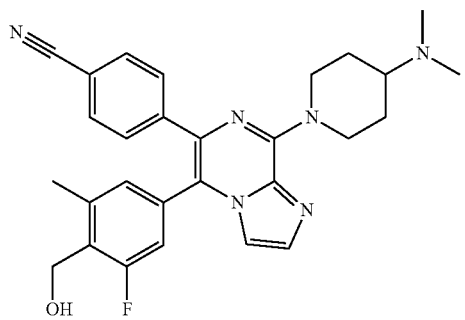 [SMILES: Cc1cc(-c2c(-c3ccc(C#N)cc3)nc(N3CCC(N(C)C)CC3)c3nccn23)cc(F)c1CO]

The title compound was prepared using similar procedures as described for Example 92 with (2-fluoro-6-methyl-4-(4,4,5,5-tetramethyl-1,3,2-dioxaborolan-2-yl)phenyl)methanol (Example 81, Step 2) replacing 2,3-dimethyl-5-(4,4,5,5-tetramethyl-1,3,2-dioxaborolan-2-yl)pyridine. The reaction mixture was purified by prep-HPLC (pH=2, acetonitrile/water+TFA) to give the desired product as the TFA salt. LC-MS calculated for $C_{28}H_{30}FN_6O$ $(M+H)^+$: m/z=485.2. found 485.2.

Example 98

4-[8-[4-(dimethylamino)piperidin-1-yl]-5-(1-methyl-2-oxo-2,3-dihydro-1H-indol-5-yl)imidazo[1,2-a]pyrazin-6-yl]benzonitrile

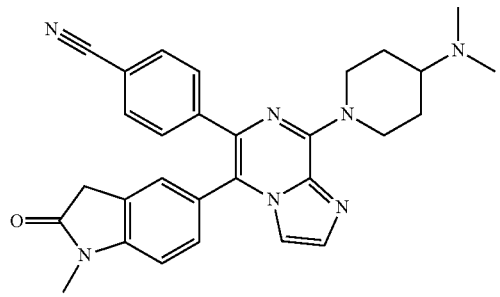 [SMILES: CN1C(=O)Cc2cc(-c3c(-c4ccc(C#N)cc4)nc(N4CCC(N(C)C)CC4)c4nccn34)ccc21]

Step 1: 1-methyl-5-(4,4,5,5-tetramethyl-1,3,2-dioxaborolan-2-yl)-1,3-dihydro-2H-indol-2-one

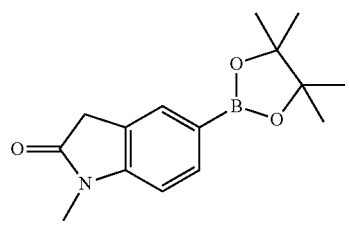

A mixture of 5-bromo-1-methyl-1,3-dihydro-2H-indol-2-one (Maybridge, cat #CC63010, 0.30 g, 1.3 mmol), 4,4,5,5,4',4',5',5'-octamethyl-[2,2']bi[[1,3,2]dioxaborolanyl](500 mg, 2.0 mmol), [1,1'-bis(diphenylphosphino)ferrocene]dichloropalladium(II) complexed with dichloromethane (1:1) (50 mg, 0.07 mmol) and potassium acetate (390 mg, 4.0 mmol) in 1,4-dioxane (10 mL) was purged with nitrogen and heated at 90° C. overnight. After cooling it was concentrated. The crude material was purified by flash chromatography on a silica gel column eluting with 0 to 25% EtOAc in hexanes to give the desired product. LC-MS calculated for $C_{15}H_{21}BNO_3$ $(M+H)^+$: m/z=274.2. found 274.1.

Step 2: 4-[8-[4-(dimethylamino)piperidin-1-yl]-5-(1-methyl-2-oxo-2,3-dihydro-1H-indol-5-yl)imidazo[1,2-a]pyrazin-6-yl]benzonitrile The title compound was prepared using similar procedures as described for Example 58, Step 5 with 1-methyl-5-(4,4,5,5-tetramethyl-1,3,2-dioxaborolan-2-yl)-1,3-dihydro-2H-indol-2-one replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{29}H_{30}N_7O$ $(M+H)^+$: m/z=492.2. found 492.2.

Example 99

4-{8-[3-(dimethylamino)piperidin-1-yl]-5-[6-(2-oxopyrrolidin-1-yl)pyridin-3-yl]imidazo[1,2-a]pyrazin-6-yl}benzonitrile

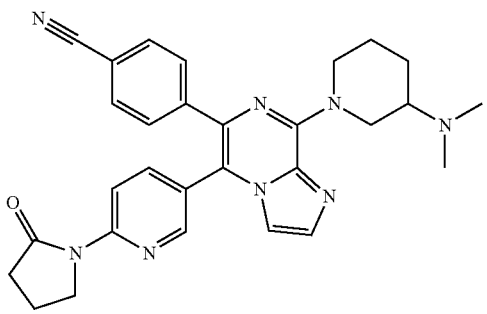 [SMILES: CN(C)C1CCCN(c2nc(-c3ccc(C#N)cc3)c(-c3ccc(N4CCCC4=O)nc3)n3ccnc23)C1]

The title compound was prepared using similar procedures as described for Example 57 with N,N-dimethylpiperidin-3-amine (ChemBridge Corp., cat #4018212) replacing N,N-dimethylpiperidin-4-amine. The reaction mixture was purified by prep-HPLC (pH=2, acetonitrile/water+TFA) to give the desired product as the TFA salt. LC-MS calculated for $C_{29}H_{31}N_8O$ $(M+H)^+$: m/z=507.3. found 507.2. $^1$H NMR (400 MHz, $CD_3OD$) δ 8.54 (d, J=8.7 Hz, 1H), 8.23 (d, J=1.7 Hz, 1H), 7.93 (dd, J=8.7, 2.4 Hz, 1H), 7.68-7.60 (m, 3H), 7.59-7.52 (m, 3H), 5.22 (d, J=12.8 Hz, 2H), 4.15 (m, 3H), 3.78 (t, J=10.3 Hz, 1H), 3.61-3.45 (m, 1H), 3.14 (s, 3H), 3.00 (s, 3H), 2.71 (t, J=8.1 Hz, 2H), 2.33-2.13 (m, 3H), 2.12-1.94 (m, 2H), 1.93-1.75 (m, 1H).

Example 100

4-{8-[4-(dimethylamino)piperidin-1-yl]-5-[6-(3-methyl-2-oxoimidazolidin-1-yl)pyridin-3-yl]imidazo[1,2-a]pyrazin-6-yl}benzonitrile

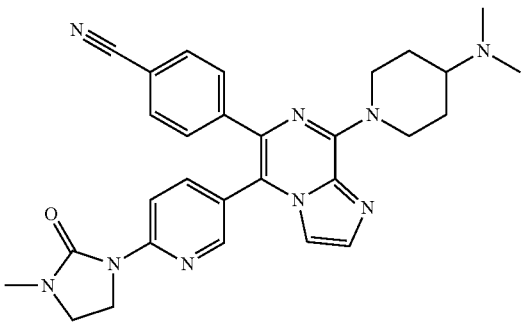

Step 1:
1-(5-bromopyridin-2-yl)-3-methylimidazolidin-2-one

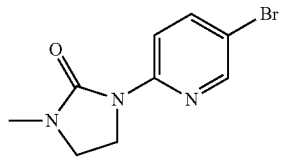

To a solution of 1-methylimidazolidin-2-one (0.210 g, 2.10 mmol) in N,N-dimethylformamide (2.1 mL) at 0° C. was added sodium hydride (60% dispersion in mineral oil, 83.9 g, 2.10 mmol) in portions. The mixture was stirred for 30 min at room temperature. Then 5-bromo-2-fluoropyridine (0.216 mL, 2.10 mmol) in N,N-dimethylformamide (0.42 mL) was added dropwise. The reaction was stirred overnight, then heated to 80° C. for 1.5 h before quenching with a methanol and water mixture. The mixture was extracted with dichloromethane, dried over magnesium sulfate and concentrated in vacuo. The crude product was purified by chromatography on silica eluting with 0-50% EtOAc in hexanes to afford the desired product. LC-MS calculated for $C_9H_{11}BrN_3O$ $(M+H)^+$: m/z=256.0. found 256.0.

Step 2: 1-methyl-3-[5-(4,4,5,5-tetramethyl-1,3,2-dioxaborolan-2-yl)pyridin-2-yl]imidazolidin-2-one

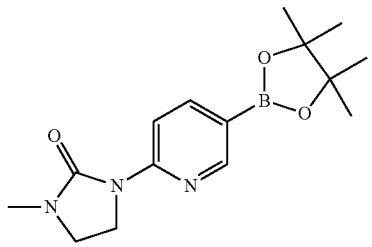

A mixture of 1-(5-bromopyridin-2-yl)-3-methylimidazolidin-2-one (220 mg, 0.84 mmol), 4,4,5,5,4',4',5',5'-octamethyl-[2,2']bi[[1,3,2]dioxaborolanyl](230 mg, 0.92 mmol), [1,1'-bis(diphenylphosphino)ferrocene]dichloropalladium (II), complex with dichloromethane (1:1) (74 mg, 0.090 mmol) and potassium acetate (200 mg, 2 mmol) in 1,4-dioxane (5 mL) was purged with nitrogen and heated at 80° C. overnight. After cooling to room temperature, it was concentrated, then diluted with EtOAc followed by filtration through Celite. The filtrate was concentrated and purified by chromatography on silica with 0-50% EtOAc in hexanes to afford the desired prod. LC-MS calculated for $C_{15}H_{23}BN_3O_3$ (M+H)$^+$: m/z=304.2. found 304.2.

Step 3: 4-{8-[4-(dimethylamino)piperidin-1-yl]-5-[6-(3-methyl-2-oxoimidazolidin-1-yl)pyridin-3-yl] imidazo[1,2-a]pyrazin-6-yl}benzonitrile The title compound was prepared using similar procedures as described for Example 58, Step 5 with 1-methyl-3-[5-(4,4,5,5-tetramethyl-1,3,2-dioxaborolan-2-yl)pyridin-2-yl]imidazolidin-2-one replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{29}H_{32}N_9O$ (M+H)$^+$: m/z=522.3. found 522.2. $^1$H NMR (400 MHz, $CD_3OD$) δ 8.40 (d, J=8.5 Hz, 1H), 8.12 (s, 1H), 7.83 (dd, J=8.8, 2.3 Hz, 1H), 7.62-7.50 (m, 6H), 5.73 (d, J=13.6 Hz, 2H), 4.12-4.00 (m, 2H), 3.66-3.53 (m, 3H), 3.33 (s, 3H), 3.25-3.11 (m, 2H), 2.94 (s, 6H), 2.24 (d, J=10.7 Hz, 2H), 1.88 (d, J=8.6 Hz, 2H).

Example 101

4-{8-[4-(dimethylamino)piperidin-1-yl]-5-quinoxalin-6-ylimidazo[1,2-a]pyrazin-6-yl}benzonitrile

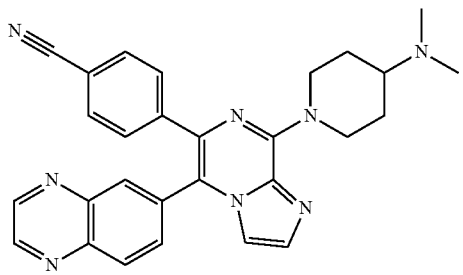 [SMILES: CN(C)C1CCN(c2nc(-c3ccc(C#N)cc3)c(-c3ccc4nccnc4c3)n3ccnc23)CC1]

The title compound was prepared using similar procedures as described for Example 58, Step 5 with 6-(4,4,5,5-tetramethyl-1,3,2-dioxaborolan-2-yl)quinoxaline (Aldrich, cat #708631) replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{28}H_{27}N_8$ (M+H)$^+$: m/z=475.2. found 475.2. $^1$H NMR (400 MHz, $CD_3OD$) δ 8.99-8.90 (m, 2H), 8.24 (d, J=8.7 Hz, 1H), 8.10 (d, J=1.6 Hz, 1H), 7.87 (dd, J=8.7, 1.8 Hz, 1H), 7.61 (d, J=1.2 Hz, 1H), 7.57-7.49 (m, 5H), 5.85-5.70 (m, 2H), 3.68-3.54 (m, 1H), 3.20 (t, J=12.5 Hz, 2H), 2.93 (s, 6H), 2.32-2.16 (m, 2H), 1.98-1.80 (m, 2H).

Example 102

4-[8-[4-(dimethylamino)piperidin-1-yl]-5-(1-methyl-2-oxo-1,2,3,4-tetrahydroquinolin-6-yl)imidazo[1,2-a]pyrazin-6-yl]benzonitrile

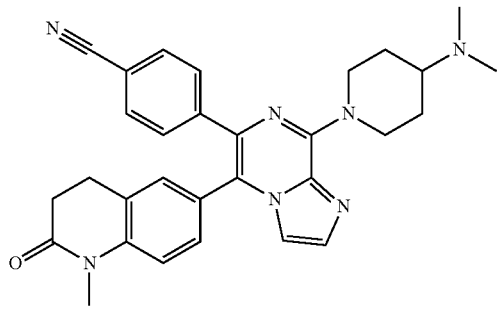

Step 1: 1-methyl-6-(4,4,5,5-tetramethyl-1,3,2-dioxaborolan-2-yl)-3,4-dihydroquinolin-2 (1H)-one

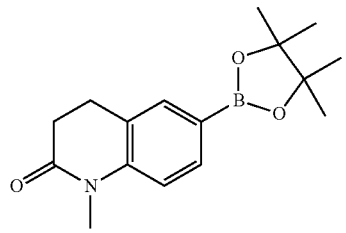 [SMILES: CN1C(=O)CCc2cc(B3OC(C)(C)C(C)(C)O3)ccc21]

A mixture of 6-bromo-1-methyl-3,4-dihydroquinolin-2 (1H)-one (Matrix Scientific, cat #101386: 0.4 g, 2 mmol), 4,4,5,5,4',4',5',5'-octamethyl-[2,2']bi[[1,3,2]dioxaborolanyl] (630 mg, 2.5 mmol), [1,1'-bis(diphenylphosphino)ferrocene]dichloropalladium(II), complex with dichloromethane (1:1) (70 mg, 0.08 mmol) and potassium acetate (490 mg, 5.0 mmol) in 1,4-dioxane (20 mL) was purged with nitrogen then heated at 90° C. overnight. After cooling it was concentrated. The crude material was purified by flash column eluting with 0 to 35% AcOEt in hexanes to give the desired product. LC-MS calculated for $C_{16}H_{23}BNO_3$ (M+H)$^+$: m/z=288.2. found 288.2.

Step 2: 4-[8-[4-(dimethylamino)piperidin-1-yl]-5-(1-methyl-2-oxo-1,2,3,4-tetrahydroquinolin-6-yl)imidazo[1,2-a]pyrazin-6-yl]benzonitrile The title compound was prepared using similar procedures as described for Example 58, Step 5 with 1-methyl-6-(4,4,5,5-tetramethyl-1,3,2-dioxaborolan-2-yl)-3,4-dihydroquinolin-2(1H)-one replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{30}H_{32}N_7O$ (M+H)$^+$: m/z=506.3. found 506.2. $^1$H NMR (400 MHz, $CD_3OD$) δ 7.63-7.58 (m, 5H), 7.51 (d, J=1.1 Hz, 1H), 7.32-7.22 (m, 3H), 5.70 (d, J=13.6 Hz, 2H), 3.60 (t, J=12.1 Hz, 1H), 3.41

(s, 3H), 3.37 (m, 2H), 3.18 (t, J=11.9 Hz, 2H), 2.94 (s, 6H), 2.68 (q, J=7.0 Hz, 2H), 2.25 (d, J=11.1 Hz, 2H), 1.97-1.80 (m, 2H).

Example 103

4-{8-[4-(dimethylamino)piperidin-1-yl]-5-[2-(hydroxymethyl)-1-methyl-1H-pyrrolo[2,3-b]pyridin-5-yl]imidazo[1,2-a]pyrazin-6-yl}benzonitrile

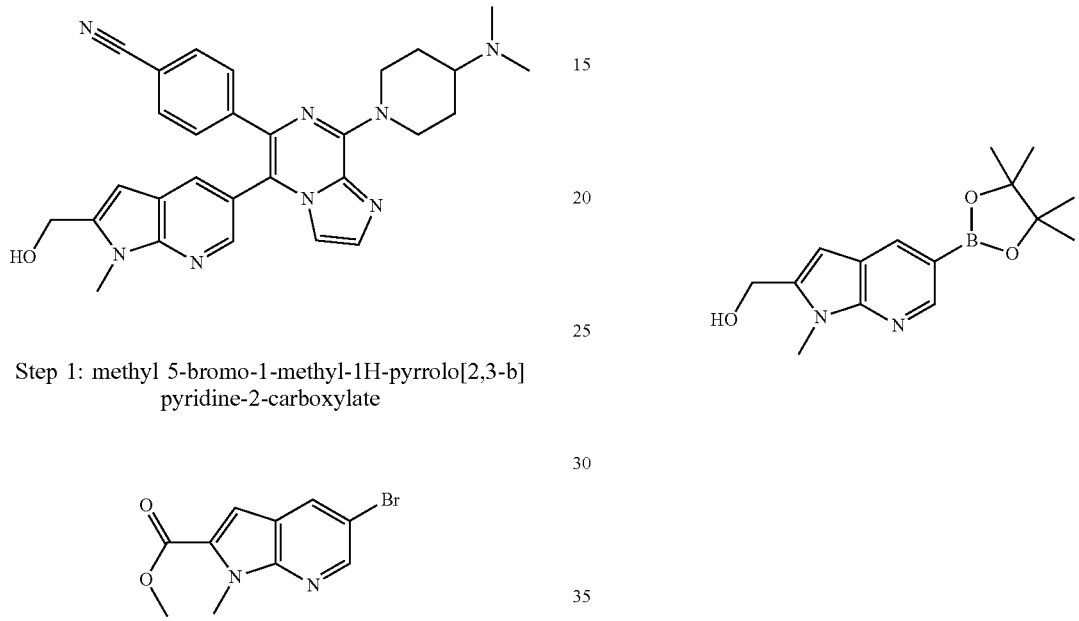

Step 1: methyl 5-bromo-1-methyl-1H-pyrrolo[2,3-b]pyridine-2-carboxylate

To a suspension of 5-bromo-1H-pyrrolo[2,3-b]pyridine-2-carboxylic acid (Adesis, cat #4-453: 101 mg, 0.419 mmol) and potassium carbonate (300 mg, 2 mmol) in acetonitrile (2 mL) was added dimethyl sulfate (75 µL, 0.80 mmol) dropwise at room temperature. The mixture was stirred at room temperature for 30 min then at 60° C. overnight. Then the reaction mixture was cooled to room temperature, filtered and the filtrate was concentrated and used directly in the next step without further purification. LC-MS calculated for $C_{10}H_{10}BrN_2O_2$ (M+H)$^+$: m/z=269.0. found 269.0.

Step 2: (5-bromo-1-methyl-1H-pyrrolo[2,3-b]pyridin-2-yl)methanol

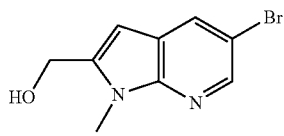

To a solution of methyl 5-bromo-1-methyl-1H-pyrrolo[2,3-b]pyridine-2-carboxylate (0.1 g, 0.4 mmol) in tetrahydrofuran (2 mL) was slowly added 1.0 M lithium tetrahydroaluminate in tetrahydrofuran (0.28 mL, 0.28 mmol) at 0° C. The reaction mixture was slowly warmed to room temperature and stirred for 30 min. Then the reaction was quenched by EtOAc, the reaction mixture was concentrated and purified by column chromatography on silica gel with 0-60% EtOAc in hexanes to afford the desired product. LC-MS calculated for $C_9H_{10}BrN_2O$ (M+H)$^+$: m/z=241.0. found 241.0.

Step 3: [1-methyl-5-(4,4,5,5-tetramethyl-1,3,2-dioxaborolan-2-yl)-1H-pyrrolo[2,3-b]pyridin-2-yl]methanol A mixture of (5-bromo-1-methyl-1H-pyrrolo[2,3-b]pyridin-2-yl)methanol (56 mg, 0.23 mmol), 4,4,5,5,4',4',5',5'-octamethyl-[2,2']bi[[1,3,2]dioxaborolanyl](65 mg, 0.26 mmol), [1,1'-bis(diphenylphosphino)ferrocene]dichloropalladium(II), complex with dichloromethane (1:1) (20. mg, 0.025 mmol) and potassium acetate (60 mg, 0.7 mmol) in 1,4-dioxane (1 mL) was purged with nitrogen and heated at 90° C. for 6 hrs. After cooling the reaction mixture was concentrated, then diluted with EtOAc followed by filtration through Celite. The filtrate was concentrated and purified by chromatography on silica gel with 0-90% EtOAc in hexanes to afford the desired product. LC-MS calculated for $C_{15}H_{22}BN_2O_3$ (M+H)$^+$: m/z=289.2. found 289.1.

Step 4: 4-{8-[4-(dimethylamino)piperidin-1-yl]-5-[2-(hydroxymethyl)-1-methyl-1H-pyrrolo[2,3-b]pyridin-5-yl]imidazo[1,2-a]pyrazin-6-yl}benzonitrile The title compound was prepared using similar procedures as described for Example 58, Step 5 with [1-methyl-5-(4,4,5,5-tetramethyl-1,3,2-dioxaborolan-2-yl)-1H-pyrrolo[2,3-b]pyridin-2-yl]methanol replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{29}H_{31}N_8O$ (M+H)$^+$: m/z=507.3. found 507.2. $^1$H NMR (400 MHz, CD$_3$OD) δ 8.10 (s, 1H), 8.05 (s, 1H), 7.61-7.47 (m, 6H), 6.55 (s, 1H), 5.71 (m, 2H), 4.86 (s, 2H), 3.93 (s, 3H), 3.61 (m, 1H), 3.24-3.11 (m, 2H), 2.94 (s, 6H), 2.25 (d, J=10.8 Hz, 2H), 1.90 (m, 2H).

Example 104

4-{8-[(3S)-3-(dimethylamino)pyrrolidin-1-yl]-5-[6-(2-oxopyrrolidin-1-yl)pyridin-3-yl]imidazo[1,2-a]pyrazin-6-yl}benzonitrile

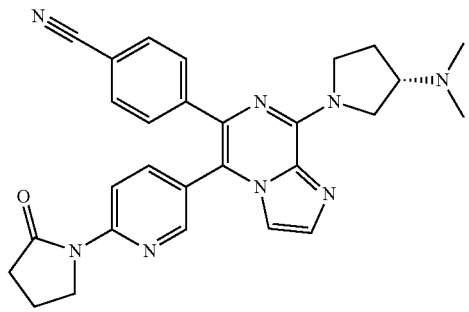 [SMILES: CN(C)[C@H]1CCN(c2nc(-c3ccc(C#N)cc3)c(-c3ccc(N4CCCC4=O)nc3)n3ccnc23)C1]

The title compound was prepared using similar procedures as described for Example 57 with (3S)—N,N-dimethylpyrrolidin-3-amine (TCI, cat #D2193) replacing N,N-dimethylpiperidin-4-amine. The reaction mixture was purified by prep-HPLC (pH=2, acetonitrile/water+TFA) to give the desired product as the TFA salt. LC-MS calculated for $C_{28}H_{29}N_8O$ (M+H)$^+$: m/z=493.2. found 493.2. $^1$H NMR (400 MHz, CD$_3$OD) δ 8.52 (d, J=8.7 Hz, 1H), 8.21 (s, 1H), 7.92 (dd, J=8.7, 2.1 Hz, 1H), 7.67-7.49 (m, 6H), 4.64 (dd, J=12.5, 7.5 Hz, 1H), 4.50 (t, J=8.7 Hz, 1H), 4.36 (dd, J=12.4, 6.7 Hz, 1H), 4.20-4.00 (m, 4H), 3.07 (s, 6H), 2.76-2.58 (m, 3H), 2.42-2.25 (m, 1H), 2.24-2.09 (m, 2H).

Example 105

4-[8-[4-(dimethylamino)piperidin-1-yl]-5-(3-ethyl-2-oxo-2,3-dihydro[1,3]oxazolo[4,5-b]pyridin-6-yl)imidazo[1,2-a]pyrazin-6-yl]benzonitrile

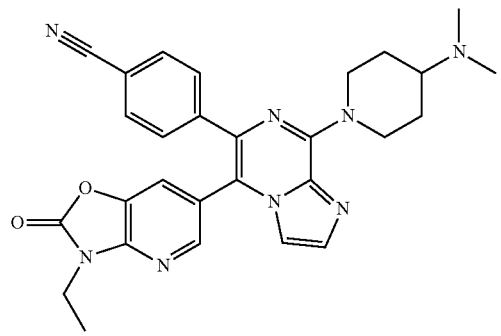 [SMILES: CCn1c(=O)oc2cc(-c3c(-c4ccc(C#N)cc4)nc(N4CCC(N(C)C)CC4)c4nccn34)cnc21]

Step 1: 6-bromo-3-ethyl[1,3]oxazolo[4,5-b]pyridin-2(3H)-one

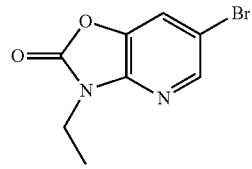

To a mixture of 6-bromo[1,3]oxazolo[4,5-b]pyridin-2(3H)-one (Ark Pharm, cat #AK-24539: 192 mg, 0.893 mmol) and cesium carbonate (440 mg, 1.3 mmol) in tetrahydrofuran (3 mL) was added iodoethane (0.4 mL, 4 mmol). The reaction mixture was stirred at 50° C. overnight. The mixture was filtered, concentrated and purified by column chromatography eluting with 0-30% EtOAc in hexanes. LC-MS calculated for $C_8H_8BrN_2O_2$ (M+H)$^+$: m/z=243.0. found 243.0.

Step 2: 3-ethyl-6-(4,4,5,5-tetramethyl-1,3,2-dioxaborolan-2-yl)[1,3]oxazolo[4,5-b]pyridin-2(3H)-one

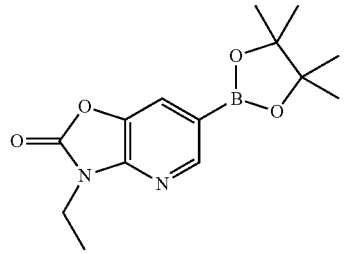 [SMILES: CCn1c(=O)oc2cc(B3OC(C)(C)C(C)(C)O3)cnc21]

A mixture of 6-bromo-3-ethyl[1,3]oxazolo[4,5-b]pyridin-2(3H)-one (81 mg, 0.33 mmol), 4,4,5,5,4',4',5',5'-octamethyl-[2,2']bi[[1,3,2]dioxaborolanyl](93 mg, 0.37 mmol), [1,1'-bis(diphenylphosphino)ferrocene]dichloropalladium (II), complex with dichloromethane (1:1) (29 mg, 0.036 mmol) and potassium acetate (90 mg, 1 mmol) in 1,4-dioxane (2 mL) was purged with nitrogen and heated at 90° C. for 6 hrs. After cooling it was concentrated, then diluted with EtOAc followed by filtration through Celite. The filtrate was concentrated and purified by chromatography on silica with 0-90% EtOAc in hexanes to afford the desired prod. LC-MS calculated for $C_{14}H_{20}BN_2O_4$ (M+H)$^+$: m/z=291.2. found 291.2.

Step 3: 4-[8-[4-(dimethylamino)piperidin-1-yl]-5-(3-ethyl-2-oxo-2,3-dihydro[1,3]oxazolo[4,5-b]pyridin-6-yl)imidazo[1,2-a]pyrazin-6-yl]benzonitrile The title compound was prepared using similar procedures as described for Example 58, Step 5 with 3-ethyl-6-(4,4,5,5-tetramethyl-1,3,2-dioxaborolan-2-yl)[1,3]oxazolo[4,5-b]pyridin-2(3H)-one replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{28}H_{29}N_8O_2$ (M+H)$^+$: m/z=509.2. found 509.2.

Example 106

4-[8-[4-(dimethylamino)piperidin-1-yl]-5-(1-methyl-1H-benzimidazol-5-yl)imidazo[1,2-a]pyrazin-6-yl]benzonitrile

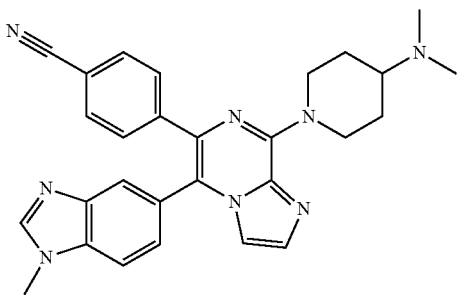 [SMILES: CN(C)C1CCN(c2nc(-c3ccc(C#N)cc3)c(-c3ccc4c(c3)ncn4C)n3ccnc23)CC1]

The title compound was prepared using similar procedures as described for Example 58, Step 5 with 1-methyl-5-(4,4,5,5-tetramethyl-1,3,2-dioxaborolan-2-yl)-1H-benzimidazole (Combi-Blocks, cat #FA-4841) replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{28}H_{29}N_8$ $(M+H)^+$: m/z=477.2. found 477.2. $^1$H NMR (400 MHz, $CD_3OD$) δ 9.18 (s, 1H), 7.98 (d, J=8.6 Hz, 1H), 7.83 (s, 1H), 7.66-7.57 (m, 2H), 7.54-7.48 (m, 4H), 7.44 (d, J=1.1 Hz, 1H), 5.79-5.68 (m, 2H), 4.14 (s, 3H), 3.67-3.53 (m, 1H), 3.18 (t, J=12.2 Hz, 2H), 2.92 (s, 6H), 2.30-2.19 (m, 2H), 1.97-1.81 (m, 2H).

Example 107

4-[8-[4-(dimethylamino)piperidin-1-yl]-5-(4-methyl-3-oxo-3,4-dihydro-2H-pyrido[3,2-b][1,4]oxazin-7-yl)imidazo[1,2-a]pyrazin-6-yl]benzonitrile

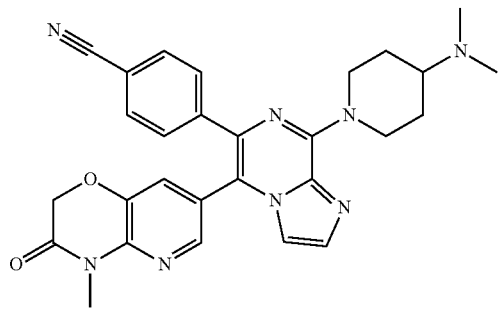

Step 1: 7-bromo-4-methyl-2H-pyrido[3,2-b][1,4]oxazin-3(4H)-one

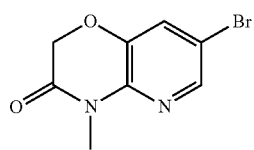

To a mixture of 7-bromo-2H-pyrido[3,2-b][1,4]oxazin-3(4H)-one (Ark Pharma, cat #AK-30821: 204 mg, 0.893 mmol) and cesium carbonate (440 mg, 1.3 mmol) in tetrahydrofuran (3 mL) was added methyl iodide (2.0 mL, 30 mmol). The mixture was stirred at 50° C. overnight. After cooling to room temperature, the reaction mixture was filtered and concentrated. The residue was used in the next step without further purification. LC-MS calculated for $C_8H_8BrN_2O_2$ $(M+H)^+$: m/z=243.0. found 242.9.

Step 2: 4-methyl-7-(4,4,5,5-tetramethyl-1,3,2-dioxaborolan-2-yl)-2H-pyrido[3,2-b][1,4]oxazin-3(4H)-one

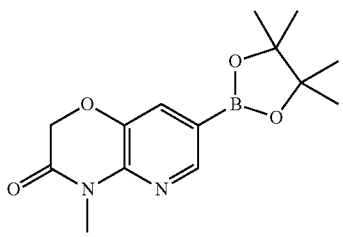 [SMILES: CN1C(=O)COc2cc(B3OC(C)(C)C(C)(C)O3)cnc21]

A mixture of 7-bromo-4-methyl-2H-pyrido[3,2-b][1,4]oxazin-3(4H)-one (200 mg, 0.8 mmol), 4,4,5,5,4',4',5',5'-octamethyl-[2,2']bi[[1,3,2]dioxaborolanyl](230 mg, 0.90 mmol), [1,1'-bis(diphenylphosphino)ferrocene]dichloropalladium(II), complex with dichloromethane (1:1) (70 mg, 0.08 mmol) and potassium acetate (300 mg, 3 mmol) in 1,4-dioxane (3 mL) was purged with nitrogen then stirred at 90° C. for 6 h. After cooling to room temperature, the reaction mixture was concentrated and the residue was dissolved in EtOAc then filtered. The filtrate was concentrated and the residue was purified by flash chromatography on a silica gel column eluting with 0-90% EtOAc in hexanes to afford the desired product. LC-MS calculated for $C_{14}H_{20}BN_2O_4$ $(M+H)^+$: m/z=291.2. found 291.1.

Step 3: 4-[8-[4-(dimethylamino)piperidin-1-yl]-5-(4-methyl-3-oxo-3,4-dihydro-2H-pyrido[3,2-b][1,4]oxazin-7-yl)imidazo[1,2-a]pyrazin-6-yl]benzonitrile The title compound was prepared using similar procedures as described for Example 58, Step 5 with 4-methyl-7-(4,4,5,5-tetramethyl-1,3,2-dioxaborolan-2-yl)-2H-pyrido[3,2-b][1,4]oxazin-3(4H)-one replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{28}H_{29}N_8O_2$ $(M+H)^+$: m/z=509.2. found 509.2. $^1$H NMR (400 MHz, $CD_3OD$) δ 7.86 (d, J=1.8 Hz, 1H), 7.66-7.53 (m, 6H), 7.44 (d, J=1.8 Hz, 1H), 5.81-5.66 (m, 2H), 4.79 (s, 2H), 3.65-3.53 (m, 1H), 3.45 (s, 3H), 3.16 (t, J=12.3 Hz, 2H), 2.91 (s, 6H), 2.29-2.17 (m, 2H), 1.93-1.78 (m, 2H).

Example 108

4-[8-[4-(dimethylamino)piperidin-1-yl]-5-(1-methyl-2-oxo-1,2,3,4-tetrahydroquinolin-7-yl)imidazo[1,2-a]pyrazin-6-yl]benzonitrile

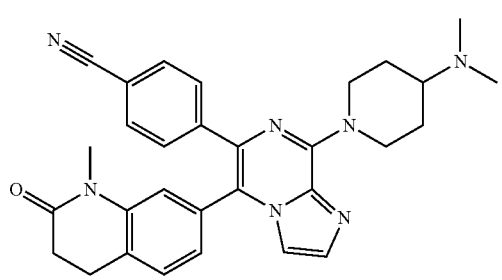 [SMILES: CN1C(=O)CCc2ccc(-c3c(-c4ccc(C#N)cc4)nc(N4CCC(N(C)C)CC4)c4nccn34)cc21]

Step 1: 1-methyl-7-(4,4,5,5-tetramethyl-1,3,2-dioxaborolan-2-yl)-3,4-dihydroquinolin-2 (H)-one

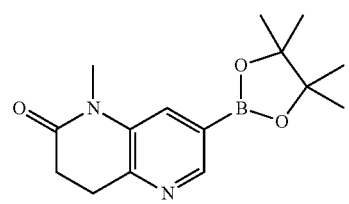 [SMILES: CN1C(=O)CCc2ncc(B3OC(C)(C)C(C)(C)O3)cc21]

A mixture of 7-bromo-1-methyl-3,4-dihydroquinolin-2 (1H)-one (Alfa Aesar, cat #H33197: 0.260 g, 1.08 mmol), 4,4,5,5,4',4',5',5'-octamethyl-[2,2']bi[[1,3,2]dioxaborolanyl] (410 mg, 1.6 mmol), [1,1'-bis(diphenylphosphino)ferrocene]dichloropalladium(II), complex with dichloromethane (1:1) (40 mg, 0.05 mmol) and potassium acetate (320 mg, 3.2 mmol) in 1,4-dioxane (10 mL) was purged with nitrogen and heated at 90° C. overnight. After cooling it was concentrated, then diluted with EtOAc followed by filtration through Celite. The filtrate was concentrated and purified by chromatography on silica with 0-50% EtOAc in hexanes to afford the desired product. LC-MS calculated for $C_{16}H_{23}BNO_3$ (M+H)$^+$: m/z=288.2. found 288.2.

Step 2: 4-[8-[4-(dimethylamino)piperidin-1-yl]-5-(1-methyl-2-oxo-1,2,3,4-tetrahydroquinolin-7-yl)imidazo[1,2-a]pyrazin-6-yl]benzonitrile The title compound was prepared using similar procedures as described for Example 58, Step 5 with 1-methyl-7-(4,4,5,5-tetramethyl-1,3,2-dioxaborolan-2-yl)-3,4-dihydroquinolin-2(1H)-one replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{30}H_{32}N_7O$ (M+H)$^+$: m/z=506.3. found 506.3.

Example 109

4-{8-[4-(dimethylamino)piperidin-1-yl]-5-[6-(4-methyl-3-oxopiperazin-1-yl)pyridin-3-yl]imidazo[1,2-a]pyrazin-6-yl}benzonitrile Step 1: 4-(5-bromopyridin-2-yl)-1-methylpiperazin-2-one To a solution of 5-bromo-2-fluoropyridine (0.100 mL, 0.972 mmol) in N,N-dimethylformamide (4.0 mL) was added triethylamine (0.284 mL, 2.04 mmol) and 1-methylpiperazin-2-one hydrochloride (0.161 g, 1.07 mmol). The resulting mixture was heated at 100° C. for 12 h then cooled to room temperature, diluted with DCM, washed with water and brine. The organic layer was dried over $Na_2SO_4$, filtered and concentrated. The residue was purified by flash chromatography on a silica gel column eluting with 0 to 100% EtoAc/Hexanes to give the desired product. LC-MS calculated for $C_{10}H_{13}BrN_3O$ (M+H)$^+$: m/z=270.0. found 270.0.

Step 2: 1-methyl-4-[5-(4,4,5,5-tetramethyl-1,3,2-dioxaborolan-2-yl)pyridin-2-yl]piperazin-2-one A mixture of 4-(5-bromopyridin-2-yl)-1-methylpiperazin-2-one (0.117 g, 0.433 mmol), 4,4,5,5,4',4',5',5'-octamethyl-[2,2']bi[[1,3,2]dioxaborolanyl](0.165 g, 0.649 mmol), [1,1'-bis(diphenylphosphino)ferrocene]dichloropalladium(II), complex with dichloromethane (1:1) (40 mg, 0.05 mmol) and potassium acetate (0.127 g, 1.30 mmol) in 1,4-dioxane (2 mL) was purged with nitrogen and heated at 90° C. overnight. After cooling it was concentrated, then diluted with EtOAc followed by filtration through Celite. The filtrate was concentrated and the residue was used in the next step without further purification.

Step 3: 4-{8-[4-(dimethylamino)piperidin-1-yl]-5-[6-(4-methyl-3-oxopiperazin-1-yl)pyridin-3-yl]imidazo[1,2-a]pyrazin-6-yl}benzonitrile The title compound was prepared using similar procedures as described for Example 58, Step 5 with 1-methyl-4-[5-(4,4,5,5-tetramethyl-1,3,2-dioxaborolan-2-yl)pyridin-2-yl]piperazin-2-one replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{30}H_{34}N_9O$ $(M+H)^+$: m/z=536.3. found 536.3.

Example 110

4-{8-[4-(dimethylamino)piperidin-1-yl]-5-[3-(hydroxymethyl)-1-methyl-1H-indazol-5-yl]imidazo[1,2-a]pyrazin-6-yl}benzonitrile

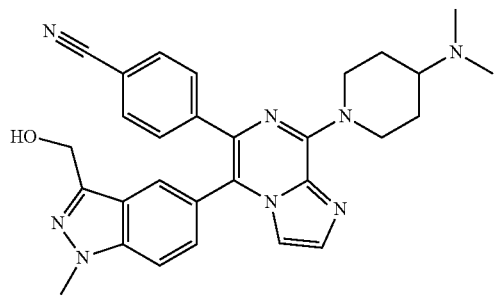 [SMILES: CN(C)C1CCN(c2nc(-c3ccc(C#N)cc3)c(-c3ccc4c(c3)c(CO)nn4C)n3ccnc23)CC1]

Step 1: methyl 5-bromo-1-methyl-1H-indazole-3-carboxylate

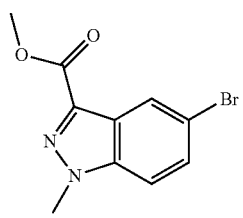

To a solution of 5-bromo-1H-indazole-3-carboxylic acid (J&W PharmLab, cat #45-0107: 210.0 mg, 0.87 mmol) and methyl iodide (200 µL, 3 mmol) in tetrahydrofuran (2 mL) was added cesium carbonate (0.42 g, 1.3 mmol). The mixture was stirred at 65° C. overnight. After filtration, the filtrate was concentrated and the residue was dissolved in THF (3 mL) and treated with sodium hydride (45 mg, 1.1 mmol) followed by addition of methyl iodide (200 µL, 3 mmol). The reaction mixture was further stirred at room temperature for 5 h before heated to 65° C. for 2 h. The reaction mixture was concentrated and used directly for next step. LC-MS calculated for $C_{10}H_{10}BrN_2O_2$ $(M+H)^+$: m/z=269.0. found 269.0.

Step 2: (5-bromo-1-methyl-1H-indazol-3-yl)methanol

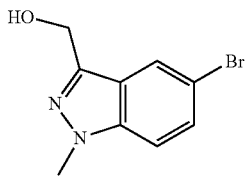

To a solution of methyl 5-bromo-1-methyl-1H-indazole-3-carboxylate (110 mg, 0.41 mmol) in tetrahydrofuran (2 mL, 20 mmol) was added lithium tetrahydroaluminate in THF (1.0 M, 120 µL, 0.12 mmol) dropwise at 0° C. The reaction mixture was stirred for 1 h, and the reaction was quenched by EtOAc, water followed by NaOH aqueous solution then extracted with EtOAc. The combined extracts were dried over $Na_2SO_4$, filtered and concentrated. The residue was purified by column chromatography eluting with 0-80% EtOAc in hexanes. LC-MS calculated for $C_9H_{10}BrN_2O$ $(M+H)^+$: m/z=241.0. found 241.0.

Step 3: [1-methyl-5-(4,4,5,5-tetramethyl-1,3,2-dioxaborolan-2-yl)-1H-indazol-3-yl]methanol

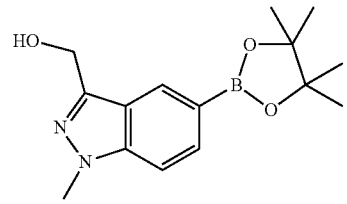 [SMILES: Cn1nc(CO)c2cc(B3OC(C)(C)C(C)(C)O3)ccc21]

A mixture of (5-bromo-1-methyl-1H-indazol-3-yl)methanol (20 mg, 0.083 mmol), 4,4,5,5,4',4',5',5'-octamethyl-[2,2']bi[[1,3,2]dioxaborolanyl](23 mg, 0.091 mmol), [1,1'-bis(diphenylphosphino)ferrocene]dichloropalladium(II) complex with dichloromethane (1:1) (7 mg, 0.008 mmol) and potassium acetate (20 mg, 0.2 mmol) in 1,4-dioxane (0.8 mL) was degassed and heated at 90° C. overnight. After cooling to room temperature, the reaction mixture was concentrated. The residue was purified by flash column chromatography eluting with 0 to 60% EtOAc in hexanes to give the desired product. LC-MS calculated for $C_{15}H_{22}BN_2O_3$ $(M+H)^+$: m/z=289.2. found 289.2.

Step 4: 4-{8-[4-(dimethylamino)piperidin-1-yl]-5-[3-(hydroxymethyl)-1-methyl-1H-indazol-5-yl]imidazo[1,2-a]pyrazin-6-yl}benzonitrile The title compound was prepared using similar procedures as described for Example 58, Step 5 with [1-methyl-5-(4,4,5,5-tetramethyl-1,3,2-dioxaborolan-2-yl)-1H-indazol-3-yl]methanol replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{29}H_{31}N_8O$ (M+H)$^+$: m/z=507.3. found 507.2. $^1$H NMR (400 MHz, CD$_3$OD) δ 7.96 (s, 1H), 7.67 (d, J=8.7 Hz, 1H), 7.63-7.55 (m, 3H), 7.52 (d, J=8.6 Hz, 2H), 7.46 (d, J=1.2 Hz, 1H), 7.36 (dd, J=8.7, 1.5 Hz, 1H), 5.70 (d, J=13.5 Hz, 2H), 4.90 (s, 2H), 4.10 (s, 3H), 3.70-3.54 (m, 1H), 3.19 (t, J=12.8 Hz, 2H), 2.94 (s, 6H), 2.26 (d, J=11.0 Hz, 2H), 1.92 (m, 2H).

Example 111

4-[8-[4-(dimethylamino)piperidin-1-yl]-5-(1-methyl-2-oxo-2,3-dihydro-1H-pyrrolo[2,3-b]pyridin-5-yl)imidazo[1,2-a]pyrazin-6-yl]benzonitrile

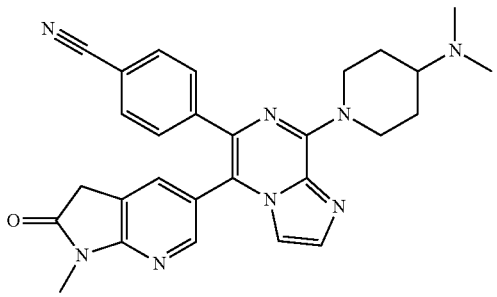 [SMILES: CN1C(=O)Cc2cc(-c3c(-c4ccc(C#N)cc4)nc(N4CCC(N(C)C)CC4)c4nccn34)cnc21]

The title compound was prepared using similar procedures as described for Example 58, Step 5 with 1-methyl-5-(4,4,5,5-tetramethyl-1,3,2-dioxaborolan-2-yl)-1,3-dihydro-2H-pyrrolo[2,3-b]pyridin-2-one (ChemBridge Corp., cat #4038124) replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{28}H_{29}N_8O$ (M+H)$^+$: m/z=493.2. found 493.2.

Example 112

4-[8-[4-(dimethylamino)piperidin-1-yl]-5-(1-methyl-1H-pyrrolo[2,3-b]pyridin-5-yl)imidazo[1,2-a]pyrazin-6-yl]benzonitrile

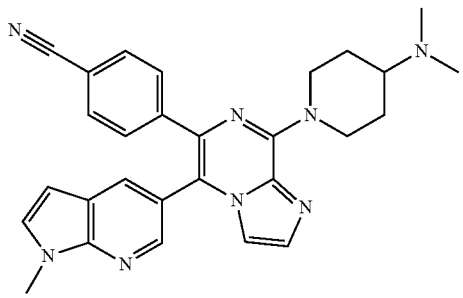 [SMILES: CN(C)C1CCN(c2nc(-c3ccc(C#N)cc3)c(-c3cnc4c(ccn4C)c3)n3ccnc23)CC1]

The title compound was prepared using similar procedures as described for Example 58, Step 5 with 1-methyl-5-(4,4,5,5-tetramethyl-1,3,2-dioxaborolan-2-yl)-1H-pyrrolo[2,3-b]pyridine (Combi-Blocks, cat #98552) replacing 1-methyl-5-(4,4,5,5-tetramethyl-1,3,2-dioxaborolan-2-yl)-1H-pyrazolo[3,4-b]pyridine. The reaction mixture was puri-fied by prep-HPLC (pH=2, acetonitrile/water+TFA) to give the desired product as the TFA salt. LC-MS calculated for $C_{28}H_{29}N_8$ (M+H)$^+$: m/z=477.2. found 477.2. $^1$H NMR (400 MHz, CD$_3$OD) δ 8.16-8.08 (m, 2H), 7.61 (d, J=1.2 Hz, 1H), 7.59-7.50 (m, 5H), 7.47 (d, J=1.2 Hz, 1H), 6.59 (d, J=3.5 Hz, 1H), 5.72 (d, J=12.8 Hz, 2H), 3.92 (s, 3H), 3.68-3.55 (m, 1H), 3.20 (t, J=12.0 Hz, 2H), 2.94 (s, 6H), 2.26 (d, J=11.9 Hz, 2H), 1.99-1.80 (m, 2H).

Example 113

4-(8-[4-(dimethylamino)piperidin-1-yl]-5-{2-[(1R)-1-hydroxyethyl]-1-methyl-1H-benzimidazol-5-yl}imidazo[1,2-a]pyrazin-6-yl)benzonitrile

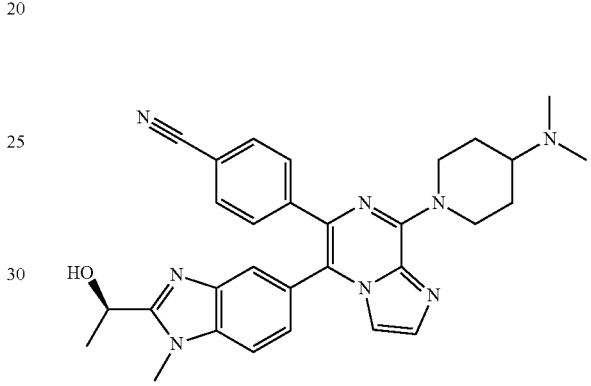

Step 1: (JR)-1-(5-bromo-1-methyl-1H-benzimidazol-2-yl)ethanol

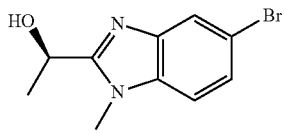

A mixture of (2R)-2-hydroxypropanamide (Aldrich, cat #436801: 186 mg, 2.09 mmol) and triethyloxonium tetrafluoroborate (Aldrich, cat #90520: 370 mg, 2.0 mmol) in tetrahydrofuran (10 mL) was stirred at room temperature for 2 hrs. After concentration, the residue was dissolved in ethanol (4.5 mL) and added to a suspension of 4-bromo-N1-methylbenzene-1,2-diamine (Combi-Blocks, cat #AN-3666: 128 mg, 0.64 mmol) in ethanol (2.1 mL). The mixture was stirred at 80° C. for 1 h then cooled to room temperature and concentrated. The residue was purified by column chromatography on a silica gel column eluting with 0-90% EtOAc in hexanes to give the desired product. LC-MS calculated for $C_{10}H_{12}BrN_2O$ (M+H)$^+$: m/z=255.0. found 255.0.

Step 2: (1R)-1-[1-methyl-5-(4,4,5,5-tetramethyl-1,3,2-dioxaborolan-2-yl)-1H-benzimidazol-2-yl]ethanol

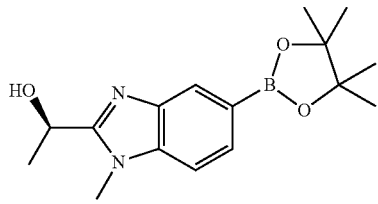 [SMILES: C[C@@H](O)c1nc2cc(B3OC(C)(C)C(C)(C)O3)ccc2n1C]

A mixture of (1R)-1-(5-bromo-1-methyl-1H-benzimidazol-2-yl)ethanol (63 mg, 0.24 mmol), 4,4,5,5,4',4',5',5'-octamethyl-[2,2']bi[[1,3,2]dioxaborolanyl](62 mg, 0.24 mmol), [1,1'-bis(diphenylphosphino)ferrocene]dichloropalladium(II) complexed with dichloromethane (1:1) (20 mg, 0.02 mmol) and potassium acetate (60 mg, 0.7 mmol) in 1,4-dioxane (4 mL) was purged with nitrogen and stirred at 80° C. overnight. After cooling to room temperature, the reaction mixture was concentrated. The residue was purified by flash column chromatography eluting with 0 to 60% EtOAc in hexanes to give the desired product. LC-MS calculated for $C_{16}H_{24}BN_2O_3$ (M+H)$^+$: m/z=303.2. found 303.2.

Step 3: 4-(8-[4-(dimethylamino)piperidin-1-yl]-5-{2-[(1R)-1-hydroxyethyl]-1-methyl-1H-benzimidazol-5-yl}imidazo[1,2-a]pyrazin-6-yl)benzonitrile The title compound was prepared using procedures analogous to those described in Example 58, Step 5 with (1R)-1-[1-methyl-5-(4,4,5,5-tetramethyl-1,3,2-dioxaborolan-2-yl)-1H-benzimidazol-2-yl]ethano 1 replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{30}H_{33}N_8O$ (M+H)$^+$: m/z=521.3. found 521.3.

Example 114

4-(8-[4-(dimethylamino)piperidin-1-yl]-5-{2-[(1S)-1-hydroxyethyl]-1-methyl-1H-benzimidazol-5-yl}imidazo[1,2-a]pyrazin-6-yl)benzonitrile

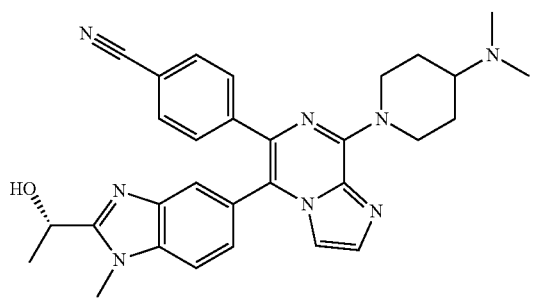 [SMILES: C[C@H](O)c1nc2cc(-c3c(-c4ccc(C#N)cc4)nc(N4CCC(N(C)C)CC4)c4nccn34)ccc2n1C]

The title compound was prepared using procedures analogous to those described in Example 113 with (2S)-2-hydroxypropanamide (Aldrich, cat #436828) replacing (2R)-2-hydroxypropanamide in Step 1. The reaction mixture was purified by prep-HPLC (pH=2, acetonitrile/water+TFA) to give the desired product as the TFA salt. LC-MS calculated for $C_{30}H_{33}N_8O$ (M+H)$^+$: m/z=521.3. found 521.3.

Example 115

4-[8-[4-(dimethylamino)piperidin-1-yl]-5-(1,2-dimethyl-1H-benzimidazol-5-yl)imidazo[1,2-a]pyrazin-6-yl]benzonitrile

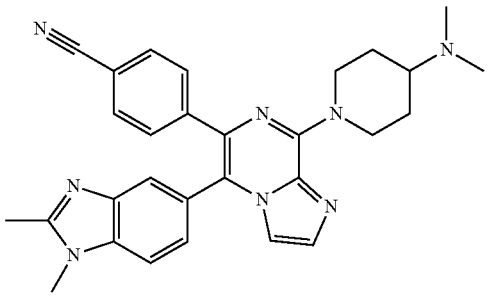

Step 1: 1,2-dimethyl-5-(4,4,5,5-tetramethyl-1,3,2-dioxaborolan-2-yl)-1H-benzimidazole

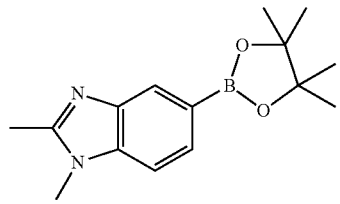

A mixture of [1,1'-bis(diphenylphosphino)ferrocene]dichloropalladium(II) complexed with dichloromethane (1:1) (40 mg, 0.04 mmol), 5-bromo-1,2-dimethyl-1H-benzimidazole (Combi-Blocks, cat #WZ-9484: 200 mg, 0.9 mmol), 4,4,5,5,4',4',5',5'-octamethyl-[2,2']bi[[1,3,2]dioxaborolanyl] (340 mg, 1.3 mmol) and potassium acetate (300 mg, 3 mmol) in 1,4-dioxane (7 mL) was purged with nitrogen then stirred at 90° C. overnight. The reaction mixture was cooled to room temperature then filtered and concentrated. The residue was purified by flash chromatography on a silica gel column eluting with 0 to 30% MeOH in DCM to give the desired product. LC-MS calculated for $C_{15}H_{22}BN_2O_2$ (M+H)$^+$: m/z=273.2. found 273.2.

Step 2: 4-[8-[4-(dimethylamino)piperidin-1-yl]-5-(1,2-dimethyl-1H-benzimidazol-5-yl)imidazo[1,2-a]pyrazin-6-yl]benzonitrile The title compound was prepared using procedures analogous to those described in Example 58, Step 5 with 1,2-dimethyl-5-(4,4,5,5-tetramethyl-1,3,2-dioxaborolan-2-yl)-1H-benzimidazole replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{29}H_{31}N_8$ (M+H)$^+$: m/z=491.3. found 491.3.

Example 116

4-[8-[4-(dimethylamino)piperidin-1-yl]-5-(5-methoxy-6-methylpyridin-3-yl)imidazo[1,2-a]pyrazin-6-yl]benzonitrile

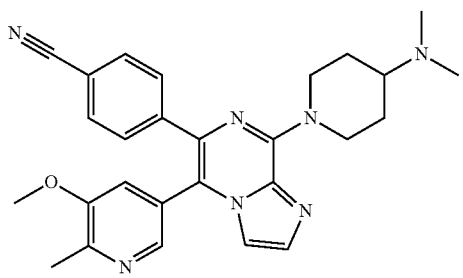 [SMILES: COc1cc(-c2c(-c3ccc(C#N)cc3)nc(N3CCC(N(C)C)CC3)c3nccn23)cnc1C]

The title compound was prepared using procedures analogous to those described in Example 92 with 3-methoxy-2-methyl-5-(4,4,5,5-tetramethyl-1,3,2-dioxaborolan-2-yl)pyridine (Anichem, cat #GS2824) replacing 2,3-dimethyl-5-(4,4,5,5-tetramethyl-1,3,2-dioxaborolan-2-yl)pyridine. The reaction mixture was purified by prep-HPLC (pH=2, acetonitrile/water+TFA) to give the desired product as the TFA salt. LC-MS calculated for $C_{27}H_{30}N_7O$ (M+H)$^+$: m/z=468.3. found 468.2.

Example 117

5-(6-(4-cyanophenyl)-8-{[(3R)-1-methylpiperidin-3-yl]methoxy}imidazo[1,2-a]pyrazin-5-yl)-2-methylnicotinonitrile

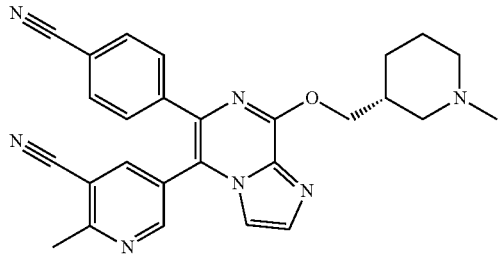 [SMILES: Cc1ncc(-c2c(-c3ccc(C#N)cc3)nc(OC[C@@H]3CCCN(C)C3)c3nccn23)cc1C#N]

Step 1: 2-methyl-5-(4,4,5,5-tetramethyl-1,3,2-dioxaborolan-2-yl)nicotinonitrile

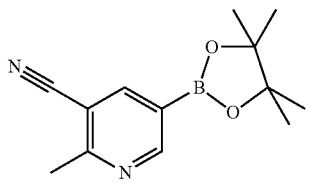 [SMILES: Cc1ncc(B2OC(C)(C)C(C)(C)O2)cc1C#N]

A suspension of 5-bromo-2-methylnicotinonitrile (Combi-Blocks, cat #PY-1861: 148 mg, 0.75 mmol), potassium acetate (220 mg, 2.3 mmol) and 4,4,5,5,4',4',5',5'-octamethyl-[2,2']bi[[1,3,2]dioxaborolanyl](290 mg, 1.1 mmol) in 1,4-dioxane (3.4 mL, 44 mmol) was degassed with stream of nitrogen for ~5 min. Then [1,1'-bis(diphenylphosphino)ferrocene]-dichloropalladium(II) complexed with dichloromethane (1:1) (30 mg, 0.04 mmol) was added, the vial was sealed and then heated at 100° C. overnight. The reaction mixture was then concentrated, diluted with ethyl acetate and filtered through celite, concentrated and used without further purification. LC-MS calculated for $C_{13}H_{18}BN_2O_2$ (M+H)$^+$: m/z=245.1. found 245.1.

Step 2. 5-(6-(4-cyanophenyl)-8-{[(3R)-1-methylpiperidin-3-yl]methoxy}imidazo[1,2-a]pyrazin-5-yl)-2-methylnicotinonitrile The title compound was prepared using procedures analogous to those described in Example 48, Step 8 with 2-methyl-5-(4,4,5,5-tetramethyl-1,3,2-dioxaborolan-2-yl)nicotinonitrile replacing 1-[5-(4,4,5,5-tetramethyl-1,3,2-dioxaborolan-2-yl)pyridin-2-yl]pyrrolidin-2-one. The reaction mixture was purified by prep-HPLC (pH=2, acetonitrile/water+TFA) to give the desired product as the TFA salt. LC-MS calculated for $C_{27}H_{26}N_7O$ (M+H)$^+$: m/z=464.2. found 464.2.

Example 118

4-[8-[4-(dimethylamino)piperidin-1-yl]-5-(5-hydroxy-6-methoxypyridin-3-yl)imidazo[1,2-a]pyrazin-6-yl]benzonitrile

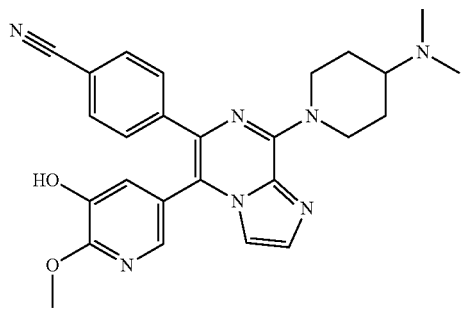 [SMILES: COc1ncc(-c2c(-c3ccc(C#N)cc3)nc(N3CCC(N(C)C)CC3)c3nccn23)cc1O]

Step 1: 2-methoxy-5-(4,4,5,5-tetramethyl-1,3,2-dioxaborolan-2-yl)pyridin-3-ol

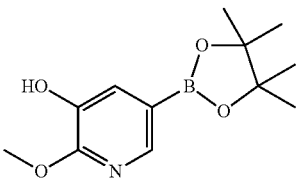

A suspension of 5-bromo-2-methoxypyridin-3-ol (AstaTech, cat #73402: 150 mg, 0.75 mmol), potassium acetate (220 mg, 2.2 mmol) and 4,4,5,5,4',4',5',5'-octamethyl-[2,2']bi[[1,3,2]dioxaborolanyl](280 mg, 1.1 mmol) in 1,4-dioxane (3.4 mL) was degassed with stream of nitrogen, then [1,1'-bis(diphenylphosphino)ferrocene]dichloropalladium(II) complexed with dichloromethane (1:1) (30 mg, 0.04 mmol) was added, the vial was sealed, and the reaction mixture was heated at 90° C. overnight. The reaction mixture was cooled to room temperature, filtered through celite and concentrated. The residue was used in the next step without further purification. LC-MS calculated for $C_{12}H_{19}BNO_4$ (M+H)$^+$: m/z=252.1. found 252.1.

Step 2: 4-[8-[4-(dimethylamino)piperidin-1-yl]-5-(5-hydroxy-6-methoxypyridin-3-yl)imidazo[1,2-a]pyrazin-6-yl]benzonitrile The title compound was prepared using procedures analogous to those described in Example 92 with 2-methoxy-5-(4,4,5,5-tetramethyl-1,3,2-dioxaborolan-2-yl)pyridin-3-ol replacing 2,3-dimethyl-5-(4,4,5,5-tetramethyl-1,3,2-dioxaborolan-2-yl)pyridine. The reaction mixture was purified by prep-HPLC (pH=2, acetonitrile/water+TFA) to give the desired product as the TFA salt. LC-MS calculated for $C_{26}H_{28}N_7O_2$ (M+H)$^+$: m/z=470.2. found 470.2.

Example 119

4-(5-(5-hydroxy-6-methoxypyridin-3-yl)-8-{[(3R)-1-methylpiperidin-3-yl]methoxy}imidazo[1,2-a]pyrazin-6-yl)benzonitrile

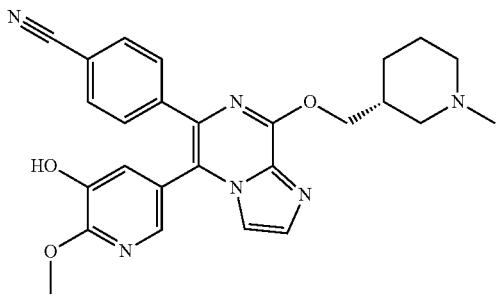 [SMILES: COc1ncc(-c2c(-c3ccc(C#N)cc3)nc(OC[C@@H]3CCCN(C)C3)c3nccn23)cc1O]

The title compound was prepared using procedures analogous to those described in Example 48, Step 8 with 2-methoxy-5-(4,4,5,5-tetramethyl-1,3,2-dioxaborolan-2-yl)pyridin-3-ol (Example 118, Step 1) replacing 1-[5-(4,4,5,5-tetramethyl-1,3,2-dioxaborolan-2-yl)pyridin-2-yl]pyrrolidin-2-one. The reaction mixture was purified by prep-HPLC (pH=2, acetonitrile/water+TFA) to give the desired product as the TFA salt. LC-MS calculated for $C_{26}H_{27}N_6O_3$ (M+H)$^+$: m/z=471.2. found 471.2.

Example A: LSD1 Histone Demethylase Biochemical Assay

LANCE LSD1/KDM1A demethylase assay—10 µL of 1 nM LSD-1 enzyme (ENZO BML-SE544-0050) in the assay buffer (50 mM Tris, pH 7.5, 0.01% Tween-20, 25 mM NaCl, 5 mM DTT) were preincubated for 1 hour at 25° C. with 0.8 µL compound/DMSO dotted in black 384 well polystyrene plates. Reactions were started by addition of 10 µL of assay buffer containing 0.4 M Biotin-labeled Histone H3 peptide substrate: ART-K(Me1)-QTARKSTGGKAPRKQLA-GGK (Biotin) SEQ ID NO:1 (AnaSpec 64355) and incubated for 1 hour at 25° C. Reactions were stopped by addition of 10 µL 1× LANCE Detection Buffer (PerkinElmer CR97-100) supplemented with 1.5 nM Eu-anti-unmodified H3K4 Antibody (PerkinElmer TRF0404), and 225 nM LANCE Ultra Streptavidin (PerkinElmer TRF102) along with 0.9 mM Tranylcypromine-HCl (Millipore 616431). After stopping the reactions plates were incubated for 30 minutes and read on a PHERAstar FS plate reader (BMG Labtech). IC$_{50}$ data for the example compounds is provided in Table 1 (+ refers to IC$_{50}$≤50 nM; ++ refers to IC$_{50}$>50 nM and ≤500 nM; +++ refers to IC$_{50}$>500 nM and ≤1000 nM).

TABLE 1

| Example No. | IC$_{50}$ (nM) |
|---|---|
| 1 | + |
| 2 | + |
| 3 | ++ |
| 4 | + |
| 5 | + |
| 6 | +++ |
| 7 | + |
| 8 | ++ |
| 9 | + |
| 10 | + |
| 11 | + |
| 12 | + |
| 13 | + |
| 14 | + |
| 15 | ++ |
| 16 | ++ |
| 17 | ++ |
| 18 | + |
| 19 | + |
| 20 | + |
| 21 | ++ |
| 22 | +++ |
| 23 | ++ |
| 24 | ++ |
| 25 | ++ |
| 26 | ++ |
| 27 | ++ |
| 28 | ++ |
| 29 | + |
| 30 | + |
| 31 | ++ |
| 32 | ++ |
| 33 | + |
| 34 | ++ |
| 35 | ++ |
| 36 | + |
| 37 | + |
| 38 | + |
| 39 | + |
| 40 | + |
| 41 | + |
| 42 | + |
| 43 | + |
| 44 | + |
| 45 | + |
| 46 | + |
| 47 | + |
| 48 | ++ |
| 49 | ++ |
| 50 | ++ |
| 51 | ++ |
| 52 | + |
| 53 | + |
| 54 | ++ |
| 55 | ++ |
| 56 | ++ |
| 57 | + |
| 58 | + |
| 59 | + |
| 60 | + |
| 61 | ++ |
| 62 | + |
| 63 | ++ |
| 64 | ++ |
| 65 | + |
| 66 | + |
| 67 | + |

TABLE 1-continued

| Example No. | IC$_{50}$ (nM) |
|---|---|
| 68 | + |
| 69 | + |
| 70 | + |
| 71 | ++ |
| 72 | + |
| 73 (mixture of diastereomers) | + |
| 74 | ++ |
| 75 | ++ |
| 76 | + |
| 77 | ++ |
| 78 (peak 1) | + |
| 78 (peak 2) | + |
| 79 (mixture of diastereomers) | + |
| 80 (mixture of diastereomers) | + |
| 81 | + |
| 82 | ++ |
| 83 | ++ |
| 84 | ++ |
| 85 | + |
| 86 | ++ |
| 87 | + |
| 88 (mixture of diastereomers) | + |
| 89 | ++ |
| 90 | + |
| 91 | + |
| 92 | + |
| 93 (racemic) | + |
| 94 | + |
| 95 (racemic) | + |
| 96 | + |
| 97 | + |
| 98 | + |
| 99 | + |
| 100 | + |
| 101 | + |
| 102 | + |
| 103 | + |
| 104 | ++ |
| 105 | + |
| 106 | + |
| 107 | + |
| 108 | ++ |
| 109 | + |
| 110 | + |
| 111 | + |
| 112 | + |
| 113 | + |
| 114 | ++ |
| 115 | + |
| 116 | ++ |
| 117 | ++ |
| 118 | + |
| 119 | + |

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound of Formula I:

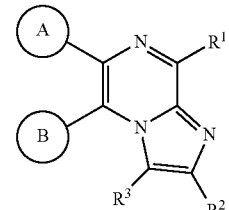

I or a pharmaceutically acceptable salt thereof, wherein:
Ring A is C$_{6-10}$ aryl or 5-10 membered heteroaryl comprising carbon and 1, 2, 3, or 4 heteroatoms selected from N, O, and S, wherein said C$_{6-10}$ aryl and 5-10 membered heteroaryl are each optionally substituted by 1, 2, 3, or 4 substituents independently selected from R$^A$;
Ring B is C$_{6-10}$ aryl; 5-10 membered heteroaryl comprising carbon and 1, 2, 3 or 4 heteroatoms selected from N, O, and S; C$_{3-10}$ cycloalkyl; or 4-10 membered heterocycloalkyl comprising carbon and 1, 2, 3 or 4 heteroatoms selected from N, O, and S; wherein said $C_{6-10}$ aryl, 5-10 membered heteroaryl, $C_{3-10}$ cycloalkyl, and 4-10 membered heterocycloalkyl are each optionally substituted by 1, 2, 3, or 4 substituents independently selected from $R^B$;

$R^1$ is halo, $C_{1-6}$ alkyl, $C_{2-6}$ alkenyl, $C_{2-6}$ alkynyl, $C_{1-6}$ haloalkyl, $Cy^1$, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, or $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $Cy^1$, halo, CN, OH, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

$R^2$ and $R^3$ are each independently selected from H, halo, $C_{1-6}$ alkyl, $C_{2-6}$ alkenyl, $C_{2-6}$ alkynyl, $C_{1-6}$ haloalkyl, $Cy^2$, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1, 2, or 3 substituents independently selected from $Cy^2$, halo, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

each $R^A$ is independently selected from halo, $C_{1-6}$ alkyl, $C_{2-6}$ alkenyl, $C_{2-6}$ alkynyl, $C_{1-6}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$, wherein said $C_{1-6}$ alkyl, $C_{2-6}$ alkenyl, and $C_{2-6}$ alkynyl are each optionally substituted by 1, 2, or 3, substituents independently selected from halo, $C_{1-6}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$;

each $R^B$ is independently selected from $Cy^3$, halo, $C_{1-6}$ alkyl, $C_{2-6}$ alkenyl, $C_{2-6}$ alkynyl, $C_{1-6}$ haloalkyl, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$, wherein said $C_{1-6}$ alkyl, $C_{2-6}$ alkenyl, and $C_{2-6}$ alkynyl are each optionally substituted by 1, 2, or 3 substituents independently selected from $Cy^3$, halo, $C_{1-6}$ haloalkyl, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$;

each $Cy^1$, $Cy^2$, $Cy^3$, and $Cy^4$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, or 4 substituents independently selected from $R^{Cy}$;

each $R^{Cy}$ is independently selected from halo, $C_{1-4}$ alkyl, $C_{1-4}$ haloalkyl, $C_{1-4}$ cyanoalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-4}$ alkyl-, $C_{3-7}$ cycloalkyl-$C_{1-4}$ alkyl-, (5-6 membered heteroaryl)-$C_{1-4}$ alkyl-, and (4-7 membered heterocycloalkyl)-$C_{1-4}$ alkyl-, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $C(=NR^{e6})NR^{c6}R^{d6}$, $NR^{c6}C(=NR^{e6})NR^{c6}R^{d6}$, $NR^{c6}R^{d6}$, $NR^{c6}C(O)R^{b6}$, $NR^{c6}C(O)OR^{a6}$, $NR^{c6}C(O)NR^{c6}R^{d6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, and $S(O)_2NR^{c6}R^{d6}$, wherein said $C_{1-4}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-4}$ alkyl-, $C_{3-7}$ cycloalkyl-$C_{1-4}$ alkyl-, (5-6 membered heteroaryl)-$C_{1-4}$ alkyl-, and (4-7 membered heterocycloalkyl)-$C_{1-4}$ alkyl- are each optionally substituted by 1, 2, or 3 substituents independently selected from $C_{1-6}$ alkyl, $C_{1-4}$ haloalkyl, $C_{1-6}$ cyanoalkyl, halo, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $C(=NR^{e6})NR^{c6}R^{d6}$, $NR^{c6}C(=NR^{e6})NR^{c6}R^{d6}$, $NR^{c6}R^{d6}$, $NR^{c6}C(O)R^{b6}$, $NR^{c6}C(O)OR^{a6}$, $NR^{c6}C(O)NR^{c6}R^{d6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, and $S(O)_2NR^{c6}R^{d6}$;

each $R^{a1}$ is independently selected from $C_{1-6}$ alkyl, $C_{2-6}$ alkenyl, $C_{2-6}$ alkynyl, and $Cy^4$; wherein said $C_{1-6}$ alkyl, $C_{2-6}$ alkenyl, and $C_{2-6}$ alkynyl are each optionally substituted with 1, 2, or 3 substituents independently selected from $Cy^4$, halo, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

each $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})$ $NR^{c7}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

or any $R^{c1}$ and $R^{d1}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c7}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$, wherein said $C_{1-6}$ alkyl, $C_{3-7}$ cycloalkyl, 4-7 membered heterocycloalkyl, $C_{6-10}$ aryl, and 5-6 membered heteroaryl are each optionally substituted by 1, 2, or 3 substituents independently selected from halo, $C_{1-4}$ alkyl, $C_{1-4}$ haloalkyl, $C_{1-4}$ cyanoalkyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c7}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

each $R^{a2}$, $R^{b2}$, $R^{c2}$, and $R^{d2}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c7}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

or any $R^{c2}$ and $R^{d2}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, phenyl, 5-6 membered heteroaryl, $C_{1-6}$ haloalkyl, halo, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c7}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$, wherein said $C_{1-6}$ alkyl, $C_{3-7}$ cycloalkyl, 4-7 membered heterocycloalkyl, phenyl, and 5-6 membered heteroaryl are each optionally substituted by 1, 2, or 3 substituents independently selected from halo, $C_{1-4}$ alkyl, $C_{1-4}$ haloalkyl, $C_{1-4}$ cyanoalkyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c7}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

each $R^{a3}$, $R^{b3}$, $R^{c3}$, and $R^{d3}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c7}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

or any $R^{c3}$ and $R^{d3}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, phenyl, 5-6 membered heteroaryl, $C_{1-6}$ haloalkyl, halo, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c7}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$, wherein said $C_{1-6}$ alkyl, $C_{3-7}$ cycloalkyl, 4-7 membered heterocycloalkyl, phenyl, and 5-6 membered heteroaryl are each optionally substituted by 1, 2, or 3 substituents independently selected from halo, $C_{1-4}$ alkyl, $C_{1-4}$ haloalkyl, $C_{1-4}$ cyanoalkyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c7}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

each $R^{a4}$, $R^{b4}$, $R^{c4}$, and $R^{d4}$ is independently selected from H, $C_{1-6}$ alkyl, $C_{1-4}$ haloalkyl, $C_{2-6}$ alkenyl, and $C_{2-6}$ alkynyl, wherein said $C_{1-6}$ alkyl, $C_{2-6}$ alkenyl, and $C_{2-6}$ alkynyl are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c7}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

or any $R^{c4}$ and $R^{d4}$ together with the N atom to which they are attached form a 4-, 5-, 6-, or 7-membered heterocycloalkyl group optionally substituted with 1, 2, or 3 substituents independently selected from $C_{1-6}$ alkyl, $C_{1-6}$ haloalkyl, halo, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c7}R^{d7}$, $S(O)R^{b7}$, $S(O)NR^{c7}R^{d7}$, $S(O)_2R^{b7}$, $NR^{c7}S(O)_2NR^{c7}R^{d7}$, and $S(O)_2NR^{c7}R^{d7}$;

each $R^{a5}$, $R^{b5}$, $R^{c5}$, and $R^{d5}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c7}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

or any $R^{c5}$ and $R^{d5}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c7}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$, wherein said $C_{1-6}$ alkyl, $C_{3-7}$ cycloalkyl, 4-7 membered heterocycloalkyl, $C_{6-10}$ aryl, and 5-6 membered heteroaryl are each optionally substituted by 1, 2, or 3 substituents independently selected from halo, $C_{1-4}$ alkyl, $C_{1-4}$ haloalkyl, $C_{1-4}$ cyanoalkyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c7}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

each $R^{a6}$, $R^{b6}$, $R^{c6}$, and $R^{d6}$ is independently selected from H, $C_{1-6}$ alkyl, $C_{1-4}$ haloalkyl, $C_{2-6}$ alkenyl, and $C_{2-6}$ alkynyl, wherein said $C_{1-6}$ alkyl, $C_{2-6}$ alkenyl, and $C_{2-6}$ alkynyl are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)OR^{a7}$, $C(=NR^{e7})NR^{c7}R^{d7}$, $NR^{c7}C(=NR^{e7})NR^{c7}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

or any $R^{c6}$ and $R^{d6}$ together with the N atom to which they are attached form a 4-, 5-, 6-, or 7-membered heterocycloalkyl group optionally substituted with 1, 2, or 3 substituents independently selected from $C_{1-6}$ alkyl, $C_{1-6}$ haloalkyl, halo, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c7}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

each $R^{a7}$, $R^{b7}$, $R^{c7}$, and $R^{d7}$ is independently selected from H, $C_{1-4}$ alkyl, $C_{1-4}$ haloalkyl, $C_{2-4}$ alkenyl, and $C_{2-4}$ alkynyl, wherein said $C_{1-4}$ alkyl, $C_{2-4}$ alkenyl, and $C_{2-4}$ alkynyl are each optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy; and each $R^{e1}$, $R^{e2}$, $R^{e3}$, $R^{e4}$, $R^{e5}$, $R^{e6}$, and $R^{e7}$ is independently selected from H, $C_{1-4}$ alkyl, and CN.

2. The compound of claim 1, or a pharmaceutically acceptable salt thereof, wherein:

Ring A is phenyl optionally substituted by 1, 2, or 3 substituents independently selected from $R^A$;

Ring B is phenyl or 5-6 membered heteroaryl comprising carbon and 1 or 2 heteroatoms selected from N; wherein said phenyl or 5-6 membered heteroaryl is optionally substituted by 1, or 2 substituents independently selected from $R^B$;

$R^1$ is halo, $C_{1-6}$ alkyl, $C_{2-6}$ alkenyl, $C_{2-6}$ alkynyl, $C_{1-6}$ haloalkyl, $Cy^1$, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, or $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $Cy^1$, halo, CN, OH, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

$R^2$ is H, halo, $C_{1-6}$ alkyl, $C_{2-6}$ alkenyl, $C_{2-6}$ alkynyl, $C_{1-6}$ haloalkyl, $Cy^2$, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, or $S(O)_2NR^{c2}R^{d2}$; wherein said $C_{1-6}$ alkyl, $C_{2-6}$ alkenyl, and $C_{2-6}$ alkynyl are each optionally substituted with 1, 2, or 3 substituents independently selected from $Cy^2$, halo, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

$R^3$ is H;

each $R^4$ is independently selected from halo, $C_{1-6}$ alkyl, $C_{2-6}$ alkenyl, $C_{2-6}$ alkynyl, $C_{1-6}$ haloalkyl, CN, $OR^{a4}$, $SR^{a4}$, $C(O)R^{b4}$, $C(O)NR^{c4}R^{d4}$, $NR^{c4}R^{d4}$, $NR^{c4}C(O)R^{b4}$, $NR^{c4}S(O)_2R^{b4}$, $S(O)R^{b4}$, $S(O)NR^{c4}R^{d4}$, $S(O)_2R^{b4}$, and $S(O)_2NR^{c4}R^{d4}$, wherein said $C_{1-6}$ alkyl, $C_{2-6}$ alkenyl, and $C_{2-6}$ alkynyl are each optionally substituted by 1, 2, or 3, substituents independently selected from halo, $C_{1-6}$ haloalkyl, CN, $OR^{a4}$, $SR^{a4}$, $C(O)R^{b4}$, $C(O)NR^{c4}R^{d4}$, $NR^{c4}R^{d4}$, $NR^{c4}C(O)R^{b4}$, $NR^{c4}S(O)_2R^{b4}$, $S(O)R^{b4}$, $S(O)NR^{c4}R^{d4}$, $S(O)_2R^{b4}$, and $S(O)_2NR^{c4}R^{d4}$;

each $R^B$ is independently selected from $Cy^3$, halo, $C_{1-6}$ alkyl, $C_{2-6}$ alkenyl, $C_{2-6}$ alkynyl, $C_{1-6}$ haloalkyl, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$, wherein said $C_{1-6}$ alkyl, $C_{2-6}$ alkenyl, and $C_{2-6}$ alkynyl are each optionally substituted by 1, 2 or 3 substituents independently selected from $Cy^3$, halo, $C_{1-6}$ alkyl, $C_{2-6}$ alkenyl, $C_{2-6}$ alkynyl, $C_{1-6}$ haloalkyl, CN, $OR^{a5}$, $SR^{a5}$, $C(O)R^{b5}$, $C(O)NR^{c5}R^{d5}$, $C(O)OR^{a5}$, $OC(O)R^{b5}$, OC(O)NR$^{c5}$R$^{d5}$, NR$^{c5}$R$^{d5}$, NR$^{c5}$C(O)R$^{b5}$, NR$^{c5}$C(O)OR$^{a5}$, NR$^{c5}$C(O)NR$^{c5}$R$^{d5}$, NR$^{c5}$S(O)R$^{b5}$, NR$^{c5}$S(O)$_2$R$^{b5}$, NR$^{c5}$S(O)$_2$NR$^{c5}$R$^{d5}$, S(O)R$^{b5}$, S(O)NR$^{c5}$R$^{d5}$, S(O)$_2$R$^{b5}$, and S(O)$_2$NR$^{c5}$R$^{d5}$;

each Cy$^1$, Cy$^2$, Cy$^3$, and Cy$^4$ is independently selected from C$_{6-10}$ aryl, C$_{3-10}$ cycloalkyl, 5-10 membered heteroaryl, and 4-10 membered heterocycloalkyl, each of which is optionally substituted with 1, 2, 3, or 4 substituents independently selected from R$^{Cy}$;

each R$^{Cy}$ is selected from halo, C$_{1-4}$ alkyl, C$_{1-4}$ haloalkyl, C$_{1-4}$ cyanoalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-4}$ alkyl-, C$_{3-7}$ cycloalkyl-C$_{1-4}$ alkyl-, (5-6 membered heteroaryl)-C$_{1-4}$ alkyl-, and (4-7 membered heterocycloalkyl)-C$_{1-4}$ alkyl-, CN, NO$_2$, OR$^{a6}$, SR$^{a6}$, C(O)R$^{b6}$, C(O)NR$^{c6}$R$^{d6}$, C(O)OR$^{a6}$, OC(O)R$^{b6}$, OC(O)NR$^{c6}$R$^{d6}$, NR$^{c6}$R$^{d6}$, NR$^{c6}$C(O)R$^{b6}$, NR$^{c6}$C(O)OR$^{a6}$, NR$^{c6}$C(O)NR$^{c6}$R$^{d6}$, NR$^{c6}$S(O)R$^{b6}$, NR$^{c6}$S(O)$_2$R$^{b6}$, NR$^{c6}$S(O)$_2$NR$^{c6}$R$^{d6}$, S(O)R$^{b6}$, S(O)NR$^{c6}$R$^{d6}$, S(O)$_2$R$^{b6}$, and S(O)$_2$NR$^{c6}$R$^{d6}$, wherein said C$_{1-4}$ alkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-4}$ alkyl-, C$_{3-7}$ cycloalkyl-C$_{1-4}$ alkyl-, (5-6 membered heteroaryl)-C$_{1-4}$ alkyl-, and (4-7 membered heterocycloalkyl)-C$_{1-4}$ alkyl- are each optionally substituted by 1, 2, or 3 substituents independently selected from C$_{1-6}$ alkyl, C$_{1-4}$ haloalkyl, C$_{1-6}$ cyanoalkyl, halo, CN, NO$_2$, OR$^{a6}$, SR$^{a6}$, C(O)R$^{b6}$, C(O)NR$^{c6}$R$^{d6}$, C(O)OR$^{a6}$, OC(O)R$^{b6}$, OC(O)NR$^{c6}$R$^{d6}$, NR$^{c6}$R$^{d6}$, NR$^{c6}$C(O)R$^{b6}$, NR$^{c6}$C(O)OR$^{a6}$, NR$^{c6}$C(O)NR$^{c6}$R$^{d6}$, NR$^{c6}$S(O)R$^{b6}$, NR$^{c6}$S(O)$_2$R$^{b6}$, NR$^{c6}$S(O)$_2$NR$^{c6}$R$^{d6}$, S(O)R$^{b6}$, S(O)NR$^{c6}$R$^{d6}$, S(O)$_2$R$^{b6}$, and S(O)$_2$NR$^{c6}$R$^{d6}$;

each R$^{a1}$ is independently selected from C$_{1-6}$ alkyl, C$_{2-6}$ alkenyl, C$_{2-6}$ alkynyl, and Cy$^4$; wherein said C$_{1-6}$ alkyl, C$_{2-6}$ alkenyl, and C$_{2-6}$ alkynyl are each optionally substituted with 1, 2, or 3 substituents independently selected from Cy$^4$, halo, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, and S(O)$_2$NR$^{c3}$R$^{d3}$;

each R$^{b1}$, R$^{c1}$, and R$^{d1}$ is independently selected from H, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl-, wherein said C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl- are each optionally substituted with 1, 2, 3, 4, or 5 substituents independently selected from C$_{1-4}$ alkyl, C$_{1-4}$ haloalkyl, C$_{1-4}$ cyanoalkyl, halo, CN, OR$^{a7}$, SR$^{a7}$, C(O)R$^{b7}$, C(O)NR$^{c7}$R$^{d7}$, C(O)OR$^{a7}$, OC(O)R$^{b7}$, OC(O)NR$^{c7}$R$^{d7}$, NR$^{c7}$R$^{d7}$, NR$^{c7}$C(O)R$^{b7}$, NR$^{c7}$C(O)NR$^{c7}$R$^{d7}$, NR$^{c7}$C(O)OR$^{a7}$, S(O)R$^{b7}$, S(O)NR$^{c7}$R$^{d7}$, S(O)$_2$R$^{b7}$, NR$^{c7}$S(O)$_2$R$^{b7}$, NR$^{c7}$S(O)$_2$NR$^{c7}$R$^{d7}$, and S(O)$_2$NR$^{c7}$R$^{d7}$;

or any R$^{c1}$ and R$^{d1}$ together with the N atom to which they are attached form a 4-, 5-, 6-, or 7-membered heterocycloalkyl group optionally substituted with 1, 2 or 3 substituents independently selected from C$_{1-6}$ alkyl, C$_{3-7}$ cycloalkyl, 4-7 membered heterocycloalkyl, C$_{6-10}$ aryl, 5-6 membered heteroaryl, C$_{1-6}$ haloalkyl, halo, CN, OR$^{a7}$, SR$^{a7}$, C(O)R$^{b7}$, C(O)NR$^{c7}$R$^{d7}$, C(O)OR$^{a7}$, OC(O)R$^{b7}$, OC(O)NR$^{c7}$R$^{d7}$, NR$^{c7}$R$^{d7}$, NR$^{c7}$C(O)R$^{b7}$, NR$^{c7}$C(O)NR$^{c7}$R$^{d7}$, NR$^{c7}$C(O)OR$^{a7}$, C(=NR$^{e7}$)NR$^{c7}$R$^{d7}$, NR$^{c7}$C(=NR$^{e7}$)NR$^{c7}$R$^{d7}$, S(O)R$^{b7}$, S(O)NR$^{c7}$R$^{d7}$, S(O)$_2$R$^{b7}$, NR$^{c7}$S(O)$_2$R$^{b7}$, NR$^{c7}$S(O)$_2$NR$^{c7}$R$^{d7}$, and S(O)$_2$NR$^{c7}$R$^{d7}$, wherein said C$_{1-6}$ alkyl, C$_{3-7}$ cycloalkyl, 4-7 membered heterocycloalkyl, C$_{6-10}$ aryl, and 5-6 membered heteroaryl are each optionally substituted by 1, 2, or 3 substituents independently selected from halo, C$_{1-4}$ alkyl, C$_{1-4}$ haloalkyl, C$_{1-4}$ cyanoalkyl, CN, OR$^{a7}$, SR$^{a7}$, C(O)R$^{b7}$, C(O)NR$^{c7}$R$^{d7}$, C(O)OR$^{a7}$, OC(O)R$^{b7}$, OC(O)NR$^{c7}$R$^{d7}$, NR$^{c7}$R$^{d7}$, NR$^{c7}$C(O)R$^{b7}$, NR$^{c7}$C(O)NR$^{c7}$R$^{d7}$, NR$^{c7}$C(O)OR$^{a7}$, C(=NR$^{e7}$)NR$^{c7}$R$^{d7}$, NR$^{c7}$C(=NR$^{e7}$)NR$^{c7}$R$^{d7}$, S(O)R$^{b7}$, S(O)NR$^{c7}$R$^{d7}$, S(O)$_2$R$^{b7}$, NR$^{c7}$S(O)$_2$R$^{b7}$, NR$^{c7}$S(O)$_2$NR$^{c7}$R$^{d7}$, and S(O)$_2$NR$^{c7}$R$^{d7}$;

each R$^{a2}$, R$^{b2}$, R$^{c2}$, and R$^{d2}$ is independently selected from H, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl-, wherein said C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl- are each optionally substituted with 1, 2, 3, 4, or 5 substituents independently selected from C$_{1-4}$ alkyl, C$_{1-4}$ haloalkyl, C$_{1-4}$ cyanoalkyl, halo, CN, OR$^{a7}$, SR$^{a7}$, C(O)R$^{b7}$, C(O)NR$^{c7}$R$^{d7}$, C(O)OR$^{a7}$, OC(O)R$^{b7}$, OC(O)NR$^{c7}$R$^{d7}$, NR$^{c7}$R$^{d7}$, NR$^{c7}$C(O)R$^{b7}$, NR$^{c7}$C(O)NR$^{c7}$R$^{d7}$, NR$^{c7}$C(O)OR$^{a7}$, S(O)R$^{b7}$, S(O)NR$^{c7}$R$^{d7}$, S(O)$_2$R$^{b7}$, NR$^{c7}$S(O)$_2$R$^{b7}$, NR$^{c7}$S(O)$_2$NR$^{c7}$R$^{d7}$, and S(O)$_2$NR$^{c7}$R$^{d7}$;

each R$^{a3}$, R$^{b3}$, R$^{c3}$, and R$^{d3}$ is independently selected from H, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl-, wherein said C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl- are each optionally substituted with 1, 2, 3, 4, or 5 substituents independently selected from C$_{1-4}$ alkyl, C$_{1-4}$ haloalkyl, C$_{1-4}$ cyanoalkyl, halo, CN, OR$^{a7}$, SR$^{a7}$, C(O)R$^{b7}$, C(O)NR$^{c7}$R$^{d7}$, C(O)OR$^{a7}$, OC(O)R$^{b7}$, OC(O)NR$^{c7}$R$^{d7}$, NR$^{c7}$R$^{d7}$, NR$^{c7}$C(O)R$^{b7}$, NR$^{c7}$C(O)NR$^{c7}$R$^{d7}$, NR$^{c7}$C(O)OR$^{a7}$, S(O)R$^{b7}$, S(O)NR$^{c7}$R$^{d7}$, S(O)$_2$R$^{b7}$, NR$^{c7}$S(O)$_2$R$^{b7}$, NR$^{c7}$S(O)$_2$NR$^{c7}$R$^{d7}$, and S(O)$_2$NR$^{c7}$R$^{d7}$;

each R$^{a4}$, R$^{b4}$, R$^{c4}$, and R$^{d4}$ is independently selected from H and C$_{1-3}$ alkyl;

each R$^{a5}$, R$^{b5}$, R$^{c5}$, and R$^{d5}$, is independently selected from H or C$_{1-3}$ alkyl;

each R$^{a6}$, R$^{b6}$, R$^{c6}$, and R$^{d6}$ is independently selected from H or C$_{1-3}$ alkyl; and each R$^{a7}$, R$^{b7}$, R$^{c7}$, and R$^{d7}$ is independently selected from H or C$_{1-3}$ alkyl.

3. The compound of claim 1, or a pharmaceutically acceptable salt thereof, wherein:

Ring A is phenyl optionally substituted by 1, 2, or 3 substituents independently selected from $R^A$;

Ring B is phenyl, pyridyl, or pyrimidinyl, each optionally substituted by 1 or 2 substituents independently selected from $R^B$;

$R^1$ is halo, $C_{1-3}$ alkyl, $Cy^1$, $OR^{a1}$, $SR^{a1}$, $C(O)NR^{c1}R^{d1}$, $NR^{c1}R^{d1}$, $NR^{c1}C(O)R^{b1}$, or $NR^{c1}C(O)NR^{c1}R^{d1}$; wherein said $C_{1-3}$ alkyl is optionally substituted with 1, 2, or 3 substituents independently selected from $Cy^1$, halo, CN, OH, $OR^{a1}$, $C(O)NR^{c1}R^{d1}$, $NR^{c1}R^{d1}$, and $NR^{c1}C(O)R^{b1}$;

$R^2$ is H, halo, $C_{1-3}$ alkyl, $C_{1-3}$ haloalkyl, $Cy^2$, $C(O)NR^{c2}R^{d2}$, $NR^{c2}R^{d2}$, or $NR^{c2}C(O)R^{b2}$; wherein said $C_{1-3}$ alkyl is optionally substituted with 1, 2, or 3 substituents independently selected from $Cy^2$, halo, CN, $OR^{a2}$, $C(O)NR^{c2}R^{d2}$, $NR^{c2}R^{d2}$, and $NR^{c2}C(O)R^{b2}$;

$R^3$ is H;

each $R^A$ is independently selected from halo, $C_{1-6}$ alkyl, $C_{2-6}$ alkenyl, $C_{2-6}$ alkynyl, $C_{1-6}$ haloalkyl, CN, $OR^{a4}$, $SR^{a4}$, $C(O)R^{b4}$, $C(O)NR^{c4}R^{d4}$, $NR^{c4}R^{d4}$, $NR^{c4}C(O)R^{b4}$, $NR^{c4}S(O)_2R^{b4}$, $S(O)R^{b4}$, $S(O)NR^{c4}R^{d4}$, $S(O)_2R^{b4}$, and $S(O)_2NR^{c4}R^{d4}$, wherein said $C_{1-6}$ alkyl, $C_{2-6}$ alkenyl, and $C_{2-6}$ alkynyl are each optionally substituted by 1, 2, or 3, substituents independently selected from halo, $C_{1-6}$ haloalkyl, CN, $OR^{a4}$, $SR^{a4}$, $C(O)R^{b4}$, $C(O)NR^{c4}R^{d4}$, $NR^{c4}R^{d4}$, $NR^{c4}C(O)R^{b4}$, $NR^{c4}S(O)_2R^{b4}$, $S(O)R^{b4}$, $S(O)NR^{c4}R^{d4}$, $S(O)_2R^{b4}$, and $S(O)_2NR^{c4}R^{d4}$;

each $R^B$ is independently selected from $Cy^3$, halo, $C_{1-6}$ alkyl, $C_{1-6}$ haloalkyl, CN, $OR^{a5}$, $C(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)R^{b5}$, $NR^{c5}S(O)_2R^b$, and $NR^{c5}S(O)_2 NR^{c5}R^{d5}$, wherein said $C_{1-6}$ alkyl is optionally substituted by 1, 2, or 3 substituents independently selected from $Cy^3$, halo, $C_{1-6}$ haloalkyl, CN, $OR^{a5}$, $C(O)NR^{c5}R^{d5}$, $NR^{c5}R^{d5}$, and $NR^{c5}C(O)R^{b5}$;

each $Cy^1$, $Cy^2$, $Cy^3$, and $Cy^4$ is independently selected from phenyl, cyclopropyl, azetidinyl, piperidinyl, pyrrolidinyl, diazapanyl, and diazaspirononanyl, each of which is optionally substituted with 1 or 2 substituents independently selected from $R^{Cy}$;

each $R^{Cy}$ is independently selected from halo, $C_{1-4}$ alkyl, $C_{1-4}$ haloalkyl, $C_{1-4}$ cyanoalkyl, CN, $OR^{a6}$, and $NR^{c6}R^{d6}$;

each $R^{a1}$ is independently selected from $C_{1-3}$ alkyl and $Cy^4$; wherein said $C_{1-3}$ alkyl is optionally substituted with 1, 2, or 3 substituents independently selected from $Cy^4$, halo, CN, and $OR^{a3}$, and $NR^{c3}R^{d3}$;

each $R^{b1}$, $R^{c1}$, and $R^{d1}$ is independently selected from H, $C_{1-3}$ alkyl, $C_{1-3}$ haloalkyl, phenyl, cyclopropyl, cyclobutyl, cyclopentyl, cyclohexyl, pyridinyl, pyrimidinyl, azetidinyl, piperidinyl, pyrrolidinyl, thiazolyl, phenyl-$C_{1-2}$ alkyl-, cyclopropyl-$C_{1-2}$ alkyl-, cyclobutyl-$C_{1-2}$ alkyl-, cyclopentyl-$C_{1-2}$ alkyl-, cyclohexyl-$C_{1-2}$ alkyl-, pyridinyl-$C_{1-2}$ alkyl-, pyrimidinyl-$C_{1-2}$ alkyl-, azetidinyl-$C_{1-2}$ alkyl-, piperidinyl-$C_{1-2}$ alkyl-, pyrrolidinyl-$C_{1-2}$ alkyl-, and thiazolyl-$C_{1-2}$ alkyl-, wherein said $C_{1-3}$ alkyl, $C_{1-3}$ haloalkyl, phenyl, cyclopropyl, cyclobutyl, cyclopentyl, cyclohexyl, pyridinyl, pyrimidinyl, azetidinyl, piperidinyl, pyrrolidinyl, thiazolyl, phenyl-$C_{1-2}$ alkyl-, cyclopropyl-$C_{1-2}$ alkyl-, cyclobutyl-$C_{1-2}$ alkyl-, cyclopentyl-$C_1$-2 alkyl-, cyclohexyl-$C_1$-2 alkyl-, pyridinyl-$C_{1-2}$ alkyl-, pyrimidinyl-$C_{1-2}$ alkyl-, azetidinyl-$C_{1-2}$ alkyl-, piperidinyl-$C_{1-2}$ alkyl-, pyrrolidinyl-$C_{1-2}$ alkyl-, and thiazolyl-$C_{1-2}$ alkyl- are each optionally substituted with 1, 2, or 3 substituents independently selected from $C_{1-3}$ alkyl, $C_{1-3}$ haloalkyl, halo, CN, $OR^{a7}$, and $NR^{c7}R^{d7}$;

or any $R^{c1}$ and $R^{d1}$ together with the N atom to which they are attached form a 4-, 5-, 6-, or 7-membered heterocycloalkyl group optionally substituted with $NR^{c7}R^{d7}$;

each $R^{a2}$, $R^{b2}$, $R^{c2}$, and $R^{d2}$ is independently selected from H, $C_{1-3}$ alkyl, $C_{1-3}$ haloalkyl, phenyl, cyclopropyl, cyclobutyl, cyclopropyl-$C_{1-2}$ alkyl-, cyclobutyl-$C_{1-2}$ alkyl-, pyridinyl, pyrimidinyl, isoxazolyl, azetidinyl, piperidinyl, and pyrrolidinyl, wherein said $C_{1-3}$ alkyl, $C_{1-3}$ haloalkyl, phenyl, cyclopropyl, cyclobutyl, cyclopropyl-$C_{1-2}$ alkyl-, cyclobutyl-$C_{1-2}$ alkyl-, pyridinyl, pyrimidinyl, isoxazolyl, azetidinyl, piperidinyl, and pyrrolidinyl are each optionally substituted with 1 or 2 substituents independently selected from $C_{1-4}$ alkyl, $C_{1-4}$ haloalkyl, $C_{1-4}$ cyanoalkyl, halo, CN, $OR^{a7}$, and $NR^{c7}R^{d7}$;

each $R^{a3}$, $R^{b3}$, $R^{c3}$, and $R^{d3}$ is independently selected from H, $C_{1-3}$ alkyl, $C_{1-3}$ haloalkyl, phenyl, cyclopropyl, cyclobutyl, cyclopropyl-$C_{1-2}$ alkyl-, cyclobutyl-$C_{1-2}$ alkyl-, pyridinyl, pyrimidinyl, isoxazolyl, azetidinyl, piperidinyl, and pyrrolidinyl, wherein said $C_{1-3}$ alkyl, $C_{1-3}$ haloalkyl, phenyl, cyclopropyl, cyclobutyl, cyclopropyl-$C_{1-2}$ alkyl-, cyclobutyl-$C_{1-2}$ alkyl-, pyridinyl, pyrimidinyl, isoxazolyl, azetidinyl, piperidinyl, and pyrrolidinyl are each optionally substituted with 1 or 2 substituents independently selected from $C_{1-4}$ alkyl, $C_{1-4}$ haloalkyl, $C_{1-4}$ cyanoalkyl, halo, CN, $OR^{a7}$, and $NR^{c7}R^{d7}$;

each $R^{a4}$, $R^{b4}$, $R^{c4}$, and $R^{d4}$ is independently selected from H and $C_{1-3}$ alkyl;

each $R^{a5}$, $R^{b5}$, $R^{c5}$, and $R^{d5}$ is independently selected from H or $C_{1-3}$ alkyl;

each $R^{a6}$, $R^{b6}$, $R^{c6}$, and $R^{d6}$ is independently selected from H or $C_{1-3}$ alkyl; and each $R^{a7}$, $R^{b7}$, $R^{c7}$, and $R^{d7}$ is independently selected from H or $C_{1-3}$ alkyl.

4. The compound of claim 1, or a pharmaceutically acceptable salt thereof, wherein Ring A is phenyl optionally substituted by 1, 2, 3, or 4 substituents independently selected from $R^A$.

5. The compound of claim 1, or a pharmaceutically acceptable salt thereof, wherein Ring A is phenyl substituted by one $R^A$.

6. The compound of claim 1, or a pharmaceutically acceptable salt thereof, wherein Ring A is phenyl substituted by CN.

7. The compound of claim 1, or a pharmaceutically acceptable salt thereof, wherein Ring B is phenyl, $C_{3-10}$ cycloalkyl, 4-10 membered heterocycloalkyl, or 5-6 membered heteroaryl, each optionally substituted by 1, 2, 3, or 4 substituents independently selected from $R^B$.

8. The compound of claim 1, or a pharmaceutically acceptable salt thereof, wherein Ring B is phenyl or 5-6 membered heteroaryl, each optionally substituted by 1, 2, 3, or 4 substituents independently selected from $R^B$.

9. The compound of claim 1, or a pharmaceutically acceptable salt thereof, wherein Ring B is phenyl, pyridyl, 3-oxo-3,4-dihydro-2H-1,4-benzoxazinyl, 2,3-dihydro-1,4-benzodioxinyl, pyrrolo[2,3-b]pyridinyl, pyrazolo[3,4-b]pyridinyl, 1,3-benzothiazolyl, 2-oxo-2,3-dihydro-1,3-benzoxazolyl, indazolyl, 2-oxo-2,3-dihydro[1,3]oxazolo[4,5-b]pyridinyl, 2,3-dihydro-1H-indenyl, 2-oxo-2,3-dihydro-1H-indolyl, quinoxalinyl, 2-oxo-1,2,3,4-tetrahydroquinolinyl, benzimidazolyl, 3-oxo-3,4-dihydro-2H-pyrido[3,2-b][1,4]oxazinyl, 2-oxo-2,3-dihydro-1H-pyrrolo[2,3-b]pyridinyl, or pyrimidinyl, each optionally substituted by 1, 2, 3, or 4 substituents independently selected from $R^B$.

10. The compound of claim 1, or a pharmaceutically acceptable salt thereof, wherein Ring B is phenyl, pyridyl, or pyrimidinyl, each optionally substituted by 1, 2, 3, or 4 substituents independently selected from $R^B$.

11. The compound of claim 1, or a pharmaceutically acceptable salt thereof, wherein Ring B is phenyl, pyridyl, 3-oxo-3,4-dihydro-2H-1,4-benzoxazinyl, 2,3-dihydro-1,4-benzodioxinyl, pyrrolo[2,3-b]pyridinyl, pyrazolo[3,4-b]pyridinyl, 1,3-benzothiazolyl, 2-oxo-2,3-dihydro-1,3-benzoxazolyl, indazolyl, 2-oxo-2,3-dihydro[1,3]oxazolo[4,5-b]pyridinyl, 2,3-dihydro-1H-indenyl, 2-oxo-2,3-dihydro-1H-indolyl, quinoxalinyl, 2-oxo-1,2,3,4-tetrahydroquinolinyl, benzimidazolyl, 3-oxo-3,4-dihydro-2H-pyrido[3,2-b][1,4]oxazinyl, 2-oxo-2,3-dihydro-1H-pyrrolo[2,3-b]pyridinyl, or pyrimidinyl, each optionally substituted by 1, 2, 3, or 4 substituents independently selected from $Cy^3$, halo, $C_{1-6}$ alkyl, $C_{1-6}$ haloalkyl, $OR^{a5}$, CN, $NR^{c5}C(O)OR^{a5}$, and $NR^{c5}R^{d5}$.

12. The compound of claim 1, or a pharmaceutically acceptable salt thereof, wherein Ring B is phenyl, pyridyl, or pyrimidinyl, each optionally substituted by one substituent selected from $Cy^3$, halo, $C_{1-6}$ alkyl, $C_{1-6}$ haloalkyl, $OR^{a5}$, and $NR^{c5}R^{d5}$.

13. The compound of claim 1, or a pharmaceutically acceptable salt thereof, wherein Ring B is phenyl, pyridyl, 3-oxo-3,4-dihydro-2H-1,4-benzoxazinyl, 2,3-dihydro-1,4-benzodioxinyl, pyrrolo[2,3-b]pyridinyl, pyrazolo[3,4-b]pyridinyl, 1,3-benzothiazolyl, 2-oxo-2,3-dihydro-1,3-benzoxazolyl, indazolyl, 2-oxo-2,3-dihydro[1,3]oxazolo[4,5-b]pyridinyl, 2,3-dihydro-1H-indenyl, 2-oxo-2,3-dihydro-1H-indolyl, quinoxalinyl, 2-oxo-1,2,3,4-tetrahydroquinolinyl, benzimidazolyl, 3-oxo-3,4-dihydro-2H-pyrido[3,2-b][1,4]oxazinyl, 2-oxo-2,3-dihydro-1H-pyrrolo[2,3-b]pyridinyl, or pyrimidinyl, each optionally substituted by 1, 2, 3, or 4 substituents independently selected from chloro, methyl, trifluoromethyl, piperidinyl, methoxy, ethyl, 2-oxopyrrolidinyl, methyl(tetrahydrofuran-2-ylmethyl)amino, fluoro, 2-oxo-1,3-oxazolidinyl, amino, cyano, hydroxymethyl, (4-(methylsulfonyl)piperazin-1-yl)methyl, hydroxy, morpholin-4-ylmethyl, $(CH_3O)(C=O)N(CH_3)$, $(CH_3O)(C=O)N(CH_3)$-methyl, 1-hydroxyethyl, cyanomethyl, 3-methyl-2-oxoimidazolidinyl or dimethylamino.

14. The compound of claim 1, or a pharmaceutically acceptable salt thereof, wherein Ring B is phenyl, pyridyl, or pyrimidinyl, each optionally substituted by chloro, methyl, trifluoromethyl, piperidinyl, methoxy, or dimethylamino.

15. The compound of claim 1, or a pharmaceutically acceptable salt thereof, wherein Ring B is phenyl substituted by methyl.

16. The compound of claim 1, or a pharmaceutically acceptable salt thereof, wherein $R^1$ is $C_{1-6}$ alkyl, $Cy^1$, $OR^{a1}$, $SR^{a1}$, $C(O)NR^{c1}R^{d1}$, $NR^{c1}R^{d1}$, $NR^{c1}C(O)R^{b1}$, or $NR^{c1}C(O)NR^{c1}R^{d1}$ wherein said $C_{1-6}$ alkyl is optionally substituted with 1, 2, or 3 substituents independently selected from $Cy^1$, halo, CN, OH, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

17. The compound of claim 1, or a pharmaceutically acceptable salt thereof, wherein $R^1$ is $C_{1-6}$ alkyl, $Cy^1$, $OR^{a1}$, $SR^{a1}$, $C(O)NR^{c1}R^{d1}$, $NR^{c1}R^{d1}$, $NR^{c1}C(O)R^{b1}$, or $NR^{c1}C(O)NR^{c1}R^{d1}$, wherein said $C_{1-6}$ alkyl is optionally substituted with $Cy^1$, OH, or $OR^{a1}$.

18. The compound of claim 1, or a pharmaceutically acceptable salt thereof, wherein $R^1$ is $OR^{a1}$.

19. The compound of claim 1, or a pharmaceutically acceptable salt thereof, wherein $R^1$ is $C_{1-6}$ alkyl substituted with 1 or 2 substituents independently selected from $Cy^1$ or $OR^{a1}$.

20. The compound of claim 1, or a pharmaceutically acceptable salt thereof, wherein $R^1$ is $Cy^1$ optionally substituted with 1 or 2 substituents independently selected from $C_{1-4}$ alkyl or $NR^{c6}R^{d6}$.

21. The compound of claim 1, or a pharmaceutically acceptable salt thereof, wherein $R^1$ is pyrrolidin-3-ylmethoxy, 2-pyrrolidin-3-ylethyl, [pyrrolidin-3-yloxy]methyl, [3-(dimethylamino)pyrrolidin-1-yl]methyl, [3-(dimethylamino)pyrrolidin-1-yl]ethyl, (1-methylpyrrolidin-3-yl)oxy, 3-(dimethylamino)propoxy, piperidin-3-ylmethoxy, [1,methylpyrrolidin-3-yl]methoxy, [1-methylpiperidin-3-yl]methoxy, [pyrrolidin-3-ylmethyl]thio, 4-(dimethylamino)piperidin-1-yl, 3-(dimethylamino)propyl](methyl)amino, [2-(1-methylpyrrolidin-2-yl)ethyl]amino, (1-methylpiperidin-4-yl)amino, 4-methyl-1,4-diazepan-1-yl, 2,7-diazaspiro[4.4]non-2-yl, 2,7-diazaspiro[3.5]non-7-yl, 3-(dimethylamino)-N-methylpyrrolidine, [2-(2-amino-1,3-thiazol-4-yl)ethyl]amino, azetidin-3-ylmethylaminocarbonyl, 3-(dimethylamino)piperidin-1-yl, [1-(2-hydroxyethyl)piperidin-3-yl]methoxy, [1-(2-cyanoethyl)piperidin-3-yl]methoxy, [1-ethylpiperidin-3-yl]methoxy, or 1-methylazetidin-3-ylaminocarbonyl.

22. The compound of claim 1, or a pharmaceutically acceptable salt thereof, wherein $R^1$ is pyrrolidin-3-ylmethoxy, 2-pyrrolidin-3-ylethyl, [pyrrolidin-3-yloxy]methyl, [3-(dimethylamino)pyrrolidin-1-yl]methyl, [3-(dimethylamino)pyrrolidin-1-yl]ethyl, (1-methylpyrrolidin-3-yl)oxy, 3-(dimethylamino)propoxy, piperidin-3-ylmethoxy, [1,methylpyrrolidin-3-yl]methoxy, [1-methylpiperidin-3-yl]methoxy, [pyrrolidin-3-ylmethyl]thio, 4-(dimethylamino)piperidin-1-yl, 3-(dimethylamino)propyl](methyl)amino, [2-(1-methylpyrrolidin-2-yl)ethyl]amino, (1-methylpiperidin-4-yl)amino, 4-methyl-1,4-diazepan-1-yl, 2,7-diazaspiro[4.4]non-2-yl, 2,7-diazaspiro[3.5]non-7-yl, 3-(dimethylamino)-N-methylpyrrolidine, [2-(2-amino-1,3-thiazol-4-yl)ethyl]amino, azetidin-3-ylmethylaminocarbonyl, or 1-methylazetidin-3-ylaminocarbonyl.

23. The compound of claim 1, or a pharmaceutically acceptable salt thereof, wherein each $R^{a1}$ is independently selected from $C_{1-6}$ alkyl, $C_{2-6}$ alkenyl, $C_{2-6}$ alkynyl, and $Cy^4$; wherein said $C_{1-6}$ alkyl, $C_{2-6}$ alkenyl, and $C_{2-6}$ alkynyl are each optionally substituted with 1, 2, or 3 substituents independently selected from $Cy^4$, halo, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$.

24. The compound of claim 1, or a pharmaceutically acceptable salt thereof, wherein each $R^{a1}$ is $C_{1-6}$ alkyl optionally substituted with 1 or 2 substituents independently selected from $Cy^4$ and $NR^{c3}R^{d3}$.

25. The compound of claim 1, or a pharmaceutically acceptable salt thereof, wherein each $R^{a1}$ is $C_{1-3}$ alkyl optionally substituted with pyrrolidinyl, piperidinyl, or dimethylamino, wherein said pyrrolidinyl and piperidinyl are each optionally substituted with 1, 2, or 3 substituents independently selected from methyl, ethyl, cyanoethyl, and hydroxyethyl.

26. The compound of claim 1, or a pharmaceutically acceptable salt thereof, wherein $R^2$ is H, $C_{1-6}$ alkyl, $C_{1-6}$ haloalkyl, $Cy^2$, or $C(O)NR^{c2}R^{d2}$, wherein said $C_{1-6}$ alkyl is optionally substituted with 1, 2, or 3 substituents independently selected from $Cy^2$, halo, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$.

27. The compound of claim 1, or a pharmaceutically acceptable salt thereof, wherein $R^2$ is H, $C_{1-6}$ alkyl, $C_{1-6}$ haloalkyl, $Cy^2$, or $C(O)NR^{c2}R^{d2}$, wherein said $C_{1-6}$ alkyl is optionally substituted with 1 or 2 substituents independently selected from $Cy^2$, CN, $OR^{a2}$, and $NR^{c2}R^{d2}$.

28. The compound of claim 1, or a pharmaceutically acceptable salt thereof, wherein $R^2$ is H, methyl, trifluoromethyl, 4-methylphenyl, cyanomethyl, methylaminocarbonyl, dimethylaminocarbonyl, cyclopropylaminocarbonyl, 1-methylazetidin-3-ylaminocarbonyl, hydroxymethyl, azetidin-1-ylmethyl, cyclopropylmethylaminomethyl, (isoxazol-3-ylamino)methyl, dimethylaminomethyl, or dimethylaminoethyl.

29. The compound of claim 1, or a pharmaceutically acceptable salt thereof, wherein $R^2$ is H.

30. The compound of claim 1, or a pharmaceutically acceptable salt thereof, wherein $R^3$ is H.

31. The compound of claim 1, or a pharmaceutically acceptable salt thereof, wherein $R^4$ is CN.

32. The compound of claim 1, or a pharmaceutically acceptable salt thereof, wherein each $R^B$ is independently selected from $Cy^3$, halo, $C_{1-6}$ alkyl, $C_{1-6}$ haloalkyl, CN, $NR^{c5}C(O)OR^{a5}$ $NR^{c5}R^{d5}$ and $OR^{a5}$.

33. The compound of claim 1, or a pharmaceutically acceptable salt thereof, wherein each $R^B$ is independently selected from $Cy^3$, halo, $C_{1-6}$ alkyl, $C_{1-6}$ haloalkyl, and $OR^{a5}$.

34. The compound of claim 1, or a pharmaceutically acceptable salt thereof, wherein $R^B$ is $C_{1-6}$ alkyl.

35. The compound of claim 1, or a pharmaceutically acceptable salt thereof, wherein $R^B$ is methyl, chloro, trifluoromethyl, piperidinyl, methoxy, ethyl, 2-oxopyrrolidinyl, methyl(tetrahydrofuran-2-ylmethyl)amino, fluoro, 2-oxo-1,3-oxazolidinyl, amino, cyano, hydroxymethyl, (4-(methylsulfonyl)piperazin-1-yl)methyl, hydroxy, morpholin-4-ylmethyl, $(CH_3O)(C=O)N(CH_3)$, $(CH_3O)(C=O)N(CH_3)$-methyl, 1-hydroxyethyl, cyanomethyl, 3-methyl-2-oxoimidazolidinyl or dimethylamino.

36. The compound of claim 1, or a pharmaceutically acceptable salt thereof, wherein $R^B$ is methyl.

37. The compound of claim 1, or a pharmaceutically acceptable salt thereof, wherein each $Cy^1$ is independently selected from 5-10 membered heteroaryl and 4-10 membered heterocycloalkyl, each of which is optionally substituted with 1, 2, 3, or 4 substituents independently selected from $R^{Cy}$.

38. The compound of claim 1, or a pharmaceutically acceptable salt thereof, wherein each $Cy^1$ is independently selected from 5-10 membered heteroaryl and 4-10 membered heterocycloalkyl, each of which is optionally substituted with 1 or 2 substituents independently selected from $C_{1-4}$ alkyl and $NR^{c6}R^{d6}$.

39. The compound of claim 1, or a pharmaceutically acceptable salt thereof, wherein $Cy^1$ is 4-10 membered heterocycloalkyl, each of which is optionally substituted with 1, 2, 3, or 4 substituents independently selected from $R^{Cy}$.

40. The compound of claim 1, or a pharmaceutically acceptable salt thereof, wherein $Cy^1$ is azetidinyl, piperidinyl, pyrrolidinyl, diazapanyl, or diazaspirononanyl, each optionally substituted with 1 or 2 substituents independently selected from $R^{Cy}$.

41. The compound of claim 1, having Formula II:

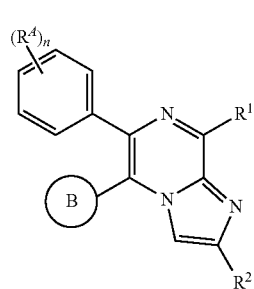

II or a pharmaceutically acceptable salt thereof, wherein n is 0, 1, 2, 3, or 4.

42. The compound of claim 41, or a pharmaceutically acceptable salt thereof, wherein group:

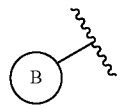

is selected from any one of Formulae (B-1) to (B-15):

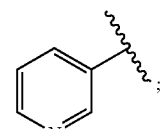
(B-1)

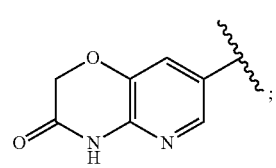
(B-2)

(B-3)

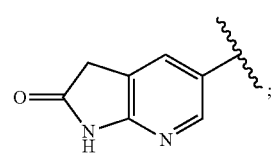
(B-4)

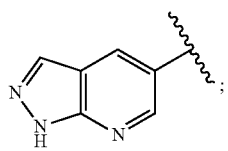 (B-5);

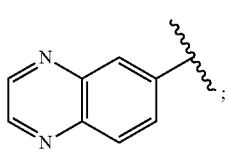 (B-6);

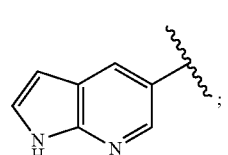 (B-7);

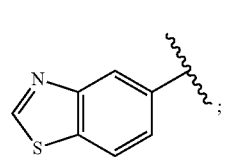 (B-8);

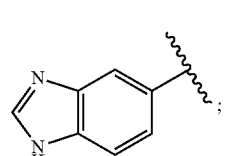 (B-9);

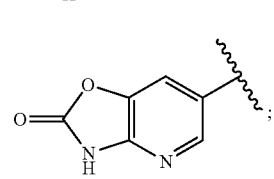 (B-10);

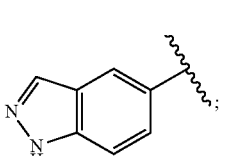 (B-11);

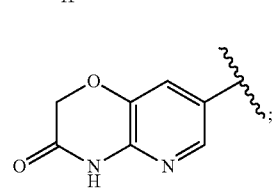 (B-12);

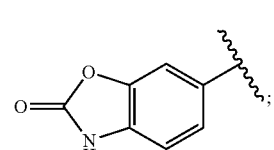 (B-13);

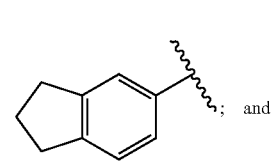 (B-14); and

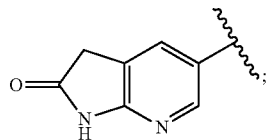 (B-15);

wherein any one of the groups of Formulae (B-1) to (B-15) is optionally substituted with 1, 2, 3, or 4 substituents independently selected from $R^B$.

43. The compound of claim 1, having Formula IIa:

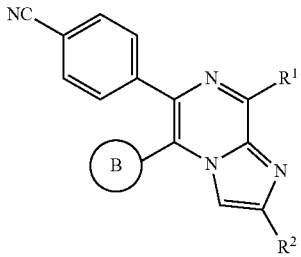

IIa or a pharmaceutically acceptable salt thereof.

44. The compound of claim 1, having Formula III:

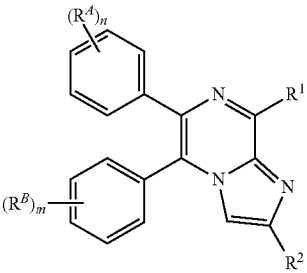

III or a pharmaceutically acceptable salt thereof, wherein n is 0, 1, 2, 3, or 4 and wherein m is 0, 1, 2, 3, or 4.

45. The compound of claim 1, having Formula IV:

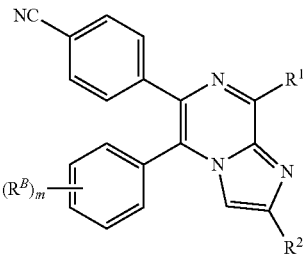

IV or a pharmaceutically acceptable salt thereof, wherein m is 0, 1, 2, 3, or 4.

46. The compound of claim 1, having Formula V:

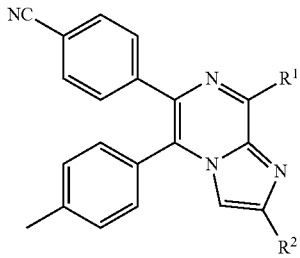

or a pharmaceutically acceptable salt thereof.

47. The compound of claim 1, having Formula VI:

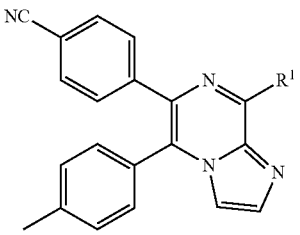

or a pharmaceutically acceptable salt thereof.

48. The compound of claim 1, having Formula VII:

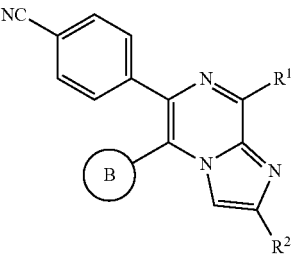

or a pharmaceutically acceptable salt thereof.

49. The compound of claim 48, or a pharmaceutically acceptable salt thereof, wherein group:

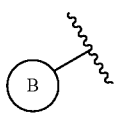

is selected from any one of Formulae (B-1a) to (B-15a):

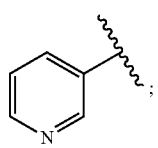
(B-1a)

-continued

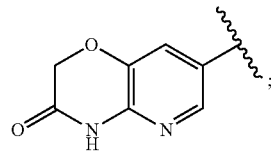
(B-2a)

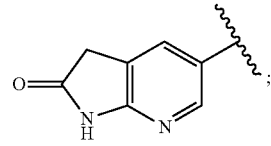
(B-3a)

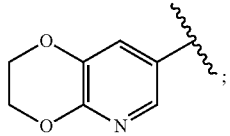
(B-4a)

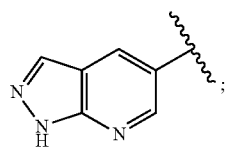
(B-5a)

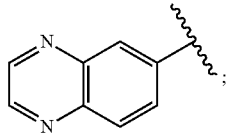
(B-6a)

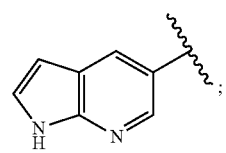
(B-7a)

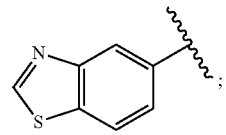
(B-8a)

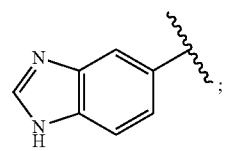
(B-9a)

(B-10a)

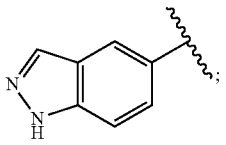
(B-11a)

-continued

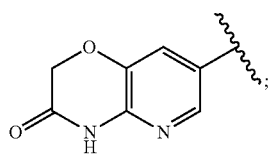 (B-12a)

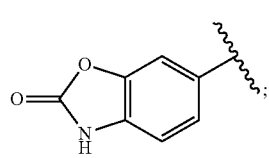 (B-13a)

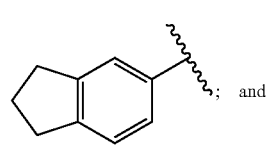 (B-14a) and

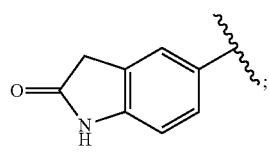 (B-15a)

wherein any one of the groups of Formulae (B-1a) to (B-15a) is optionally substituted with 1, 2, 3, or 4 substituents independently selected from $R^B$.

50. The compound of claim 1 selected from:
4-{5-(4-methylphenyl)-8-[(3R)-pyrrolidin-3-ylmethoxy]imidazo[1,2-a]pyrazin-6-yl}benzonitrile;
4-[5-(4-methylphenyl)-8-(2-pyrrolidin-3-ylethyl)imidazo[1,2-a]pyrazin-6-yl]benzonitrile;
4-(5-(4-methylphenyl)-8-{[(3R)-pyrrolidin-3-yloxy]methyl}imidazo[1,2-a]pyrazin-6-yl)benzonitrile;
4-[8-{[(3S)-3-(dimethylamino)pyrrolidin-1-yl]methyl}-5-(4-methylphenyl)imidazo[1,2-a]pyrazin-6-yl]benzonitrile;
4-[8-{[(3R)-3-(dimethylamino)pyrrolidin-1-yl]methyl}-5-(4-methylphenyl)imidazo[1,2-a]pyrazin-6-yl]benzonitrile;
4-[8-{2-[(3R)-3-(dimethylamino)pyrrolidin-1-yl]ethyl}-5-(4-methylphenyl)imidazo[1,2-a]pyrazin-6-yl]benzonitrile;
4-{5-(4-methylphenyl)-8-[(1-methylpyrrolidin-3-yl)oxy]imidazo[1,2-a]pyrazin-6-yl}benzonitrile;
4-[8-[3-(dimethylamino)propoxy]-5-(4-methylphenyl)imidazo[1,2-a]pyrazin-6-yl]benzonitrile;
4-{5-(4-methylphenyl)-8-[(3R)-piperidin-3-ylmethoxy]imidazo[1,2-a]pyrazin-6-yl}benzonitrile;
4-{5-(4-methylphenyl)-8-[(3S)-piperidin-3-ylmethoxy]imidazo[1,2-a]pyrazin-6-yl}benzonitrile;
4-(5-(4-methylphenyl)-8-{[(3R)-1-methylpyrrolidin-3-yl]methoxy}imidazo[1,2-a]pyrazin-6-yl)benzonitrile;
4-(5-(4-methylphenyl)-8-{[(3R)-1-methylpiperidin-3-yl]methoxy}imidazo[1,2-a]pyrazin-6-yl)benzonitrile;
4-(5-(4-methylphenyl)-8-{[(3R)-pyrrolidin-3-ylmethyl]thio}imidazo[1,2-a]pyrazin-6-yl)benzonitrile;
4-[8-[4-(dimethylamino)piperidin-1-yl]-5-(4-methylphenyl)imidazo[1,2-a]pyrazin-6-yl]benzonitrile;
4-[8-[[3-(dimethylamino)propyl](methyl)amino]-5-(4-methylphenyl)imidazo[1,2-a]pyrazin-6-yl]benzonitrile;
4-(5-(4-methylphenyl)-8-{[2-(1-methylpyrrolidin-2-yl)ethyl]amino}imidazo[1,2-a]pyrazin-6-yl)benzonitrile;
4-{5-(4-methylphenyl)-8-[(1-methylpiperidin-4-yl)amino]imidazo[1,2-a]pyrazin-6-yl}benzonitrile;
4-[8-(4-methyl-1,4-diazepan-1-yl)-5-(4-methylphenyl)imidazo[1,2-a]pyrazin-6-yl]benzonitrile;
4-[8-(2,7-diazaspiro[4.4]non-2-yl)-5-(4-methylphenyl)imidazo[1,2-a]pyrazin-6-yl]benzonitrile;
4-[8-(2,7-diazaspiro[3.5]non-7-yl)-5-(4-methylphenyl)imidazo[1,2-a]pyrazin-6-yl]benzonitrile;
(3R)—N-[6-(4-cyanophenyl)-5-(4-methylphenyl)imidazo[1,2-a]pyrazin-8-yl]-3-(dimethylamino)-N-methylpyrrolidine-1-carboxamide;
(3S)—N-[6-(4-cyanophenyl)-5-(4-methylphenyl)imidazo[1,2-a]pyrazin-8-yl]-3-(dimethylamino)-N-methylpyrrolidine-1-carboxamide;
4-[8-{[2-(2-amino-1,3-thiazol-4-yl)ethyl]amino}-5-(4-methylphenyl)imidazo[1,2-a]pyrazin-6-yl]benzonitrile;
N-(azetidin-3-ylmethyl)-6-(4-cyanophenyl)-5-(4-methylphenyl)imidazo[1,2-a]pyrazine-8-carboxamide;
6-(4-cyanophenyl)-N-(1-methylazetidin-3-yl)-5-(4-methylphenyl)imidazo[1,2-a]pyrazine-8-carboxamide;
4-{(5-phenyl)-8-[(3R)-pyrrolidin-3-ylmethoxy]imidazo[1,2-a]pyrazin-6-yl}benzonitrile;
4-{5-(4-chlorophenyl)-8-[(3R)-pyrrolidin-3-ylmethoxy]imidazo[1,2-a]pyrazin-6-yl}benzonitrile;
4-{8-[(3R)-pyrrolidin-3-ylmethoxy]-5-[4-(trifluoromethyl)phenyl]imidazo[1,2-a]pyrazin-6-yl}benzonitrile;
4-{5-(4-piperidin-1-ylphenyl)-8-[(3R)-pyrrolidin-3-ylmethoxy]imidazo[1,2-a]pyrazin-6-yl}benzonitrile;
4-{5-(4-methoxyphenyl)-8-[(3R)-pyrrolidin-3-ylmethoxy]imidazo[1,2-a]pyrazin-6-yl}benzonitrile;
4-{5-[2-(dimethylamino)pyrimidin-5-yl]-8-[(3R)-pyrrolidin-3-ylmethoxy]imidazo[1,2-a]pyrazin-6-yl}benzonitrile;
4-(5-[6-(dimethylamino)pyridin-3-yl]-8-{[(3R)-1-methylpyrrolidin-3-yl]methoxy}imidazo[1,2-a]pyrazin-6-yl)benzonitrile;
4-{2-methyl-5-(4-methylphenyl)-8-[(3R)-pyrrolidin-3-ylmethoxy]imidazo[1,2-a]pyrazin-6-yl}benzonitrile;
4-[5-(4-methylphenyl)-8-[(3R)-pyrrolidin-3-ylmethoxy]-2-(trifluoromethyl)imidazo[1,2-a]pyrazin-6-yl]benzonitrile;
4-{2,5-bis(4-methylphenyl)-8-[(3R)-pyrrolidin-3-ylmethoxy]imidazo[1,2-a]pyrazin-6-yl}benzonitrile;
4-{2-(cyanomethyl)-5-(4-methylphenyl)-8-[(3R)-pyrrolidin-3-ylmethoxy]imidazo[1,2-a]pyrazin-6-yl}benzonitrile;
6-(4-cyanophenyl)-N-methyl-5-(4-methylphenyl)-8-[(3R)-pyrrolidin-3-ylmethoxy]imidazo-[1,2-a]pyrazine-2-carboxamide;
6-(4-cyanophenyl)-N,N-dimethyl-5-(4-methylphenyl)-8-[(3R)-pyrrolidin-3-ylmethoxy]imidazo[1,2-a]pyrazine-2-carboxamide;
6-(4-cyanophenyl)-N-cyclopropyl-5-(4-methylphenyl)-8-[(3R)-pyrrolidin-3-ylmethoxy]imidazo[1,2-a]pyrazine-2-carboxamide;
6-(4-cyanophenyl)-N-(1-methylazetidin-3-yl)-5-(4-methylphenyl)-8-[(3R)-pyrrolidin-3-ylmethoxy]imidazo[1,2-a]pyrazine-2-carboxamide;
4-{2-(hydroxymethyl)-5-(4-methylphenyl)-8-[(3R)-pyrrolidin-3-ylmethoxy]imidazo[1,2-a]pyrazin-6-yl}benzonitrile;
4-{2-[(dimethylamino)methyl]-5-(4-methylphenyl)-8-[(3R)-pyrrolidin-3-ylmethoxy]imidazo[1,2-a]pyrazin-6-yl}benzonitrile;

4-{2-(azetidin-1-ylmethyl)-5-(4-methylphenyl)-8-[(3R)-pyrrolidin-3-ylmethoxy]imidazo[1,2-a]pyrazin-6-yl}benzonitrile;
4-{2-{[(cyclopropylmethyl)amino]methyl}-5-(4-methylphenyl)-8-[(3R)-pyrrolidin-3-ylmethoxy]imidazo[1,2-a]pyrazin-6-yl}benzonitrile;
4-{2-[(isoxazol-3-ylamino)methyl]-5-(4-methylphenyl)-8-[(3R)-pyrrolidin-3-ylmethoxy]imidazo[1,2-a]pyrazin-6-yl}benzonitrile;
4-(2-[(dimethylamino)methyl]-5-(4-methylphenyl)-8-{[(3R)-1-methylpyrrolidin-3-yl]methoxy}imidazo[1,2-a]pyrazin-6-yl)benzonitrile; and
4-{2-[2-(dimethylamino)ethyl]-5-(4-methylphenyl)-8-[(3R)-pyrrolidin-3-ylmethoxy]imidazo[1,2-a]pyrazin-6-yl}benzonitrile, or a pharmaceutically acceptable salt of any of the aforementioned.

51. The compound of claim 1 selected from:
4-{8-{[(3R)-1-methylpiperidin-3-yl]methoxy}-5-[6-(2-oxopyrrolidin-1-yl)pyridin-3-yl]imidazo[1,2-a]pyrazin-6-yl}benzonitrile;
4-(5-(4-methyl-3-oxo-3,4-dihydro-2H-1,4-benzoxazin-7-yl)-8-{[(3R)-1-methylpiperidin-3-yl]methoxy}imidazo[1,2-a]pyrazin-6-yl)benzonitrile;
4-(5-(2,3-dihydro-1,4-benzodioxin-6-yl)-8-{[(3R)-1-methylpiperidin-3-yl]methoxy}imidazo[1,2-a]pyrazin-6-yl)benzonitrile;
4-(5-[6-(dimethylamino)pyridin-3-yl]-8-{[(3R)-1-methylpiperidin-3-yl]methoxy}imidazo[1,2-a]pyrazin-6-yl)benzonitrile;
4-(8-{[(3R)-1-methylpiperidin-3-yl]methoxy}-5-{6-[methyl(tetrahydrofuran-2-ylmethyl)amino]pyridin-3-yl}imidazo[1,2-a]pyrazin-6-yl)benzonitrile;
4-[8-{[(3R)-1-methylpiperidin-3-yl]methoxy}-5-(1-methyl-1H-pyrrolo[2,3-b]pyridin-5-yl)imidazo[1,2-a]pyrazin-6-yl]benzonitrile;
4-[8-{[(3R)-1-methylpiperidin-3-yl]methoxy}-5-(1-methyl-1H-pyrazolo[3,4-b]pyridin-5-yl)imidazo[1,2-a]pyrazin-6-yl]benzonitrile;
4-(5-(1,3-benzothiazol-5-yl)-8-{[(3R)-1-methylpiperidin-3-yl]methoxy}imidazo[1,2-a]pyrazin-6-yl)benzonitrile;
4-{8-{[(3S)-3-(dimethylamino)pyrrolidin-1-yl]methyl}-5-[6-(2-oxopyrrolidin-1-yl)pyridin-3-yl]imidazo[1,2-a]pyrazin-6-yl)}benzonitrile;
4-{8-[4-(dimethylamino)piperidin-1-yl]-5-[6-(2-oxopyrrolidin-1-yl)pyridin-3-yl]imidazo[1,2-a]pyrazin-6-yl}benzonitrile;
4-[8-[4-(dimethylamino)piperidin-1-yl]-5-(1-methyl-1H-pyrazolo[3,4-b]pyridin-5-yl)imidazo[1,2-a]pyrazin-6-yl]benzonitrile;
4-[8-[4-(dimethylamino)piperidin-1-yl]-5-(3-methyl-2-oxo-2,3-dihydro-1,3-benzoxazol-6-yl)imidazo[1,2-a]pyrazin-6-yl]benzonitrile;
4-[8-[4-(dimethylamino)piperidin-1-yl]-5-(4-methyl-3-oxo-3,4-dihydro-2H-1,4-benzoxazin-7-yl)imidazo[1,2-a]pyrazin-6-yl]benzonitrile;
4-[8-{[(3R)-1-ethylpiperidin-3-yl]methoxy}-5-(1-methyl-1H-pyrrolo[2,3-b]pyridin-5-yl)imidazo[1,2-a]pyrazin-6-yl]benzonitrile;
4-[8-[4-(dimethylamino)piperidin-1-yl]-5-(5-fluoro-3-methyl-2-oxo-2,3-dihydro-1,3-benzoxazol-6-yl)imidazo[1,2-a]pyrazin-6-yl]benzonitrile;
4-[8-{[(3R)-1-ethylpiperidin-3-yl]methoxy}-5-(3-methyl-2-oxo-2,3-dihydro-1,3-benzoxazol-6-yl)imidazo[1,2-a]pyrazin-6-yl]benzonitrile;
4-[8-{[(3R)-1-(2-cyanoethyl)piperidin-3-yl]methoxy}-5-(3-methyl-2-oxo-2,3-dihydro-1,3-benzoxazol-6-yl)imidazo[1,2-a]pyrazin-6-yl]benzonitrile;
4-[8-{[(3R)-1-(2-hydroxyethyl)piperidin-3-yl]methoxy}-5-(1-methyl-1H-indazol-5-yl)imidazo[1,2-a]pyrazin-6-yl]benzonitrile;
4-[8-[4-(dimethylamino)piperidin-1-yl]-5-(3-methyl-2-oxo-2,3-dihydro[1,3]oxazolo[4,5-b]pyridin-6-yl)imidazo[1,2-a]pyrazin-6-yl]benzonitrile;
4-{8-[4-(dimethylamino)piperidin-1-yl]-5-[6-(2-oxo-1,3-oxazolidin-3-yl)pyridin-3-yl]imidazo[1,2-a]pyrazin-6-yl}benzonitrile;
4-{5-(3-amino-1-methyl-1H-indazol-5-yl)-8-[4-(dimethylamino)piperidin-1-yl]imidazo[1,2-a]pyrazin-6-yl}benzonitrile;
5-(6-(4-cyanophenyl)-8-{[(3R)-1-methylpiperidin-3-yl]methoxy}imidazo[1,2-a]pyrazin-5-yl)-2-methylbenzonitrile;
4-(5-[3-(hydroxymethyl)-4-methylphenyl]-8-{[(3R)-1-methylpiperidin-3-yl]methoxy}imidazo[1,2-a]pyrazin-6-yl)benzonitrile;
4-(5-{4-methyl-3-{[4-(methylsulfonyl)piperazin-1-yl]methyl}phenyl)-8-{[(3R)-1-methylpiperidin-3-yl]methoxy}imidazo[1,2-a]pyrazin-6-yl)benzonitrile;
4-(5-[4-(hydroxymethyl)-3-methylphenyl]-8-{[(3R)-1-methylpiperidin-3-yl]methoxy}imidazo[1,2-a]pyrazin-6-yl)benzonitrile;
4-(5-(3-hydroxy-2,3-dihydro-1H-inden-5-yl)-8-{[(3R)-1-methylpiperidin-3-yl]methoxy}imidazo[1,2-a]pyrazin-6-yl)benzonitrile;
4-(5-[4-(hydroxymethyl)phenyl]-8-{[(3R)-1-methylpiperidin-3-yl]methoxy}imidazo[1,2-a]pyrazin-6-yl)benzonitrile;
4-{8-{[(3R)-1-methylpiperidin-3-yl]methoxy}-5-[4-(morpholin-4-ylmethyl)phenyl]imidazo[1,2-a]pyrazin-6-yl}benzonitrile;
methyl [5-(6-(4-cyanophenyl)-8-{[(3R)-1-methylpiperidin-3-yl]methoxy}imidazo[1,2-a]pyrazin-5-yl)-2-methylphenyl]methylcarbamate;
methyl [4-(6-(4-cyanophenyl)-8-{[(3R)-1-methylpiperidin-3-yl]methoxy}imidazo[1,2-a]pyrazin-5-yl)phenyl]methylcarbamate;
4-(5-(2-hydroxy-2,3-dihydro-1H-inden-5-yl)-8-{[(3R)-1-methylpiperidin-3-yl]methoxy}imidazo[1,2-a]pyrazin-6-yl)benzonitrile;
4-(5-(7-fluoro-3-hydroxy-2,3-dihydro-1H-inden-5-yl)-8-{[(3R)-1-methylpiperidin-3-yl]methoxy}imidazo[1,2-a]pyrazin-6-yl)benzonitrile;
4-(5-(1-hydroxy-2,3-dihydro-1H-inden-5-yl)-8-{[(3R)-1-methylpiperidin-3-yl]methoxy}imidazo[1,2-a]pyrazin-6-yl)benzonitrile;
4-(5-[3-fluoro-4-(hydroxymethyl)-5-methylphenyl]-8-{[(3R)-1-methylpiperidin-3-yl]methoxy}imidazo[1,2-a]pyrazin-6-yl)benzonitrile;
4-(5-[3-fluoro-4-(morpholin-4-ylmethyl)phenyl]-8-{[(3R)-1-methylpiperidin-3-yl]methoxy}imidazo[1,2-a]pyrazin-6-yl)benzonitrile;
4-(5-[3,5-difluoro-4-(hydroxymethyl)phenyl]-8-{[(3R)-1-methylpiperidin-3-yl]methoxy}imidazo[1,2-a]pyrazin-6-yl)benzonitrile;
4-(5-(5-fluoro-6-methoxypyridin-3-yl)-8-{[(3R)-1-methylpiperidin-3-yl]methoxy}imidazo[1,2-a]pyrazin-6-yl)benzonitrile;
methyl [4-(6-(4-cyanophenyl)-8-{[(3R)-1-methylpiperidin-3-yl]methoxy}imidazo[1,2-a]pyrazin-5-yl)-2-fluorobenzyl]methylcarbamate;

4-(5-[4-(1-hydroxyethyl)-3-methylphenyl]-8-{[(3R)-1-methylpiperidin-3-yl]methoxy}imidazo[1,2-a]pyrazin-6-yl)benzonitrile;

4-(5-[3-(1-hydroxyethyl)-4-methylphenyl]-8-{[(3R)-1-methylpiperidin-3-yl]methoxy}imidazo[1,2-a]pyrazin-6-yl)benzonitrile;

4-(5-(7-fluoro-1-hydroxy-2,3-dihydro-1H-inden-5-yl)-8-{[(3R)-1-methylpiperidin-3-yl]methoxy}imidazo[1,2-a]pyrazin-6-yl)benzonitrile;

4-(5-[2-fluoro-4-(morpholin-4-ylmethyl)phenyl]-8-{[(3R)-1-methylpiperidin-3-yl]methoxy}imidazo[1,2-a]pyrazin-6-yl)benzonitrile;

4-(5-[2-(hydroxymethyl)-4-methylphenyl]-8-{[(3R)-1-methylpiperidin-3-yl]methoxy}imidazo[1,2-a]pyrazin-6-yl)benzonitrile;

4-(5-[3-(cyanomethyl)-4-methylphenyl]-8-{[(3R)-1-methylpiperidin-3-yl]methoxy}imidazo[1,2-a]pyrazin-6-yl)benzonitrile;

4-[8-[4-(dimethylamino)piperidin-1-yl]-5-(5,6-dimethylpyridin-3-yl)imidazo[1,2-a]pyrazin-6-yl]benzonitrile;

4-[8-[4-(dimethylamino)piperidin-1-yl]-5-(2-hydroxy-2,3-dihydro-1H-inden-5-yl)imidazo[1,2-a]pyrazin-6-yl]benzonitrile;

4-[8-[4-(dimethylamino)piperidin-1-yl]-5-(5-hydroxy-6-methylpyridin-3-yl)imidazo[1,2-a]pyrazin-6-yl]benzonitrile;

4-[8-[4-(dimethylamino)piperidin-1-yl]-5-(3-hydroxy-2,3-dihydro-1H-inden-5-yl)imidazo[1,2-a]pyrazin-6-yl]benzonitrile;

4-{8-[4-(dimethylamino)piperidin-1-yl]-5-[3-(hydroxymethyl)-4-methylphenyl]imidazo[1,2-a]pyrazin-6-yl}benzonitrile;

4-{8-[4-(dimethylamino)piperidin-1-yl]-5-[3-fluoro-4-(hydroxymethyl)-5-methylphenyl]imidazo[1,2-a]pyrazin-6-yl}benzonitrile;

4-[8-[4-(dimethylamino)piperidin-1-yl]-5-(1-methyl-2-oxo-2,3-dihydro-1H-indol-5-yl)imidazo[1,2-a]pyrazin-6-yl]benzonitrile;

4-{8-[3-(dimethylamino)piperidin-1-yl]-5-[6-(2-oxopyrrolidin-1-yl)pyridin-3-yl]imidazo[1,2-a]pyrazin-6-yl}benzonitrile;

4-{8-[4-(dimethylamino)piperidin-1-yl]-5-[6-(3-methyl-2-oxoimidazolidin-1-yl)pyridin-3-yl]imidazo[1,2-a]pyrazin-6-yl}benzonitrile;

4-{8-[4-(dimethylamino)piperidin-1-yl]-5-quinoxalin-6-ylimidazo[1,2-a]pyrazin-6-yl}benzonitrile;

4-[8-[4-(dimethylamino)piperidin-1-yl]-5-(1-methyl-2-oxo-1,2,3,4-tetrahydroquinolin-6-yl)imidazo[1,2-a]pyrazin-6-yl]benzonitrile;

4-{8-[4-(dimethylamino)piperidin-1-yl]-5-[2-(hydroxymethyl)-1-methyl-1H-pyrrolo[2,3-b]pyridin-5-yl]imidazo[1,2-a]pyrazin-6-yl}benzonitrile;

4-{8-[(3S)-3-(dimethylamino)pyrrolidin-1-yl]-5-[6-(2-oxopyrrolidin-1-yl)pyridin-3-yl]imidazo[1,2-a]pyrazin-6-yl}benzonitrile;

4-[8-[4-(dimethylamino)piperidin-1-yl]-5-(3-ethyl-2-oxo-2,3-dihydro[1,3]oxazolo[4, 5-b]pyridin-6-yl)imidazo[1,2-a]pyrazin-6-yl]benzonitrile;

4-[8-[4-(dimethylamino)piperidin-1-yl]-5-(1-methyl-1H-benzimidazol-5-yl)imidazo[1,2-a]pyrazin-6-yl]benzonitrile;

4-[8-[4-(dimethylamino)piperidin-1-yl]-5-(4-methyl-3-oxo-3,4-dihydro-2H-pyrido[3,2-b][1,4]oxazin-7-yl)imidazo[1,2-a]pyrazin-6-yl]benzonitrile;

4-[8-[4-(dimethylamino)piperidin-1-yl]-5-(1-methyl-2-oxo-1,2,3,4-tetrahydroquinolin-7-yl)imidazo[1,2-a]pyrazin-6-yl]benzonitrile;

4-{8-[4-(dimethylamino)piperidin-1-yl]-5-[6-(4-methyl-3-oxopiperazin-1-yl)pyridin-3-yl]imidazo[1,2-a]pyrazin-6-yl}benzonitrile;

4-{8-[4-(dimethylamino)piperidin-1-yl]-5-[3-(hydroxymethyl)-1-methyl-1H-indazol-5-yl]imidazo[1,2-a]pyrazin-6-yl}benzonitrile;

4-[8-[4-(dimethylamino)piperidin-1-yl]-5-(1-methyl-2-oxo-2,3-dihydro-1H-pyrrolo [2,3-b]pyridin-5-yl)imidazo[1,2-a]pyrazin-6-yl]benzonitrile;

4-[8-[4-(dimethylamino)piperidin-1-yl]-5-(1-methyl-1H-pyrrolo[2,3-b]pyridin-5-yl)imidazo[1,2-a]pyrazin-6-yl]benzonitrile;

4-(8-[4-(dimethylamino)piperidin-1-yl]-5-{2-[(1R)-1-hydroxyethyl]-1-methyl-1H-benzimidazol-5-yl}imidazo[1,2-a]pyrazin-6-yl)benzonitrile;

4-(8-[4-(dimethylamino)piperidin-1-yl]-5-{2-[(1S)-1-hydroxyethyl]-1-methyl-1H-benzimidazol-5-yl}imidazo[1,2-a]pyrazin-6-yl)benzonitrile;

4-[8-[4-(dimethylamino)piperidin-1-yl]-5-(1,2-dimethyl-1H-benzimidazol-5-yl)imidazo[1,2-a]pyrazin-6-yl]benzonitrile;

4-[8-[4-(dimethylamino)piperidin-1-yl]-5-(5-methoxy-6-methylpyridin-3-yl)imidazo[1,2-a]pyrazin-6-yl]benzonitrile;

5-(6-(4-cyanophenyl)-8-{[(3R)-1-methylpiperidin-3-yl]methoxy)}imidazo[1,2-a]pyrazin-5-yl)-2-methylnicotinonitrile;

4-[8-[4-(dimethylamino)piperidin-1-yl]-5-(5-hydroxy-6-methoxypyridin-3-yl)imidazo[1,2-a]pyrazin-6-yl]benzonitrile; and 4-(5-(5-hydroxy-6-methoxypyridin-3-yl)-8-{[(3R)-1-methylpiperidin-3-yl]methoxy}imidazo[1,2-a]pyrazin-6-yl)benzonitrile;

or a pharmaceutically acceptable salt thereof.

52. A pharmaceutical composition comprising a compound of claim 1, or a pharmaceutically acceptable salt thereof, and at least one pharmaceutically acceptable carrier or excipient.

53. A method of inhibiting lysine specific demethylase-1 comprising contacting a compound of claim 1, or a pharmaceutically acceptable salt thereof, with said lysine specific demethylase-1.

* * * * *

UNITED STATES PATENT AND TRADEMARK OFFICE
CERTIFICATE OF CORRECTION

PATENT NO. : 9,695,180 B2
APPLICATION NO. : 14/795466
DATED : July 4, 2017
INVENTOR(S) : Liangxing Wu et al.

It is certified that error appears in the above-identified patent and that said Letters Patent is hereby corrected as shown below:

In the Claims

Column 159, Line 23, Claim 3, delete "$R^{b4}$" and insert -- $R^{b4}$, --;

Column 159, Line 33, Claim 3, delete "$NR^{c5}S(O)_2R^b$," and insert -- $NR^{c5}S(O)_2R^{b5}$, --;

Column 159, Line 63, Claim 3, delete "cyclopentyl-$C_1$-2" and insert -- cyclopentyl-$C_{1-2}$ --;

Column 159, Line 63, Claim 3, delete "cyclohexyl-$C_1$-2" and insert -- cyclohexyl-$C_{1-2}$ --.

Column 163, Line 35, Claim 32, after "$NR^{c5}C(O)OR^{a5}$" insert -- , --.

Column 170, Line 11, Claim 50, delete "(3R)—" and insert -- (3R)- --;

Column 170, Line 14, Claim 50, delete "(3S)—" and insert -- (3S)- --.

Column 174, Line 2, Claim 51, delete "[4, 5-b]" and insert -- [4,5-b] --;

Column 174, Line 20, Claim 51, delete "pyrrolo [2,3-b]" and insert -- pyrrolo[2,3-b] --.

Signed and Sealed this
Twenty-first Day of November, 2017

Joseph Matal
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 1

<210> SEQ ID NO 1
<211> LENGTH: 20
<212> TYPE: PRT
<213> ORGANISM: Artificial Sequence
<220> FEATURE:
<223> OTHER INFORMATION: synthetic peptide

<400> SEQUENCE: 1

Gln Thr Ala Arg Lys Ser Thr Gly Gly Lys Ala Pro Arg Lys Gln Leu
 1               5                  10                  15

Ala Gly Gly Lys
            20
```